US006410033B1

(12) United States Patent
Cochran

(10) Patent No.: US 6,410,033 B1
(45) Date of Patent: Jun. 25, 2002

(54) RECOMBINANT INFECTIOUS BOVINE RHINOTRACHEITIS VIRUS

(75) Inventor: Mark D. Cochran, Carlsbad, CA (US)

(73) Assignee: Syntro Corporation, San Diego, CA (US)

( * ) Notice: Subject to any disclaimer, the term of this patent is extended or adjusted under 35 U.S.C. 154(b) by 0 days.

(21) Appl. No.: 08/379,647

(22) PCT Filed: Feb. 2, 1995

(86) PCT No.: PCT/US95/01491

§ 371 (c)(1),
(2), (4) Date: Aug. 5, 1996

(87) PCT Pub. No.: WO95/21261

PCT Pub. Date: Aug. 10, 1995

Related U.S. Application Data

(63) Continuation-in-part of application No. 08/334,428, filed on Nov. 4, 1994, now Pat. No. 5,834,305, and a continuation-in-part of application No. 08/191,866, filed on Feb. 4, 1994, now Pat. No. 5,783,195, which is a continuation of application No. 08/037,707, filed on Mar. 25, 1993, now abandoned, which is a continuation of application No. 07/649, 380, filed on Jan. 31, 1991, now abandoned, which is a continuation of application No. 07/078,519, filed on Jul. 27, 1987, now abandoned.

(51) Int. Cl.[7] ........................ A61K 39/265; C12N 7/04; C12N 15/63

(52) U.S. Cl. .................. 424/229.1; 435/236; 435/320.1

(58) Field of Search .............................. 435/320.1, 236; 424/229.1

(56) References Cited

U.S. PATENT DOCUMENTS

| | | | | | |
|---|---|---|---|---|---|
| 4,703,011 A | | 10/1987 | Kit et al. | | |
| 4,769,331 A | | 9/1988 | Roizman et al. | | |
| 4,824,667 A | | 4/1989 | Kit et al. | | |
| 4,877,737 A | | 10/1989 | Shih et al. | | |
| 5,593,873 A | | 1/1997 | Cochran et al. | | |
| 5,599,544 A | | 2/1997 | Cochran et al. | | |
| 5,783,195 A | * | 7/1998 | Cochran et al. | ......... | 424/229.1 |
| 5,804,372 A | | 9/1998 | Cochran et al. | | |
| 5,874,279 A | | 2/1999 | Cochran et al. | | |
| 6,210,961 B1 | * | 4/2001 | Cochran et al. | ......... | 435/320.1 |

FOREIGN PATENT DOCUMENTS

| | | |
|---|---|---|
| EP | 0316658 | 5/1989 |
| EP | 0326127 | 8/1989 |
| EP | 0547446 | 6/1993 |
| WO | 9221751 | 12/1992 |
| WO | 9302104 | 2/1993 |
| WO | 9400586 | 1/1994 |

OTHER PUBLICATIONS

E.A. Petrovskis, et al., (1986) Deletions in Vaccine Strains of Pseudorabies Virus and Their Effect on Synthesis of Glycoprotein gp63. J. Virol. 60:1166–1169 (Exhibit 9).

T. Ben–Porat, et al., (1986) Role of Glycoproteins of Pseudorabies Virus in Eliciting Neutralizing Antibodies. Virology 154:325–334 (Exhibit 10).

R.W. Price and A. Khan, (1981) Resistance of Peripheral Autonomic Neurons To In Vivo Productive Infection by Herpes Simplex Virus Mutants Deficient in Thymidine Kinase Activity. Infection and Immunity 34:571–580 (Exhibit 11).

R.B. Tenser, et al. (1983) The Role of Pseudorabies Virus Thymidine Kinase Expression in Trigeminal Ganglion Infection. J. Gen. Virol. 64:1369–1373 (Exhibit 12).

B. Lomniczi, et al., (1984) Deletions in the Genomes of Pseudorabies Virus Vaccine Strains and Existence of Four Isomers of the Genomes. J. Of Virol. 49:970–979 (Exhibit 13).

B. Roizman, et al., (1983) Bioengineering of Herpes Simplex Virus Variants for Potential Use as Live Vaccines. Cold Spring Harbor Conference on New Approaches to Viral Vaccines, Sep., pp. 275–281 (Exhibit 14).

R.L. Thompson, et al. (1983) Physical Location of a Herpes Simplex Virus Type–1 Gene Function(s) Specifically Associated with a 10 Million–Fold Increase in HSV Neurovirulence, Virology 131:180–192 (Exhibit 15).

K. Fukuchi, et al., (1985) The Structure of Marek Disease Virus DNA: The Presence of Unique Expansion in Non-pathopagenic Viral DNA. Proc. Natl. Acad. Sci, U.S.A. 82:751–754 (Exhibit 16).

J.M. Koomey, et al., (1984) Deletion of DNA Sequences in a Non–oncogenic Variant of *Herpesvirus saimiri*. J. of Virol. 50:662–665 (Exhibit 17).

F. Zucjerman, et al., (1989) Vaccination and Control of Aujeszky's Disease, "Role of Pseudorabies Virus Glycoproteins in Immune Response," J.T. van Oirschot (ed. Kluwer Academic Publishers, London, pp. 107–117 (Exhibit 18).

M. Kit, et al. (1990) Bovine Herpesvirus–1 (BHV–1)—Based viral Vector Which Expresses Foot and Mouth Disease Virus (FMDV) Epitopes on Surface on Virus Particles. Cold Spring Harbor Conference on Modern Approaches to New Vaccines incuding AIDS, Sep. p. 106 (Exhibit 19).

U.V. Wirth, et al., (1989) Spatial and Temporal Distribution of Bovine Herpesvirus 1 Transcripts, J. Of Virology 63:4882–4889 (Exhibit 20).

(List continued on next page.)

*Primary Examiner*—Terry McKelvey
(74) *Attorney, Agent, or Firm*—Pamela G. Salkeld

(57) ABSTRACT

The present invention provides a recombinant infectious bovine rhinotracheitis designated S-IBR-052 (ATCC Accession No. VR 2443). The present invention also provides a vaccine which comprises an effective immunizing amount of the recombinant infectious bovine rhinotracheitis virus designated S-IBR-052 and a suitable carrier.

The present invention provides homology vectors, methods of immunization and a method of distinguishing an animal vaccinated with the vaccines of the present invention from an animal infected with a naturally-occurring infectious bovine rhinotracheitis virus.

30 Claims, 75 Drawing Sheets

OTHER PUBLICATIONS

B. Moss, (1991) Vaccinia Virus: A Tool for Research and Vaccine Development. Science 252:1662–1667 (Exhibit 21).

M.L. Cook and J.G. Stevens., (1976) Latent Herpes Infections Following Experimental Viraemia. J. Gen. Virol. 31:75–80 (Exhibit 22).

R. W. Honess, (1984) Herpes Simplex and 'The Herpes Complex': Diverse Observation and a Unifying Hypothesis. J. Gene. Virol. 65:2077–2107 (Exhibit 23).

R. C. Desrosiers, et al., (1985) Synthesis of Bovine Growth Hormone in Primates by Using a Herpesvirus Vector. Molecular and Cellular Biology 5: 2796–2803 (Exhibit 24).

D.R. Thomsen, et al., (1987) Pseudorabies Virus as a Live Virus Vector for Expression of Foreign Genes. Gene 57:261–265 (Exhibit 25).

J.P. Weir and P.R. Narayanan, (1988) The Use of β–galactosidase as a Marker Gene to Define the Regulatory Sequences of the Herpes Simplex Virus Type 1 Glycoprotein C Gene in Recombinant Herpesviruses. Nucleic Acids Research 16:10267–10282 (Exhibit 26).

R.R. Spaete and E.S. Mocarske, (1987) Insertion and Deletion Mutagenesis of the Human Cytomegalovirus Genome. Proc. Natl. Acad. Sci. USA 84:7213–7217 (Exhibit 27).

M. Shih, et al., (1984) Expression of Hepatitis B Virus S Gene by Herpes Simplex Virus Type 1 Vectors Carrying the α and β–regulated Gene Chimeras. Proc. Natl. Acad. Sci. U.S.A. 81:5867–5870 (Exhibit 28).

S.J. Edwards, et al., (1988) Plasmodium Falciparum Antigens in Recombinant HSV–1, Technological Advances in Vaccine Development pp. 223–234 (Exhibit 29).

D.R. Fitzpatrick, et al., (1988) Expression of Bovine Herpesvirus 1 Glycoproteins gI and GIII in Transfected Murine Cells. J. Of Virol. 62:4239–4248 (Exhibit 30).

Federal Register, May 9, 1990; 55: No. 90, pp. 19245–19253 (Exhibit 31).

S, Kit, et al., (1990) Gene–deleted IBRV Marker Vaccine. Veterinary Record 127:363–364 (Exhibit 32).

L.J. Bello, et al., (1992) Bovine Herpesvirus 1 as a Live Virus Vector for Expression of Foreign Genes, Virology 190:666–673.

S. Kit, et al., (1992) Expression of Porcine Pseudorabies Virus Genes by a Bovine Herpesvirus–1 (Infectious Bovine Rhinotracheitis Virus) Vector. Arch. Virol. 124:1–20.

S. Kit, et al., (1991) Modified–live Infectious Bovine Rhinotracheitis Virus Vaccine Expressing Monomer And Dimer Forms of Foot–And Mouth Disease Capsid Protein Epitopes On Surface of Hybrid Virus Particles. Arch. Virol. 120:1–17.

M. Schwyzer, (1993) Genome Map Of Bovine Herpesvirus 1. O'Brien, S.J. (Ed.). Genetic Maps: Locus Maps of Complex Genomes, Sixth Edition, No. 1. Viruses. Cold Spring Harbor Laboratory Press: Plainview, New York, U.S.A. pp. 166–170.

Van Drunen Littel–Van Den Hurk S., et al., (1983) Bovine Herpesvirus–1 Vaccines. Immun. And Cell Biology 71:405–420.

J.T. Van Oirshot, et al., (1990) Agricultural Biotechnology in Focus in the Netherlands, Dekker, J.J., et al. (Eds.), Pudoc Wageningen (Unnumbered pages).

C.A. Whetstone, et al., (1992) Latency and Reactivation of a Thymidine Kinase–Negative Bovine Herpesvirus 1 Deletion Mutant. Arch. Virol. 122:207–214.

* cited by examiner

TTAAGCCGTTGCCGTGGCCGGTCGCCATGGTGACTATAGTCACGTGTGGCCGGATAGGCCGCG
                     MetValThrIle...........

GCGCCTTCCAGGCAAGCCCAGACGTGCCGCGGGTGTGGCGTTCCTTGCCGAGCAG
AGCCGGGGCGCTGACGCGCAAGCGCGGCTGGGGACGACGGTCGTTGTCTTCGATCACGCCCTA
GTAAAAACGGGCGAAGGGCTGCACGTCGACGTCAAGCGCCGGCTGGCTT
TTGTCGACACAGCCCCTTGGCCGGGGGCGCCTTAGCCGCACCGCCAACCGGCGAG
TGGGTCAGCTGTGGTCGACGGCTACAAACTGCTGAAACTCGGCCCGCGAGGGCTCGGCCC
TTCCACATGTGGGTTTTTGCGCCGGTCTGTACGCGCCTATTTTGCGCACATTGCC
GCCACGACGCGCTTGGTTTACGCGCAGCTGGACTGTTTGCGGAGCGCGTGGCGG
CTCCCGCGGCCCTAGCCCGCTTCCGGATACCCGACACTC
CCTGAGCTGGTGCCCCGCCAAACGCGAGCCCGGTCTACGAAGTCGTAGACCGCGGG
CGGCGCGCCCCCGGCCTATATCCTTAAAGGCCGTTGCTTCATTGCTTTGTGACC
CATGTGCTATCCTTAAAGGACCATGTTCCGCAGGGCACCCCCAACCGGTGATCAGCACAGTGCC
GCGCCGAGGACAGAGGCCACCGCCGGCCACGAGCAAGAAGACCCCTGTCCGATGCGAGGGGG
GTTGAGCAGCTGGCTGCCGACTCTTTACAGTGCCGCCACGAGCAAGAAGACCCCTGTATGCTA
TCGTCCCCGGGACTATTTCCGGTGGTGCCCCTCGTCCAAGCCTGCTGCTGGTGAAAGTTC
                                      ...........ProSerProCysTrp...

CCGCTCCCCGGCGCGAGTCCCGACCGAACTGGGGCGGCAGTTCACTTTGAATGTGTTCCCG
CGGCCGCCGACCGCTGCAGTTCTTTACGACGGTTCATTCATTCGTTAAGCTT

FIG. 3

| IBR US2 | 115 | H-MWVFGAADLYAPIFAHI |
| HSV-1 US2 | 124 | H-LWVVGAADLCVPFLEYA |
| PRV US2 | 148 | H-LWILGAADLCDQVLLAA |
| HSV-2 US2 | 123 | H-LWVVGAADLCVPFFEYA |
| MDV US2 | 132 | HSLWIVGAADICRIALECI |

```
                                                                                       HindIII
                                                                                       ┌/───┐
IBR Cooper   HindIII O TGAGCGCGCCGCTGCATGCTGGTGCGAACTCACGCCGAGCGCGTGCGAGCAAGCTT
                                           ||||||||||||||||||||||||||||||||||||||||
IBR Nasalgen HindIII K CTAGTAAAAACGGCGAAGGGCTGGTGCGAACTCACGCCGAGCGCGTGCGAGCAAGCTT
                       |||||||||||||||||||||||
IBR Cooper   HindIII K CTAGTAAAAACGGCGAAGGGCTGCACGTCGACGTCAACGTCAAGCCAGCGGCGCGGTGG L  V  K  T  A  K  G  C  T  S  T  S  T  S  S  Q  R  R  G  W
                                          |
                                       US2 (58)
```

| DNA | Origin | Sites | Size |
|---|---|---|---|
| Vector | pSP65 | SmaI - HindIII | ~2975 BP |
| Fragment 1 | IBR HindIII A | NcoI - BamHI | ~860 BP |
| Fragment 2 | HSV-1 BamHI N | PvuII - BamHI | ~490 BP |
| Fragment 3 | Tn5 | BglII - BamHI | ~1541 BP |
| Fragment 4 | HSV-1 BamHI Q | SmaI - SmaI | ~784 BP |
| Fragment 5 | IBR HindIII A | BglII - StuI | ~1741 BP |

FIG. 7A

| 7A |
|---|
| 7B |
| 7C |
| 7D |
| 7E |
| 7F |
| 7G |
| 7H |

FIG. 7

GCGATCATGCCTGCCCCCGGACCGGGACACCTTGGCCGCCCGTCGCCCTAATCCTGCTCTGC
              MetProAlaArg..........

GGGCCGCCCGTTTGCGCCCCGCCCCGACGACCTCTGTTTCGCCGACGTGCGCCAC
TGGCATGGCGCCCTCCCCGCCCCGCTGGGGCGTCCTGAACCTAGCGGCCTCGATTTGAC
CTCGCGGGTTTCGGTGCGCGGTGGAGCTTCGCGCCCTGCGCCTTGCCCCTTCTTGACA
TGGCGGAGAGACGGTGGTGCCCGGCGACCCCGAGCCCACGTCGTCGACGTCGCTGGGCT
TACCAAGACGGGACTGCATGTGCCTCTGCATATCGCCAGTACTTTAACTGCACGGGG
GGCGCGTGCCCGGCCAAAACGTCTGCGCCGGGCTCTCTGAGACCGCATCGCGGTGGC
TTTGAACCTCCGACTACGCGCTCTACTTCCTTGGGACGTCGCTAGTACTGCGCCCTGTAC
GACCGCGGGACCTACATCTATGTGGGGCGCCGACATCCACAAATACCCCTGCGGCGCAGC
GTCACGCTCATGTGCCCTGCCACCAAGAGCGGACCCGCCCTCTGACAGAGACGAGGCTC
GGTGTGCCCTGCCACCAAGAGCGGACCCGCCCTCTGACAGAGACGACGCCACC
GGCGACTGGCCGCGCTGCTTCCCCGCCCGACCCTGTTGAGGTTGACGCGGTGTGGGCAAC
GTAAGCGCCGAGAGCTGGGCCTGCCCGACCCGATCGACTACGCCGGAAGGGGTGAG
GTCGAAGTGCTGAGGACGAATTGCCCAGATCGCTGCGCCCGGGCTCTCTTTAGCGAAACCTGCCGCAGGACGACCCC
GACCCCCACGGGCCCGAATCGCTGCTGCGCCCGTTGCGCCAAGACGTCCTGACGGTG
ACCGGCCACGGGCCCGAATCGCTGCTGCGCCCGTTGCGCCAAGACGTCCTGACGGTG
CCCCTCAATCTGCCCGCGAGACCCCCGGTGGTGGCCACCGAGTTTGGCTCTTTGGC
AACTCCCGCGCTCGAGACCCCCGGTGGTGGCCACCGAGTTTGGCTCTTTGGC
GCTCGCCGATGACGCGCCGGGCATTCTCATCGGCTCCGCCTCGCTGCTGG
CTGCCCGATGACGCGCCGGGCATTCTCATCGGCTCCGCCTCGCTGCTGG
TGCTGCTGTTTCGCTGGTGATCGTCGCCAGTTCGCCAAGAGCAACCCGCGTACGAGCCGATG
GGCTGCTCGACGCGCCGCCACGTTCGTCGCCAAGAGCAACCCGCGTACGAGCCGATG
CTCAGCCGTCTGATCGCCGGCACCCCCACGCCCGACCCCGCTGTCCCGGCGTTTACAAT

..SerVal---
AAACAG

FIG. 8

```
IBR gpG     95   VGWAYQDGDCMVPLAYRQYFNCTGGALPGNVLCA
                 | |   ||||| ||  ||||| | | | | |  |
PRV gpX     89   VAWFFDGGHCKVPLVHREYYGCPGDAMPSVETCT
                 |     | |  ||  | || || ||    |  ||
HSV-2 gpG  111   VTYYRLTRACRQPILLRQYGGCRGGEPPSPKTCG
                 V        C  P    R Y  C G    P    C
```

| DNA | Origin | Sites | Size |
|---|---|---|---|
| Vector | pSP64/65 | XbaI - XbaI | ~2999 BP |
| Fragment 1 | HCMV XbaI B | PstI - EcoRV | ~182 BP |
| Fragment 2 | IBR HindIII K | MluI - XhoI | ~2121 BP |
| Fragment 3 | PRV BamHI #2 | XhoI - BamHI | ~121 BP |
| Fragment 4 | PRV BamHI #7 | NdeI - SalI | ~760 BP |

FIG. 11A

| 11A |
|---|
| 11B |
| 11C |
| 11D |
| 11E |
| 11F |
| 11G |
| 11H |

FIG. 11

Fragment 1    GCG-TTT GAG ATT TCT GTC-CCG ACT AAA TTC ATG-TCG CGC GAT AGT

GGT-GTT TAT CGC CGA TAG-AGA TGG CGA TAT TGG-AAA AAT CGA TAT TTG-AAA ATA TGG

FIG. 11D

| DNA | Origin | Sites | Size |
|---|---|---|---|
| Vector | pSP64 | HindIII - SmaI | ~2965 BP |
| Fragment 1 | IBR HindIII K | HindIII - XhoI | ~3593 BP |
| Fragment 2 | PRV BamHI #7 | SalI - NdeI* | ~ 753 BP |
| Fragment 3 | pJF751 | BalI - BamHI | ~3347 BP |
| Fragment 4 | HCMV XbaI B | AvaII - PstI | ~1191 BP |
| Fragment 5 | IBR HindIII K | XhoI - NdeI | ~ 785 BP |

*resected with ExoIII/S1

FIG. 12A

| 12A |
|---|
| 12B |
| 12C |
| 12D |
| 12E |
| 12F |
| 12G |
| 12H |

FIG. 12

| DNA | Origin | Sites | Size |
|---|---|---|---|
| Vector | pSP64 | HindIII - SmaI | ~2965 BP |
| Fragment 1 | IBR HindIII K | MluI - SmaI | ~ 888 BP |
| Fragment 2 | PRV BamHI #7 | SalI - NdeI* | ~ 753 BP |
| Fragment 3 | pJF751 | BalI - BamHI | ~ 3347 BP |
| Fragment 4 | HCMV XbaI B | AvaII - PstI | ~1191 BP |
| Fragment 5 | IBR HindIII K | XhoI - NdeI | ~ 785 BP |

*resected with ExoIII/S1

FIG. 13A

| 13A |
|---|
| 13B |
| 13C |
| 13D |
| 13E |
| 13F |
| 13G |
| 13H |

FIG. 13

| DNA | Origin | Sites | Size |
|---|---|---|---|
| Vector | pSP64 | HindIII – SmaI | ~2965 BP |
| Fragment 1 | IBR HindIII K | MluI – SmaI | ~ 888 BP |
| Fragment 2 | IBR HindIII K | XhoI – NdeI | ~ 785 BP |

FIG. 14A

| 14A |
|---|
| 14B |
| 14C |
| 14D |
| 14E |

```
GTGGAAGCTTGGGACTACTGCCTAGTCGTTACTTCGGACCGTTTGGTGCGCGGTCACC
GACCACACGCGCCCCGAGCCGCAGCCCGACGCTCCCGAGCCAGCCAGCCCACCGCTCACC
AGCGAGCCGGCGGGGSGCCCACCGGCCCGCGCCCTGGCTTGTGTGGTGCTGGCGCGGCG
CTTGGACTCGCGGGACTGGGCATCGGCAGCCCCTCGCCGTTCGGCCCCGTGTGCGCGCCGC
GCAAGCCAGAAGCCACCTACGACATCCCTCAACCCCTTCGGCCCCGTATACACCAGCTTG
CCGACCAACGAGCCGCTCGACGTGGTGCCAGTTAGCGACGAATTTCCCTCGAC
GAAGACTCTTTTGCGGATGACGACAGCGACGATGACCCCGCTAGCAACCCCCTGCG
GATGCCTACGACCTCGCCGGCCCCCAGCCAACTAGCGGGTTTGCGCGAGCCCCTGCC
AACGGCACGCGCTCGAGTCGCTCTGGGTTCAAAGTTTGGTTTAGGACCCGCTTGAAGAC
GATGCCCGCGCCAGCGCGCGACCCCCGGCCCCCCCGCGCTGTGCCGTCTGACGCGACTC
AAGTCCATCCCGCTAGCGCGCCCCCCGCCCCCCCCGCGCTAGGCCGCGACTC
.....IleLeuArg---

GCGTGTAGGGCTGCATATAAATGGAGCGCTCACACAAAGCCTCGTGCCGGCTGCTTCGAAG
```

FIG. 15B

```
HSV-1 gpE 262  WLRFDVPTSCAEMRIYESCLYHPQLPECLSPADAPC--AASTWTSRLAVRSY
               |||   | |    ||| ||||||  || |||  ||    |   |   | |
PRV     gI 265  WYYARAPPRCLLYYVYEPCIYHPRAPECLRPVDPACSFTSPARAALVARRAY
                ||   |    |   |   |||   ||| |    |||    |     | |
VZV    gpI 378  WLYVPIDPTCQPMRLYSTCLYHPNAPQCLSHMNSGCTFTSPHLAQRVASTVY
                ||      |     |   ||||   || |      |  |||     |  |
IBR    gpE 303  WYFLRTAGDCALIRIYETCIFHPEAPACLHPADAQCSFASPYRSETVYSRLY
                 |        |        | ||  | ||      |              |
                 W        C        Y  HP P  CL       C           Y
```

FIG. 16B

| DNA | Origin | Sites | Size |
|---|---|---|---|
| Vector | pSP64/pSP65 | SmaI - SmaI | ~3015 BP |
| Fragment 1 | IBR HindIII K | NdeI - HindIII | ~3647 BP |
| Fragment 2 | IBR SmaI 2.5KB | HindIII- SacI | ~ 832 BP |

FIG. 17A

| 17A |
|---|
| 17B |
| 17C |
| 17D |
| 17E |

FIG. 17

| DNA | Origin | Sites | Size |
|---|---|---|---|
| Vector | pSP65 | SmaI − HindIII | ~2975 BP |
| Fragment 1 | IBR HindIII K | SmaI − SmaI | ~1704 BP |
| Fragment 2 | PRV BamHI #10 | SalI − BamHI | ~413 BP |
| Fragment 3 | pJF751 | BamHI − PvuII | ~3010 BP |
| Fragment 4 | PRV BamHI #7 | NdeI − SalI | ~754 BP |
| Fragment 5 | IBR SmaI 2.5KB | NheI − BglI | ~742 BP |

FIG. 18A

| 18A |
|---|
| 18B |
| 18C |
| 18D |
| 18E |
| 18F |
| 18G |

FIG. 18

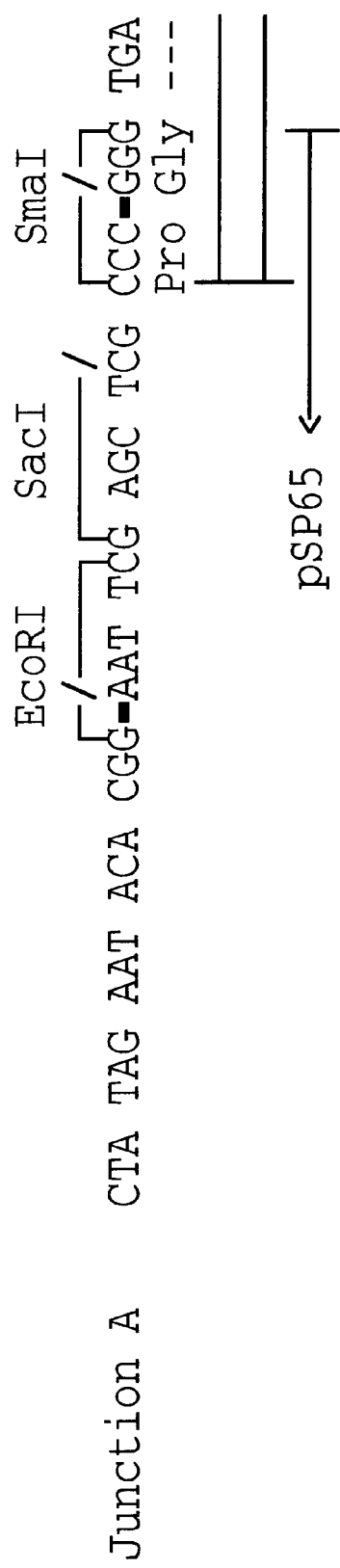
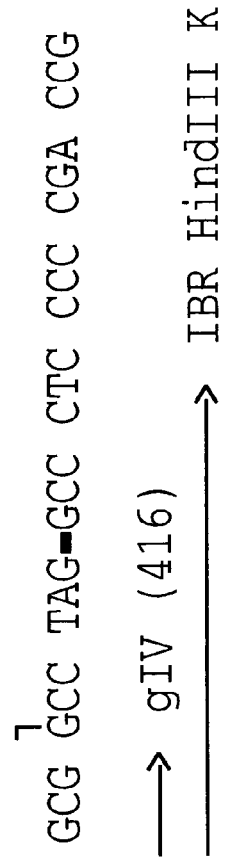
FIG. 18C

FIG. 21

| 21A |
|-----|
| 21B |

FIG. 21A

AGGAACAAAGTTGTTCAACACAGCAGCAGGCGAACAGAGACCCAAAGGCAGAGGCGACACCGAACCCA
AAATGGAATATTGGAAACACACAAAAACAGCAAACAACCACCAACAATGAAACCGAAACAACCAGAGGCAA
MetGluTyrTrpLys..........

ACACAGTAGCAAGGTTACAAATATCATAAATGTACACCTTCTGGACAATAACATCAACAATATTATTAGTC
ATTTTATAATGATATTGACAAACTTAATTCAAGAGAACAATCATAATAATTAATGTTGCAGGAAATAA
GAAAGAATTCGCGGCAATAGACACCAAGATTCAGAGGACCTCGGATGACATTGGAACCTCAATACAGTC
AGGAATAAATACAAGACTTCTCACAATTCAGAGTCATGTTCAAAACTATATCCACTATCACTAACACAA
CAAATGTCAGATCTCAGAGAATTTATCAATGATCTAACAATAAAAGAGAACATCAAGAAGTGCCAATAC
AGAGAATGACTCATGATGAGTATAGAGAGTCCTAAGATAAGTAGTTAATCCCAATCAATAATCAATACA
CCCATCTCTAACAAGTAGTCTTAAGATAAGTAGTCCTAAGATAAGTAGTTAATACCAGGGCCAGTTTATTAGCAACATCTACTACA
GTAAATGGCTGTGTATTAGAATCCCATGGGCTGTCAAAATATAGGAAATCTTACCAAGTACTACAAATAGGATAATTACTATAAATTC
TCACCCAGGCTGTCAAAATATAGGGCTGTCAAAATATAGGAAATCTTACCAAGTACTACAAATATTAATATTGATGATAATAGGAAATCTTGC
GGACCTAGTACCCAGAGTCACACATATCAGTGTTTATCAGTTATGCTCAACACCAAAAGTTGATGAGAGATCCGATT
TCTCTGGCACTATTGAATACAGATGTTTATCAGTTACTTGACATTGTACTTGACATTGTACTAATAATGGATTAATTATAACAACAAG
ATGCATCAACAGTATTGAGGATATTGAGGATATTGACTTGTCACTAATAATGGATTAATTATAACAACAAG

GTTTACAAATAATAATATAACTTTTGATAAACCGTATGCAGCATTGTATCCATCAGTAGGACCAGGAATC
TATTATAAGGGTAAAGTTATCTTTCTCGGATATGGAGGTCTAGAGCATGAGAAACGGAGACGTAATAT
GTAATACAACTGGTTGTCCTGGCAAAACACAGAGACTGTAATCAGGCTTCTTATAGCCCATGGTTCTC
AAATAGGAGAATGGTAAACTCTATTATTGTTGTTGATAAAGGCATAGATGCAACTTTTAGTTGAGGGTG
TGGACTATTCCAATGAGCCAAAATTATTGGGGATCAGAAGGAAGATTACTTTTATTAGGTGACAGAATAT
ACATATATACTAGATCCACAAGTTGGCACAGTAAATTACCATCACGGCTAGGGTAATTGATATTTCTGATTATAA
TAATATAAGAATAAATTGGACTTGGCATAACAGAGTTTACACTGATGCATATCCGTAAACCATCGGGAGTG
CATTCATGCCCAGACGGATGTATAACTCTCACAAAAGTCTAGAGAACACTTCCAGCTGCATATAAACAATTGTATC
TTGTATCAGTAATTCTTTGACTAATTCTCACAAAAGTCTAGAGAACACTTCCAGCTGCATATAAACAATTGTATC
AAATAGAATAAATGAATTAGCTATATATAAACAGAATAAATCACAGAATAAATCACAGAAGTTTGAATACGTTTCAAC
ACACATTATGATAAAGGGTATTGTTTTCATATAGTAGAAATAAATCACAGAAGTTTGAATACGTTTCAAC
CTATGTTATTCAAAACAGAAGTTCCAAAAAACTGCAGCTAAANTGATCATCGCATATCGGATGCCAGATG

ACATTAAAAAGAGACCACCAGACACAACACAGGAGATGATGCAAGATATAAAGGAATAAT

........ProLysAsnCysSer---

FIG. 21B

| 26A |
| 26B |

RECOMBINANT INFECTIOUS BOVINE RHINOTRACHEITIS VIRUS

This application is a national stage application under 35 U.S.C. 371 of PCT International Application No. PCT/US95/01491, filed Feb. 2, 1995, a continuation-in-part of U.S. Ser. No. 08/191,866, filed Feb. 4, 1994, now U.S. Pat. No. 5,783,195, and a continuation-in-part of U.S. Ser. No. 08/334,428, filed Nov. 4, 1994, now U.S. Pat. No. 5,834,305, which is a continuation of U.S. Ser. No. 08/037,707, filed Mar. 25, 1993, now abandoned, which is a continuation of U.S. Ser. No. 07/649,380, filed Jan. 31, 1991, now abandoned, which is a continuation of U.S. Ser. No. 07/078,519, filed Jul. 27, 1987, now abandoned.

Within this application several publications are referenced by arabic numerals within parentheses. Full citations for these publications may be found at the end of the specification immediately preceding the claims. The disclosures of these publications are hereby incorporated by reference into this application in order to more fully describe the state of the art to which this invention pertains.

BACKGROUND OF THE INVENTION

The ability to isolate viral DNA and clone this isolated DNA into bacterial plasmids has greatly expanded the approaches available to make viral vaccines. The methods used to make the present invention involve modifying cloned viral DNA sequences by insertions, deletions and single or multiple base changes. The modified DNA is then reinserted into the viral genome to render the virus non-pathogenic. The resulting live virus may then be used in a vaccine to elicit an immune response in a host animal and to protect the animal against a disease.

One group of animal viruses, the herpesviruses or Herpetoviridae, is an example of a class of viruses amenable to this approach. These viruses contain 100,000 to 200,000 base pairs of DNA as their genetic material. Importantly, several regions of the genome have been identified that are nonessential for the replication of virus in vitro in cell culture. Modifications in these regions of the DNA may lower the pathogenicity of the virus, i.e., attenuate the virus. For example, inactivation of the thymidine kinase gene renders human herpes simplex virus non-pathogenic (28), and pseudorabies virus of swine non-pathogenic (29).

Removal of part of the repeat region renders human herpes simplex virus non-pathogenic (30,31). A repeat region has been identified in marek's disease virus that is associated with viral oncogenicity (32). A region in herpesvirus saimiri has similarly been correlated with oncogenicity (33). Removal of part of the repeat region renders pseudorabies virus non-pathogenic (U.S. Pat. No. 4,877,737, issued Oct. 31, 1989). A region in pseudorabies virus has been shown to be deleted in naturally-occurring vaccine strains (11,3) and it has been shown that these deletions are at least partly responsible for the lack of pathogenicity of these strains.

It is generally agreed that herpesviruses contain non-essential regions of DNA in various parts of the genome, and that modifications of these regions can attenuate the virus, leading to a non-pathogenic strain from which a vaccine may be derived. The degree of attenuation of the virus is important to the utility of the virus as a vaccine. Deletions which cause too much attenuation of the virus will result in a vaccine that fails to elicit an adequate immune-response. Although several examples of attenuating deletions are known, the appropriate combination of deletions is not readily apparent.

Infectious bovine rhinotracheitis (IBR) virus, an alpha-herpesvirus with a class D genome, is an important pathogen of cattle. It has been associated with respiratory, ocular, reproductive, central nervous system, enteric, neonatal, and dermal diseases (34). Cattle are the normal hosts of infectious bovine rhinotracheitis virus, however it also infects goats, swine, water buffalo, wildebeest, mink, and ferrets. Experimental infections have been established in mule deer, goats, swine, ferrets, and rabbits (35).

Conventional modified live virus vaccines have been widely used to control diseases caused by infectious bovine rhinotracheitis virus. However, these vaccine viruses may revert to virulence. More recently, killed virus infectious bovine rhinotracheitis vaccines have been used, but their efficacy appears to be marginal.

Infectious bovine rhinotracheitis virus has been analyzed at the molecular level as reviewed in Ludwig (36). A restriction map of the genome is available in this reference, which will aid in the genetic engineering of infectious bovine rhinotracheitis according to the methods provided by the present invention.

As reported in the current literature, infectious bovine rhinotracheitis virus has been engineered to contain a thymidine kinase deletion (43,44) and a deletion in the gIII gene (45,46). However, no evidence has been presented for the deletions in the US2, repeat, gG, or gE regions. In the subject application, usefulness of such deletions for both the attenuation of infectious bovine rhinotracheitis virus and for the development of gene deleted marker vaccines is demonstrated.

As with other herpesviruses, infectious bovine rhinotracheitis virus can become latent in healthy animals which makes them potential carriers of the virus. For this reason it is clearly advantageous to be able to distinguish animals vaccinated with non-virulent virus from animals infected with disease-causing wild type virus. The development of differential vaccines and companion diagnostic tests has proven valuable in the management of pseudorabies disease (47). A similar differential marker vaccine would be of great value in the management of infectious bovine rhinotracheitis disease. The construction of differential diagnostics has focused on the deletion of glycoproteins. Theoretically, the glycoprotein chosen to be the diagnostic marker should have the following characteristics: (1) the glycoprotein and its gene should be non-essential for the production of infectious virus in tissue culture; (2) the glycoprotein should elicit a major serological response in the animal; and (3) the glycoprotein should not be one that makes a significant contribution to the protective immunity. Four major infectious bovine rhinotracheitis virus glycoproteins (gI, gII, gIII, and gIV) have been described in the literature (48). Three of these genes, gI, gIII, and gIV, have been sequenced and shown to be homologous to the HSV glycoproteins gB, gC, and gD, respectively. Although it has been suggested that the gII protein is analogous to HSV gE, no sequence evidence has been presented to confirm that suggestion (48). The gB and gD homologues are essential genes and would not be appropriate as deletion marker genes. The gC gene of herpesviruses has been shown to make a significant contribution to protective immunity as a target of neutralizing antibody (49) and as a target of cell-mediated immunity (50). Therefore, the gC gene is not desirable as a deletion marker gene. As indicated above, Kit et al. (45) have described the deletion of the infectious bovine rhinotracheitis virus gIII as a marker gene. It would be expected that such a deletion would compromise the efficacy of an infectious bovine rhinotracheitis vaccine.

For pseudorabies virus (PRV) the criteria for a deletion marker gene are best met by the glycoprotein X (51). Wirth et al. (52) suggests the existence of a "gX homologue of HSV-1" in the infectious bovine rhinotracheitis virus. It is not clear what is meant by this because although there is a PRV gX gene, there is no reported HSV-1 gX gene or gX homologous gene. In any case, no sequence evidence is presented to support this suggestion. Clear evidence of homologues of PRV gX (HSV-2 gG) and PRV gI (HSV gE) in infectious bovine rhinotracheitis virus and their usefulness as diagnostic markers is demonstrated.

The present invention provides a method of producing a fetal-safe, live recombinant infectious bovine rhinotracheitis virus which comprises treating viral DNA from a naturally-occurring live infectious bovine rhinotracheitis virus so as to delete from the virus DNA corresponding to the US2 region of the naturally-occurring infectious bovine rhinotracheitis virus. The present invention also provides viruses in which (1) DNA corresponding to the US2 region of naturally-occurring infectious bovine rhinotracheitis virus has been deleted, and (2) DNA encoding gG and/or gE has been altered or deleted. Such viruses are useful in vaccines which need diagnostic markers and are safe for use in pregnant animals.

The ability to engineer DNA viruses with large genomes, such as vaccinia virus and the herpesviruses, has led to the finding that these recombinant viruses can be used as vectors to deliver immunogens to animals (53). The herpesviruses are attractive candidates for development as vectors because their host range is primarily limited to a single target species (54), and they have the capacity for establishing a latent infection (55) that could provide for stable in vivo expression of a desired cloned polypeptide. Herpesviruses have been engineered to express a variety of foreign gene products, such as bovine growth hormone (56), human tissue plasminogen activator (57), and *E. coli* β-galactosidase (58,59). In addition, possible immunogenic polypeptides have been expressed by herpesviruses. Whealy et al. (60) expressed portions of the human immunodeficiency virus type 1 envelope glycoprotein in pseudorabies virus (PRV) as fusions to the PRV glycoprotein III. The hepatitis B virus surface antigen (61) and a hybrid human malaria antigen from Plasmodium falciparum have been expressed in herpes simplex virus type 1 (HSV-1) (62). The infectious bovine rhinotracheitis viruses described above may be used as vectors for the insertion of genes encoding antigens from microorganisms causing important cattle diseases. Such recombinant viruses would be multivalent vaccines protecting against infectious bovine rhinotracheitis as well as other diseases. Kit et al. (63) have described the expression of a Foot and Mouth disease antigen in infectious bovine rhinotracheitis virus. In some of the prior applications from which the subject application claims priority (which precedes the Kit publication by at least three years), the use of infectious bovine rhinotracheitis virus to express several foreign genes including the *E. coli* β-galactosidase (lacZ) gene, the TN5 neomycin resistance gene, and antigens from bovine rota virus, and parainfluenza type 3 virus (see U.S. Ser. No. 06/933,107, filed Nov. 20, 1986, now abandoned and U.S. Ser. No. 07/078,519, filed Jul. 27, 1987, now abandoned) is described. These applications precede the Kit publication by at least three years. The viruses described in this application provide a combination of attenuation, differentiation and multivalency. These properties make such viruses useful as vaccines for the management of cattle diseases.

SUMMARY OF THE INVENTION

The present invention provides a recombinant infectious bovine rhinotracheitis designated S-IBR-052 (ATCC Accession No. VR 2443). The present invention also provides a vaccine which comprises an effective immunizing amount of the recombinant infectious bovine rhinotracheitis virus designated S-IBR-052 and a suitable carrier.

The present invention provides homology vectors, methods of immunization and a method of distinguishing an animal vaccinated with the vaccines of the present invention from an animal infected with a naturally-occurring infectious bovine rhinotracheitis virus.

BRIEF DESCRIPTION OF THE INVENTION

FIG. 1: Details of the infectious bovine rhinotracheitis Cooper Strain. Diagram of infectious bovine rhinotracheitis genomic DNA showing the unique long, internal repeat, unique short, and Terminal repeat regions. Restriction maps for the enzymes HindIII, EcoRI, and XbaI are indicated (7). Fragments are lettered in order of decreasing size. The unique short region is also expanded for inclusion of more detail. The location of several genes is also indicated, they are unique short 2 (US2), immediate early genes (IE) (20), glycoprotein G (gG), glycoprotein IV (gIV) (17), glycoprotein E (gE). Note that due to the inversion of the short region, which includes the unique short, internal, and terminal repeats, four half molar HindIII fragments are present (HindIII D, C, F, and H).

FIG. 2: Details of S-IBR-002. Diagram of S-IBR-002 genomic DNA showing the unique long, internal repeat, unique short, and Terminal repeat regions. Restriction maps for the enzymes HindIII, EcoRI, and XbaI are indicated (7). Fragments are lettered in order of decreasing size. The EcoRI B and F fragments are expanded for inclusion of more detail. The ~800 BP repeat deletions are indicated by deltas. Note that due to the inversion of the short region, which includes the unique short, internal, and terminal repeats, four half molar HindIII fragments are present (HindIII D, C, F, and H).

FIG. 3 SEQ ID NO. 1: DNA sequence (SEQ ID NO: 19) of the IBR; Unique Short 2 gene. The sequence of the first 1080 base pairs of the HindIII K fragment, reading from the HindIII K/HindIII O junction, are shown. The unique short 2 (US2) gene is transcribed toward the HindIII K/HindIII O junction as indicated in FIG. 1. The sequence has been reversed and complemented in order to show the translation start and termination of US2 gene.

FIGS. 4A–4B SEQ ID NOS: 2–6:

Homology between the infectious bovine rhinotracheitis US2 (SEQ ID NO. 2) protein and the US2 proteins of HSV-1, (SEQ ID NO: 3) PRV (SEQ ID NO: 4), HSV-2(SEQ ID NO: 5), and marek's disease virus, (SEQ ID NO. 6). (FIG. 4A) Matrix plot of the amino acid sequence of the invectious bovine rhinotracheitis US2 protein (309) against the amino acid sequence of the HSV-1 US2 protein (291) (8). (FIG. 4B) Alignment of the conserved region between infectious bovine rhinotracheitis US2 protein, HSV-1 US2 protein, PRV US2 protein (256 amino acids) (21), HSV-2 US2 protein (291) (9), and marek's disease virus US2 protein (270 amino acids)(SEQ ID NOS: 20–24)(1).

FIGS. 5A–5B SEQ ID NOS: 7–9:

Details of the Nasalgen deletion. Diagram of infectious bovine rhinotracheitis genomic DNA showing the unique long, internal repeat, unique short, and terminal repeat regions. A restriction map for the enzyme HindIII is indicated. Fragments are lettered in order of decreasing size. The unique short region is expanded for inclusion of more detail. The location of the deletion in the Nasalgen HindIII K fragment is shown. Three regions of DNA sequence are also shown (SEQ ID NOS: 25–27). The first line (SEQ ID NO: 7) shows the first 60 base pairs upstream of the HindIII O/HindIII D junction in the infectious bovine rhinotracheitis Cooper strain. The second line (SEQ ID NO: 8) shows the first 60 base pairs upstream of the HindIII K/HindIII D junction in the Nasalgen strain. The third line (SEQ ID NO: 9) shows 60base pairs flanking the DNA encoding amino acid 59 of the infectious bovine rhinotracheitis US2 gene in the infectious bovine rhinotracheitis Cooper strain.

FIG. 6: Details of S-IBR-027. Diagram of S-IBR-027 genomic DNA showing the unique long, internal repeat, unique short, and terminal repeat regions. Restriction maps for the enzymes HindIII, EcoRI, and XbaI are indicated (7). Fragments are lettered in order of decreasing size. The unique short region is also expanded for inclusion of more detail. The location of several genes is also indicated, they are unique short 2 (US2), immediate early genes (IE) (20), glycoprotein G (gG), glycoprotein IV (gIV) (17), glycoprotein E (gE). The unique short region and repeat region deletions are indicated by deltas. The location of the approximately 1200 BP deletion of the US2 gene is shown in the expanded region. Note that due to the inversion of the short region, which includes the unique short, internal, and terminal repeats, four half molar HindIII fragments are present (HindIII D, C, F, and H).

FIGS. 7A–7H SEQ ID NOS. 10–15:

Detailed description of the DNA insertion in Homology Vector 129-71.5. Diagram showing the orientation of DNA fragments assembled in plasmid 129-71.5. The origin of each fragment is indicated in the table. The sequences (SEQ ID NOS. 10–15) located at each of the junctions between fragments is also shown. The restriction sites used to generate each fragment as well as synthetic linker sequences which were used to join the fragments are described for each junction (SEQ ID NOS: 28–33). The synthetic linker sequences are underlined by a heavy bar. The location of several gene coding regions and regulatory elements is also given. The following two conventions are used: numbers in parentheses, ( ), refer to amino acids, and restriction sites in brackets, [ ], indicate the remnants of sites which were destroyed during construction. The following abbreviations are used: polyadenylation signal (pA), infectious bovine rhinotracheitis virus (IBR), Herpes simplex virus type 1 (HSV-1), thymidine kinase (TK), neomycin resistance (NEO), bacterial transposon Tn5 (Tn5).

FIG. 8 SEQ ID NO. 16: DNA sequence of the IBR glycoprotein G gene (SEQ ID NO: 34). The sequence of approximately 1400 base pairs of the HindIII K fragment, starting approximately 2800 base pairs downstream of the HindIII K/HindIII O junction, are shown. The glycoprotein G (gG) gene is transcribed away from the HindIII K/HindIII O junction as indicated in FIG. 1. The translational start and termination of the gG gene are indicated.

FIGS. 9A–9B SEQ ID NOS: 17–19:

Homology between the IBR gG protein, the gX protein of PRV and the gG protein of HSV-2. (FIG. 9A) Matrix plot of the amino acid sequence of the IBR gG protein (441) against the amino acid sequence of the PRV gX protein (498) (12). (FIG. 9B) Alignment of the conserved region between IBR gG (SEQ ID NO: 17) protein, PRV (SEQ ID NO: 18) protein, and HSV-2 (SEQ ID NO: 19) gG protein (699) (9). Note that IUPAC-IUB Biochemical Nomenclature Commission conventions are used.

FIG. 10:

Western blot of proteins released into the medium of IBR and PRV infected cells, showing the absence of gG in S-PRV-013, S-IBR-035, S-IBR-036, S-IBR-037, and S-IBR-038 but its presence in S-PRV-160 and wild type S-IBR-000. Lanes (A) 0.5 μg purified gG, (B) blank lane, (C) S-PRV-160, (D) S-PRV-013, (E) pre-stained molecular weight markers, (F) 0.5 μg purified gG, (G) S-IBR-038, (H) S-IBR-037, (I) S-IBR-036, (J) S-IBR-035, (K) S-IBR-000, (L) uninfected MDBK cells, (M) pre-stained molecular weight markers. Media samples were prepared as described in the PREPARATION OF HERPESVIRUS CELL LYSATES. The concentrated media from the infection of one 6 cm dish of infected cells was loaded in each sample lane except for samples S-PRV-013 and S-PRV-160 for which the media from two 6 cm dishes were loaded.

FIGS. 11A–11H SEQ ID NOS: 20–25:

Detailed description of the DNA insertion in Plasmid 459-12.6. Diagram showing the orientation of DNA fragments assembled in plasmid 459-12.6. The origin of each fragment is indicated in the table. The sequences (SEQ ID NOS: 20–25) located at each of the junctions between fragments is also shown. The restriction sites used to generate each fragment as well as synthetic linker sequences which were used to join the fragments are described for each junction (SEQ ID NOS: 38–43). The synthetic linker sequences are underlined by a heavy bar. The location of several gene coding regions and regulatory elements is also given. The following two conventions are used: numbers in parentheses, ( ), refer to amino acids, and restriction sites in brackets, [ ], indicate the remnants of sites which were destroyed during construction. The following abbreviations are used: unique glycoprotein G (gG), glycoprotein III (gIII), glycoprotein X (gX), polyadenylation signal (pA), infectious bovine rhinotracheitis virus (IBR), pseudorabies virus (PRV), and human cytomegalovirus (HCMV).

FIGS. 12A–12H SEQ ID NOS. 26, 27 and 29–32:

Detailed description of the DNA insertion in Homology Vector 439-01.31. Diagram showing the orientation of DNA fragments assembled in plasmid 439-01.31. The origin of each fragment is indicated in the table. The sequences (SEQ ID NOS. 26, 27 and 29–32) located at each of the junctions between fragments is also shown. The restriction sites used to generate each fragment as well as synthetic linker sequences which were used to join the fragments are described for each junction (SEQ ID NOS: 44–49). The synthetic linker sequences are underlined by a heavy bar. The location of several gene coding regions and regulatory elements is also given. The following two conventions are used: numbers in parentheses, ( ), refer to amino acids, and restriction sites in brackets, [ ], indicate the remnants of sites which were destroyed during construction. The following abbreviations are used: unique short 2 (US2), glycoprotein G (gG), glycoprotein IV (gIV), polyadenylation signal (pA), infectious bovine rhinotracheitis virus (IBR), pseudorabies virus (PRV), and human cytomegalovirus (HCMV).

FIGS 13A–13H SEQ ID NOS. 29–32, 33 and 34:

Detailed description of the DNA insertion in Homology Vector 439-21.69. Diagram showing the orientation of DNA fragments assembled in plasmid 439-21.69. The origin of each fragment its indicated in the table. The sequences (SEQ ID NOS: 29–32, 33 and 34) located at each of the junctions between fragments is also shown. The restriction sites used to generate each fragment as well as synthetic linker sequences which were used to join the fragments are described for each junction (SEQ ID NOS: 50–55). The synthetic linker sequences are underlined by a heavy bar. The location of several gene coding regions and regulatory elements is also given. The following two conventions are used: numbers in parentheses, ( ), refer to amino acids, and restriction sites in brackets, [ ], indicate the remnants of sites which were destroyed during construction. The following abbreviations are used: unique short 2 (US2), glycoprotein G (gG), glycoprotein IV (gIV), polyadenylation signal (pA), infectious bovine rhinotracheitis virus (IBR), pseudorabies virus (PRV), and human cytomegalovirus (HCMV).

FIGS. 14A–14E SEQ ID NOS: 32, 33 and 35:

Detailed description of the DNA insertion in Homology Vector 439-70.4. Diagram showing the orientation of DNA fragments assembled in plasmid 439-70.4. The origin of each fragment is indicated in the table. The sequences (SEQ ID NOS. 32, 33 and 35) located at each of the junctions between fragments is also shown. The restriction sites used to generate each fragment as well as synthetic linker sequences which were used to join the fragments are described for each junction. The synthetic linker sequences are underlined by a heavy bar. The location of several gene coding regions and regulatory elements is also given. The following two conventions are used: numbers in parentheses, ( ), refer to amino acids, and restriction sites in brackets, [ ], indicate the remnants of sites which were destroyed during construction. The following abbreviations are used: glycoprotein G (gG), glycoprotein IV (gIV), and infectious bovine rhinotracheitis virus (IBR).

FIGS. 15A–15B SEQ ID NO. 36:

DNA sequence of the IBR glycoprotein E gene (SEQ ID NOS: 59–67. The sequence of 2038 base pairs of the IBR unique short region, starting approximately 1325 base pairs upstream in the HindIII K/HindIII F junction in the HindIII K fragment, are shown. The glycoprotein E (gE) gene is transcribed toward the HindIII K/HindIII F junction as indicated in FIG. 1. The translation start and termination of the gE gene are indicated. Note that IUPAC-IUB Biochemical Nomenclature Commission conventions are used.

FIGS. 16A–16B SEQ ID NO. 37–40:

Homology between the IBR gE (SEQ ID NO. 40) protein and the gE protein of HSV-1 (SEQ ID NO. 37), the gI protein of VZV (SEQ ID NO. 39), and the gI protein of PRV. (FIG 16A) Matrix plot of the amino acid sequence of the IBR gE protein (617) against the amino acid sequence of the PRV (SEQ ID NO. 38) gI protein (577) (64). (FIG. 16B) Alignment of the conserved region between IBR gE protein PRV gI protein, and VZV gI protein (SEQ ID NOS. 61–64) (37).

FIGS. 17A–17E SEQ ID NOS: 41–43:

Detailed description of a plasmid containing the gE gene. Diagram showing the orientation of DNA fragments to be assembled in the gE-containing plasmid. The origin of each fragment is indicated in the table. The sequences (SEQ ID NOS. 41–43) located at each of the junctions between fragments are also shown. The restriction sites used to generate each fragment are described for each junction (SEQ ID NOS. 65–67). The location of several gene coding regions and regulatory elements is also given. The following two conventions are used: numbers in parentheses, ( ), refer to amino acids, and restriction sites in brackets, [ ], indicate the remnants of sites which were destroyed during construction. The following abbreviations are used: unique glycoprotein E (gE), glycoprotein IV (gIV), and infectious bovine rhinotracheitis virus (IBR).

FIGS. 18A–18G SEQ ID NOS. 44–48:

Detailed description of the DNA insertion in the homology vector 536-03.5. Diagram showing the orientation of DNA fragments to be assembled in the homology vector. The origin of each fragment is indicated in the table. The sequences (SEQ ID NOS. 44–48) located at each of the junctions between fragments is also shown. The restriction sites used to generate each fragment as well as synthetic linker sequences which were used to join the fragments are described for each junction (SEQ ID NOS: 68–72). The synthetic linker sequences are underlined by a heavy bar. The location of several gene coding regions and regulatory elements is also given. The following two conventions are used: numbers in parentheses, ( ), refer to amino acids, and restriction sites in brackets, [ ], indicate the remnants of sites which were destroyed during construction. The following abbreviations are used: glycoprotein E (gE), immediate early promoter (IE), infectious bovine rhinotracheitis virus (IBR), and pseudorabies virus (PRV).

FIG. 19:

Construction of Recombinant S-IBR-004 Virus. S-IBR-004 is an IBR recombinant virus carrying an inserted foreign gene (NEO) under the control of the PRV gX promoter. A new XbaI site was created at the short unique region and the original SacI site was deleted.

FIG. 20:

Construction of Recombinant S-IBR-008 Virus. S-IBR-008 is a recombinant IBR virus that has a bovine rotavirus glycoprotein gene and the plasmid vector inserted in the XbaI site on the unique long region. A site specific deletion was created at the [SacI] site due to the loss of NEO gene in the small unique region.

FIGS. 21A–21B SEQ ID NO. 49:

Sequence of the PI-3 (SF-4 Strain) HN Gene (SEQ ID NOS: 73–74). Note that IUPAC-IUB Biochemical Nomenclature Commission conventions are used.

FIGS. 22A–22C:

Details of S-IBR-018 Construction.

A. First line shows the IBR (Cooper Strain) BamHI-C fragment map. Second line shows the construction of the alpha-4 promoter on the PI-3 HN gene and its insertion into the HindIII site in BamHI-C. Also shown are the beta-gal and neomycin (NEO) gene constructions under the control of the gX promoter that were put into the XbaI site and used as selectable markers to purify the recombinant virus.

B. The BamHI-C fragment map of S-IBR-018 after insertion of the PI-3 HN, beta-gal, and neomycin genes.

C. The S-IBR-018 genome showing the location of the three inserted foreign genes.

Legend: B=BamHI; H=HindIII; X=XbaI; S=StuI; UL=unique long region; US=unique short region; IR=internal repeat region; TR=terminal repeat region.

FIGS. 23A–23C:

Details of S-IBR-019 Construction.

A. First line shows the IBR (Cooper Strain) BamHI-C fragment map. Second line shows the construction of the alpha-4 promoter on the PI-3 F gene and its insertion into the HindIII site in BamHI-C. Also shown are the beta-gal and neomycin (NEO) gene constructions under the control of the gX promoter that were put into the XbaI site and used as selectable markers to purify the recombinant virus.

B. The BamHI-C fragment map of S-IBR-019 after insertion of the PI-3 F, beta gal, and neomycin genes.

C. The S-IBR-019 genome showing the location of the three inserted foreign genes.

FIG. 24:

Detailed description of the DNA insertion in Homology Vector 591-21.20. The diagram shows the orientation of DNA fragments assembled in plasmid 591-21.20. The origin of each fragment is described in the MATERIALS AND METHODS section. The sequences located at the junctions between each fragment are shown (SEQ ID NOS: 75–77). The restriction sites used to generate each fragment as well as synthetic linker sequences which were used to join the fragments are described for each junction. The synthetic linker sequences are underlined by a double bar. The location of the Tk gene coding region is also given. The following two conventions are used: numbers in parenthesis ( ) refer to amino acids, and restriction sites in brackets [ ] indicate the remnants of sites which were destroyed during construction. The following abbreviation is used, infectious bovine rhinotracheitis virus (IBR).

FIGS. 25A–25B:

Detailed description of the marker gene insertion in Homology Vector 591-46.12. The diagram shows the orientation of DNA fragments assembled in the marker gene. The origin of each fragment is described in the MATERIALS AND METHODS section. The sequences located at the junctions between each fragment and at the ends of the marker gene are shown. The restriction sites used to generate each fragment are indicated at the appropriate junction. The location of the uidA gene coding region is also given. The following two conventions are used: numbers in parenthesis ( ) refer to amino acids, and restriction sites in brackets [ ] indicate the remnants of sites which were destroyed during construction. The following abbreviations are used, pseudorabies virus (PRV), uronidase A gene (uidA), *Escherichia coli* (*E. coli*), herpes simplex virus type 1 (HSV-1), poly adenylation signal (pA), and glycoprotein X (gX).

Legend: B=Ba HI; H=HindIII; X=XbaI; S=StuI; UL=unique long region; US=unique short region; IR=internal repeat region; TR=terminal repeat region.

FIGS. 26A–26B:

Detailed description of the DNA insertion in the homology vector 523-78.72. Diagram showing the orientation of DNA fragments to be assembled in the homology vector. The origin of each fragment is indicated in the table. The sequences located at each of the junctions between fragments is also shown. The restriction sites used to generate each fragment as well as synthetic linker sequences which were used to join then fragments are described for each junction (SEQ ID NO: 78). The synthetic linker sequences are underlined by a heavy bar. The location of several gene coding regions and regulatory elements is also given. The following two conventions are used: numbers in parentheses, ( ), refer to amino acids, and restriction sites in brackets, [ ], indicate the remnants of sites which were destroyed during construction. The following abbreviations are used: glycoprotein D (gD), glycoprotein E (gE), infectious bovine rhinotracheitis virus (IBRV).

FIG. 27:

Restriction Enzyme Map of the IBRV BamHI C Fragment. The restriction map shows non-essential regions within the BamHI C fragment (21.1 kb). The BamHI C fragment contains part of the unique long region, all of the internal repeat region and part of the unique short region of IBRV. The HindIII restriction enzyme site within the 3.9 kb ApaI restriction fragment within the larger BamHI-KpnI subfragment was used as an insertion site for foreign genes in S-IBR-018, S-IBR-019, S-IBR-069, S-IBR-071, S-IBR-074, S-IBR-086. The EcoRV restriction enzyme site within the smaller KpnI-BamHI subfragment within the repeat region of IBRV is used as an insertion site for foreign genes in S-IBR-072. The XbaI restriction enzyme site within the 3.9 kb ApaI restriction fragment within the larger BamHI-KpnI subfragment was used as an insertion site for foreign genes in S-IBR-018 and S-IBR-019.

DETAILED DESCRIPTION OF THE INVENTION

The present invention provides a recombinant infectious bovine rhinotracheitis (IBR) virus designated S-IBR-052 (ATCC Accession No. VR 2443).

S-IBR-052 was deposited on Feb. 4, 1994 pursuant to the Budapest Treaty on the International Deposit of Microorganisms for the Purposes of Patent Procedure with the Patent Culture Depository of the American Type Culture Collection, 10801 University Blvd., Manassas, Va. 20110-2209, U.S.A. under ATCC Accession No. VR 2443.

The present invention provides a recombinant infectious bovine rhinotracheitis virus, further comprising a foreign DNA sequence inserted into the IBR virus genomic DNA, wherein the foreign DNA sequence is inserted within a BamHI C fragment of the infectious bovine rhinotracheitis virus genomic DNA and is capable of being expressed in a infectious bovine rhinotracheitis virus infected host cell.

In one embodiment the foreign DNA is inserted within a larger BamHI-KpnI subfragment of the BamHI C fragment of the infectious bovine rhinotracheitis virus genomic DNA. In another embodiment the foreign DNA sequence is inserted within a HindIII site located within the larger BamHI-KpnI subfragment of the infectious bovine rhinotracheitis virus genomic DNA. In another embodiment the foreign DNA sequence is inserted within a XbaI site located within the larger BamHI-KpnI subfragment of the infectious bovine rhinotracheitis virus genomic DNA.

In one embodiment the foreign DNA is inserted within a smaller KpnI-BamHI subfragment of the BamHI C fragment of the infectious bovine rhinotracheitis virus genomic DNA. In another embodiment the foreign DNA sequence is inserted within a EcoRV site located within smaller KpnI-BamHI subfragment of the infectious bovine rhinotracheitis virus genomic DNA.

In another embodiment the infectious bovine rhinotracheitis virus genomic DNA contains a deletion or deletions in a non-essential region of the infectious bovine rhinotracheitis virus. In one embodiment the deletion is in either the US2, gG or gE gene regions.

In another embodiment the infectious bovine rhinotracheitis virus further comprises a foreign DNA sequence inserted into an open reading frame encoding infectious bovine rhinotracheitis virus thymidine kinase.

For purposes of this invention, "a recombinant infectious bovine rhinotracheitis virus capable of replication" is a live infectious bovine rhinotracheitis virus which has been generated by the recombinant methods well known to those of skill in the art, e.g., the methods set forth in HOMOLOGOUS RECOMBINATION PROCEDURE FOR GENERATING RECOMBINANT HERPESVIRUS in *Materials and Methods* and has not had genetic material essential for the replication of the recombinant infectious bovine rhinotracheitis virus deleted.

For purposes of this invention, "an insertion site which is not essential for replication of the infectious bovine rhinotracheitis virus" is a location in the infectious bovine rhinotracheitis viral genome where a sequence of DNA is not necessary for viral replication, for example, complex protein binding sequences, sequences which code for reverse transcriptase or an essential glycoprotein, DNA sequences necessary for packaging, etc.

Figure 1:
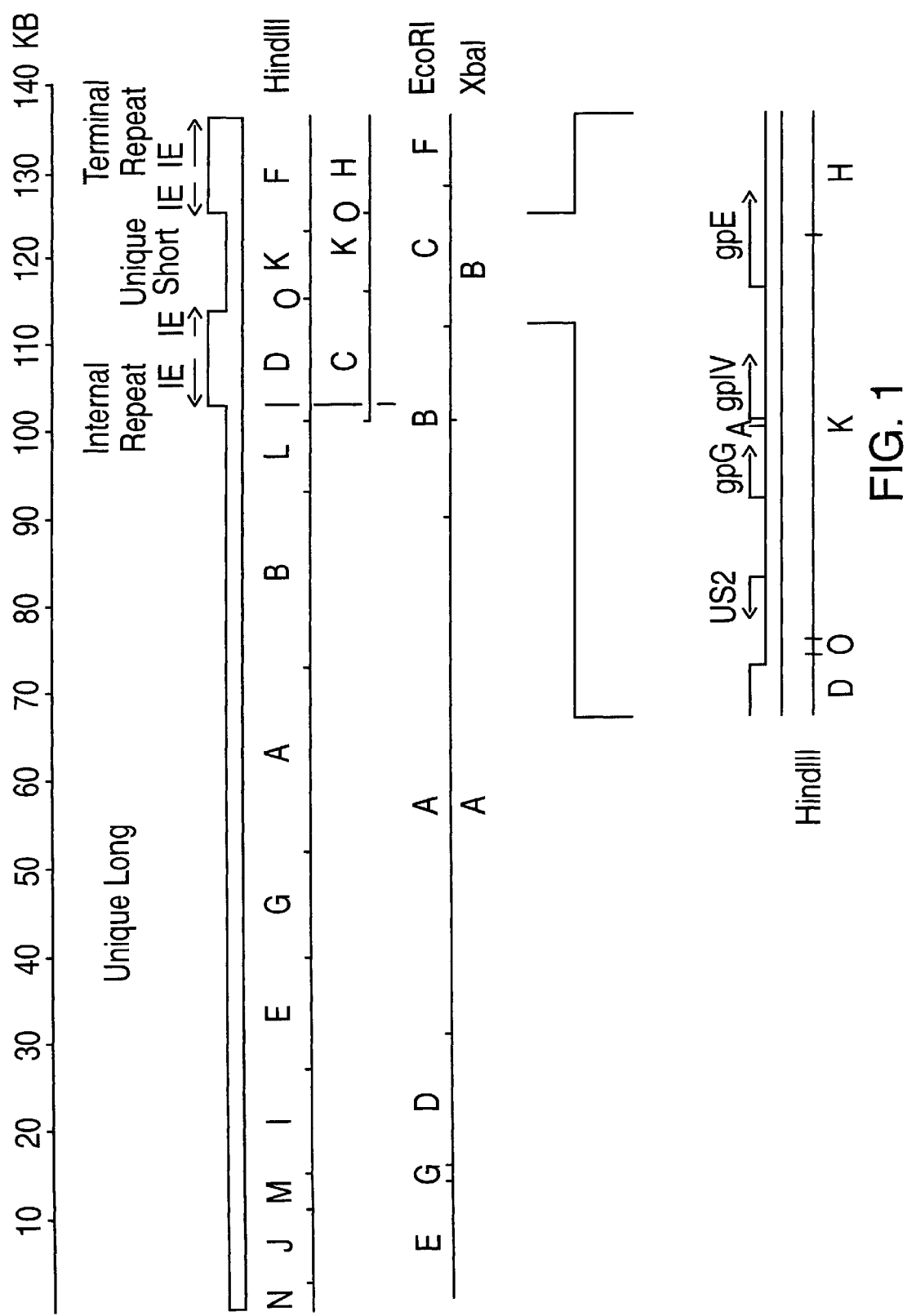

For purposes of this invention, an "open reading frame" is a segment of DNA which contains codons that can be transcribed into RNA which can be translated into an amino acid sequence and which does not contain a termination codon.

The present invention provides a recombinant infectious bovine rhinotracheitis virus comprising viral DNA from a naturally-occurring infectious bovine rhinotracheitis virus in which DNA encoding gG glycoprotein has been altered or deleted so that upon replication the recombinant infectious bovine rhinotracheitis virus produces no gG glycoprotein. The DNA encoding gG glycoprotein may be deleted or foreign DNA may be inserted into the DNA encoding gG glycoprotein. The DNA encoding gG glycoprotein may be deleted and foreign DNA may be inserted in place of the deleted DNA encoding gG glycoprotein.

The present invention further provides a recombinant infectious bovine rhinotracheitis virus comprising viral DNA from a naturally-occurring infectious bovine rhinotracheitis virus in which DNA encoding gG glycoprotein has been altered or deleted and DNA encoding the gE glycoprotein has been altered or deleted so that upon replication the recombinant infectious bovine rhinotracheitis virus produces no gG glycoprotein and no gE glycoprotein. The DNA encoding gG glycoprotein may be deleted or foreign DNA may be inserted into the DNA encoding gG glycoprotein. The DNA encoding gE glycoproteian may be deleted and foreign DNA may be inserted in place of the deleted DNA encoding gE glycoprotein.

The present invention further provides a recombinant infectious bovine rhinotracheitis virus comprising viral DNA from a naturally-occurring infectious bovine rhinotracheitis virus in which DNA encoding gG glycoprotein has been altered or deleted so that upon replication the recombinant infectious bovine rhinotracheitis virus produces no gG glycoprotein, DNA corresponding to the US2 region of the naturally-occurring infectious bovine rhinotracheitis virus has been deleted, and DNA encoding the gE glycoprotein has been altered or deleted.

The present invention also provides a recombinant infectious bovine rhinotracheitis virus comprising viral DNA from a naturally-occurring infectious bovine rhinotracheitis virus in which (1) DNA corresponding to the US2 region of the naturally-occurring infectious bovine rhinotracheitis virus has been deleted, and (2) DNA encoding gG glycoprotein has been altered or deleted. The DNA encoding the gG glycoprotein may be deleted or foreign DNA may be inserted in place of the deleted DNA encoding gG glycoprotein. Foreign DNA may be inserted in place of the deleted DNA corresponding to the US2 region of the naturally-occurring infectious bovine rhinotracheitis virus.

The present invention also provides a recombinant infectious bovine rhinotracheitis virus comprising viral DNA from a naturally-occurring infectious bovine rhinotracheitis virus in which (1) DNA corresponding to the US2 region of the naturally-occurring infectious bovine rhinotracheitis virus has been deleted, and (2) DNA encoding gE glycoprotein has been altered or deleted. The DNA encoding the gG glycoprotein may be deleted or foreign DNA may be inserted in place of the deleted DNA encoding gE glycoprotein. Foreign DNA may be inserted in place of the deleted DNA corresponding to the US2 region of the naturally-occurring infectious bovine rhinotracheitis virus.

The present invention also provides S-IBR-037, a recombinant infectious bovine rhinotracheitis virus comprising viral DNA from a naturally-occurring infectious bovine rhinotracheitis virus in which (1) DNA corresponding to the US2 region of the naturally-occurring infectious bovine rhinotracheitis virus has been deleted, and (2) DNA encoding gG glycoprotein has been deleted. S-IBR-037 was deposited on Apr. 16, 1991 pursuant to the Budapest Treaty on the International Deposit of Microorganisms for the Purposes of Patent Procedure with the Patent Culture Depository of the American Type Culture Collection, 10801 University Blvd., Manassas, Va. 20110-2209, U.S.A. under ATCC Accession No. VR 2320.

The present invention also provides a recombinant infectious bovine rhinotracheitis virus comprising viral DNA from a naturally-occurring infectious bovine rhinotracheitis virus in which (1) DNA corresponding to the US2 region of the naturally-occurring infectious bovine rhinotracheitis virus has been deleted and a foreign DNA sequence which encodes *Escherichia coli* β-galactosidase has been inserted in place of the deleted DNA encoding gG glycoprotein, and (2) DNA encoding gG glycoprotein has been altered or deleted. The present invention also provides two examples of such viruses, S-IBR-035 and S-IBR-036.

The present invention further provides a recombinant infectious bovine rhinotracheitis virus comprising viral DNA from a naturally-occurring infectious bovine rhinotracheitis virus in which DNA encoding gE glycoprotein has been altered or deleted so that upon replication the recombinant infectious bovine rhinotracheitis virus produces no gE glycoprotein. The DNA encoding gE glycoprotein may be deleted or foreign DNA may be inserted in the DNA encoding gE glycoprotein. The DNA encoding gE glycoprotein may be deleted and foreign DNA may be inserted in place of the deleted DNA encoding gE glycoprotein.

The present invention further provides a recombinant infectious bovine rhinotracheitis virus comprising viral DNA from a naturally-occurring infectious bovine rhinotracheitis virus in which DNA encoding gE glycoprotein has been altered or deleted so that upon replication the recombinant infectious bovine rhinotracheitis virus produces no gE glycoprotein and DNA corresponding to the US2 region of the naturally-occurring infectious bovine rhinotracheitis virus has been deleted.

The present invention further provides a recombinant infectious bovine rhinotracheitis virus comprising viral DNA from a naturally-occurring infectious bovine rhinotracheitis virus from which DNA in the unique short region of the naturally-occurring infectious bovine rhinotracheitis virus has been deleted. Foreign DNA may be inserted into the DNA of the recombinant infectious bovine rhinotracheitis virus. The foreign DNA may be inserted into the XbaI site in the long unique region. The foreign DNA may be a sequence which encodes bovine rotavirus glycoprotein 38; this sequence may be inserted into the XbaI site in the long unique region.

The present invention provides S-IBR-008, a recombinant infectious bovine rhinotracheitis virus comprising viral DNA from a naturally-occurring infectious bovine rhinotracheitis virus from which DNA corresponding to the unique short region of the naturally-occurring infectious bovine rhinotracheitis virus has been deleted and in which a foreign DNA sequence which encodes bovine rotavirus glycoprotein 38 has been inserted into the XbaI site in the long unique region. S-IBR-008 was deposited on Jun. 18, 1986 pursuant to the Budapest Treaty on the International Deposit of Microorganisms for the Purposes of Patent Procedure with the Patent Culture Depository of the American Type Culture Collection, 10801 University Blvd., Manassas, Va. 20110-2209, U.S.A. under ATCC Accession No. VR 2141.

The present invention further provides a recombinant infectious bovine rhinotracheitis virus comprising viral DNA from a naturally-occurring infectious bovine rhinotracheitis virus from which (1) DNA corresponding to the US2 region of the naturally-occurring infectious bovine rhinotracheitis virus has been deleted and (2) at least a portion of both repeat sequences has been deleted. The present invention further provides an example of such a recombinant virus, designated S-IBR-027. S-IBR-027 was deposited on Apr. 17, 1991 pursuant to the Budapest Treaty on the International Deposit of Microorganisms for the Purposes of Patent Procedure with the Patent Culture Depository of the American Type Culture Collection, 10801 University Blvd., Manassas, Va. 20110-2209, U.S.A. under ATCC Accession No. VR 2322.

The present invention further provides a recombinant IBR virus comprising viral DNA from a naturally-occurring IBR virus from which at least a portion of both repeat sequences has been deleted.

The present invention further provides a recombinant infectious bovine rhinotracheitis virus comprising viral DNA from a naturally-occurring IBR virus from which (1) at least a portion of both repeat sequences has been deleted and (2) DNA encoding one or more EcoRV restriction sites has been deleted. The present invention further provides an example of such a recombinant virus, designated S-IBR-002. S-IBR-002 was deposited on Jun. 18, 1986 pursuant to the Budapest Treaty on the International Deposit of Microorganisms for the Purposes of Patent Procedure with the Patent Culture Depository of the American Type Culture Collection, 10801 University Blvd., Manassas, Va. 20110-2209, U.S.A. under ATCC Accession No. VR 2140.

The present invention further provides a recombinant infectious bovine rhinotracheitis virus comprising. viral DNA from a naturally-occurring infectious bovine rhinotracheitis virus from which (1) at least a portion of both repeat sequences has been deleted and (2) wherein foreign DNA has been inserted into the DNA of the recombinant infectious bovine rhinotracheitis virus. The foreign DNA may be a sequence which encodes the Tn5 NEO gene.

The present invention further provides S-IBR-020, a recombinant infectious bovine rhinotracheitis virus comprising viral DNA from a naturally-occurring IBR virus from which (1) at least a portion of both repeat sequences has been deleted and (2) wherein a foreign DNA sequence which encodes the Tn5 NEO gene has been inserted into the DNA of the recombinant infectious bovine rhinotracheitis virus.

The present invention also provides a recombinant infectious bovine rhinotracheitis virus comprising viral DNA from a naturally-occurring infectious bovine rhinotracheitis virus from which (1) at least a portion of both repeat sequences has been deleted, (2) wherein a foreign DNA sequence which encodes the Tn5 NEO gene has been inserted into the DNA of the recombinant infectious bovine rhinotracheitis virus, and (3) wherein at least a portion of the thymidine kinase gene has been deleted.

The present invention also provides a recombinant infectious bovine rhinotracheitis virus comprising viral DNA from a naturally-occurring infectious bovine rhinotracheitis virus from which (1) at least a portion of both repeat sequences has been deleted, (2) wherein a foreign DNA sequence which encodes the Tn5 NEO gene has been inserted into the DNA of the recombinant infectious bovine rhinotracheitis virus, and (3) wherein at least a portion of the thymidine kinase gene has been deleted. The subject invention provides an example of such a recombinant virus, designated S-IBR-028. S-IBR-028 was deposited on May 14, 1991 pursuant to the Budapest Treaty on the International Deposit of Microorganisms for the Purposes of Patent Procedure with the Patent Culture Depository of the American Type Culture Collection, 10801 University Blvd., Manassas, Va. 20110-2209, U.S.A. under ATCC Accession No. VR 2326.

The present invention further provides a recombinant infectious bovine rhinotracheitis virus comprising viral DNA from a naturally-occurring IBR virus in which a foreign DNA sequence which encodes the Tn5 NEO gene has been inserted into the viral DNA. The Tn5 NEO gene may be under the control of an inserted, upstream, pseudorabies virus glycoprotein X promoter. The subject invention further provides an example of a recombinant virus wherein the Tn5 NEO gene is under the control of an inserted, upstream, pseudorabies virus glycoprotein X promoter, designated S-IBR-004. S-IBR-004 was deposited on May 23, 1986 pursuant to the Budapest Treaty on the International Deposit of Microorganisms for the Purposes of Patent Procedure with the Patent Culture Depository of the American Type Culture Collection, 10801 University Blvd., Manassas, Va. 20110-2209, U.S.A. under ATCC Accession No. VR 2134.

The subject invention further provides a recombinant infectious bovine rhinotracheitis virus comprising viral DNA from a naturally-occurring infectious bovine rhinotracheitis virus in which a foreign DNA sequence which encodes the *Escherichia coli* β-galactosidase and Tn5 NEO genes, and the parainfluenza type 3 virus hemagglutinin gene, HN, has been inserted into the viral DNA. The subject invention provides an example of such a recombinant virus, designated S-IBR-018.

The subject invention further provides a recombinant infectious bovine rhinotracheitis virus comprising viral DNA from a naturally-occurring infectious bovine rhinotracheitis virus in which a foreign DNA sequence which encodes the *Escherichia coli* β-galactosidase and Tn5 NEO genes, and the parainfluenza type 3 virus fusion gene, F, has been inserted into the viral DNA. The subject invention provides an example of such a recombinant virus, designated S-IBR-019.

The recombinant viruses of the subject invention were derived from the Cooper Strain. However, other infectious bovine rhinotracheitis viruses, such as the LA strain or the 3156 strain, may also be used.

The invention further provides a foreign DNA sequence or foreign RNA which encodes a polypeptide. Preferably, the polypeptide is antigenic in the animal. Preferably, this antigenic polypeptide is a linear polymer of more than 10 amino acids linked by peptide bonds which stimulates the animal to produce antibodies.

The invention further provides a recombinant infectious bovine rhinotracheitis virus capable of replication which contains a foreign DNA encoding a polypeptide which is a detectable marker. Preferably the detectable marker is the polypeptide *E. coli* β-galactosidase.

For purposes of this invention, a "polypeptide which is a detectable marker" includes the bimer, trimer and tetramer form of the polypeptide. *E. coli* β-galactosidase is a tetramer composed of four polypeptides or monomer sub-units.

The invention further provides a recombinant infectious bovine rhinotracheitis virus capable of replication which contains foreign DNA encoding an antigenic polypeptide which is or is from *Serpulina hyodysenteriae*, Foot and Mouth Disease Virus, Hog Cholera Virus, Swine Influenza Virus, African Swine Fever Virus or *Mycoplasma hyopneumoniae*.

The invention further provides for a recombinant infectious bovine rhinotracheitis virus capable of replication which contains foreign DNA encoding pseudorabies virus (PRV) g50 (gD). This recombinant infectious bovine rhinotracheitis virus can be further engineered to contain foreign DNA encoding a detectable marker, such as *E. coli* β-galactosidase.

In one embodiment of the recombinant infectious bovine rhinotracheitis virus the foreign DNA sequence encodes a cytokine. In another embodiment the cytokine is chicken myelomonocytic growth factor (cMGF) or chicken interferon (cIFN). Cytokines include, but are not limited to: transforming growth factor beta, epidermal growth factor family, fibroblast growth factors, hepatocyte growth factor, insulin-like growth factors, B-nerve growth factor, platelet-derived growth factor, vascular endothelial growth factor, interleukin 1, IL-1 receptor antagonist, interleukin 2, interleukin 3, interleukin 4, interleukin 5, interleukin 6, IL-6 soluble receptor, interleukin 7, interleukin 8, interleukin 9, interleukin 10, interleukin 11, interleukin 12, interleukin 13, angiogenin, chemokines, colony stimulating factors, granulocyte-macrophage colony stimulating factors, erythropoietin, interferon, interferon gamma, leukemia inhibitory factor, oncostatin M, pleiotrophin, secretory leukocyte protease inhibitor, stem cell factor, tumor necrosis factors, and soluble TNF receptors. These cytokines are from humans, bovine, equine, feline, canine, porcine or avian. Recombinant IBRV expressing cytokines is useful to enhance the immune response when combined with vaccines containing anitgens of disease causing microorganisms.

The present invention further provides a recombinant infectious bovine rhinotracheitis virus which comprises a foreign DNA sequence inserted into a non-essential site of the infectious bovine rhinotracheitis virus genome, wherein the foreign DNA sequence encodes an antigenic polypeptide derived from a human pathogen and is capable of being expressed in a host infected by the recombinant infectious bovine rhinotracheitis virus.

Recombinant infectious bovine rhinotracheitis virus expressing cytokines is used to enhance the immune response either alone or when combined with vaccines containing cytokines or antigen genes of disease causing microorganisms.

Antigenic polypeptide of a human pathogen which are derived from human herpesvirus include, but are not limited to: hepatitis B virus and hepatitis C virus hepatitis B virus surface and core antigens, hepatitis C virus, human immunodeficiency virus, herpes simplex virus-1, herpes simplex virus-2, human cytomegalovirus, Epstein-Barr virus, Varicella-Zoster virus, human herpesvirus-6, human herpesvirus-7, human influenza, measles virus, hantaan virus, pneumonia virus, rhinovirus, poliovirus, human respiratory syncytial virus, retrovirus, human T-cell leukemia virus, rabies virus, mumps virus, malaria (*Plasmodium falciparum*), *Bordetella pertussis*, Diptheria, *Rickettsia prowazekii*, *Borrelia berfdorferi*, Tetanus toxoid, malignant tumor antigens.

In one embodiment of the invention, a recombinant infectious bovine rhinotracheitis virus contains the foreign DNA sequence encoding hepatitis B virus core protein.

The antigenic polypeptide of an equine pathogen is derived from equine influenza virus, or equine herpesvirus. In one embodiment the antigenic polypeptide is equine influenza neuraminidase or hemagglutinin. Examples of such antigenic polypeptide are: equine influenza virus type A/Alaska 91 neuraminidase and hemagglutinin, equine influenza virus type A/Prague 56 neuraminidase and hemagglutinin, equine influenza virus type A/Miami 63 neuraminidase, equine influenza virus type A/Kentucky 81 neuraminidase and hemagglutinin, equine herpesvirus type 1 glycoprotein B, and equine herpesvirus type 1 glycoprotein D, *Streptococcus equi*, equine infectious anemia virus, equine encephalitis virus, equine rhinovirus and equine rotavirus.

The present invention further provides an antigenic polypeptide which includes, but is not limited to: hog cholera virus gE1, hog cholera virus gE2, swine influenza virus hemagglutinin, neuraminidase, matrix and nucleoprotein, pseudorabies virus gB, gC and gD, and PRRS virus ORF7.

The present invention further provides a recombinant infectious bovine rhinotracheitis virus which comprises a foreign DNA sequence inserted into a non-essential site of the infectious bovine rhinotracheitis virus genome, wherein the foreign DNA sequence encodes an antigenic polypeptide derived from bovine respiratory syncytial virus or bovine parainfluenza virus, and is capable of being expressed in a host infected by the recombinant infectious bovine rhinotracheitis virus.

For example, the antigenic polypeptide is derived from bovine respiratory syncytial virus attachment protein (BRSV G), bovine respiratory syncytial virus fusion protein (BRSV F), bovine respiratory syncytial virus nucleocapsid protein (BRSV N), bovine parainfluenza virus type 3 fusion protein, and the bovine parainfluenza virus type 3 hemagglutinin neuraminidase.

In one embodiment the recombinant infectious bovine rhinotracheitis virus is designated S-IBR-071. In another embodiment the recombinant infectious bovine rhinotracheitis virus is designated S-IBR-072. In another embodiment the recombinant infectious bovine rhinotracheitis virus is designated S-IBR-073.

The present invention further provides a recombinant infectious bovine rhinotracheitis virus which comprises a foreign DNA sequence inserted into a non-essential site of the infectious bovine rhinotracheitis genome, wherein the foreign DNA sequence encodes bovine viral diarrhea virus (BVDV) glycoprotein 48 or glycoprotein 53, and wherein the foreign DNA sequence is capable of being expressed in a host infected by the recombinant infectious bovine rhinotracheitis virus.

In one embodiment the recombinant infectious bovine rhinotracheitis virus is designated S-IBR-069. In another embodiment the recombinant infectious bovine rhinotracheitis virus is designated S-IBR-074. In another embodiment the recombinant infectious bovine rhinotracheitis virus is designated S-IBR-086.

The present invention further provides a recombinant infectious bovine rhinotracheitis virus in which the foreign DNA sequence encodes an antigenic polypeptide which includes, but is not limited to: Marek's disease virus (MDV) gA, marek's disease virus gB, Marek's disease virus gD, Newcastle disease virus (NDV) HN, Newcastle disease virus F, infectious laryngotracheitis virus (ILT) gB, infectious laryngotracheitis virus gI, infectious laryngotracheitis virus gD, infectious bursal disease virus (IBDV) VP2, infectious bursal disease virus VP3, infectious bursal disease virus VP4, infectious bursal disease virus polyprotein, infectious bronchitis virus (IBV) spike, infectious bronchitis virus matrix, avian encephalomyelitis virus, avian reovirus, avian paramyxovirus, avian influenza virus, avian adenovirus, fowl pox virus, avian coronavirus, avian rotavirus, chick anemia virus, Salmonella spp. *E. coli*, Pasteurella spp., Bordetella spp., Eimeria spp., Histomonas spp., Trichomonas spp., Poultry nematodes, cestodes, trematodes, poultry mites/lice, and poultry protozoa.

The invention further provides that the inserted foreign DNA sequence is under the control of an endogenous infectious bovine rhinotracheitis virus promoter. In one embodiment the foreign DNA sequence is under control of a heterologous promoter. In another embodiment the heterologous promoter is a herepesvirus promoter.

For purposes of this invention, promoters include but is not limited to: herpes simplex virus type I ICP4 protein promoter, a pseudorabies virus glycoprotein X promoter, PRV gX, HCMV immediate early, marek's disease virus gA, marek's disease virus gB, marek's disease virus gD, infectious laryngotracheitis virus gB, BHV-1.1 VP8 and infectious laryngotracheitis virus gD.

The subject invention also provides a vaccine which comprises a suitable carrier and an effective immunizing amount of any of the recombinant viruses of the present invention. The vaccine may contain either inactivated or live recombinant virus.

Suitable carriers for the recombinant virus are well known in the art and include proteins, sugars, etc. One example of such a suitable carrier is a physiologically balanced culture medium containing one or more stabilizing agents such as hydrolyzed proteins, lactose, etc. Preferably, the live vaccine is created by taking tissue culture fluids and adding stabilizing agents such as stabilized, hydrolyzed proteins. Preferably, the inactivated vaccine uses tissue culture fluids directly after inactivation of the virus.

The subject invention also provides a vaccine which comprises a suitable carrier and an effective immunizing amount of a recombinant virus comprising viral DNA from a naturally-occurring infectious bovine rhinotracheitis virus in which DNA encoding gG glycoprotein has-been altered or deleted so that upon replication the recombinant infectious bovine rhinotracheitis virus produces no gG glycoprotein.

The subject invention provides a vaccine which comprises a suitable carrier and an effective immunizing amount of a recombinant infectious bovine rhinotracheitis virus comprising viral DNA from a naturally-occurring infectious bovine rhinotracheitis virus in which DNA encoding gG glycoprotein has been altered or deleted and DNA encoding the gE glycoprotein has been altered or deleted so that upon replication the recombinant infectious bovine rhinotracheitis virus produces no gG glycoprotein and no gE glycoprotein.

The subject invention also provides a vaccine which comprises a suitable carrier and an effective immunizing amount of a recombinant infectious bovine rhinotracheitis virus comprising viral DNA from a naturally-occurring infectious bovine rhinotracheitis virus in which DNA encoding gG glycoprotein has been altered or deleted so that upon replication the recombinant infectious bovine rhinotracheitis virus produces no gG glycoprotein, DNA corresponding to the US2 region of the naturally-occurring infectious bovine rhinotracheitis virus has been deleted, and DNA encoding the gE glycoprotein has been altered or deleted.

The subject invention further provides a vaccine which comprises a suitable carrier and an effective immunizing amount of a recombinant infectious bovine rhinotracheitis virus comprising viral DNA from a naturally-occurring infectious bovine rhinotracheitis virus in which (1) DNA corresponding to the US2 region of the naturally-occurring infectious bovine rhinotracheitis virus has been deleted, and (2) DNA encoding gG glycoprotein has been altered or deleted.

The subject invention also provides a vaccine which comprises a suitable carrier and an effective immunizing amount of a recombinant infectious bovine rhinotracheitis virus comprising viral DNA from a naturally-occurring infectious bovine rhinotracheitis virus in which DNA encoding gE glycoprotein has been altered or deleted so that upon replication the recombinant infectious bovine rhinotracheitis virus produces no gE glycoprotein.

The subject invention provides a vaccine which comprises a suitable carrier and an effective immunizing amount of a recombinant infectious bovine rhinotracheitis virus comprising viral DNA from a naturally-occurring infectious bovine rhinotracheitis virus in which DNA encoding gE glycoprotein has been altered or deleted so that upon replication the recombinant infectious bovine rhinotracheitis virus produces no gE glycoprotein and DNA corresponding to the US2 region of the naturally-occurring infections bovine rhinotracheitis virus has been deleted.

The subject invention also provides a vaccine which comprises a suitable carrier and an effective immunizing amount of a recombinant infectious bovine rhinotracheitis virus comprising viral DNA from a naturally-occurring infectious bovine rhinotracheitis virus from which DNA corresponding to the US2 region of the naturally-occurring infectious bovine rhinotracheitis virus has been deleted.

The subject invention provides a vaccine which comprises a suitable carrier and an effective immunizing amount of a recombinant infectious bovine rhinotracheitis virus comprising viral DNA from a naturally-occurring infectious bovine rhinotracheitis virus from which at least a portion of both repeat sequences has been deleted.

The subject invention further provides a vaccine which comprises a suitable carrier and an effective immunizing amount of a recombinant infectious bovine rhinotracheitis virus comprising viral DNA from a naturally-occurring infectious bovine rhinotracheitis virus in which a foreign DNA sequence which encodes the Tn5 NEO gene has been inserted into the viral DNA.

The subject invention also provides a vaccine which comprises a suitable carrier and an effective immunizing amount of a recombinant infectious bovine rhinotracheitis virus comprising viral DNA from a naturally-occurring infectious bovine rhinotracheitis virus in which a foreign DNA sequence which encodes the *Escherichia coli* β-galactosidase and Tn5 NEO genes, and the parainfluenza type 3 virus hemagglutinin gene, HN, has been inserted into the viral DNA.

The subject invention also provides a vaccine which comprises a suitable carrier and an effective immunizing amount of a recombinant infectious bovine rhinotracheitis virus comprising viral DNA from a naturally-occurring infectious bovine rhinotracheitis virus in which a foreign DNA sequence which encodes the *Escherichia coli* β-galactosidase and Tn5 NEO genes, and the parainfluenza type 3 virus fusion gene, F, has been inserted into the viral DNA.

All of the vaccines described hereinabove and hereinbelow may contain either inactivated or live recombinant virus. The vaccines may be administered by any of the methods well known to those skilled in the art, for example, by intramuscular, subcutaneous, intraperitoneal, or intravenous injection.

Alternatively, the vaccine may be administered intranasally or orally.

The present invention also provides a method of immunizing an animal against infectious bovine rhinotracheitis virus which comprises administering to the animal an effective immunizing dose of any of the vaccines of the present invention. The animal may be a bovine.

As defined herein an animal includes, but is not limited to: a human, swine, bovine, equine, caprine or ovine. For purposes of this invention, this includes immunizing the animal against the virus or viruses which cause the disease or diseases: pseudorabies, transmissible gastroenteritis, swine rotavirus, swine parvovirus, *Serpulina hyodysenteriae*, bovine viral diarrhea, Newcastle disease, swine influenza, PRRS, bovine respiratory synctial virus, bovine parainfluenza virus type 3, foot and mouth disease, hog cholera, African swine fever or *Mycoplasma hyopneumoniae*. For purposes of this invention, the method of immunizing also includes immunizing the animal against human pathogens, feline pathogens, bovine pathogens, equine pathogens, avian pathogens described in the preceding part of this section.

Recombinant infectious bovine rhinotracheitisV is useful as a vaccine against feline or canine diseases when foreign antigens from the following diseases or disease organisms are expressed in the IBRV vector, including but not limited to feline herpesvirus, feline leukemia virus, feline immunodeficiency virus (FIV) and *Dirofilaria immiitis* (heartworm). Disease causing microorganisms in dogs include, but are not limited to canine herpesvirus, canine distemper, canine adenovirus type 1 (hepatitis), adenovirus type 2 (respiratory disease), parainfluenza, leptospira canicola, icterohemorragia, parvovirus, coronavirus, *Borrelia burgdorferi*, canine herpesvirus, *Bordetella bronchiseptica, Dirofilaria immitis* (heartworm) and rabies virus. FIV env and gag genes expressed in infectious bovine rhinotracheitisV is useful as a vaccine against feline immunodeficiency and is useful to express the FIV env and gag protein antigens for use in a diagnostic assay. D. immitis p39 and 22kD genes expressed in IBRV is useful as a vaccine against heartworm in dogs and cats and is useful to express the D. immitis p39 and 22kD protein antigens for use in a diagnostic assay.

Recombinant IBRV is useful as a vaccine against avian diseases when foreign antigens from the following diseases or disease organisms are expressed in the IBRV vector: Chick anemia virus, Avian encephalomyelitis virus, Avian reovirus, Avian paramyxoviruses, Avian influenza virus , Avian adenovirus, Fowl pox virus, Avian coronavirus, Avian rotavirus, Salmonella spp *E coli*, Pasteurella spp, Haemophilus spp, Chlamydia spp, Mycoplasma spp, Campylobacter spp, Bordetella spp, Poultry nematodes, cestodes, trematodes, Poultry mites/lice, Poultry protozoa (Eimeria spp, Histomonas spp, Trichomonas spp).

Recombinant IBRV is useful as a vaccine against equine diseases when foreign antigens from the following diseases or disease organisms are expressed in the IBRV vector: *Streptococcus equi*, equine infectious anemia virus, equine encephalitis virus, equine rhinovirus and equine rotavirus.

The method comprises administering to the animal an effective immunizing dose of the vaccine of the present invention. The vaccine may be administered by any of the methods well known to those skilled in the art, for example, by intramuscular, subcutaneous, intraperitoneal or intravenous injection. Alternatively, the vaccine may be administered intranasally or orally.

The present invention also provides a host cell infected with a recombinant infectious bovine rhinotracheitis virus capable of replication. In one embodiment, the host cell is a mammalian cell. Preferably, the mammalian cell is a Vero cell. Preferably, the mammalian cell is an ESK-4 cell, PK-15 cell or EMSK cell.

For purposes of this invention a "host cell" is a cell used to propagate a vector and its insert. Infecting the cells was accomplished by methods well known to those of skill in the art, for example, as set forth in INFECTION—TRANSFECTION PROCEDURE in *Material and Methods*.

Methods for constructing, selecting and purifying recombinant infectious bovine rhinotracheitis viruses described above are detailed below in *Materials and Methods*.

The subject invention also provides a method for distinguishing an animal vaccinated with a vaccine which comprises an effective immunizing amount of a recombinant virus of the present invention from an animal infected with a naturally-occurring IBR virus which comprises analyzing a sample of a body fluid from the animal for the presence of gG glycoprotein of infectious bovine rhinotracheitis virus and at least one other antigen normally expressed in an animal infected by a naturally-occurring infectious bovine rhinotracheitis virus, identifying antigens which are present in the body fluid, and determining whether gG glycoprotein is present in the body fluid. The presence of antigens which are normally expressed in an animal by a naturally-occurring infectious bovine rhinotracheitis virus and the absence of gG glycoprotein in the body fluid is indicative of an animal vaccinated with the vaccine and not infected with a naturally-occurring infectious bovine rhinotracheitis virus. The presence of antigens and gG glycoprotein in the body fluid may be determined by detecting in the body fluid antibodies specific for the antigens and gG glycoprotein.

One of the vaccines that is useful in this method is a vaccine which comprises a suitable carrier and an effective immunizing amount of a recombinant virus comprising viral DNA from a naturally-occurring infectious bovine rhinotracheitis virus in which DNA encoding gG glycoprotein has been altered or deleted so that upon replication the recombinant infectious bovine rhinotracheitis virus produces no gG glycoprotein. Another vaccine that is useful in this method is a vaccine which comprises a suitable carrier and an effective immunizing amount of a recombinant infectious bovine rhinotracheitis virus comprising viral DNA from a naturally-occurring infectious bovine rhinotracheitis virus in which DNA encoding gG glycoprotein has been altered or deleted and DNA encoding the gE glycoprotein has been altered or deleted so that upon replication the recombinant infectious bovine rhinotracheitis virus produces no gG glycoprotein and no gE glycoprotein. Yet another vaccine that is useful in this method is a vaccine which comprises a suitable carrier and an effective immunizing amount of a recombinant infectious bovine rhinotracheitis virus comprising viral DNA from a naturally-occurring infectious bovine rhinotracheitis virus in which DNA encoding gG glycoprotein has been altered or deleted so that upon replication the recombinant infectious bovine rhinotracheitis virus produces no gG glycoprotein, DNA corresponding to the US2 region of the naturally-occurring infectious bovine rhinotracheitis virus has been deleted, and DNA encoding the gE glycoprotein has been altered or deleted. Still another vaccine that is useful in this method is a vaccine which comprises a suitable carrier and an effective immunizing amount of a recombinant infectious bovine rhinotracheitis virus comprising viral DNA from a naturally-occurring infectious bovine rhinotracheitis virus in which (1) DNA corresponding to the US2 region of the naturally-occurring infectious bovine rhinotracheitis virus has been deleted, and (2) DNA encoding gG glycoprotein has been altered or deleted.

The present invention also provides a method for distinguishing an animal vaccinated with a vaccine which comprises an effective immunizing amount of a recombinant virus of the present invention from an animal infected with a naturally-occurring infectious bovine rhinotracheitis virus which comprises analyzing a sample of a body fluid from the animal for the presence of gE glycoprotein of infectious bovine rhinotracheitis virus and at least one other antigen normally expressed in an animal infected by a naturally-occurring infectious bovine rhinotracheitis virus, identifying antigens which are present in the body fluid and determining whether gE glycoprotein is present in the body fluid. The presence of antigens which are normally expressed in an animal by a naturally-occurring infectious bovine rhinotracheitis. virus and the absence of gE glycoprotein in the body fluid is indicative of an animal vaccinated with the vaccine and not infected with a naturally-occurring infectious bovine rhinotracheitis virus. The presence of antigens and gE glycoprotein in the body fluid may be determined by detecting in the body fluid antibodies specific for the antigens and gE glycoprotein.

One of the vaccines useful in this method is a vaccine which comprises a suitable carrier and an effective immunizing amount of a recombinant infectious bovine rhinotracheitis virus comprising viral DNA from a naturally-occurring infectious bovine rhinotracheitis virus in which DNA encoding gG glycoprotein has been altered or deleted and DNA encoding the gE glycoprotein has been altered or deleted so that upon replication the recombinant infectious bovine rhinotracheitis virus produces no gG glycoprotein and no gE glycoprotein. Another vaccine that is useful in this method is a vaccine which comprises a suitable carrier and an effective immunizing amount of a recombinant infectious bovine rhinotracheitis virus comprising viral DNA from a naturally-occurring infectious bovine rhinotracheitis virus in which DNA encoding gG glycoprotein has been altered or deleted so that upon replication the recombinant infectious bovine rhinotracheitis virus produces no gG glycoprotein, DNA corresponding to the US2 region of the naturally-occurring infectious bovine rhinotracheitis virus has been deleted, and DNA encoding the gE glycoprotein has been altered or deleted. Yet another vaccine that is useful in this method is a vaccine which comprises a suitable carrier and an effective immunizing amount of a recombinant infectious bovine rhinotracheitis virus comprising viral DNA from a naturally-occurring infectious bovine rhinotracheitis virus in which DNA encoding gE glycoprotein has been altered or deleted so that upon replication the recombinant infectious bovine rhinotracheitis virus produces no gE glycoprotein. Still another vaccine that is useful in this method is a vaccine which comprises a suitable carrier and an effective immunizing amount of a recombinant infectious bovine rhinotracheitis virus comprising viral DNA from a naturally-occurring infectious bovine rhinotracheitis virus in which DNA encoding gE glycoprotein has been altered or deleted so that upon replication the recombinant infectious bovine rhinotracheitis virus produces no gE glycoprotein and DNA corresponding to the US2 region of the naturally-occurring infectious bovine rhinotracheitis virus has been deleted.

The present invention also provides isolated DNA encoding the gG glycoprotein of infectious bovine rhinotracheitis virus. The subject invention also provides purified recombinant gG glycoprotein encoded by the DNA encoding the gG glycoprotein of infectious bovine rhinotracheitis virus. The subject invention further provides a recombinant cloning vector which comprises the DNA encoding the gG glycoprotein of infectious bovine rhinotracheitis virus. The subject invention also provides a recombinant expression vector which comprises the DNA encoding the gG glycoprotein of infectious bovine rhinotracheitis virus. The subject invention provides a host cell which comprises the recombinant expression vector which comprises the DNA encoding the gG glycoprotein of infectious bovine rhinotracheitis virus.

The subject invention also provides a method of producing a polypeptide which comprises growing the host cell which comprises the recombinant expression vector which comprises the DNA encoding the gG glycoprotein of infectious bovine rhinotracheitis virus under conditions such that the recombinant expression vector expresses gG glycoprotein and recovering the gG glycoprotein so expressed.

The subject invention also provides an antibody directed to an epitope of the purified gG glycoprotein of infectious bovine rhinotracheitis virus encoded by the DNA encoding the gG glycoprotein of infectious bovine rhinotracheitis virus. The antibody may be a monoclonal antibody.

The subject invention also provides a method of detecting the presence or absence of gG glycoprotein of infectious bovine rhinotracheitis virus in a sample which comprises contacting the sample with an antibody directed to an epitope of the purified gG glycoprotein of infectious bovine rhinotracheitis virus encoded by the DNA encoding the gG glycoprotein of infectious bovine rhinotracheitis virus under conditions such that the antibody forms a complex with any gG glycoprotein present in the sample and detecting the presence or absence of such complex. The sample may be bovine-derived.

The subject invention also provides isolated DNA encoding the gE glycoprotein of infectious bovine rhinotracheitis virus. The subject invention also provides purified recombinant gE glycoprotein encoded by the DNA encoding the gE glycoprotein of infectious bovine rhinotracheitis virus. The subject invention further provides a recombinant cloning vector which comprises the DNA encoding the gE glycoprotein of infectious bovine rhinotracheitis virus. The subject invention provides a recombinant expression vector which comprises the DNA encoding the gE glycoprotein of infectious bovine rhinotracheitis virus. The subject invention also provides a host cell which comprises the recombinant expression vector which comprises the DNA encoding the gE glycoprotein of infectious bovine rhinotracheitis virus.

The subject invention also provides a method of producing a polypeptide which comprises growing the host cell which comprises the recombinant expression vector which comprises the DNA encoding the gE glycoprotein of infectious bovine rhinotracheitis virus under conditions such that the recombinant expression vector expresses gE glycoprotein and recovering the gE glycoprotein so expressed.

The subject invention also provides an antibody directed to an epitope of the purified gE glycoprotein of infectious bovine rhinotracheitis virus encoded by the DNA encoding the gE glycoprotein of infectious bovine rhinotracheitis virus. The antibody may be a monoclonal antibody.

The subject invention also provides a method of detecting the presence or absence of gE glycoprotein of infectious bovine rhinotracheitis virus in a sample which comprises contacting the sample with an antibody directed to an epitope of the purified gE glycoprotein of infectious bovine rhinotracheitis virus encoded by the DNA encoding the gE glycoprotein of infectious bovine rhinotracheitis virus under conditions such that the antibody forms a complex with any gE glycoprotein present in the sample and detecting the presence or absence of such complex. The sample may be bovine-derived.

The subject invention also provides a method of producing a fetal-safe, live recombinant infectious bovine rhinotracheitis virus which comprises treating viral DNA from a naturally-occurring live infectious bovine rhinotracheitis virus so as to delete from the virus DNA corresponding to the US2 region of the naturally-occurring infectious bovine rhinotracheitis virus.

The subject invention also provides isolated DNA encoding the US2 gene of an infectious bovine rhinotracheitis virus. The present invention further provides a homology vector for producing a recombinant infectious bovine rhinotracheitis virus by inserting foreign DNA into the genomic DNA of an infectious bovine rhinotracheitis virus which comprises a double-stranded DNA molecule consisting essentially of double-stranded foreign DNA encoding RNA which does not naturally occur in an animal into which the recombinant infectious bovine rhinotracheitis is introduced, with at one end of the foreign DNA, double-stranded infectious bovine rhinotracheitis viral DNA homologous to genomic DNA located at one side of a site on the genomic DNA which is not essential for replication of the infectious bovine rhinotracheitis virus and at the other end of the foreign DNA, double-stranded infectious bovine rhinotracheitis viral DNA homologous to genomic DNA located at the other side of the same site on the genomic DNA. The double-stranded foreign DNA may further comprise a promoter. The promoter can be from HSV-1 ICP4, Human cytomegalovirus immediate early gene or pseudorabies virus glycoprotein X gene. The double-stranded foreign DNA may further comprise a polyadenylation signal. The polyadenylation signal may be from HSV-1 thymidine kinase gene or pseudorabies virus glycoprotein X gene. The subject invention also provides a homology vector wherein the RNA encodes a polypeptide. The polypeptide may be a detectable marker such as *Escherichia coli* β-galactosidase or bacterial transposon neomycin resistance protein. The DNA which encodes the polypeptide may be flanked on each side by restriction sites permitting said DNA to be cut out with a restriction endonuclease which cuts at a limited number of sites on the genome. The subject invention further provides for a homology vector wherein the upstream double-stranded infectious bovine rhinotracheitis viral DNA is homologous to genomic DNA present within the approximately 860 bp NcoI to BamHI subfragment of the HindIII A fragment of infectious bovine rhinotracheitis virus and the downstream double-stranded infectious bovine rhinotracheitis viral DNA is homologous to genomic DNA present within the approximately 1741 bp BglII to StuI subfragment of the HindIII A fragment of infectious bovine rhinotracheitis virus.

The subject invention further provides a homology vector wherein upstream double-stranded foreign DNA which comprises a promoter and downstream double-stranded foreign DNA which comprises a polyadenylation signal flank on each side double-stranded foreign DNA which encodes a detectable marker. The invention further a homology vector wherein the upstream promoter is homologous to genomic DNA present within the approximately 490 bp PvuII to BamHI subfragment of the BamHI N fragment of HSV-1 and the downstream polyadenylation signal is homologous to genomic DNA present within the approximately 784 bp SmaI to SmaI subfragment of the BamHI Q fragment of HSV-1. The invention further provides a homology vector wherein the DNA which encodes a detectable marker is homologous to the approximately 1541 bp BglII to BamHI fragment of Tn5.

The subject invention also provides a homology vector wherein the upstream double-stranded infectious bovine rhinotracheitis viral DNA is homologous to genomic DNA present within the approximately 3593 bp HindIII to XhoI subfragment of the HindIII K fragment of infectious bovine rhinotracheitis virus and the downstream double-stranded infectious bovine rhinotracheitis viral DNA is homologous to genomic DNA present within the approximately 785 bp XhoI to NdeI subfragment of the HindIII K fragment of infectious bovine rhinotracheitis virus. The invention further provides a homology vector wherein upstream double-stranded foreign DNA which comprises a promoter and downstream double-stranded foreign DNA which comprises a polyadenylation signal flank on each side double-stranded foreign DNA which encodes a detectable marker. This upstream promoter is homologous to genomic DNA present within the approximately 1191 bp AvaII to PstI subfragment of the XbaI B fragment of HCMV and the downstream polyadenylation sequence is homologous to genomic DNA present within the approximately 753 bp SalI to NdeI subfragment of the BamHI #7 fragment of PRV. The DNA which encodes a detectable marker is homologous to the approximately 3347 bp BalI to BamHI fragment of pJF751.

The invention further provides a homology vector wherein the upstream double-stranded infectious bovine rhinotracheitis viral DNA is homologous to genomic DNA present within the approximately 888 bp MluI to SmaI subfragment of the HindIII K fragment of infectious bovine rhinotracheitis virus and the downstream double-stranded infectious bovine rhinotracheitis viral DNA is homologous to genomic DNA present within the approximately 785 bp XhoI to NdeI subfragment of the HindIII K fragment of infectious bovine rhinotracheitis virus. The upstream double-stranded foreign DNA may comprise a promoter and double-stranded foreign DNA which comprise a polyadenylation signal flank on each side double-stranded foreign DNA which encodes a detectable marker. The subject invention also provides a homology vector wherein the upstream promoter is homologous to genomic DNA present within the approximately 1191 bp AvaII to PstI subfragment of the XbaI B fragment of HCMV and the downstream polyadenylation signal is homologous to genomic DNA present within the approximately 753 bp SalI to NdeI subfragment of the BamHI #7 fragment of PRV. The DNA which encodes a detectable marker is homologous to the approximately 3347 bp BalI to BamHI fragment of pJF571.

The present invention further provides a homology vector wherein the upstream double-stranded infectious bovine rhinotracheitis viral DNA is homologous to genomic DNA present within the approximately 1704 bp SmaI to SmaI subfragment of the HindIII K fragment of infectious bovine rhinotracheitis virus and the downstream double-stranded infectious bovine rhinotracheitis viral DNA is homologous to genomic DNA present within the approximately 742 bp NheI to BglI subfragment of the SmaI 2.5KB fragment of infectious bovine rhinotracheitis virus. The present invention further provides a homology vector wherein upstream double-stranded foreign DNA which comprises a promoter and downstream double-stranded foreign DNA which comprises a polyadenylation signal flank on each side double-stranded foreign DNA which encodes a detectable marker. The upstream promoter is homologous to genomic DNA present within the approximately 413 bp SalI to BamHI subfragment of the BamHI #10 fragment of PRV and the downstream polyadenylation signal is homologous to genomic DNA present within the approximately 754 bp NdeI to SalI subfragment of the BamHI #7 fragment of PRV. The detectable marker is homologous to the approximately 3010 bp BamHI to PvuII fragment of pJF751.

The present invention provides for a homology vector for producing a recombinant infectious bovine rhinotracheitis virus by deleting DNA which encodes a detectable marker which had been inserted into the genomic DNA of an infectious bovine rhinotracheitis virus comprising a double-stranded DNA molecule consisting essentially of double-stranded infectious bovine rhinotracheitis viral DNA homologous to the genomic DNA which flank on each side the DNA to be deleted. The subject invention further provides a homology vector wherein the upstream double-stranded infectious bovine rhinotracheitis viral DNA is homologous to genomic DNA present within the approximately 888 bp MluI to SmaI subfragment of the HindIII K fragment of infectious bovine rhinotracheitis virus and the downstream double-stranded infectious bovine rhinotracheitis viral DNA is homologous to genomic DNA present within the approximately 785 bp XhoI to NdeI subfragment of the HindIII K fragment of infectious bovine rhinotracheitis virus.

In a preferred embodiment the homology vectors are designated 691-096.2, 756-11.17, and 769-73.3.

The present invention also provides a method of immunizing an animal against infectious bovine rhinotracheitis virus which comprises administering to the animal an effective immunizing dose of any of the vaccines of the present invention. The animal may be a bovine. The subject invention also provides a recombinant infectious bovine rhinotracheitis virus comprising viral DNA from a naturally-occurring infectious bovine rhinotracheitis virus from which at least a portion of both repeat sequences have been deleted, specifically, wherein DNA encoding one or more EcoRV restriction sites has been deleted, and wherein foreign DNA has been inserted into the DNA of the recombinant virus. The foreign DNA may be a DNA sequence which encodes bovine viral diarrhea virus glycoprotein g53. The subject invention provides an example of such a recombinant infectious bovine rhinotracheitis virus, designated S-IBR-032.

The subject invention provides a recombinant infectious bovine rhinotracheitis virus comprising viral DNA from a naturally-occurring infectious bovine rhinotracheitis virus from which DNA from the US2 gene, the gE glycoprotein gene and the gG glycoprotein gene have been deleted so that upon replication, the recombinant infectious bovine rhinotracheitis virus produces no gE glycoprotein and no gG glycoprotein. A Foreign DNA sequence may be inserted in place of the deleted DNA which encodes gE glycoprotein. The foreign DNA sequence that may be inserted can be a foreign DNA sequence which encodes *Escherichia coli* β-galactosidase. The subject invention provides an example of such a recombinant virus, designated S-IBR-039.

The subject invention further provides a recombinant infectious bovine rhinotracheitis virus comprising viral DNA from a naturally-occurring IBR virus in which DNA from the US2, gE glycoprotein gene, the gG glycoprotein gene and the thymidine kinase gene has been deleted so that upon replication, the recombinant infectious bovine rhinotracheitis virus produces no gE glycoprotein, no gG glycoprotein and no thymidine kinase. The subject invention provides an example of such a recombinant virus, designated S-IBR-045. A foreign DNA sequence may be inserted in place of the deleted DNA encoding gE glycoprotein. The foreign DNA sequence may encode *Escherichia coli* β-galactosidase. The subject invention provides an example of such a recombinant virus, designated S-IBR-044. The foreign DNA sequence may encode bovine viral diarrhea virus g53 glycoprotein. The subject invention provides an example of such a recombinant virus, designated S-IBR-046. The foreign DNA sequence may encode Parainfluenza virus type 3 fusion protein and Parainfluenza virus type 3 hemagglutinin protein. The subject application provides an example of such a virus, designated S-IBR-047. The foreign DNA sequence may encode Bovine respiratory syncytial virus fusion protein, Bovine respiratory syncytial virus attachment protein and Bovine respiratory syncytial virus nucleocapsid protein. The subject invention provides an example of such a recombinant virus, designated S-IBR-049. The foreign DNA sequence may encode *Pasteurella haemolytica* leukotoxin and *Pasteurella haemolytica* iron regulated outer membrane proteins. The subject invention provides an example of such a recombinant virus, designated S-IBR-051.

The subject invention also provides a recombinant infectious bovine rhinotracheitis virus comprising viral DNA from a naturally-occurring IBR virus from which DNA from the US2 gene, the gE glycoprotein gene, the gG glycoprotein gene and the thymidine kinase gene have been deleted so that upon replication, the recombinant IBR virus produces no gE glycoprotein, no gG glycoprotein and no thymidine kinase. The subject invention provides for a foreign DNA sequence inserted in place of the DNA which encodes thymidine kinase. The foreign DNA sequence may encode *Escherichia coli* β-glucuronidase. The present invention further provides a recombinant virus wherein a foreign DNA sequence is inserted in place of the DNA encoding gE glycoprotein. The foreign DNA sequence may encode *Escherichia coli* β-galactosidase. The present invention further provides an example of such a recombinant virus, designated S-IBR-043.

The subject invention also provides a vaccine which comprises an effective immunizing amount of any of the recombinant viruses of the present invention and a suitable carrier. The vaccine may contain either inactivated or live recombinant virus.

The present invention provides a vaccine which comprises an effective immunizing amount of recombinant virus protective against bovine respiratory disease complex and a suitable carrier. A recombinant virus may be a recombinant IBR virus and the recombinant virus can consist essentially of any or all of the recombinant viruses of the present invention.

The subject invention also provides for a vaccine which comprises an effective immunizing amount of a recombinant virus and non-recombinant virus protective against bovine respiratory disease complex and a suitable carrier.

The subject invention further provides a vaccine which comprises an effective immunizing amount of a recombinant IBR virus and non-recombinant virus protective against bovine respiratory disease complex and a suitable carrier. The recombinant IBR virus can consist essentially of any or all of the recombinant viruses of the subject invention.

For purposes of this invention, the infectious diseases that contribute to bovine respiratory disease complex include infectious bovine rhinotracheitis, parainfluenza type 3 virus, bovine viral diarrhea virus, bovine respiratory syncytial virus and *Pasteurella haemolytica*.

For purposes of the present invention, non-recombinant viruses can include, but are not limited to, conventionally derived viruses which include killed virus, inactivated bacterins, and modified live viruses.

The subject invention further provides for a method of immunizing an animal against infectious bovine rhinotracheitis which comprises administering to the animal an immunizing dose of any of the vaccines of the present invention. The subject invention further provides a method of immunizing an animal against Parainfluenza type 3 which comprises administering to the animal an immunizing dose of the vaccine of the present invention that contains the IBR virus encoding antigens for Parainfluenza type 3 virus. The subject invention further provides a method of immunizing an animal against bovine viral diarrhea which comprises administering to the animal an immunizing dose of the vaccine of the present invention that contains the IBR virus encoding antigens for bovine viral diarrhea virus. The subject invention further provides a method of immunizing an animal against bovine respiratory syncytial virus disease which comprises administering to the animal an immunizing dose of the vaccine of the present invention that contains the IBR virus encoding antigens for bovine respiratory syncytial virus. The subject invention further provides for a method of immunizing an animal against Pneumonic pasteurellosis which comprises administering to the animal an immunizing dose of the vaccine of the present invention that contains the IBR virus encoding antigens for *Pasteurella haemolytica*.

The invention further provides a method of immunizing an animal against bovine respiratory disease complex which comprises administering to an animal an immunizing dose of the vaccine containing the recombinant IBR viruses of the present invention or the recombinant viruses of the present invention and non-recombinant viruses. For purposes of this invention, the animal may be a bovine. The invention further provides a method for distinguishing an animal vaccinated with a vaccine which comprises an effective immunizing amount of a recombinant virus of the present invention from an animal infected with a naturally-occurring IBR virus which comprises analyzing a sample of a body fluid from the animal for the presence of gE glycoprotein of IBR virus and at least one other antigen normally expressed in an animal infected by a naturally-occurring IBR virus, identifying antigens which are present in the body fluid and determining whether gE glycoprotein is present in the body fluid, the presence of antigens which are normally expressed in an animal by a naturally-occurring IBR virus and the absence of gE glycoprotein in the body fluid being indicative of an animal vaccinated with the vaccine and not infected with a naturally-occurring IBR virus.

The present invention also provides a vaccine which comprises an effective immunizing amount of the recombinant infectious bovine rhinotracheitis virus S-IBR-052 and a suitable carrier. The vaccine may contain either inactivated or live infectious bovine rhinotracheitis S-IBR-052.

In general, the vaccine of this invention contains an effective immunizing amount of S-IBR-052 virus from about $10^3$ to $10^8$ PFU/dose. Preferably, the effective immunizing amount is from about $10^4$ to $10^7$ or $10^4$ to $10^6$ PFU/dose for the live vaccine. Preferably, the live vaccine is created by taking tissue culture fluids and adding stabilizing agents such as stabilized, hydrolyzed proteins. Preferably, the inactivated vaccine uses tissue culture fluids directly after inactivation of the virus.

The present invention also provides a method of immunizing an animal, particularly a bovine, against disease caused by infectious bovine rhinotracheitis virus which comprises administering to the animal an effective immunizing dose of the vaccine comprising S-IBR-052.

The present invention provides a method of enhancing an immune response which comprises administering to a subject an effective dose of a recombinant infectious bovine rhinotracheitis virus and a suitable carrier.

The present invention also provides a method for distinguishing an animal vaccinated with the infectious bovine rhinotracheitis virus S-IBR-052 from an animal infected with naturally-occurring infectious bovine rhinotracheitis virus. This method comprises analyzing a sample of a body fluid from the animal for the presence of IBRV gG or gE and at least one other antigen which is normally expressed in an animal infected by a naturally-occurring infectious bovine rhinotracheitis virus and determining whether the antigen and gG or gE are present in the body fluid. The presence of the antigen and the absence of gG or gE in the body fluid is indicative of an animal vaccinated with the vaccine and not infected with a naturally-occurring infectious bovine rhinotracheitis virus.

The presence of the antigen and of gG or gE in the body fluid may be determined by various methods, for example, by detecting in the body fluid antibodies specific for the antigen and for gG or gE.

Methods for constructing, selecting and purifying infectious bovine rhinotracheitis viruses, including S-IBR-052, are detailed in the Materials and Methods section which follows. Furthermore, Example 25 of the specification contains detailed characterization of recombinant infectious bovine rhinotracheitis virus S-IBR-052.

EXPERIMENTAL DETAILS

Materials and Methods
Preparation of IBR Virus Stock Samples

IBR virus stock samples were prepared by infecting MDBK cells at a multiplicity of infection of 0.01 PFU/cell in Dulbecco's Modified Eagle Medium (DMEM) containing 2 mM glutamine, 100 units/ml penicillin, 100 units/ml streptomycin (these components were obtained from Irvine Scientific or an equivalent supplier, and hereafter are referred to as complete DME medium) plus 1% fetal bovine serum. After cytopathic effect was complete, the medium and cells were harvested and the cells were pelleted at 3000 rpm for 5 minutes in a clinical centrifuge. Cells were resuspended in 1/10 the original volume of medium, and an equal volume of skim milk (9% skim milk powder in $H_2O$ weight/volume) was added. The virus sample was frozen at $-70°$ C. The titers were usually about $10^8$ PFU/ml.

Preparation of Herpesvirus DNA

For herpesvirus DNA preparation, a confluent monolayer of cells (MDBK for IBR virus or Vero for PRV) in a 25 $cm^2$ flask or 60 mm petri dish was infected with 100 gl of virus sample. After overnight incubation, or when the cells were showing 100% cytopathic effect, the cells were scraped into the medium. The cells and medium were centrifuged at 3000 rpm for 5 minutes in a clinical centrifuge. The medium was decanted, and the cell pellet was gently resuspended in 0.5 ml of solution containing 0.5% NONIDET P-40™ (NP-40, purchased from Sigma Chemical Co., St. Louis, Mo.). The sample was incubated at room temperature for 10 minutes. Ten $\mu l$ of a stock solution of RNase A (Sigma) was added (stock was 10 mg/ml, boiled for 10 minutes to inactivate DNAse). The sample was centrifuged to pellet nuclei. The DNA pellet was removed with a pasteur pipette or wooden stick and discarded. The supernatant fluid was decanted into a 1.5 ml Eppendorf tube containing 25 $\mu l$ of 20% sodium dodecyl sulfate (Sigma) and 25 $\mu l$ proteinase-K (10 mg/ml; Boehringer Mannheim). The sample was mixed and incubated at 37° C. for 30–60 minutes. An equal volume of water-saturated phenol was added and the sample was mixed briefly. The sample was centrifuged in an Eppendorf minifuge for 5 minutes at full speed. The upper aqueous phase was removed to a new Eppendorf tube, and two volumes of absolute ethanol were added and the tube put at $-20°$ C. for 30 minutes to precipitate nucleic acid. The sample was centrifuged in an Eppendorf minifuge for 5 minutes. The supernatant was decanted, and the pellet was washed with ~300 μl of 80% ethanol, followed by centrifugation in an Eppendorf minifuge for 5 minutes. The supernatant was decanted, and the pellet was air dried and rehydrated in ~16 μl $H_2O$. For the preparation of larger amounts of DNA, the procedure was scaled up to start with a 850 $cm^2$ roller bottle of MDBK cells. The DNA was stored in 0.01 M tris pH 7.5, 1 mM EDTA at 4° C.

Preparation of Herpesvirus Cell Lysates

For cell lysate preparation, serum free medium was used. A confluent monolayer of cells (MDBK for IER virus or Vero for PRV) in a 25 $cm^2$ flask or a 60 mm petri dish was infected with 100 μl of virus sample. After cytopathic effect was complete, the medium and cells were harvested and the cells were pelleted at 3000 rpm for 5 minutes in a clinical centrifuge. For media samples medium was concentrated approximately 10-fold by filtration with a centricon-10 microconcentrator (Amicon). For cell samples the cell pellet was resuspended in 250 μl of disruption buffer (2% sodium dodecyl sulfate, 2% β-mercaptoethanol). The samples were sonicated for 30 seconds on ice and stored at −20° C.

Western Blotting Procedure

Samples of lysates, controls and protein standards were run on a polyacrylamide gel according to the procedure of Laemmli (2). After gel electrophoresis the proteins were transferred according to Sambrook (14). The primary antibody was a mouse hyper-immune serum raised against chemically-synthesized gG peptides (amino acids 232–252 and 267–287) linked to keyhole limpet hemocyanin. The secondary antibody was a goat anti-mouse alkaline phosphatase coupled antibody.

Molecular Biological Techniques

Techniques for the manipulation of bacteria and DNA, including such procedures as digestion with restriction endonucleases, gel electrophoresis, extraction of DNA from gels, ligation, phosphorylation with kinase, treatment with phosphatase, growth of bacterial cultures, transformation of bacteria with DNA, and other molecular biological methods are described by Maniatis (6). Except as noted, these were used with minor variation.

Ligation

DNA was joined together by the action of the enzyme T4 DNA ligase (BRL). Ligation reactions contained various amounts of DNA (from 0.2 to 20 μg), 20 mM Tris pH 7.5, 10 mM $MgCl_2$, 10 mM dithiothreitol (DTT), 200 μM ATP and 20 units T4 DNA ligase in 10–20 μl final reaction volume. The ligation proceeded for 3–16 hours at 15° C.

DNA Sequencing

Sequencing was performed using the BRL Sequenase Kit and $^{35}S$-dATP (NEN). Reactions using both the dGTP mixes and the dITP mixes were performed to clarify areas of compression. Alternatively, compressed areas were resolved on formamide gels. Templates were double-stranded plasmid subclones or single stranded M13 subclones, and primers were either made to the vector just outside the insert to be sequenced, or to previously obtained sequence. Sequence obtained was assembled and compared using Dnastar software. Manipulation and comparison of sequences obtained was performed with Superclone and Supersee programs from Coral Software.

Southern Blotting of DNA

The general procedure for Southern blotting was taken from Maniatis (6). DNA was blotted to nitrocellulose filters and hybridized to appropriate, labeled DNA probes. Probes for southern blots were prepared using either the Nonradioactive DNA Labeling and Detection Kit of Boehringer Mannheim or the nick translation kit of Bethesda Research Laboratories (BRL). In both cases the manufacturers' recommended procedures were followed.

DNA Transfection for Generating Recombinant Virus

The method is based upon the calcium phosphate procedure of Graham and Van der Eb (24) with the following modifications. Virus and/or plasmid DNA were diluted to 298 μl in 0.01 M Tris pH 7.5, 1 mM EDTA. Forty μl 2M $CaCl_2$ was added followed by an equal volume of 2×HEPES buffered saline (10 g N-2-hydroxyethyl piperazine N'-2-ethanesulfonic acid (HEPES), 16 g NaCl, 0.74 g KCl, 0.25 g $Na_2HPO_4$ .$2H_2O$, 2 g dextrose per liter $H_2O$ and buffered with NaOH to pH 7.4). The mixture was then incubated on ice for 10 minutes, and then added dropwise to an 80% confluent monolayer of MDBK or rabbit skin (RS) cells growing in a 60 mm petri dish under 5 ml of medium (DME plus 2% fetal bovine serum). The cells were incubated 4 hours at 37° C. in a humidified incubator containing 5% $CO_2$. The cells were then washed with three 5 ml aliquots of 1×PBS (1.15 g $Na_2HPO_4$, 0.2 g $KH_2PO_4$, 0.8 g NaCl, 0.2 g KCl per liter $H_2O$), and fed with 5 ml of medium (DME plus 2% fetal bovine serum). The cells were incubated at 37° C. as above for 3–7 days until cytopathic effect from the virus was 50–100%. Virus was harvested as described above for the preparation of virus stocks. This stock was referred to as a transfection stock and was subsequently screened for recombinant virus by the BLUOGAL™ SCREEN FOR RECOMBINANT IBR VIRUS.

Homologous Recombination Procedure for Generating Recombinant Herpesvirus

This method relies upon the homologous recombination between herpesvirus DNA and plasmid homology vector DNA which occurs in tissue culture cells co-transfected with these elements. From 0.1–1.0 μg of plasmid DNA containing foreign DNA flanked by appropriate herpesvirus cloned sequences (the homology vector) were mixed with approximately 0.3 μg of intact herpesvirus DNA. The DNAs were diluted to 298 μl in 0.01 M Tris pH 7.5, 1 mM EDTA and transfected into MDBK cells according to the DNA TRANSFECTION FOR GENERATING RECOMBINANT VIRUS (see above).

Direct Ligation Procedure for Generating Recombinant Herpesvirus

Rather than using homology vectors and relying upon homologous recombination to generate recombinant virus, the technique of direct ligation to engineer herpesviruses was also developed. In this instance, a cloned foreign gene did not require flanking herpesvirus DNA sequences but only required that it have restriction sites available to cut out the foreign gene fragment from the plasmid vector. A compatible restriction enzyme was used to cut herpesvirus DNA. A requirement of the technique was that the restriction enzyme used to cut the herpesvirus DNA must cut at a limited number of sites. XbaI, which cuts IBR virus DNA in one place was used. EcoRV which cuts IBR virus DNA in two places was used. For PRV XbaI and HindIII, both of which cut in two places was used. Restriction sites previously introduced into herpesviruses by other methods may also be used. The herpesvirus DNA was mixed with a 30-fold molar excess of plasmid DNA (typically 5 μg of virus DNA to 10 μg of plasmid DNA), and the mixture was cut with the appropriate restriction enzyme. The DNA mixture was phenol extracted and ethanol precipitated to remove restriction enzymes, and ligated together according to the ligation procedure detailed above. The ligated DNA mixture was then resuspended in 298 μl 0.01 M Tris pH 7.5, 1 mM EDTA and transfected into cells (MDBK or RS for IBR virus and Vero for PRV) according to the DNA TRANSFECTION FOR GENERATING RECOMBINANT VIRUS (see above). The direct ligation procedure may also be used to delete DNA from herpesviruses. Non-essential DNA which is flanked by appropriate restriction enzyme sites may be deleted by digesting the virus DNA with such enzymes and religation. The frequency of engineered viruses generated by the direct ligation procedure is high enough that screening can be accomplished by restriction enzyme analysis of randomly picked plaques from the transfection stock.

Bluogal™ Screen for Recombinant Herpesvirus

When the E.coli β-galactosidase (lacZ) marker gene was incorporated into a recombinant virus the plaques containing recombinants were visualized by a simple assay. The chemical BLUOGAL™ (GIBCO-Bethesda Research Labs) was incorporated (200 μg/ml) into the agarose overlay during the plaque assay, and plaques that expressed active β-galactosidase turned blue. The blue plaques were then picked onto fresh cells (MDBK for IBR virus and Vero for PRV) and purified by further blue plaque isolations. In recombinant virus strategies in which the E.coli β-galactosidase marker gene is removed, the assay involves plaque purifying white plaques from a background of parental blue plaques. In both cases viruses were typically purified with three rounds of plaque purification.

Screen for Recombinant Herpesvirus Expressing Enzymatic Marker Genes

When the E. coli β-galactosidase (lacZ) or β-glucuronidase (uidA) marker gene was incorporated into a recombinant virus the plaques containing recombinants were visualized by a simple assay. The enzymatic substrate was incorporated (300 μg/ml) into the agarose overlay during the plaque assay. For the lacZ marker gene the substrate BLUOGAL™ (halogenated indolyl-β-D-galactosidase, Bethesda Research Labs) was used. For the uidA marker gene the substrate X-Glucuro Chx (5-bromo-4-chloro-3-indolyl-β-D-glucuronic acid Cyclohexylammonium salt, Biosynth AG) was used. Plaques that expressed active marker enzyme turned blue. The blue plaques were then picked onto fresh cells and purified by further blue plaque isolation. In recombinant virus strategies in which the enzymatic marker gene is removed the assay involves plaque purifying white plaques from a background of parental blue plaques. In both cases viruses were typically purified with three rounds of plaque purification.

Antibody Screen for Recombinant Herpesvirus

A third method for screening the recombinant virus stock was to look directly for the expression of the foreign gene with antibodies. Herpesvirus plaques were spotted and picked by inserting a toothpick through the agarose above the plaque and scraping the plaque area on the dish. Viruses were then rinsed from the toothpick by inserting the toothpick into a well of a 96-well microtiter dish (Falcon Plastics) containing a confluent monolayer of tissue culture cells that had been washed 3 times in DME medium without serum. It was important for the virus to grow without serum at this stage to allow the immunological procedure to work. After cytopathic effect was complete, the plates were put at −70° C. to freeze and lyse the cells. The medium was thawed, and the freeze/thaw procedure was repeated a second time. Then 50–100 microliters of medium were removed from each well and filtered under vacuum through a nitrocellulose membrane (S&S BA85) using a DotBlot~ apparatus (BRL). The filter blots were soaked in a blocking solution of 0.01 M Tris pH 7.5, 0.1 M NaCl, 3% bovine serum albumin at room temperature for two hours with shaking. The filter blots were then placed in a sealable bag (Sears SEAL-A-MEAL™ or equivalent), and 10 mls of the blocking solution that contained 10 microliters of antibody specific for the foreign protein were added. After overnight incubation at room temperature with shaking, the blot was washed 3 times with 100 mls 0.01 M Tris, pH 7.5, 0.1 M NaCl, 0.05% Tween 20 detergent (Sigma). The blot was put in another sealable bag and 10 mls blocking solution containing $10^6$ counts per minute of $^{125}$I-protein A (New England Nuclear) were added. After allowing the protein A to bind to the antibody for 2 hours at room temperature with shaking, the blot was washed as above, dried, and overlayed with an X-ray film and an intensifying screen (Dupont) and autoradiographed for 1–3 days at −70° C. The film was developed by standard procedures. Virus from the positive wells which contained the recombinant virus was further purified.

Selection of G418 Resistant IBR Virus

The antibiotic G418 (GIBCO) has a wide range of inhibitory activity on protein synthesis. However, recombinant viruses expressing the aminoglycosidase 3'-phosphotransferase, encoded by the NEO gene of the transposable element Tn5, are resistant to G418. The transfection stocks of recombinant viruses were grown on MDBK cells in the presence of 500 μg/ml G418 in complete DME medium plus 1% fetal bovine serum. After one or two days at 37° C., plaques from the dishes inoculated with the highest dilution of virus were picked for virus stocks. The selection was repeated a second or third time. The virus stocks generated from the G418 selection were tested for NEO gene insertion by the SOUTHERN BLOTTING OF DNA hybridization procedure described above.

Construction of Deletion Viruses

The strategy used to construct deletion viruses involved the use of either homologous recombination and/or direct ligation techniques. Initially a virus was constructed via homologous recombination, in which the DNA to be deleted was replaced with a marker gene such as E. coli β-galactosidase (lacZ) or β-glucuronidase (uidA). A second virus was then constructed in which the marker gene was deleted either by homologous recombination or via direct ligation. The advantage of this strategy is that both viruses may be purified by the SCREEN FOR RECOMBINANT HERPESVIRUS EXPRESSING ENZYMATIC MARKER GENES. The first virus is purified by picking blue plaques from a white plaque background, the second virus is purified by picking white plaques from a blue plaque background.

Several homology vectors were constructed for the purpose of deleting the gG, gE and Tk gene coding regions. A detailed description of these homology vectors follows.

IBR Virus gE Plasmid

A plasmid may be generated for the purpose of constructing a recombinant cloning vector which expresses the IBR virus glycoprotein E (gE). This plasmid may be used to insert the IBR virus gE gene into S-PRV-002 (U.S. Pat. No. 4,877,737). The plasmid will contain the gE gene flanked by XbaI restriction sites. When this plasmid is used with S-PRV-002 and the restriction enzyme XbaI according to the DIRECT LIGATION PROCEDURE FOR GENERATING RECOMBINANT HERPESVIRUS the resulting recombinant will express the IBR virus gE. A detailed description of the plasmid is given in FIGS. 17A–17E. It may be constructed, utilizing standard recombinant DNA techniques (6), by joining restriction fragments from the following sources. The plasmid vector is derived from an approximately 2999 base pair XbaI to XbaI restriction fragment of a hybrid cloning vector derived from pSP64 and pSP65 (Promega). The hybrid cloning vector was constructed by joining an approximately 1369 base pair PvuI to SmaI fragment from pSP64 with the approximately 1652 base pair PvuI to SmaI fragment from pSP65. Fragment 1 is an approximately 3647 base pair NdeI to HindIII restriction sub-fragment of the IBR virus HindIII restriction fragment K (7). Fragment 2 is an approximately 832 base pair HindIII to SacI restriction sub-fragment of an IBR virus 2400 base pair SmaI restriction fragment. This SmaI fragment has been cloned into the SmaI site of the plasmid pSP64 (Promega). This plasmid is designated PSY1645. PSY1645 was deposited on Jul. 16, 1991 pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. 68650. Note that the lacZ marker gene is flanked by XbaI sites located at Junction B and Junction E in this plasmid permitting the marker gene to be cut out with XbaI.

Purification of IBR Virus gG gG was purified from the tissue culture medium of infected MDBK cells. Confluent MDBK cells in serum-free medium were infected at a multiplicity of infection equal to 5, with wild-type, Cooper strain of IBR virus. The cells and media were harvested at approximately twenty-two hours after infection, when the cells showed considerable cytopathic effect and the fluids were centrifuged at 5000 rpm for 15 minutes.

The supernatant fluid was concentrated approximately 10-fold by ultrafiltration through an Amicon ym-30 membrane, and dialyzed against 10 mM $NaPO_4$ pH 7.2. The dialysate was treated for 20 minutes at 0° C. with 70% perchloric acid to a final concentration of 0.2M perchloric acid, then centrifuged at 12,000 rpm for 20 minutes. The supernatant fluid was then dialyzed against 20mM Tris pH 9.5.

The acid-soluble proteins were separated by column chromatography on a DEAE-Sephacel anion exchange column using a liner gradient elution: 0 to 100% A to B where A=20 mM Tris pH 9.5 and B=20 mM Tris pH 9.5/800 mM NaCl. The gG eluted at approximately 35–40% B. Peak fractions were assayed by Western blot using anti gG peptide sera. Reactive fractions were combined and dialyzed against 5 mM Tris pH 7.0. The sample was then concentrated 10-fold by lyophilization and stored at −20° C.

ELISA Assay

A standard enzyme-linked immunosorbent assay (ELISA) protocol was used to determine the immune status of cattle following vaccination and challenge.

A purified gG antigen solution (100 μl at 1 ng/μl in PBS) was allowed to absorb to the wells of microtiter dishes for 18 hours at 4° C. The coated wells were rinsed one time with PBS. Wells were blocked by adding 250 μl of PBS containing 1% BSA (Sigma) and incubating 1 hour at 37° C. The blocked wells were rinsed one time with PBS containing 0.02% Tween 20. 50 μl of test serum (previously diluted 1:2 in PBS containing 1% BSA) were added to the wells and incubated 1 hour at 37° C. The antiserum was removed and the wells were washed 3 times with PBS containing 0.02% Tween 20. 50 μl of a solution containing anti-bovine IgG coupled to horseradish peroxidase (diluted 1:500 in PBS containing 1% BSA, Kirkegaard and Perry Laboratories, Inc.) was added to visualize the wells containing antibody against the specific antigen. The solution was incubated 1 hour at 37° C., then removed and the wells were washed 3 times with PBS containing 0.02% Tween 20. 100 μl of substrate solution (ATBS, Kirkegaard and Perry Laboratories, Inc.) were added to each well and color was allowed to develop for 15 minutes. The reaction was terminated by addition of 0.1M oxalic acid. The color was read at absorbance 410 nm on an automatic plate reader.

Procedure for Generating Monoclonal Antibodies

To produce monoclonal antibodies, 8 to 10 week old BALB/c female mice were vaccinated intraperitoneally seven times at two to four week intervals with $10^7$ PFU of S-PRV-160. Three weeks after the last vaccination, mice were injected intraperitoneally with 40 μg of purified gG. Spleens were removed from the mice three days after the last antigen dose.

Splenocytes were fused with mouse NS1/Ag4 plasmacytoma cells by the procedure modified from Oi and Herzenberg, (39). Splenocytes and plasmacytoma cells were pelleted together by centrifugation at 300×g for 10 minutes. One ml of a 50% solution of polyethylene glycol (m.w. 1300–1600) was added to the cell pellet with stirring over one minute. Dulbecco's modified Eagles's medium (5 ml) was added to the cells over three minutes. Cells were pelleted by centrifugation at 300×g for 10 minutes and resuspended in medium with 10% fetal bovine serum and containing 100 μM hypoxanthine, 0.4 μM aminopterin and 16 μM thymidine (HAT). Cells (100 μl) were added to the wells of eight to ten 96-well tissue culture plates containing 100 μl of normal spleen feeder layer cells and incubated at 37° C. Cells were fed with fresh HAT medium every three to four days.

Hybridoma culture supernatants were tested by the ELISA ASSAY in 96-well microtiter plates coated with 100 ng of purified gG. Supernatants from reactive hybridomas were further analyzed by black-plaque assay and by Western Blot. Selected hybridomas were cloned twice by limiting dilution. Ascetic fluid was produced by intraperitoneal injection of $5\times10^6$ hybridoma cells into pristane-treated BALB/c mice.

Method for cDNA Cloning Bovine Rotavirus g38 Gene

The Calf Nebraska strain of bovine rotavirus (USDA) was propagated on MA-104 cells (Rhesus monkey kidney cells from MA Bioproducts). Confluent monolayers were infected at a multiplicity of infection of greater than 10 in DMEM containing 5 micrograms/ml trypsin. Cells were incubated with virus for 48 hours or until a cytopathic effect was obtained. Media and cell debris were collected and centrifuged at 10,000×g for 20 minutes at 4° C. The supernatant containing the rotavirus was then centrifuged at 10,000×g in a preparative Beckman Ti45 rotor at 4° C. Virus pellets were resuspended in SM medium (50 mM Tris-HCl pH 7.5, 100 mM KCl, 10 mM MgCl) and homogenized lightly in a Dounce-type homogenizer. The resuspended virus was centrifuged at 10,000×g for 10 minutes then loaded onto 25–50% CsCl gradients in SM buffer. Gradients were centrifuged at 100,000×g for 4 hours at 20° C. The two blue-white bands representing intact virions and cores of rotavirus were collected, diluted, and the CsCl gradient procedure was repeated a second time. Virus obtained from the second gradient was dialyzed overnight against SM buffer at 4° C.

Dialyzed bovine rotavirus was twice extracted with an equal volume of SDS/phenol, then twice more with chloroform:isoamylalcohol (24:1). The double stranded RNA was precipitated with ethanol in the presence of 0.2 M sodium acetate, centrifuged and resuspended in water. The yield was typically 100 micrograms from 1,000 $cm^2$ of infected cells.

160 micrograms of double-stranded bovine rotavirus RNA obtained from the above procedure was mixed with one microgram each of two synthetic oligonucleotide primers in a volume of 160 microliter (sequences of primers were:

5'-GGGAATTCTGCAGGTCACATCATACAATTCT AATCTAAG-3' (SEQ ID NO: 1) and 5'-GGGAATTCTGCAGGCTTTAAAAGAGAGAATTT CCGTTTGGCTA-3' (SEQ ID NO: 2) derived from the published sequence of bovine rotavirus (40). The RNA-primer mixture was boiled for 3 minutes in a water bath then chilled on ice. Additions of 25 microliters of 1 M Tris-HCl pH 8.3, 35 microliters of 1 M KCl, 10 microliters of 0.25 M $MgCl_2$, 7 microliters of 0.7 M 2-mercaptoethanol, 7 microliters of 20 mM dNTP's, and 6 microliters of reverse transcriptase (100 units) were made sequentially. The reaction was incubated at 42° C. for 1.5 hours then 10 microliters of 0.5 M EDTA pH 8.0 was added and the solution was extracted once with chloroform:phenol (1:1). The aqueous layer was removed and to it 250 microliters of 4 M ammonium acetate and 1.0 ml of 95% ethanol was added, the mixture was frozen in dry ice and centrifuged in the cold. The resulting pellet was resuspended in 100 microliters of 10 mM Tris-HCl pH 7.5 and the ammonium acetate precipitation procedure was repeated. The pellet was resuspended in 100 microliters of 0.3 M KOH and incubated at room temperature overnight, then at 37° C. for 2 hours. The solution was brought to neutral pH by addition of 10 microliters of 3.0 M HCl and 25 microliters of 1.0 M Tris-HCl pH 7.5 The resulting single-stranded cDNA was then precipitated two times by the above-described ammonium acetate-ethanol procedure. The pellet obtained was resuspended in 50 microliters of 10 mM Tris-HCl pH 7.5, 100 mM NaCl, 1 mM EDTA, boiled in a water bath for 2 minutes, then incubated at 59° C. for 16 hours. The solution was lyophilized to a volume of 15 microliters and the resulting double-stranded cDNA was run on a 1.0% agarose gel (Sigma agarose Type II). The ethidium bromide-stained DNA migrating at 1,000–1,100 base pair length was excised from the gel and electroeluted in a CBS electroeluter device. The solution was lyophilized, and the cDNA was resuspended in 25 microliters of water. To this solution was added 2 microliters of 1.0 M Tris-HCl pH 7.5, 2 microliters of 1 M KCl, 1 microliter of 0.25 M $MgCl_2$, 1 microliter of 20 mM dNTP's and 5 units of *E. coli* DNA polymerase I. The reaction was incubated at room temperature for 15 minutes, then chloroform/phenol extracted and ammonium acetate-ethanol precipitated as described above. The resulting cDNA was tailed with dCTP using terminal deoxynucleotide transferase (BRL buffer and enzyme used). The reaction was stopped with 2 microliters of 0.5 M EDTA, chloroform/phenol extracted and precipitated with sodium acetate in the presence of 10 micrograms of carrier tRNA. The resuspended cDNA was mixed with 200 ng of dGMP-tailed Pst I cut pBR322 (BRL catalog #5355SA) in 200 microliters of 10 mM Tris-HCl pH 7.5, 100 mM NaCl, 1 mM EDTA, heated to 65° C. for 5 minutes, then 57° C. for 2 hours. The annealed cDNA-vector pBR322 was transformed onto *E. coli* DH-1 cells prepared for high efficiency transformation. Colonies that showed sensitivity to ampicillin and tetracycline resistance were grown and DNA was prepared and cut with Pst I to determine the size of the cDNA insert. Several clones having Pst I inserts of 1,050–1,100 base pairs were analyzed and found to have identical restriction enzyme digest patterns. For one of these clones, the 1,100 base pair PstI insert was subcloned into a M13 phage sequencing vector. Part of the DNA sequence of this clone was determined and was found to be identical to the published sequence (40).

CDNA Cloning cDNA cloning refers to the methods used to convert RNA molecules into DNA molecules following state of the art procedures. Applicants' methods are described in Gubler and Hoffman (23). Bethesda Research Laboratories (Gaithersburg, Md.) have designed a cDNA Cloning Kit that is very similar to the procedures used by applicants and contains the best set of reagents and protocols to duplicate the results.

For cloning virus mRNA species, a host cell line sensitive to infection by the virus was infected at 5–10 plaque forming units per cell. When cytopathic effect was evident, but before total destruction, the medium was removed and the cells were lysed in 10 mls lysis buffer (4 M guanidine thiocyanate, 0.1% antifoam A, 25 mM sodium citrate pH 7.0, 0.5% N-lauroyl sarcosine, 0.1 M beta-mercaptoethanol). The cell lysate was poured into a sterilized Dounce homogenizer and homogenized on ice 8–10 times until the solution was homogenous. For RNA purification, 8 mls of cell lysate were gently layered over 3.5 mls of CsCl solution (5.7 M CsCl, 25 mM sodium citrate pH 7.0) in a Beckman SW41 centrifuge tube. The samples were centrifuged for 18 hours at 20° C. at 36,000 rpm in a Beckman SW41 rotor. The tubes were put on ice and the supernatants from the tubes were carefully removed by aspiration to leave the RNA pellet undisturbed. The pellet was resuspended in 400 microliters glass distilled water, and 2.6 mls of guanidine solution (7.5 M guanidine-HCl, 25 mM sodium citrate pH 7.0, 5 mM dithiothreitol) were added. Then 0.37 volumes of 1 M acetic acid were added, followed by 0.75 volumes of cold ethanol and the sample was put at −20° C. for 18 hours to precipitate RNA. The precipitate was collected by centrifugation in a Sorvall centrifuge for 10 min at 4° C. at 10,000 rpm in an SS34 rotor. The pellet was dissolved in 1.0 ml distilled water, recentrifuged at 13,000 rpm, and the supernatant saved. RNA was reextracted from the pellet 2 more times as above with 0.5 ml distilled water, and the supernatants were pooled. A 0.1 volume of 2 M potassium acetate solution was added to the sample followed by 2 volumes of cold ethanol and the sample was put at −20° C. for 18 hours. The precipitated RNA was collected by centrifugation in the SS34 rotor at 4° C. for 10 minutes at 10,000 rpm. The pellet was dissolved in 1 ml distilled water and the concentration taken by absorption at A260/280. The RNA was stored at −70° C.

mRNA containing polyadenylate tails (poly-A) was selected using oligo-dT cellulose (Pharmacia #27 5543-0). Three milligrams of total RNA was boiled and chilled and applied to a 100 mg oligo-dT cellulose column in binding buffer (0.1 M Tris pH 7.5, 0.5 M LiCl, 5 mM EDTA pH 8.0, 0.1% lithium dodecyl sulfate). The retained poly-$A^+$ RNA was eluted from the column with elution buffer (5 mM Tris pH 7.5, 1 mM EDTA pH 8.0, 0.1% sodium dodecyl sulfate). This mRNA was reapplied to an oligo-dT column in binding buffer and eluted again in elution buffer. The sample was precipitated with 200 mM sodium acetate and 2 volumes cold ethanol at −20° C. for 18 hours. The RNA was resuspended in 50 microliters distilled water.

Ten micrograms poly-$A^+$ RNA was denatured in 20 mM methyl mercury hydroxide for 6 minutes at 22° C. Beta-mercaptoethanol was added to 75 mM and the sample was incubated for 5 min at 22° C. The reaction mixture for first strand cDNA synthesis in 0.25 ml contained 1 microgram oligo-dT primer (P-L Biochemicals) or 1 microgram synthetic primer, 28 units placental ribonuclease inhibitor (Bethesda Research Labs #5518SA), 100 mM Tris pH 8.3, 140 mM KCl, 10 mM $MgCl_2$, 0.8 mM dATP, dCTP, dGTP, and dTTP (Pharmacia), 100 microcuries $^{32}P$-labelled dCTP (New England Nuclear #NEG-013H), and 180 units AMV reverse transcriptase (Molecular Genetics Resources #MG 101). The reaction was incubated at 42° C. for 90 minutes, and then was terminated with 20 mM EDTA pH 8.0. The sample was extracted with an equal volume of phenol/chloroform (1:1) and precipitated with 2 M ammonium acetate and 2 volumes of cold ethanol −20° C. for 3 hours. After precipitation and centrifugation, the pellet was dissolved in 100 microliters distilled water. The sample was loaded onto a 15 ml G-100 Sephadex column (Pharmacia) in buffer (100 mM Tris pH 7.5, 1 mM EDTA pH 8.90, 100 mM NaCl). The leading edge of the eluted DNA fractions were pooled, and DNA was concentrated by lyophilization until the volume was about 100 microliters, then the DNA was precipitated with ammonium acetate plus ethanol as above.

The entire first strand sample was used for second strand reaction which follow the Gubler and Hoffman (23) method except that 50 micrograms/ml dNTP's, 5.4 units DNA polymerase I (Boehringer Mannheim #642-711), and 100 units/ml E. coli DNA ligase (New England Biolabs #205) in a total volume of 50 microliters were used. After second strand synthesis, the cDNA was phenol/chloroform extracted and precipitated. The DNA was resuspended in 10 microliters distilled water, treated with 1 microgram RNase A for 10 minutes at 22° C., and electrophoresed through a 1% agarose gel (Sigma Type II agarose) in 40 mM Tris-acetate buffer pH 6.85. The gel was stained with ethidium bromide, and DNA in the expected size range was excised from the gel and electroeluted in 8 mM Tris-acetate pH 6.85. Electroeluted DNA was lyophilized to about 100 microliters, and precipitated with ammonium acetate and ethanol as above. The DNA was resuspended in 20 microliters water.

Oligo-dC tails were added to the DNA to facilitate cloning. The reaction contained the DNA, 100 mM potassium cacodylate pH 7.2, 0.2 mM dithiothreitol, 2 mM $CaCl_2$, 80 micromoles dCTP, and 25 units terminal deoxynucleotidyl transferase (Molecular Genetic Resources #S1001) in 50 microliters. After 30 minutes at 37° C., the reaction was terminated with 10 mM EDTA, and the sample was phenol/chloroform extracted and precipitated as above.

The dc-tailed DNA sample was annealed to 200 ng plasmid vector pBR322 that contained oligo-dG tails (Bethesda Research Labs #5355 SA/SB) in 200 microliters of 0.01 M Tris pH 7.5, 0.1 M NaCl, 1 mM EDTA pH 8.0 at 65° C. for 2 minutes and then 57° C. for 2 hours. Fresh competent E. coli DH-1 cells were prepared and transformed as described by Hanahan (41) using half the annealed cDNA sample in twenty 200 microliter aliquots of cells. Transformed cells were plated on L-broth agar plates plus 10 micrograms/ml tetracycline. Colonies were screened for the presence of inserts into the ampicillin gene using Ampscreen (Bethesda Research Labs #5537 UA), and the positive colonies were picked for analysis.

Polymerase Fill-in Reaction

DNA was resuspended in buffer containing 50 mM Tris pH 7.4, 50 mM KCl, 5 mM $MgCl_2$, and 400 micromolar each of the four deoxynucleotides. Ten units of Klenow DNA polymerase (BRL) were added and the reaction was allowed to proceed for 15 minutes at room temperature. The DNA was then phenol extracted and ethanol precipitated as above.

Cloning of Bovine Viral Diarrhea Virus g53 and g48 Genes

The bovine viral diarrhea (BVDV) g53 gene was cloned essentially as described earlier (see CDNA CLONING) using the random priming method (6). Viral RNA prepared from BVDV Singer strain grown in MADIN-DARBY bovine kidney (MDBK) cells was converted to cDNA using the random priming method. The cDNA was used for second strand reaction (23) and the resulting double stranded DNA was used cloned as described in the cDNA CLONING procedure. From this procedure a series of clones were obtained that comprised parts of the genome of BVDV. The location of the gene for g53 gene has been published (66) and this sequence information was used to locate and isolate the g53 encoding region from the 449 kilodalton primary translation product open reading frame contained in the complete cDNA clone.

The bovine viral diarrhea g48 and g53 genes were cloned by a PCR CLONING procedure essentially as described by Katz et al. (J. Virology 64: 1808–1811 (1990)) for the HA gene of human influenza. Viral RNA prepared from BVD virus Singer strain grown in Madin-Darby bovine kidney (MDBK) cells was first converted to cDNA utilizing an oligonucleotide primer specific for the target gene. The cDNA was then used as a template for polymerase chain reaction (PCR) cloning (67) of the targeted region. The PCR primers were designed to incorporate restriction sites which permit the cloning of the amplified coding regions into vectors containing the appropriate signals for expression in IBRV. One pair of oligonucleotides were required for each coding region. The g48 gene coding region (amino acids 1–226) from the BVDV Singer strain (66) was cloned using the following primers: 5'-ACGTCGGATCCCTTACCAAACCACGTCTTACTCTTGTTTTCC-3' (SEQ ID NO: 3) for cDNA priming and combined with 5'-ACATAGGATCCCATGGGAGAAAACATAACACAGTGGAACC-3' (SEQ ID NO: 4) for PCR. The g53 gene coding region (amnio acids 1–394) from the BVDV Singer strain (66) was cloned using the following primers: 5'-CTTGGATCCTCATCCATACTGAGTCCCTGAGGCCTTCTGTTC-3' (SEQ ID NO: 5) for cDNA priming and combined with 5'-CATAGATCTTGTGGTGCTGTCCGACTTCGCA-3' (SEQ ID NO: 6) for PCR. Note that this general strategy is used to clone the coding region of g48 and g53 genes from other strains of BVDV.

Cloning of Bovine Respiratory Syncytial Virus Fusion Protein and Nucleocapsid Protein Genes The bovine respiratory virus (BRSV) fusion (F), attachment (G), an nucleocapsid protein (N) genes have been cloned essentially as described by Katz et al. (Journal of Virology, volume 64, 1808–1811 (1990)) for the HA gene of human influenza. Viral RNA prepared from virus grown in bovine nasal turbinate (BT) cells was first converted to cDNA utilizing an oligo nucleotide primer specific for the target gene. The cDNA was then used as a template for polymerase chain reaction (PCR) cloning (67) of the targeted region. The PCR primers were designed to incorporate restriction sites which permit the cloning of the amplified coding regions into vectors containing the appropriate signals for expression in IBRV. One pair of oligo nucleotides was required for each coding region. The N gene coding region from the BRSV strain 375 (ATCC No. VR 1339) was cloned utilizing the following primers: 5'-CGTCGGATCCCTCACAGTTCCACATCATTGTCTTTGGGAT-3' (SEQ ID NO: 7) for cDNA priming and combined with 5'-CTTAGGATCCCATGGCTCTTAGCAAGGTCAAACTAAATGAC-3' (SEQ ID NO: 8) for PCR. The G gene coding region from the BRSV strain 375 (ATCC No. VR 1339) was cloned utilizing the following primers: 5'-CGTTGGATCCCTAGATCTGTGTAGTTGATTGATTTGTGTGA-3' (SEQ ID NO: 9) for cDNA priming and combined with 5'-CTCTGGATCCTCATACCCATCATCTTAAATTCAAGACATTA-3' (SEQ ID NO: 10) for PCR. The F gene from strain 375 (ATCC NO. VR 1339) of BRSV was cloned utilizing the following primers: 5'-TGCAGGATCCTCATTT ACTAAAGGAAAGATTGTTGAT-3' (SEQ ID NO: 11) for cDNA priming and combined with 5'-CTCTGG ATCCTACAGCCATGAGGATGATCATCAGC-3' (SEQ ID NO: 12) for PCR. Note that this general strategy may be used to clone the coding region of F and N genes from other strains of BRSV.

Cloning of Parainfluenza-3 Virus Fusion and Hemagglutinin Genes

The parainfluenza-3 virus fusion (F) and hemagglutinin (HN) genes were cloned by a cDNA CLONING procedure as described in Examples 16 and 17 and also by a PCR CLONING procedure essentially as described by Katz et al. (Journal of Virology, volume 64, 1808–1811 (1990)) for the HA gene of human influenza. Viral RNA prepared from virus grown in Madin-Darby bovine kidney (MDBK) cells was first converted to cDNA utilizing an oligonucleotide primer specific for the target gene. The cDNA was then used as a template for polymerase chain reaction (PCR) cloning (67) of the targeted region. The PCR primers were designed to incorporate restriction sites which permit the cloning of the amplified coding regions into vectors containing the appropriate signals for expression in IBRV. One pair of oligonucleotides were required for each coding region. The F gene coding region from the PI-3 strain SF-4 (VR-281) was cloned using the following primers: 5'-TTATGGATCCTGCTGCTGTGTTGAACAACTTTGT-3' (SEQ ID NO: 13) for CDNA priming combined with 5'-CCGCGGATCCCATGACCATCACAACCATAATCAT AGCC-3' (SEQ ID NO: 14) for PCR. The HN gene coding region from PI-3 strain SF-4 (VR-281) was cloned utilizing the following primers: 5'-CGTCGGATCCCTTAGCTGCAG TTTTTTGGAACTTCTGTTTTGA-3' (SEQ ID NO: 15) for cDNA priming and combined with 5'-CATAGGATCCCATGGAATATTGGAAACACAC AAACAGCAC-3' (SEQ ID NO: 16) for PCR. Note that this general strategy is used to clone the coding region of F and HN genes from other strains of PI-3.

Cloning of *Pasteurella Haemolytica* Leukotoxin and Iron Regulated Outer Membrane Protein(S)

The *Pasteurella haemolytica* strain A1 leukotoxin gene was cloned from a genomic DNA sample. Genomic DNA was prepared from *P. haemolytica* A1 cells grown in culture (68) by the methods described in Maniatis et al. (1982). The purified *P. haemolytica* DNA was then used as a template for polymerase chain reaction (PCR) cloning (67) of the targeted leukotoxin gene. The PCR primers were designed so that restriction endonuclease sites were incorporated that allow the cloning of the 102 kilodalton toxin portion of the gene into vectors containing the appropriate signals for expression in IBR. The *P. haemolytica* A1 (ATTC 43279 biotype A, serotype 1) leukotoxin gene was cloned utilizing the following primers: 5'-TATAGAT CTTAGACTTACAACCCTAAAAAAC-3' (SEQ ID NO: 17) and 5'-CGTGG ATCCAACTCTATAATGTGTGAAACAATATAG-3' (SEQ ID NO: 18) for PCR. Note that this general strategy is used to clone the coding regions for the leukotoxin gene of all *P. haemolytica* serotypes.

The *P. haemolytica* A1 iron regulated outer membrane proteins (IRP) of 3 major polypeptides with molecular weights of 35, 70 and 100 kilodaltons. The DNA coding for the array of *P. haemolytica* genes can be cloned in *Escherichia coli* using plasmid vectors essentially as described in Maniatis et al. (1982). The clone library is constructed by partial digestion of the genomic DNA. The IRP genes can be isolated from this library of *P. haemolytica* clones by screening for the production of iron regulated outer membrane antigens by a colony enzyme-linked immunosorbent assay blot method with antiserum that is specific to the IRPs. This antiserum may be obtained by eluting antibodies derived from polyclonal antiserum raised against whole *P. haemolytica* or membrane enriched fractions but selectively bound to the IRPs on Western blots (69). The specificity of the antibodies can be verified by immunoblot screening of *P. haemolytica* polypeptides from iron restricted and iron induced cultures.

Vaccination Studies in Calves with Inactivated IBR Virus

Calves, seronegative to IBR virus, were housed in facilities secure from IBR virus exposure. Groups of four calves were vaccinated intramuscularly with vaccines containing $10^{7.3}$ or $10^{8.0}$ plaque forming units of inactivated IBR virus formulated with an oil adjuvant. A second vaccination was given 21 days later; four calves were maintained as unvaccinated controls. At 21 days after the second vaccination, animals were challenged intranasally with virulent wild-type IBR virus. After vaccination and challenge, animals were observed and the injection site was palpated weekly. Blood samples were taken on days 0, 7, 21, 28, and 42 post vaccination. After challenge, animals were observed daily for clinical signs of IBR. Blood samples were taken on days 7 and 13 post challenge. Nasal swabs were collected on days 3, 6, 9, and 12 post challenge.

Homology Vector 129-71.5

The plasmid 129-71.5 was constructed for the purpose of deleting a portion of the TK gene coding region from the IBR virus. It incorporates a selectable marker, the bacterial transposon neomycin resistance gene, flanked by IBR virus DNA. Upstream of the marker gene is an approximately 860 base pair fragment of IBR virus DNA which ends with sequences encoding amino acids 1–62 of the TK primary translation product. Downstream of the marker gene is an approximately 1741 base pair fragment of IBR virus DNA which begins with sequences encoding amino acids 156–367 of the TK primary translation product. When this plasmid is used according to the HOMOLOGOUS RECOMBINATION PROCEDURE FOR GENERATING RECOMBINANT HERPESVIRUS, it will replace the DNA coding for amino acids 63–155 of the TK primary translation product with DNA coding for the marker gene. Note that the marker gene will be under the control of the herpes simplex type 1 alpha-4 immediate early gene promoter (5). A detailed description of the plasmid is given in FIGS. 7A–7H. It was constructed from the indicated DNA sources utilizing standard recombinant DNA techniques (6). It may be constructed by joining restriction fragments from the following sources with the synthetic DNA sequences indicated in FIGS. 7A–7H. The plasmid vector is derived from an approximately 2975 base pair SmaI to HindIII restriction fragment of pSP65 (Promega). Fragment 1 is an approximately 860 base pair NcoI to BamHI restriction fragment of the IBR virus HindIII restriction fragment A (7). This fragment is located on an approximately 5500 base pair ClaI to NruI fragment contained in the IBR virus HindIII A fragment. Fragment 2 is an approximately 490 base pair PvuII to BamHI restriction sub-fragment of the HSV-1 BamHI restriction fragment N (5). Note that the HSV-1 oriS region has been removed from this fragment by deletion of the sequences between the SmaI sites located 1483 and 128 base pairs away from the PvuII end (10). Fragment 3 is an approximately 1541 base pair BglII to BamHI restriction fragment of plasmid pNEO (P.L. Biochemicals, Inc.). Fragment 4 is an approximately 784 base pair SmaI to SmaI restriction sub-fragment of the HSV-1 BamHI restriction fragment Q (10). Note that this fragment is oriented such that the polyadenylation sequence (AATAAA) is located closest to junction D. Fragment 5 is an approximately 1741 base pair BglII to StuI restriction sub-fragment from the IBR HindIII restriction fragment A (7).

Plasmid 459-12.6

The plasmid 459-12.6 was generated for the purpose of constructing a recombinant cloning vector which expresses the IBR virus glycoprotein G. This was accomplished by inserting the IBR virus gG gene into S-PRV-013 (U.S. Ser. No. 07/823,102 filed Jan. 27, 1986). Plasmid 459-12.6 contains a chimeric gene under the control of the IBR virus gG promoter. The chimeric gene expresses a fusion protein consisting of the first 362 amino acids of IBR virus gG fused to amino acids 421–467 of the PRV gIII (13) followed by amino acids 480–498 of the PRV gX (12). The chimeric gene is flanked by HindIII restriction sites. When this plasmid is used with S-PRV-013 and the restriction enzyme HindIII according to the DIRECT LIGATION PROCEDURE FOR GENERATING RECOMBINANT HERPESVIRUS the resulting recombinant will express the IBR virus gG. A detailed description of the plasmid is given in FIGS. 11A–11H. It was constructed from the indicated DNA sources utilizing standard recombinant DNA techniques (6). It may be constructed by joining restriction fragments from the following sources with the synthetic DNA sequences indicated in FIGS. 11A–11H. The plasmid vector is derived from an approximately 2999 base pair XbaI to XbaI restriction fragment of a hybrid cloning vector derived from pSP64 and pSP65 (Promega). The hybrid cloning vector was constructed by joining approximately 1369 base pair PvuI to SmaI fragment from pSP64 with the approximately 1652 base pair PvuI to SmaI fragment from pSP65. Fragment 1 is an approximately 182 base pair PstI to EcoRV restriction sub-fragment of the HCMV XbaI restriction fragment B (16). Fragment 2 is an approximately 2121 base pair MluI to XhoI restriction sub-fragment of the IBR virus HindIII restriction fragment K (7) Fragment 3 is an approximately 121 base pair XhoI to BamHI restriction sub-fragment of the PRV BamHI restriction fragment #2 (3). Fragment 4 is an approximately 760 base pair NdeI to SalI restriction sub-fragment of the PRV BamHI restriction fragment #7 (3).

Homology Vector 439-01.31

The plasmid 439-01.31 was constructed for the purpose of deleting a portion of the gG gene coding region from the IBR virus. It incorporates an *E.coli* β-galactosidase marker gene flanked by IBR virus DNA. Downstream of the marker gene is an approximately 3593 base pair fragment of IBR virus DNA which ends with sequences encoding the first 262 amino acids of the gG primary translation product. Upstream of the marker gene is an approximately 785 base pair fragment of IBR virus DNA which begins with sequences encoding the last 80 amino acids of the gG primary translation product. When this plasmid is used according to the HOMOLOGOUS RECOMBINATION PROCEDURE FOR GENERATING RECOMBINANT HERPESVIRUS it will replace the DNA coding for amino acids 263–361 of the gG primary translation product with DNA coding for the marker gene. Note that the β-galactosidase (lacZ) marker gene will be under the control of the human cytomegalovirus immediate early gene promoter. A detailed description of the plasmid is given in FIGS. 12A–12H. It was constructed from the indicated DNA sources utilizing standard recombinant DNA techniques (6). It may be constructed by joining restriction fragments from the following sources with the synthetic DNA sequences indicated in FIGS. 12A–12H. The plasmid vector is derived from an approximately 2965 base pair HindIII to SmaI restriction fragment of pSP64 (Promega). Fragment 1 is an approximately 3593 base pair HindIII to XhoI restriction fragment of the IBR HindIII restriction fragment K (7). Fragment 2 is an approximately 753 base pair SalI to NdeI restriction fragment of the PRV BamHI restriction fragment #7 (3). Note that this fragment was resected with Exonuclease III/S1 nuclease digestion such that approximately 57 base pairs were removed from the NdeI end. Fragment 3 is an approximately 3347 base pair BalI to BamHI restriction fragment of plasmid pJF751 (38). Fragment 4 is an approximately 1191 base pair AvaI to PstI restriction fragment from the HCMV XbaI restriction fragment E (16). Fragment 5 is an approximately 785 base pair XhoI to NdeI restriction fragment from the IBR HindIII restriction fragment K (7). Note that the lacZ marker gene is flanked by XbaI sites located at Junction B and Junction E in this plasmid permitting the marker gene to be cut out with XbaI.

Homology Vector 439-21.69

The plasmid 439-21.69 was constructed for the purpose of deleting a portion of the gG gene coding region from the IBR virus. It incorporates an *E.coli* β-galactosidase (lacZ) marker gene flanked by IBR virus DNA. Downstream of the marker gene is an approximately 888 base pair fragment of IBR virus DNA which begins approximately 1042 base pairs upstream of the initiation codon of the gG gene and ends approximately 154 base pairs upstream of the initiation codon of the gG gene. Upstream of the marker gene is an approximately 785 base pair fragment of IBR virus DNA which begins with sequences encoding the last 80 amino acids of the gG primary translation product. When this plasmid is used according to the HOMOLOGOUS RECOMBINATION PROCEDURE FOR GENERATING RECOMBINANT HERPESVIRUS it will replace the DNA coding for amino acids 1–361 of the gG primary translation product with DNA coding for the marker gene. Note that the β-galactosidase (lacZ) marker gene will be under the control of the human cytomegalovirus immediate early gene promoter. A detailed description of the plasmid is given in FIGS. 13A–13H. It was constructed from the indicated DNA sources utilizing standard recombinant DNA techniques (6). It may be constructed by joining restriction fragments from the following sources with the synthetic DNA sequences indicated in FIGS. 13A–13H. The plasmid vector is derived from an approximately 2965 base pair HindIII to SmaI restriction fragment of pSP64 (Promega). Fragment 1 is an approximately 3593 base pair HindIII to XhoI restriction fragment of the IBR HindIII restriction fragment K (7). Fragment 2 is an approximately 753 base pair SalI to NdeI restriction fragment of the PRV BamHI restriction fragment #7 (3). Note that this fragment was resected with Exonuclease III/S1 nuclease digestion such that approximately 57 base pairs were removed from the NdeI end. Fragment 3 is an approximately 3347 base pair BalI to BamHI restriction fragment of plasmid pJF751 (38). Fragment 4 is an approximately 1191 base pair AvaI to PstI restriction fragment from the HCMV XbaI restriction fragment E (16). Fragment 5 is an approximately 785 base pair XhoI to NdeI restriction fragment from the IBR HindIII restriction fragment K (7). Note that the lacZ marker gene is flanked by XbaI sites located at Junction B and Junction E in this plasmid permitting the marker gene to be cut out with XbaI.

Homology Vector 439-70.4

The plasmid 439-70.4 was constructed for the purpose of deleting the *E.coli* β-galactosidase (lacZ) marker gene from S-IBR-035 virus. It incorporates two regions of IBR viral DNA which flank the marker gene in S-IBR-035. The first region is an approximately 888 base pair fragment of IBR virus DNA which begins approximately 1042 base pairs upstream of the initiation codon of the gG gene and ends approximately 154 base pairs upstream of the initiation codon of the gG gene. The second region is an approximately 785 base pair fragment of IBR virus DNA which begins with sequences encoding the last 80 amino acids of the gG primary translation product. When this plasmid is used in conjunction with S-IBR-035 DNA according to the HOMOLOGOUS RECOMBINATION PROCEDURE FOR GENERATING RECOMBINANT HERPESVIRUS it will delete the DNA coding for the E. coli β-galactosidase (lacZ) marker gene. A detailed description of the plasmid is given in FIGS. 14A–14E. It was constructed from the indicated DNA sources utilizing standard recombinant DNA techniques (6). It may be constructed by joining restriction fragments from the following sources with the synthetic DNA sequences indicated in FIGS. 14A–14E. The plasmid vector is derived from an approximately 2965 base pair HindIII to SmaI restriction fragment of pSP64 (Promega). Fragment 1 is an approximately 3593 base pair HindIII to XhoI restriction fragment of the IBR HindIII restriction fragment K (7). Fragment 2 is an approximately 785 base pair XhoI to NdeI restriction fragment from the IBR HindIII restriction fragment K (7).

Homology Vector 523-78.72

The plasmid 523-78.72 was constructed for the purpose of deleting a portion of the gE coding region from the IBR virus. It was also used to insert foreign DNA into IBRV. Plasmid 523-78.72 was constructed by digestion of the plasmid 536-03.5 with the enzyme XbaI followed by religation to remove the lacZ marker gene. It incorporates two regions of IBR viral DNA which flanked the marker gene in S-IBR-039. The first region is an approximately 1704 base pair fragment of IBR virus DNA which ends with sequences encoding amino acids 1–76 of the gE primary translation product. The second region is an approximately 742 base pair fragment of IBR virus DNA which begins with sequences encoding amino acids 548–617 of the gE primary translation product. When the plasmid 523-78.72 is used with S-IBR-039 according to the HOMOLOGOUS RECOMBINATION PROCEDURE FOR GENERATING RECOMBINANT HERPESVIRUS, it will delete the DNA coding for the *E. coli* β-galactosidase (lacZ) marker gene. A detailed description of plasmid 523-78.72 is given in FIGS. 26A–26B. It may be constructed utilizing standard recombinant DNA techniques (6), by joining restriction fragments from the following sources with the synthetic DNA sequences indicated in FIGS. 26A–26B. The plasmid vector 523-78.72 is derived from an approximately 2975 base pair SmaI to HindIII restriction fragment of pSP65 (Promega). Fragment 1 is an approximately 1704 base pair SmaI to SmaI restriction sub-fragment of the IBR HindIII restriction fragment K (7). Fragment 2 is an approximately 742 base pair NheI to BglI sub-fragment of an IBR virus 2500 base pair SmaI fragment.

Homology Vector 536-03.5

The plasmid 536-03.5 was constructed for the purpose of deleting a portion of the gE gene coding region from the IBR virus. It incorporates an *E.coli* β-galactosidase (lacZ) marker gene flanked by IBR virus DNA. Upstream of the marker gene is an approximately 1704 base pair fragment of IBR virus DNA which ends with sequences encoding amino acids 1–76 of the gE primary translation product. Downstream of the marker gene is an approximately 742 base pair fragment of IBR virus DNA which begins with sequences encoding amino acids 548–617 of the gE primary translation product. When this plasmid is used according to the HOMOLOGOUS RECOMBINATION PROCEDURE FOR GENERATING RECOMBINANT HERPESVIRUS, it will replace the DNA coding for amino acids 77–547 of the gE primary translation product with DNA coding for the marker gene. Note that the β-galactosidase (lacZ) marker gene will be under the control of the PRV gX. A detailed description of the plasmid is given in FIGS. 18A–18G. It may be constructed utilizing standard recombinant DNA techniques (6), by joining restriction fragments from the following sources with the synthetic DNA sequences indicated in FIGS. 18A–18G. The plasmid vector is derived from an approximately 2975 base pair SmaI to HindIII restriction fragment of psP65 (Promega). Fragment 1 is an approximately 1704 base pair SmaI to SmaI restriction subfragment of the IBR HindIII restriction fragment K (7). Fragment 2 is an approximately 413 base pair SalI to BamHI restriction fragment #7 (3). Fragment 5 is an approximately 742 base pair NheI to BglI sub-fragment of an IBR virus 2400 base pair SmaI fragment. This SmaI fragment has been cloned into the SmaI site of the plasmid pSP64 (Promega). This plasmid is designated PSY1645. PSY1645 was deposited on Jul. 16, 1991 with the American Type Culture Collection. Note that the lacZ marker gene is flanked by XbaI sites located at Junction B and Junction E in this plasmid permitting the marker gene to be cut out with XbaI.

Homology Vector 591-21.20

The plasmid 591-21.20 was constructed for the purpose of deleting a portion of the IBR thymidine kinase gene. It may also be used to insert foreign DNA into IBR. It contains a unique BglII restriction enzyme site into which foreign DNA may be inserted. It may be constructed utilizing standard recombinant DNA techniques (6, 14) by joining restriction fragments from the following sources with the synthetic DNA sequences indicated in FIG. 24. The plasmid vector is derived from an approximately 2999 base pair SalI to SalI restriction fragment of pSP64 (Promega). Fragment 1 is an approximately 1400 base pair SalI to NarI restriction subfragment contained on the approximately 2700 base pair SalI-SalI restriction subfragment of the IBR HindIII restriction fragment A (72). Fragment 2 is an approximately 1215 base pair BglIII to SalI restriction subfragment contained on the approximately 2700 base pair SalI-SalI restriction subfragment of the IBR HindIII restriction fragment A (72).

Homology Vector 552-46.12

The plasmid 591-46.12 was constructed for the purpose of deleting a portion of the Tk gene coding region from the IBR virus. It incorporates an *E. coli* β-glucuronidase (uidA) marker gene flanked by IBR virus DNA. The uidA marker gene was inserted into the homology vector 591-21.20 at the unique BglII site. The marker gene is oriented in the same direction as the Tk gene in the homology vector. A detailed description of the marker gene is given in FIGS. 25A–25B. It may be constructed utilizing standard recombinant DNA techniques (6, 14) by joining restriction fragments from the following sources with the synthetic DNA sequences indicated in FIGS. 25A–25B. Fragment 1 is an approximately 404 base pair SalI to EcoRI restriction subfragment of the PRV BamHI restriction fragment #10 (3). Note that the EcoRI site was introduced at the location indicated in FIGS. 12A–12H by PCR cloning. Fragment 2 is an approximately 1823 base pair EcoRI to SmaI fragment of the plasmid pRAJ260 (Clonetech). Note that the EcoRI and SmaI sites were introduced at the locations indicated in FIGS. 25A–25B by PCR cloning. Fragment 3 is an approximately 784 base pair SmaI to SmaI restriction subfragment of the HSV-1 BamHI restriction fragment Q (10). Note that this fragment is oriented such that the polyadenylation sequence (AATAAA) is located closest to junction C.

Homology Vector 691-096.2

The homology vector 691-096.2 was constructed for the purpose of inserting foreign DNA into the unique long of IBRV. It was constructed utilizing standard recombinant DNA techniques (6), by joining restriction fragments from the following sources. The plasmid vector was derived from an approximately 2485 base pair NaeI to PvuII restriction fragment of pSP65 (Promega). Fragment 1 is an approximately 3900 base pair ApaI to ApaI restriction sub-fragment within the larger BamHI-KpnI subfragment of the IBRV BamHI restriction fragment C (7). Foreign DNA is inserted into a unique HindIII or XbaI restriction endonuclease site within the ApaI to ApaI restriction subfragment.

Homology Vector 756-11.17

The homology vector 756-11.17 was constructed for the purpose of inserting foreign DNA into the gG deletion within the unique short region of IBRV and was derived from homology vector 439-70.4. It incorporates an E. coli uidA marker gene and PI-3 HN (amino acids 1–573) and F genes (amino acids 4–450) flanked by IBRV DNA. The first IBRV region is an approximately 888 base pair fragment of IBR virus DNA which begins approximately 1042 base pairs upstream of the initiation codon of the gG gene and ends approximately 154 base pairs upstream of the initiation codon of the gG gene. The second IBRV region is an approximately 785 base pair fragment of IBR virus DNA which begins with sequences encoding the last 80 amino acids of the gG primary translation product. Inserted into the IBRV gG deletion region between the first and second regions is a synthetic polylinker adding restriction endonuclease sites for SwaI-BglII-SwaI-HindIII-BamHI-SpeI. The lacZ gene was inserted into the SwaI site of the polylinker, and the PI-3 F and HN genes were inserted into the HindIII site of the polylinker. The PI-3 F and HN genes were isolated by CLONING OF PARAINFLUENZA-3 FUSION AND HEMAGGLUTININ GENES. The homology vector 756-11.17 was constructed utilizing standard recombinant DNA techniques (6), by joining restriction fragments from the following sources. The plasmid vector was derived from an approximately 2965 base pair HindIII to SmaI restriction fragment of pSP64 (Promega) Fragment 1 is an approximately 3593 base pair HindIII to XhoI restriction fragment of the IBRV HindIII restriction fragment K (7). Fragment 2 is a HSV-1 TK promoter lacZ gene DNA fragment inserted into the SwaI site of the synthetic polylinker. Fragment 3 is a HCMV IE promoter PI-3 F gene/PRV gX promoter PI-3 HN gene DNA fragment inserted into the HindIII site of the synthetic polylinker. Fragment 4 is an approximately 785 base pair XhoI to NdeI restriction fragment of the IBRV HindIII restriction fragment K (7).

Homology Vector 769-73.1

The homology vector 769-73.1 was constructed for the purpose of inserting foreign DNA into the repeat region of IBRV. It was constructed utilizing standard recombinant DNA techniques (6), by joining restriction fragments from the following sources. The plasmid vector was derived from an approximately 2792 base pair SmaI to PvuII restriction fragment of pSP65 (Promega). Fragment 1 is an approximately 2900 base pair NruI to XhoI restriction sub-fragment within the smaller KpnI-BamHI subfragment of the IBRV BamHI restriction fragment C (7). A synthetic polylinker was inserted into a unique EcoRV site within the 2900 base pair NruI to XhoI fragment. The synthetic polylinker provides unique restriction sites: SwaI-BglII-SwaI-HindIII-BamHI-SpeI.

EXAMPLES

Example 1

S-IBR-002

Figure 2:
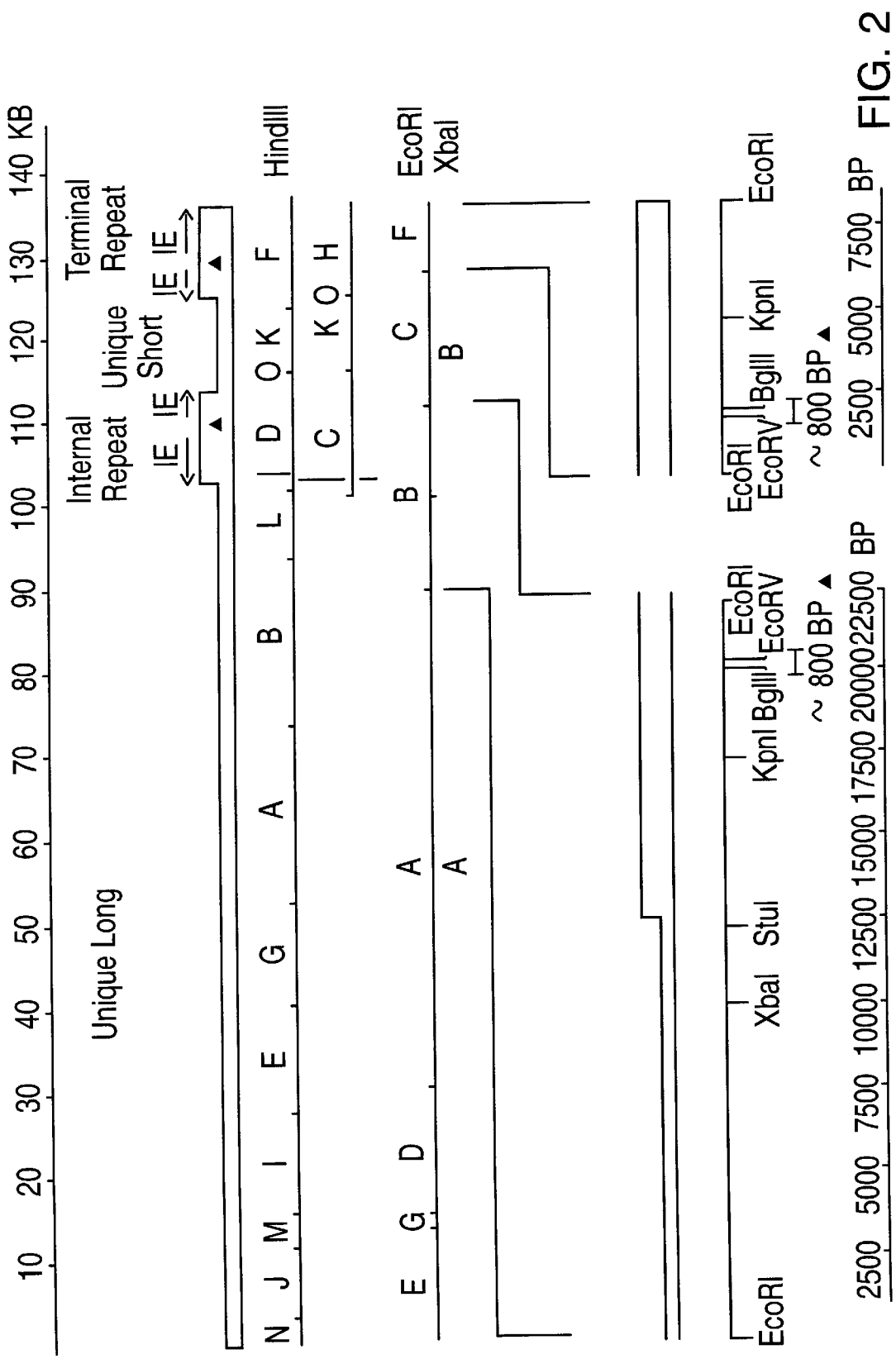

S-IBR-002 is an IBR virus that has a deletion of approximately 800 bp in the repeat region of the genome. This deletion removes the only two EcoRV restriction sites on the virus genome and an adjacent BglII site (FIG. 2).

To construct this virus, the DIRECT LIGATION PROCEDURE FOR GENERATING RECOMBINANT HERPESVIRUS was performed. Purified IBR virus DNA (Cooper strain) digested with EcoRV restriction enzyme was mixed with DraI-restriction enzyme-digested plasmid DNA containing the E.coli β-galactosidase (lacZ) gene under the control of the HSV-1 TK promoter. After ligation the mixture was used to transfect animal cells and the transfection stock was screened for recombinant IBR virus by the SOUTHERN BLOTTING OF DNA procedure. The final result of the purification was the recombinant IBR virus designated S-IBR-002. It was shown by Southern hybridization that this virus does not carry any foreign genes. Restriction enzyme analysis also showed that the insertion sites (EcoRV) in both repeats were deleted. FIG. 2 shows the restriction map of the EcoRI B fragment which contains the EcoRV restriction sites and the map of S-IBR-002 which lacks the EcoRV sites. S-IBR-002 was deposited on Jun. 18, 1986 pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. VR 2140.

A study was conducted to determine the safety and serological response of young calves following intramuscular administration of S-IBR-002. These results are presented in Table 1. Three calves were inoculated intramuscularly with $10^7$ PFU of S-IBR-002. Clinical signs of IBR and febrile response were absent in these calves, as well as in the contact control calf. All three calves developed significant neutralizing antibody to IBR virus but the contact control remained seronegative. These results suggest that S-IBR-002 is useful as a vaccine against IBR disease.

TABLE 1

Serologic and Clinical Response of Young Calves Following Vaccination with S-IBR-002

| Virus Construct | Calf # | Clinical and Febrile response | Virus Isolation[a] | Antibody Titer Days Post Inoculation | | | | |
|---|---|---|---|---|---|---|---|---|
| | | | | 0 | 7 | 14 | 21 | 28 |
| S-IBR-002 | 28 | NONE | (—) | <2 | <4 | 6 | 5 | 3 |
| | 30 | NONE | (—) | <2 | <4 | 6 | <2 | 6 |
| | 94 | NONE | (—) | <2 | <4 | 6 | 3 | 8 |
| Control | 32 | NONE | (—) | <4 | <4 | <4 | <2 | <4 |

[a]From nasal swabs and peripheral blood leukocytes.

Example 2

Unique Short 2 Gene

The unique short region of IBR virus contains a gene homologous to the US2 gene of several other herpesviruses. In the studies described below deletion of the IBR unique short 2 gene (US2) may render the virus safe for use in pregnant cows, as determined by direct fetal inoculation.

Figures 4A, 4B:
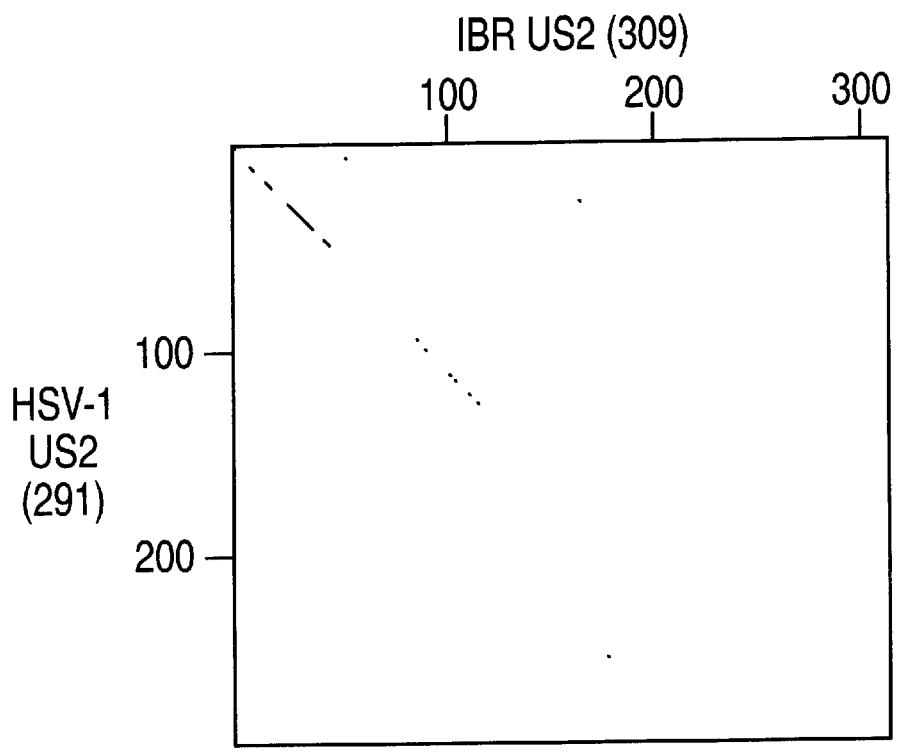

Observing that the Nasalgen IBR vaccine strain will not cause abortion when used in IBR-susceptible pregnant cows at various stages of gestation (18,65), the genomic lesion responsible for this property are determined. The genome of this virus are characterized by restriction mapping and DNA sequence analysis. It was determined that a major portion of the IBR virus US2 gene was deleted from the Nasalgen virus. Restriction mapping of the Nasalgen virus indicated that the HindIII K fragment contained an approximately 800 base pair deletion. The deletion was localized to the end of the HindIII K Fragment located next to the HindIII O fragment (see FIG. 1). Therefore, the HindIII K fragment from the Cooper strain was subcloned and this region was sequenced. The first 1080 base pairs of the fragment were found to contain an open reading frame (ORF) coding for 309 amino acids (see FIG. 3). The ORF is 68% G+C and encodes a protein with a predicted molecular weight of 46,094. Comparison of the sequence of the predicted protein with sequences of gene products of HSV-1, PRV, HSV-2, and marek's disease virus in the unique short region indicated that this ORF is homologous to the herpesvirus US2 gene (see FIGS. 4A–4B). Although the function of the herpesvirus US2 gene is not known, the gene has been shown to be nonessential for growth of HSV in cell culture (4,19). The US2 gene has also been shown to be deleted in the PRV vaccine strains Norden and Bartha (11).

Figures 5, 5A:
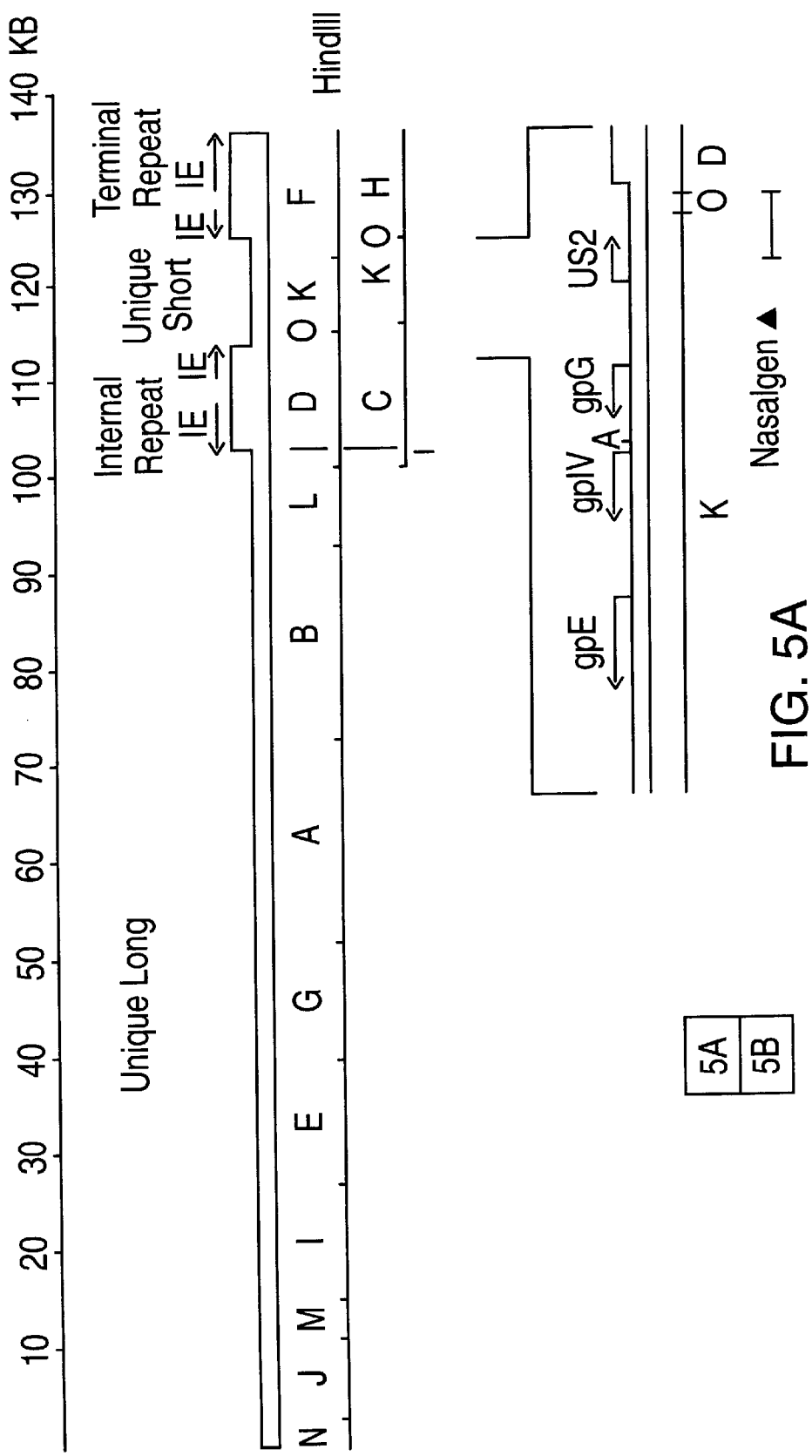

The HindIII K fragment from the Nasalgen virus was subcloned and the deletion region was sequenced. When the sequence obtained from the Nasalgen strain was compared to the sequence obtained from the Cooper strain (see FIGS. 5A–5B), it was possible to determine that amino acids 59 to 309 of the US2 gene had been deleted. It was also determined that most of the HindIII O fragment had also been deleted.

Cattle studies have shown that the Nasalgen virus will not cause abortion when used in IBR-susceptible pregnant cows at various stages of gestation (18). Since the only major difference between the wild-type IBR strain and the Nasalgen strain resides in the deletion of the US2 gene, this gene may be involved in the fetal virulence observed for the wild type virus.

Example 3

S-IBR-027

Figure 6:
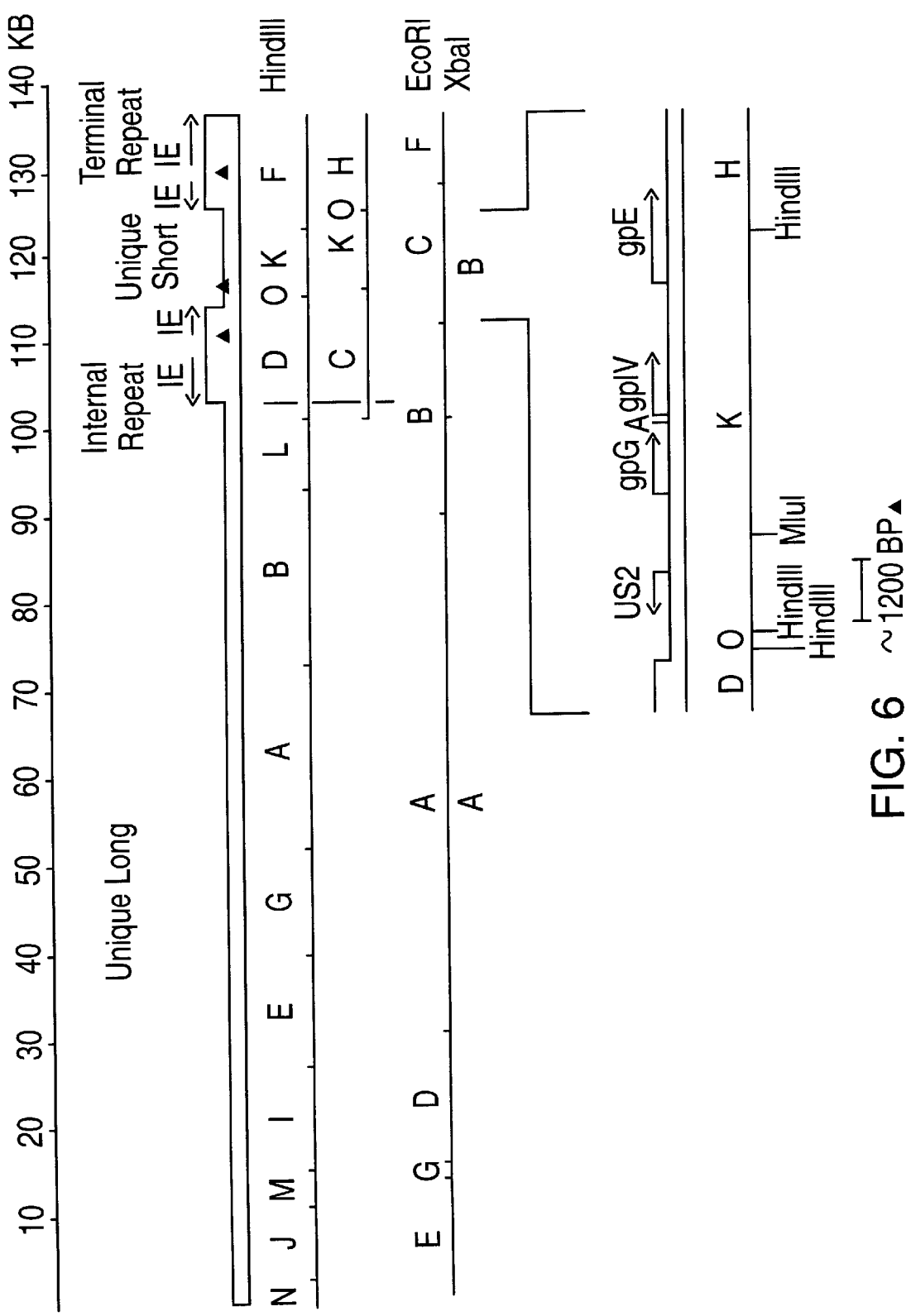
Figure 7B:
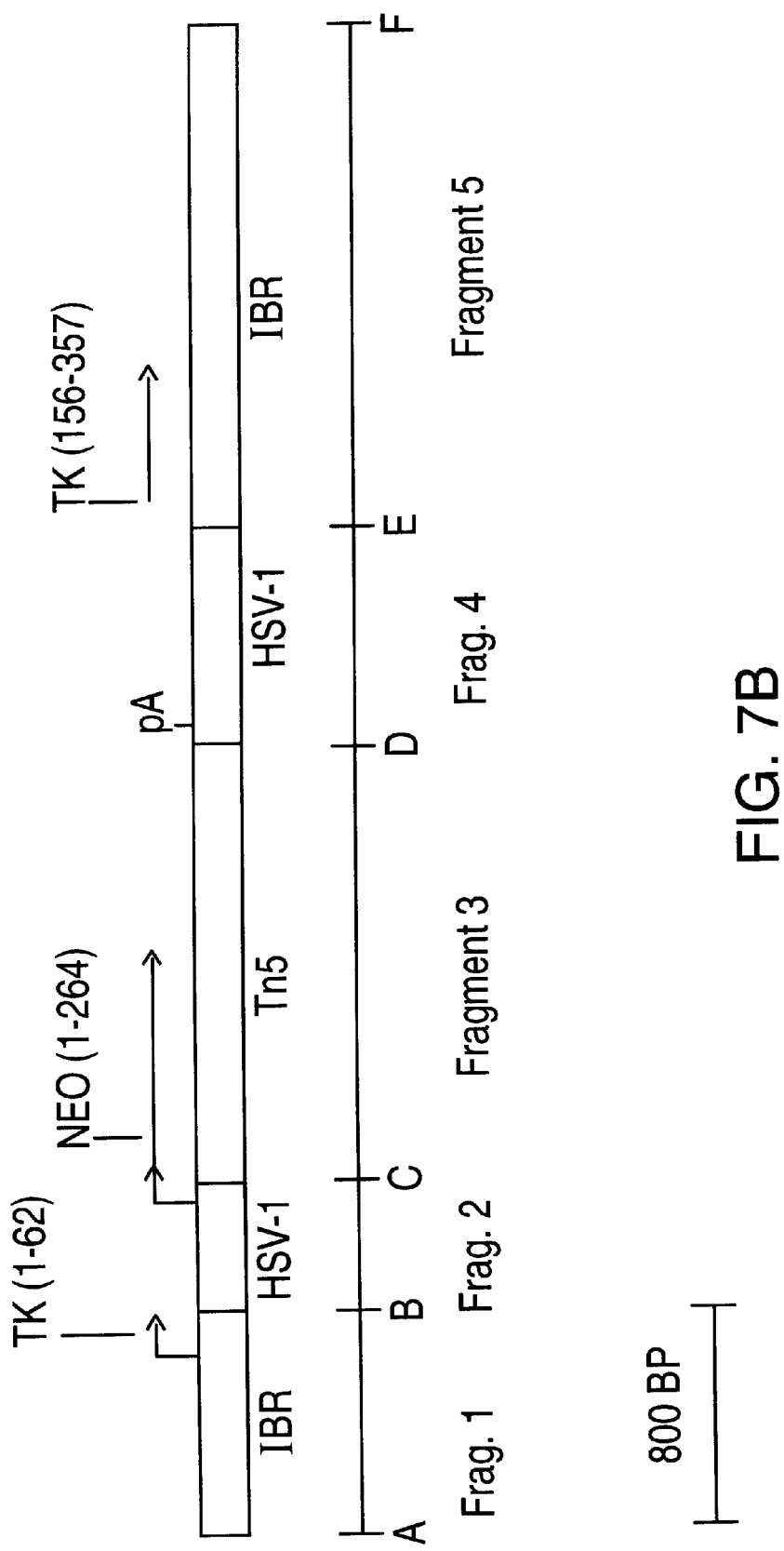
Figure 7C:
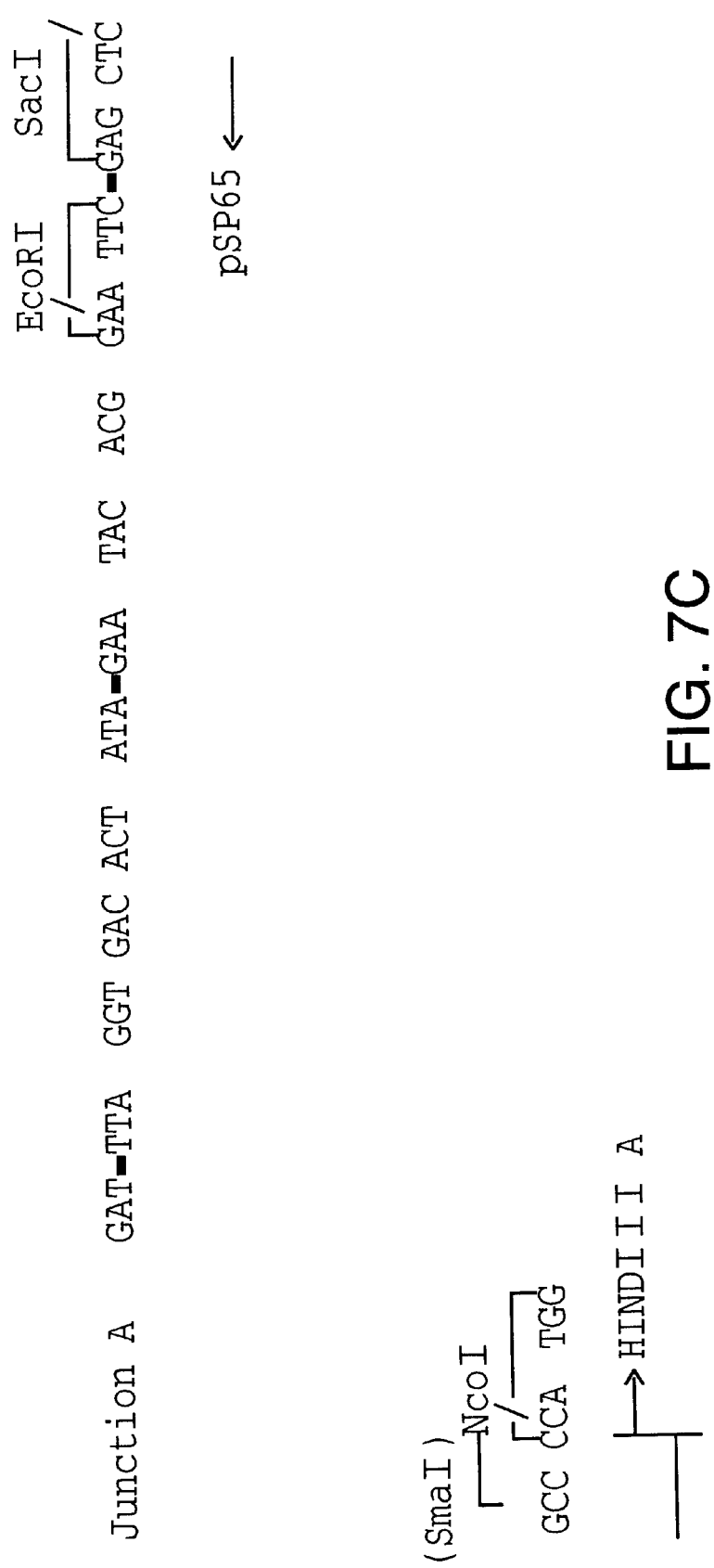
Figure 7D:
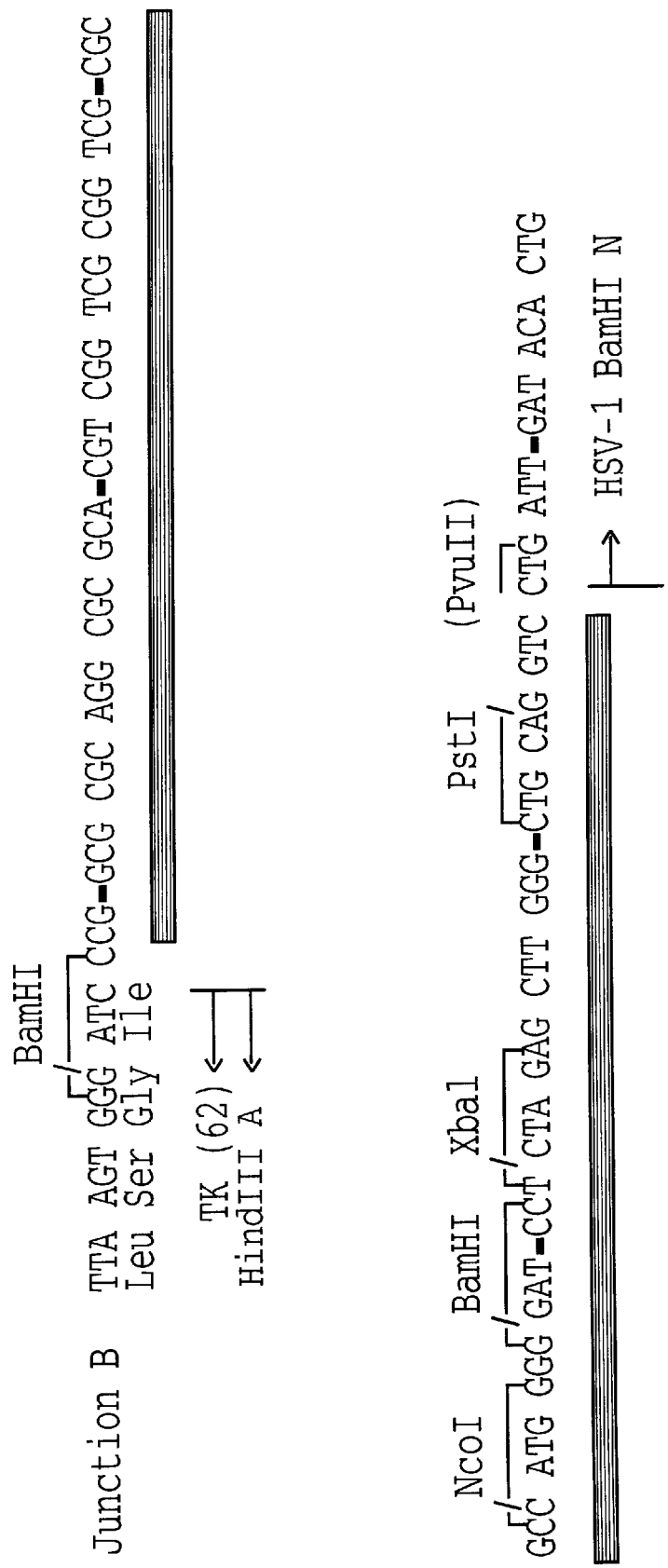
Figure 7E:
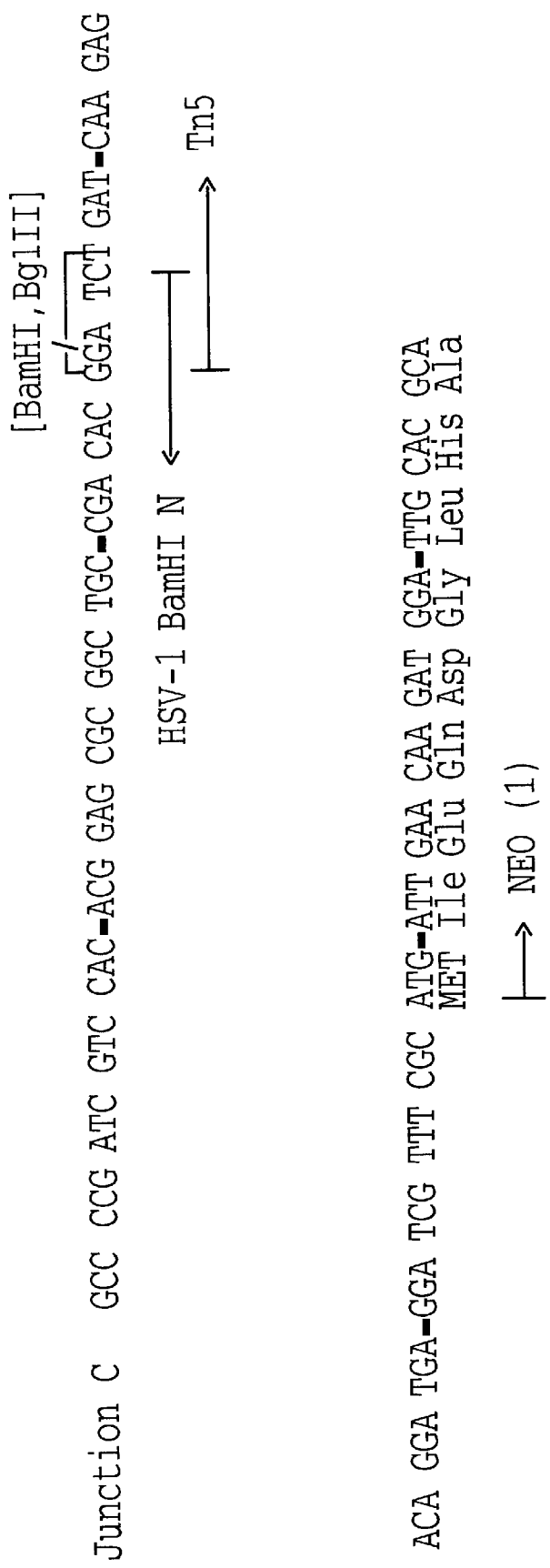
Figure 7F:
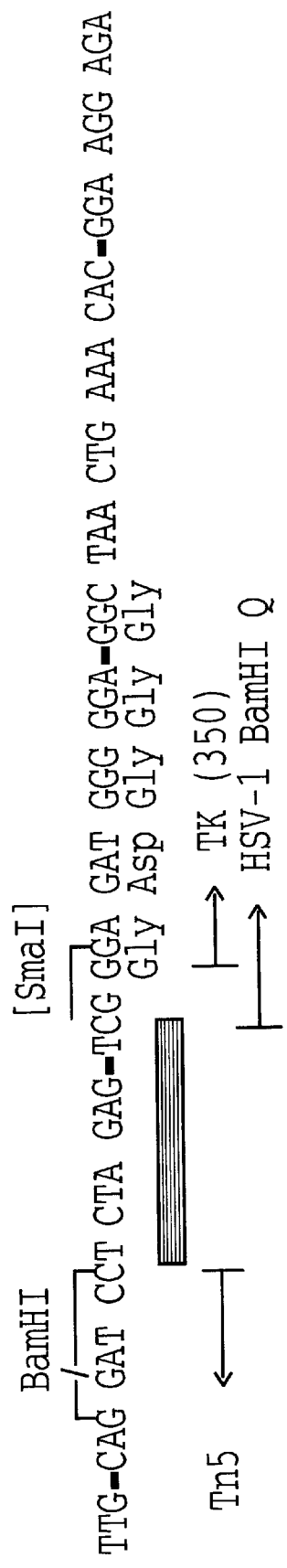
Figure 7G:
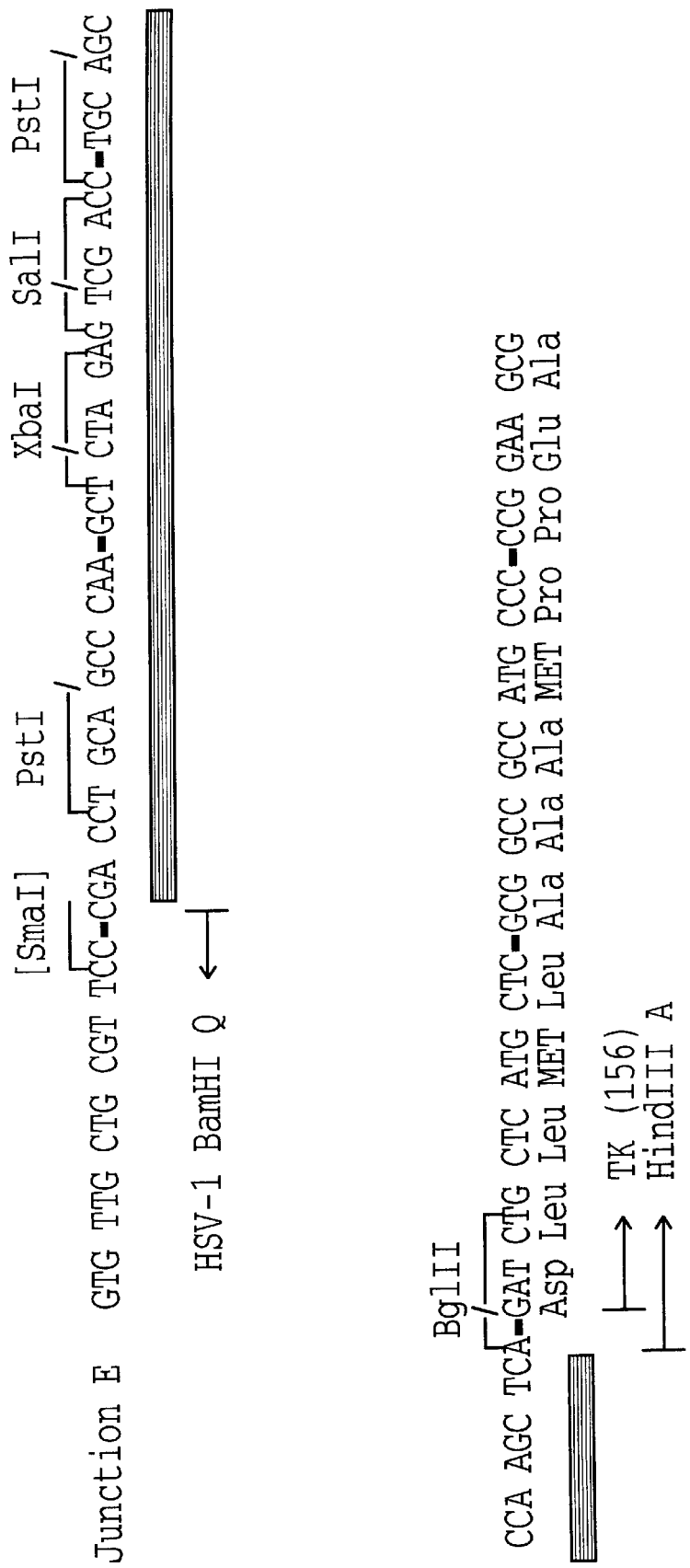
Figure 7H:
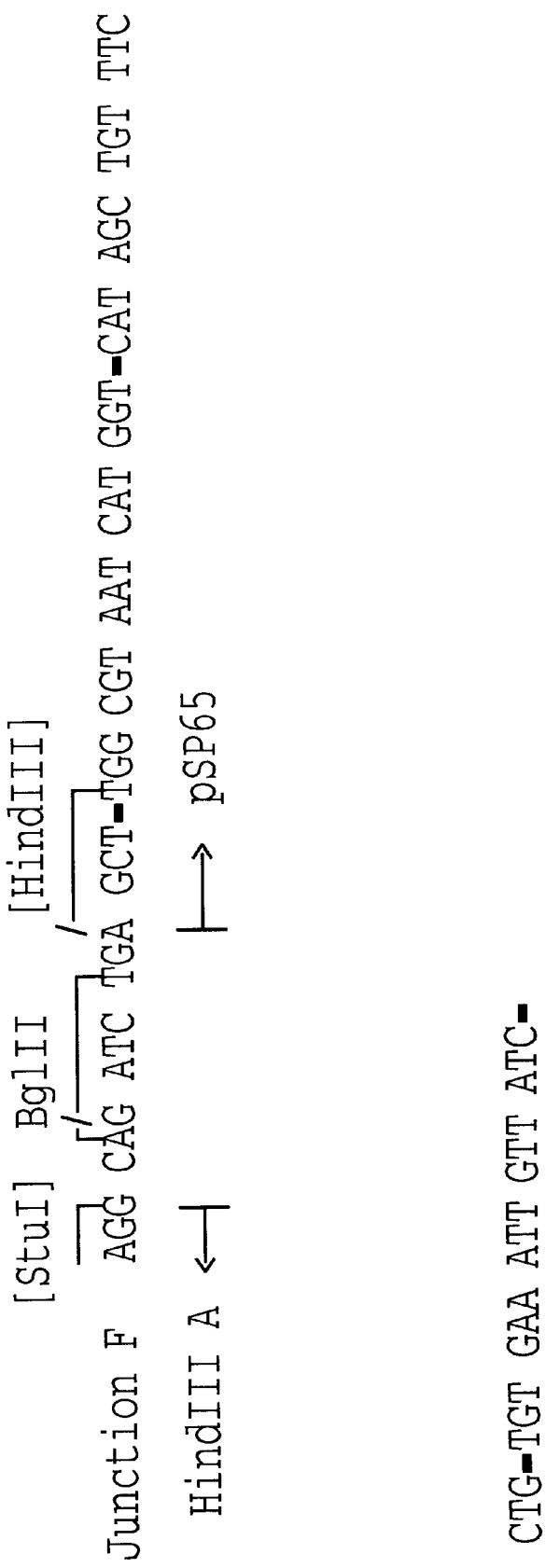

S-IBR-027 is an IBR virus that has a deletion of approximately 800 bp in the repeat regions and approximately 1200 bp in the short unique region of the genome. The deletion in the short unique region removes the US2 gene (FIG. 6). The repeat deletion was derived from the parental virus S-IBR-002 and is described in Example 2.

To construct this virus, the HOMOLOGOUS RECOMBINATION PROCEDURE FOR GENERATING RECOMBINANT HERPESVIRUS was performed. A homology vector containing the bacterial transposon Tn5 NEO (aminoglycosidase 3'-phosphotransferase) gene under the control of the HSV $\alpha 4$ promoter flanked by sequences from the IBR virus TK gene was constructed. The IBR virus homology regions were derived from the TK gene. The upstream homology included the first amino acid of the TK gene (15) and extended approximately 800 base pairs upstream of the TK coding region. The downstream homology included amino acids 156 to 357 and extended downstream of the TK coding region approximately 60 base pairs. S-IBR-002 DNA was mixed with the homology vector and transfected into rabbit skin cells as indicated in the methods. The transfection stock was selected according to the SELECTION OF G418 RESISTANT IBR VIRUS. Individual clones were picked after one round of selection and analyzed by the SOUTHERN BLOTTING OF DNA procedure. When a probe derived from the NEO gene was used in this analysis, one clone was found which did not hybridize to the NEO probe but had a HindIII restriction digestion pattern clearly distinct from the parental S-IBR-002. Further analysis indicated that the NEO had not been inserted into the TK region, however an approximately 1200 base pair deletion had occurred in the HindIII K fragment.

In order to characterize the HindIII K deletion, that fragment was subcloned and subjected to restriction mapping. Utilizing a series of oligonucleotide probes derived from the wild type sequence it was determined that approximately 1200 base pairs were deleted from the end of the HindIII K fragment adjacent to the HindIII K/HindIII O junction (see FIG. 6). This deletion removes the entire coding region of the US2 gene. S-IBR-027 was deposited on Apr. 17, 1991 pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. VR 2322.

Direct fetal inoculation is the most sensitive test for determining the safety of live, IBR vaccines as regards their use in pregnant cows or in calves nursing pregnant cows. Three virus constructs were tested for fetal safety by inoculating directly into the bovine fetus, following laparotomy to expose the uterus. Abortion occurring within seven days after inoculation was considered to be surgically-induced. If fetuses aborted after this time, tissue samples were removed and cultured for the presence of the IBR construct. Caesarean sections were performed on cows with fetuses surviving for greater than 30 days post-inoculation. Fetal tissue was removed for virus culturing and blood samples were taken for evaluation of serum antibody to IBR virus.

The S-IBR-027 construct described above was tested, as well as two other constructs, S-IBR-020 and S-IBR-028. The S-IBR-020 construct was derived from the Cooper strain of IBR virus by making deletions in the repeat regions of the DNA and by inserting the Tn5 NEO gene. The S-IBR-028 construct was derived from the Cooper strain of IBR virus by making deletions in the repeat region of the DNA and in the TK gene. The Tn5 NEO gene was also inserted into the TK deletion.

The following results were obtained from studies with the three virus constructs. In the studies with S-IBR-020, two fetuses were inoculated, one at approximately 130–140 days gestation and the other at approximately 170–180 days gestation. The younger fetus aborted twenty days after inoculation, but virus could not be recovered from tissue samples of this fetus (Table 2). The other fetus was live and appeared normal when it was surgically removed 60 days post-inoculation. In studies with S-IBR-027, four fetuses, ranging in age from 125 days to >250 days, were inoculated (Table 2). All fetuses survived and appeared normal. In studies with S-IBR-028, three fetuses, ranging in age from 140 days to >250 days, were inoculated. The youngest and eldest fetuses survived and appeared normal, however the fetus inoculated at 160–170 days gestation aborted nine days after inoculation.

Direct fetal inoculation is the most sensitive test for measuring the safety of live, IBR viruses used in pregnant cows. To date, the gene(s) involved in fetal virulence has not been reported. IBR viruses was engineered with deletions in three different regions of IBR virus DNA and then determined the effect of the gene deletion. All three virus constructs tested have a deletion in the repeat region of the DNA and two constructs do not have TK activity. One fetus inoculated with each of the TK-constructs has aborted. In contrast, the construct with deletions in the repeat regions and the US2 gene (S-IBR-027) has been inoculated into four fetuses with no adverse reactions.

TABLE 2

Safety of IBR Viruses for Bovine Fetuses

| Construct | Fetal Age[a] | Results |
| --- | --- | --- |
| S-IBR-020 | 130–140 Days | Fetus aborted Day 20 post-inoculation; no virus isolated |
| | 170–180 Days | Normal, live fetus 60 days post-inoculation |
| S-IBR-027 | 125–135 Days | Normal, live fetus 60 days post-inoculation |
| | 150–160 Days | Normal, live calf born 56 days post-inoculation |
| | 220–240 Days | Normal, live calf born 30 days post-inoculation |
| | >250 Days | Normal, live calf born 30 days post-inoculation |
| S-IBR-028 | 140–150 Days | Normal, live fetus 60 days post-inoculation |
| | 160–170 Days | Fetus aborted Day 9 post-inoculation; no virus isolated |
| | >250 Days | Normal, live calf born 12 days post-inoculation |

[a]Approximate age at time of virus inoculation

S-IBR-027 is safe for fetal inoculation in contrast to S-IBR-020 and S-IBR-028 which are not. Although all three viruses were engineered by similar approaches, the distinguishing difference of S-IBR-027 is the deletion of the US2 gene. Nasalgen virus, which was generated by independent methods, is also safe for use in IBR-susceptible pregnant cows, has been deleted in the US2 gene.

Although the S-IBR-027 and Nasalgen have the similar property of fetal safety, S-IBR-027 offers additional advantages. The major portion of the US2 gene (251 out of 309 amino acids) has been deleted in the Nasalgen virus. This deletion would clearly inactivate the gene, however the remaining portion of the gene may make it more likely to revert to virulence via recombination with other viruses. The complete coding region of the US2 has been deleted from S-IBR-027 making it less likely that this gene could be restored and revert the virus to virulence. The S-IBR-027 construct also carries an important deletion in the repeat region, which is not present in the Nasalgen virus. A deletion in the analogous region of the pseudorabies virus (PRV) has been shown to be valuable in attenuating PRV for swine (see U.S. Pat. No. 4,877,737). This deletion has also been shown to attenuate IBR for cattle as seen in the testing of S-IBR-002 (see Example 1).

Example 4
S-IBR-028

S-IBR-028 is an IBR virus that has a deletion of approximately 800 bp in the repeat regions and approximately 250 bp in the TK region of the genome. The deletion in the TK region inactivates the TK gene. The repeat deletion was derived from the parental virus S-IBR-002 and is described in Example 2.

To construct this virus, the HOMOLOGOUS RECOMBINATION PROCEDURE FOR GENERATING RECOMBINANT HERPESVIRUS was performed. A homology vector containing the bacterial transposon Tn5 NEO (aminoglycosidase 3-phosphotransferase) gene under the control of the HSV-1 α4 gene promoter flanked by sequences from the IBR virus TK gene was constructed. The IBR virus homology regions were derived from the TK gene. The upstream homology included amino acids 1 to 62 of the TK gene (15) and extended approximately 674 base pairs upstream of the TK coding region. The downstream homology included amino acids 156 to 357 and extended downstream of the TK coding region approximately 1138 base pairs. S-IBR-002 DNA was mixed with the homology vector 129-71.5 and transfected into rabbit skin cells as indicated in the methods. The transfection stock was selected according to the SELECTION OF G418 RESISTANT IBR VIRUS.

Individual clones were picked after two rounds of selection and analyzed by the SOUTHERN BLOTTING OF DNA procedure. Several clones were assayed for TK activity by a $^{14}$C-thymidine incorporation assay (29). One clone which was negative for TK activity was chosen and characterized by digestion with HindIII and XbaI. The restriction endonuclease analysis confirmed that the NEO gene had been inserted into the TK gene. This clone, designated S-IBR-028, was deposited on May 14, 1991 pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. VR 2326.

Example 5
Glycoprotein G Gene

Deletion of the PRV gX gene has been shown to be valuable both as an attenuating lesion and as a negative serological marker (see U.S. Ser. No. 192,866, filed May 11, 1988 now U.S. Pat. No. 5,047,237 issued Sep. 10, 1991). In the studies described below the unique short region of IBR virus was shown to contain a gene homologous to the gX gene of PRV.

Figures 9A, 9B:
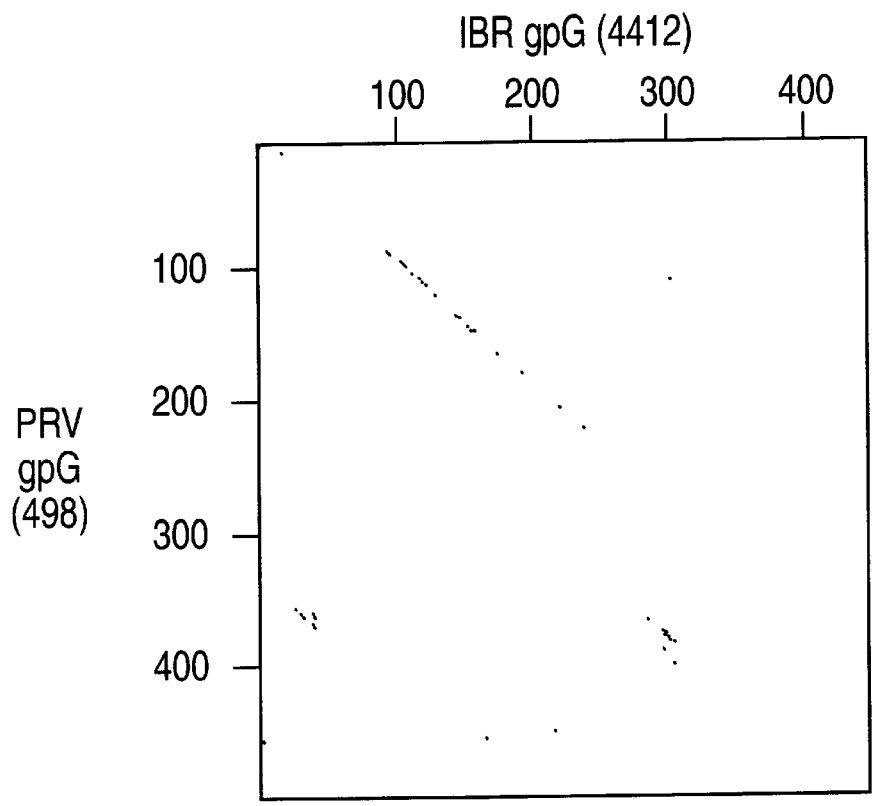

The sequence of an approximately 1400 base pair region of the IBR HindIII K fragment (see FIG. 8), located approximately 2800 base pairs downstream of the HindIII K/HindIII O junction was determined. This region was found to contain an ORF coding for 441 amino acids translated in the direction away from the HindIII K/HindIII O junction (see FIG. 1). The ORF is 69% G+C and encodes a protein with a predicted molecular weight of 58,683. Comparison of the sequence of the predicted protein with sequences of gene products of HSV-2 and PRV in the unique short region indicated that this ORF is homologous to the herpesvirus gG gene (see FIGS. 9A–9B). The complete gG gene resides on an approximately 2800 base pair MluI to NdeI sub-fragment of the IBR virus HindIII K fragment. This subfragment has been cloned as a blunt ended fragment into the plasmid pSP64. This plasmid is designated PSY1643. PSY1643 was deposited on Jul. 16, 1991 pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. 68652. This plasmid may be used to confirm the sequence of the gG gene. The sequence of the gG gene may also be confirmed by comparing the appropriate DNA sequence of the wild type virus S-IBR-000 (Cooper strain with the sequence of the gG deleted virus S-IBR-037 (ATCC Accession No. 2320).

Figure 10:
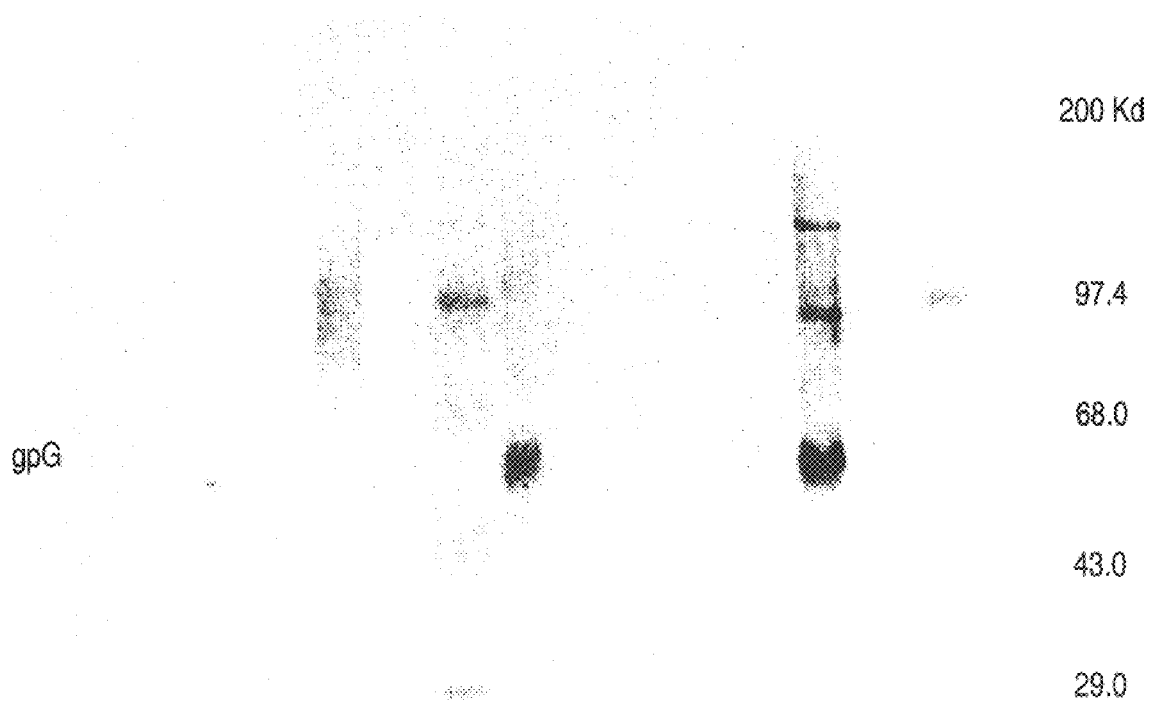
Figure 11B:
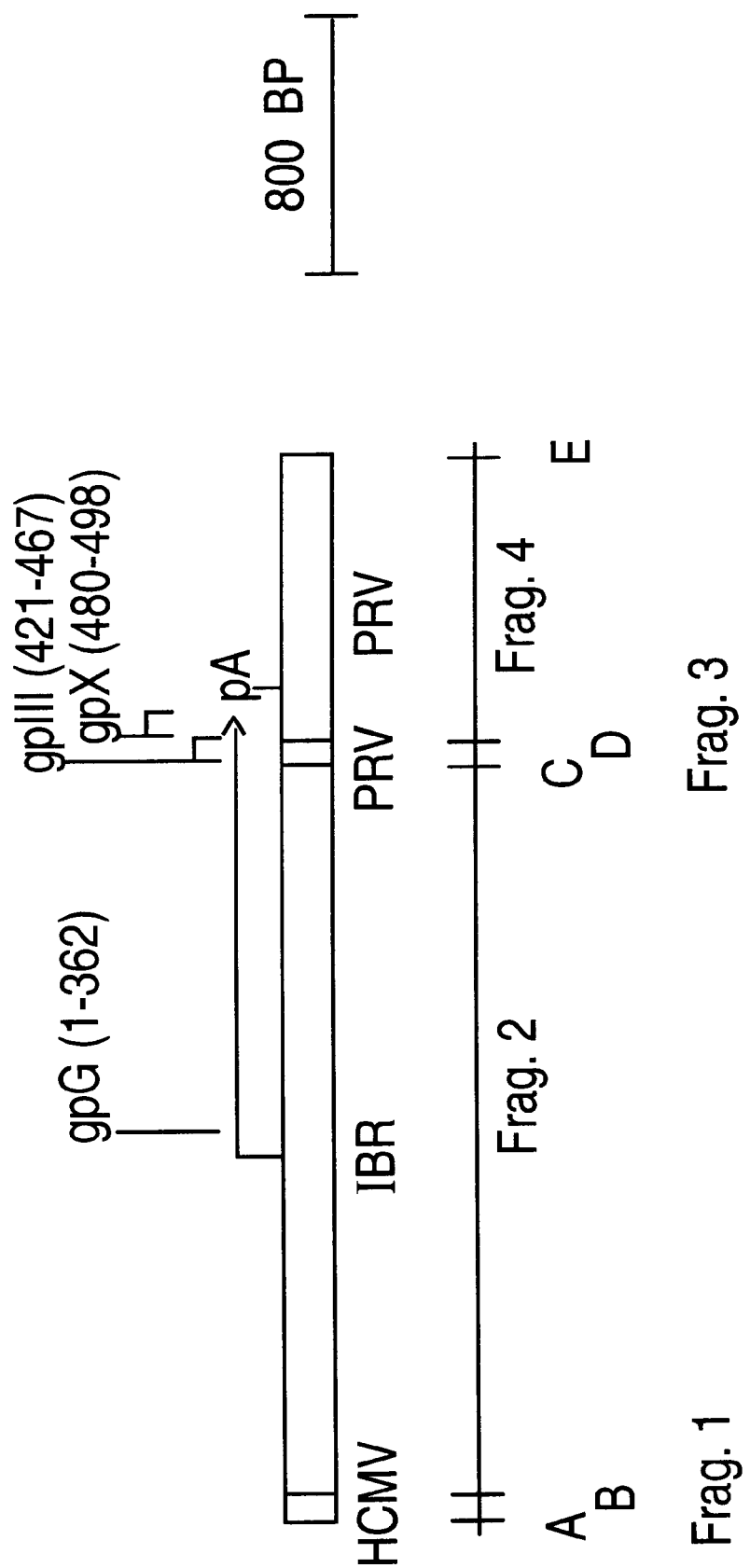
Figure 11C:
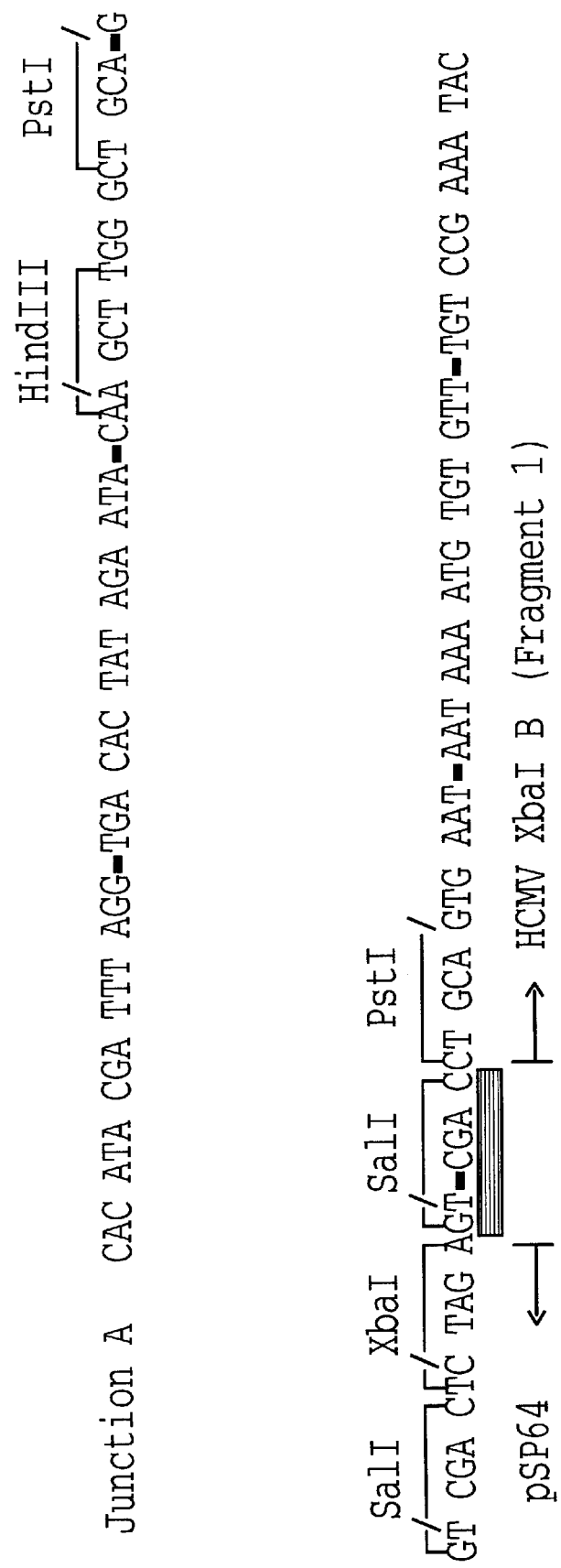
Figure 11E:
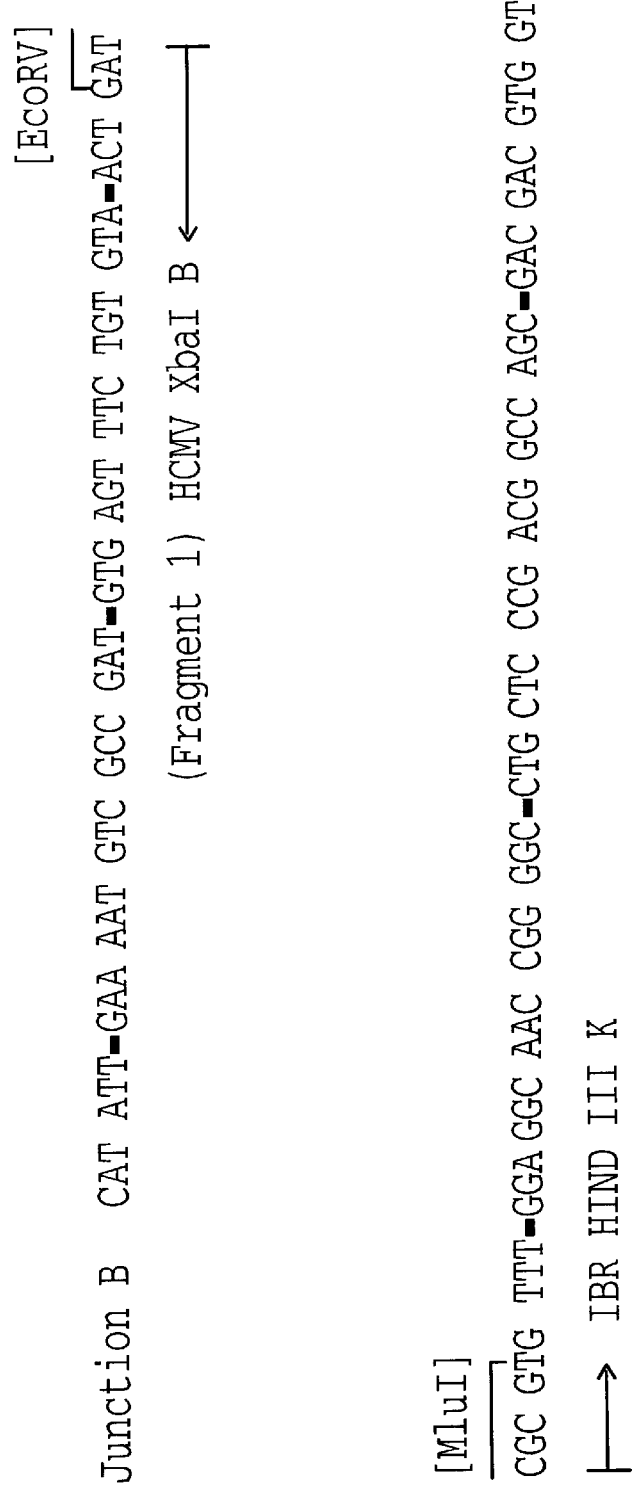
Figure 11F:
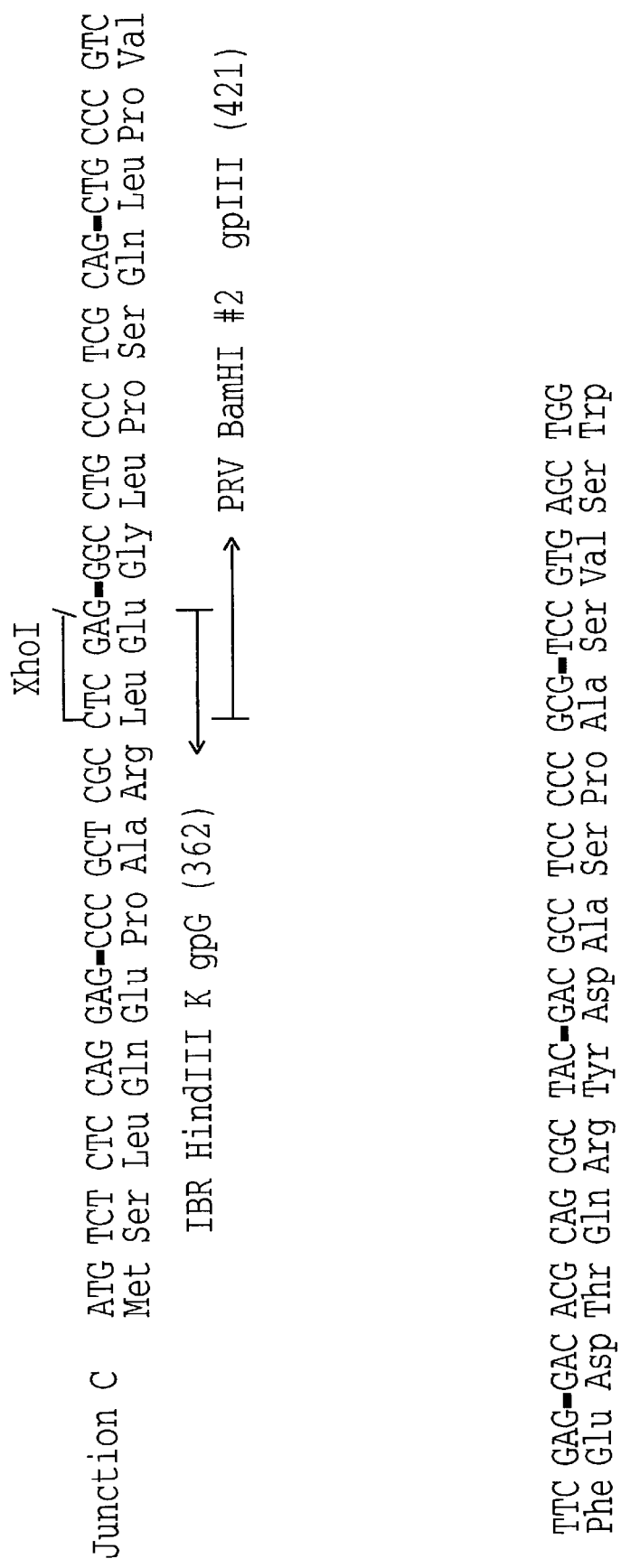
Figure 11G:
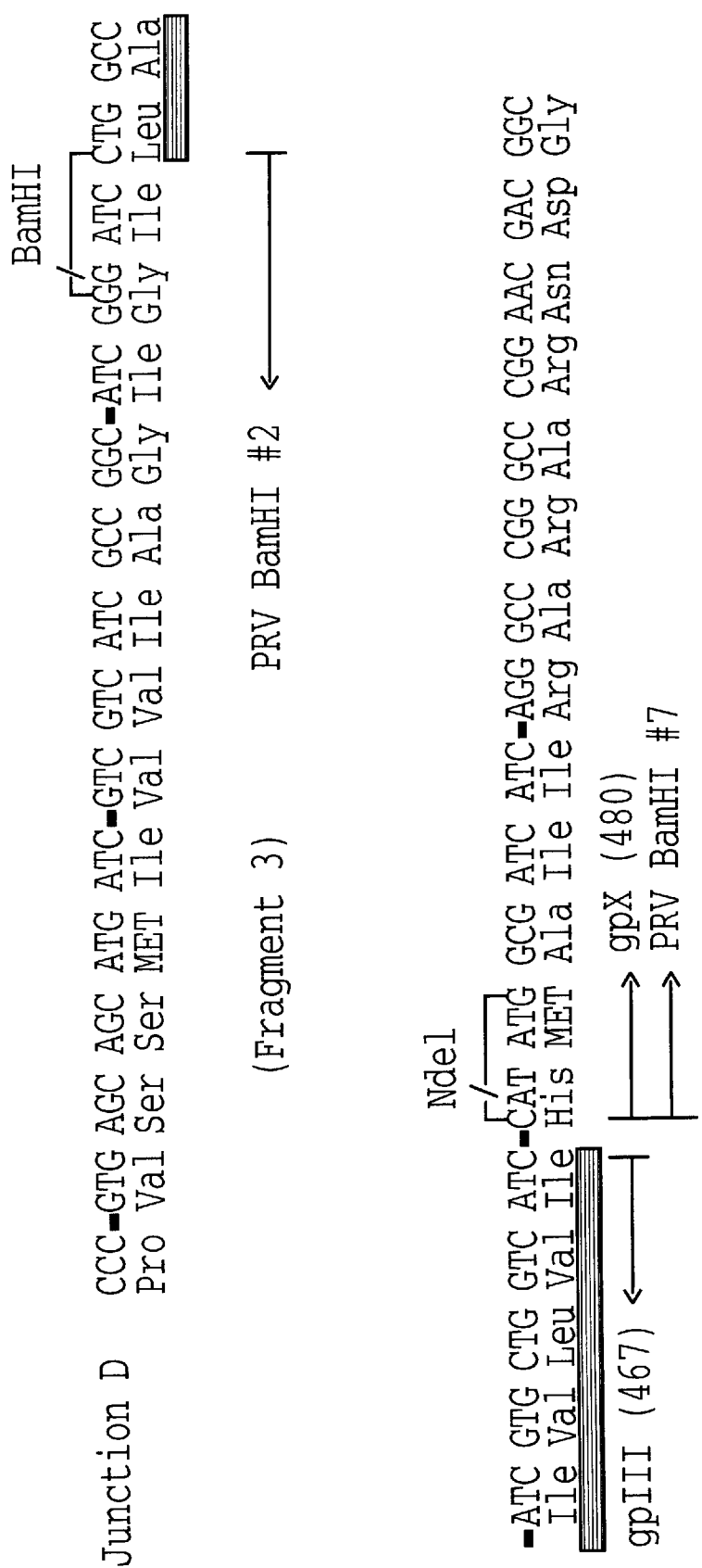
Figure 11H:
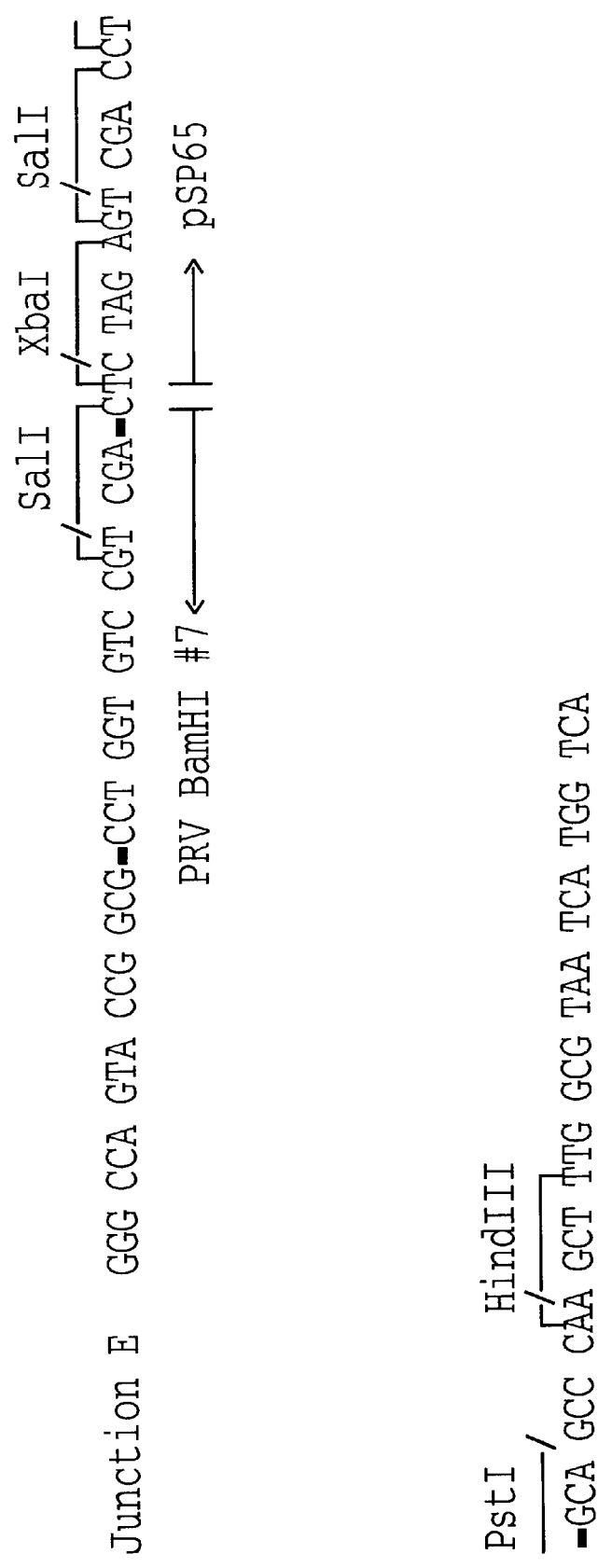
Figure 12B:
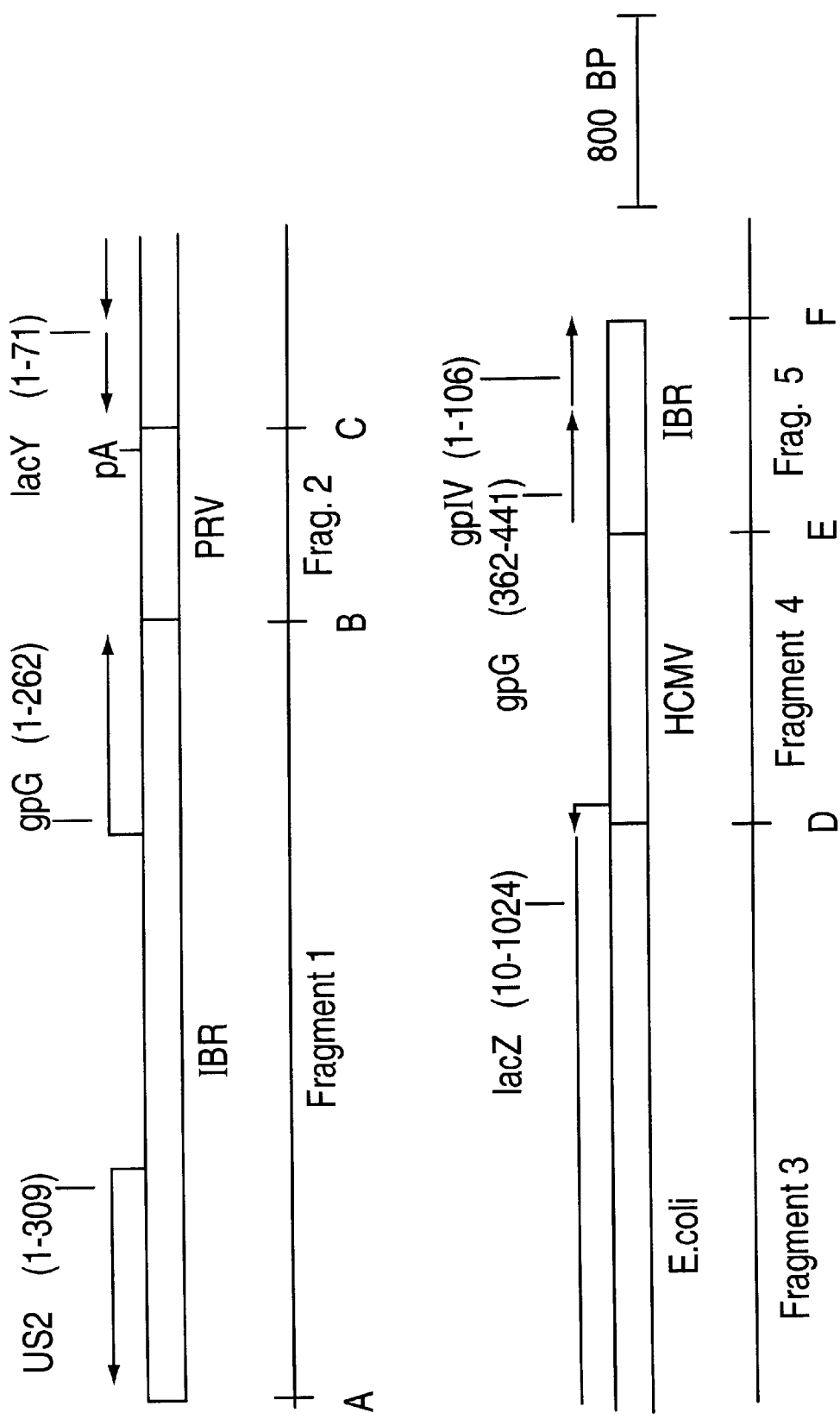
Figure 12C:
Figure 12D:
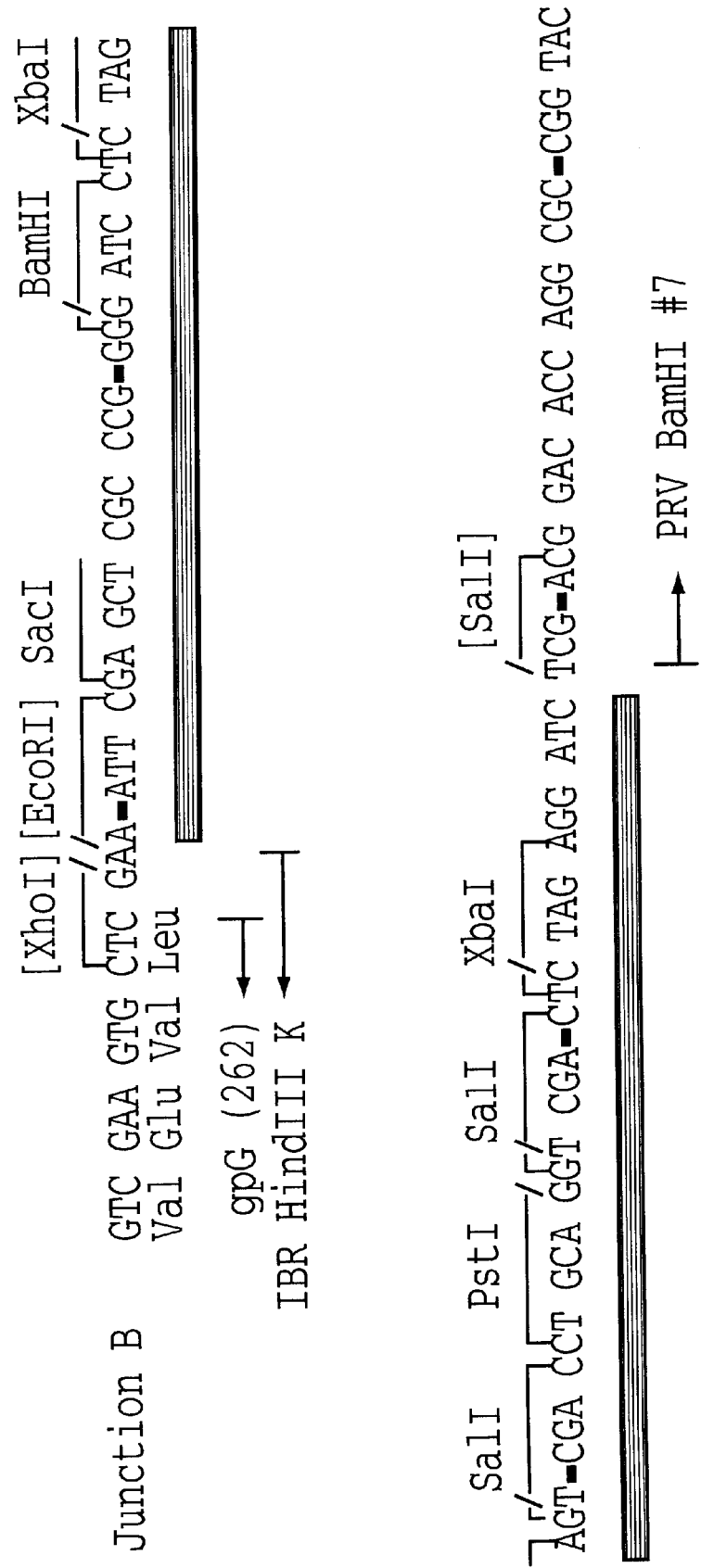
Figure 12E:
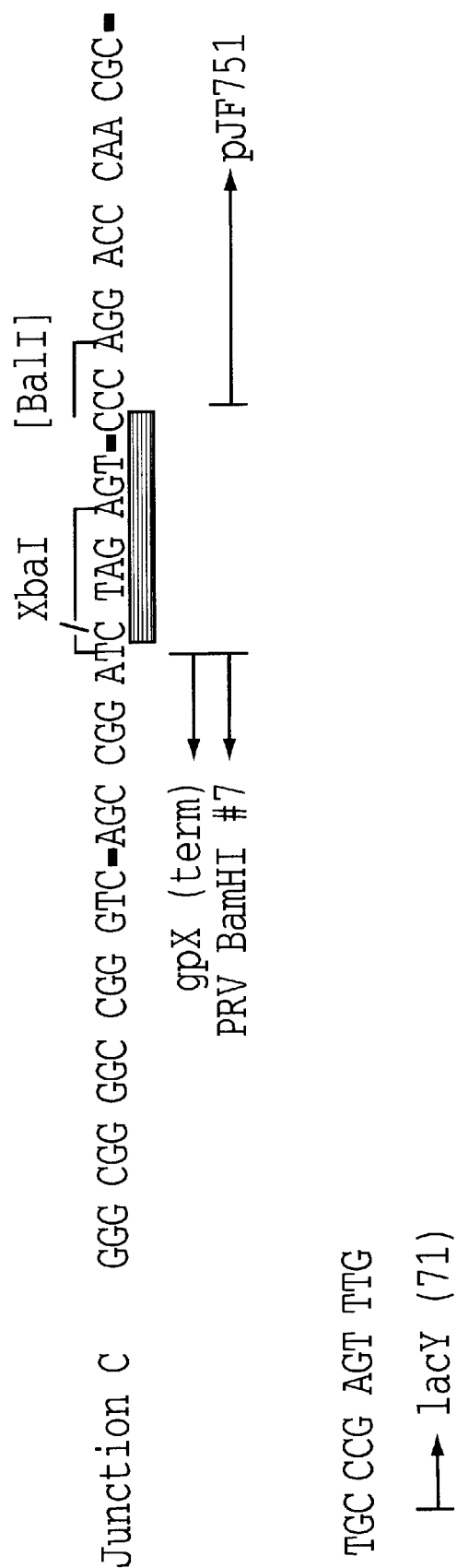
Figure 12F:
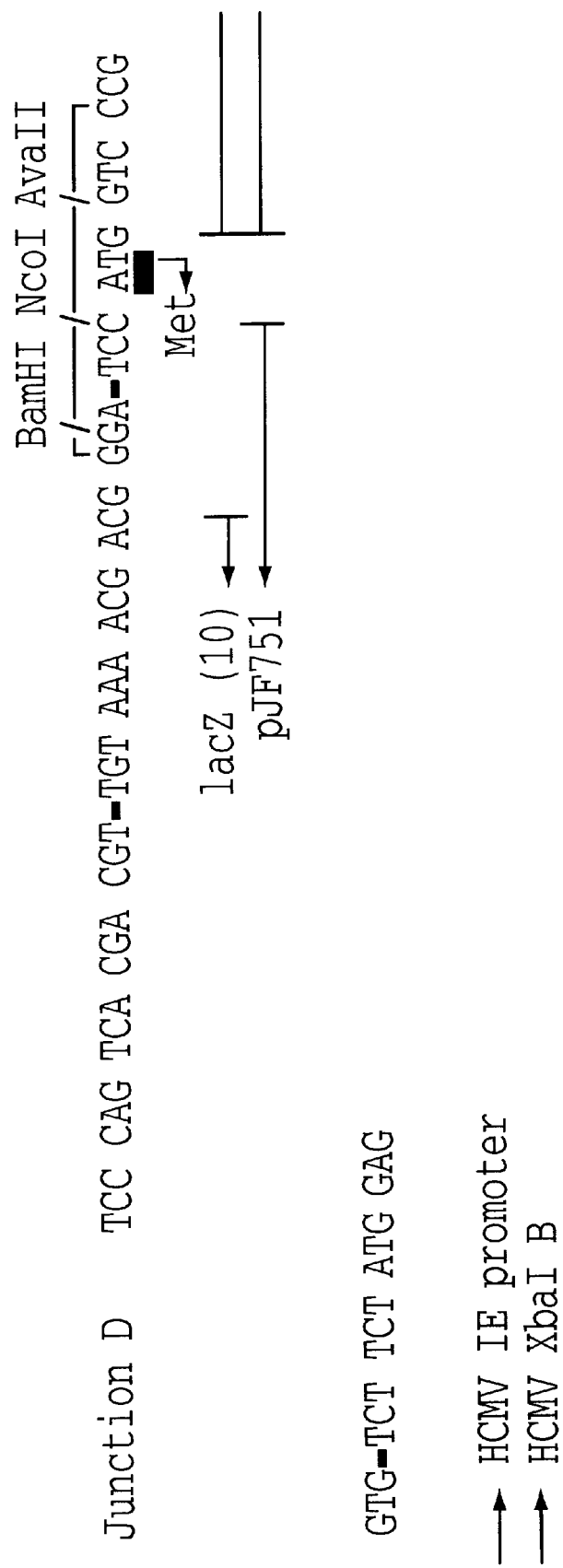
Figure 12G:
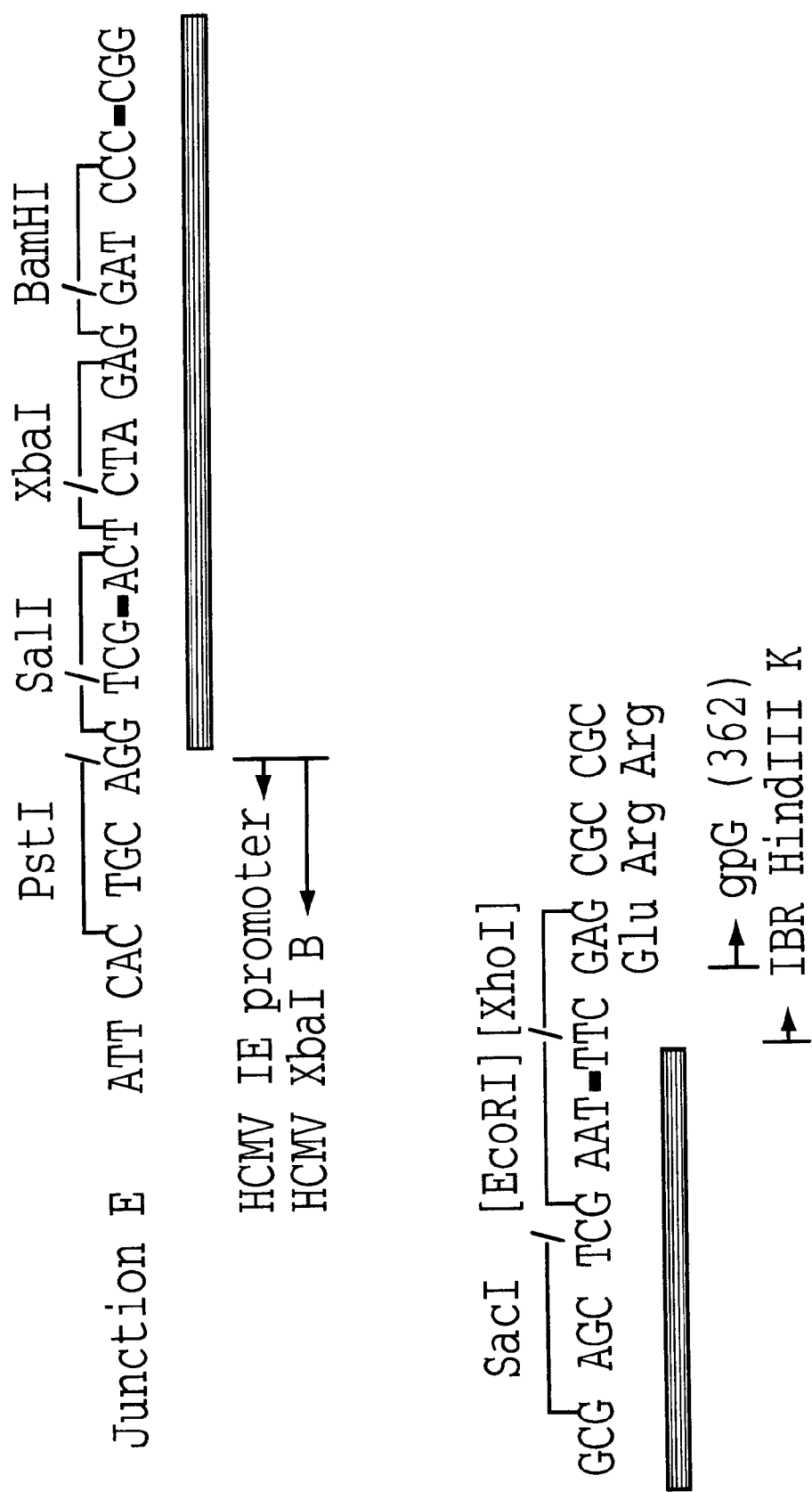
Figure 12H:
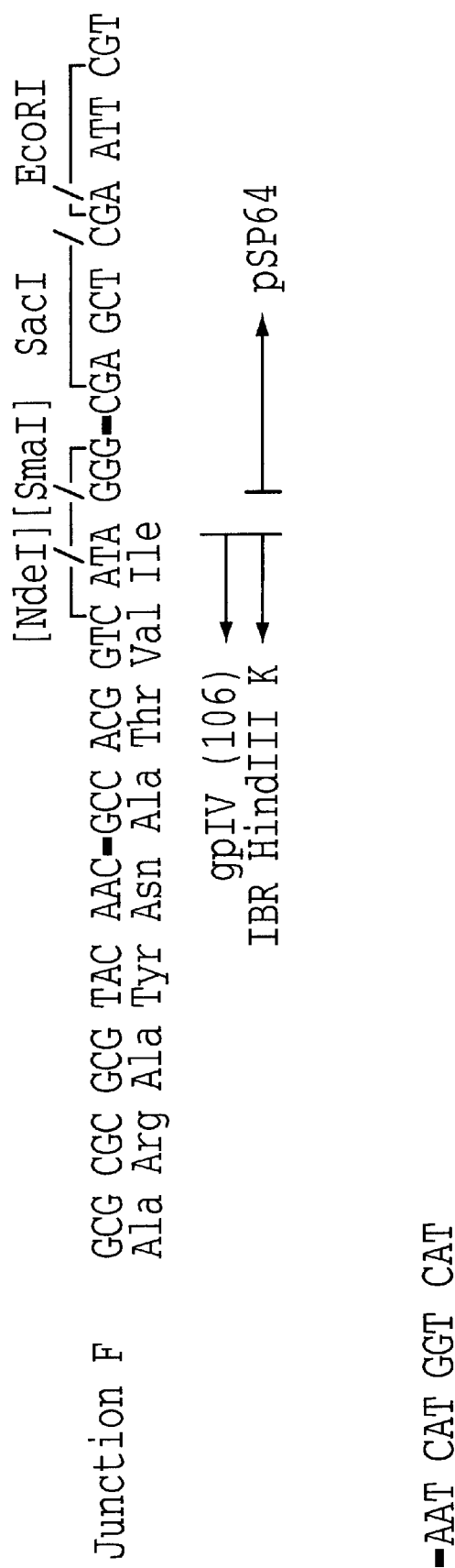
Figure 13B:
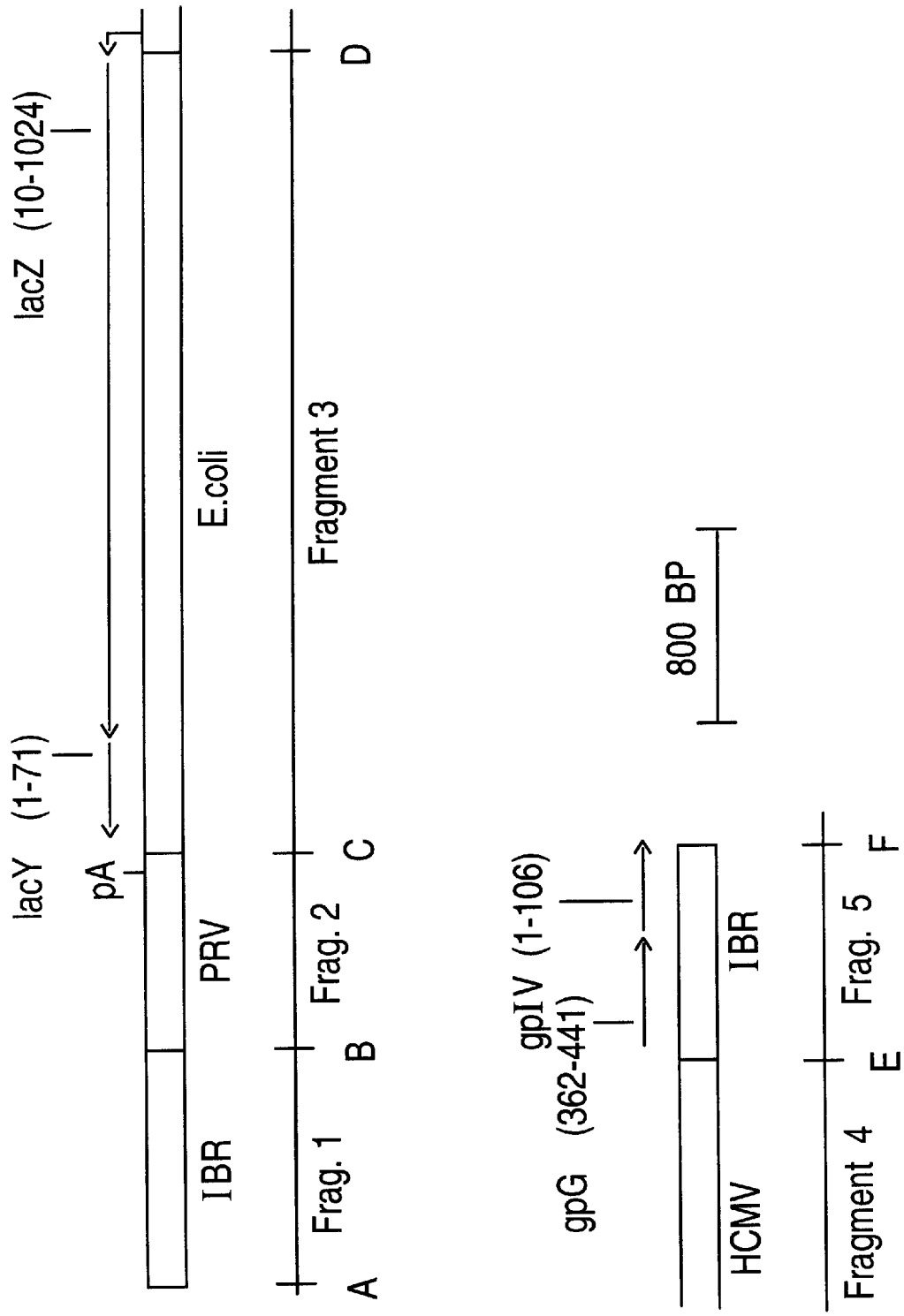
Figure 13C:
Figure 13D:
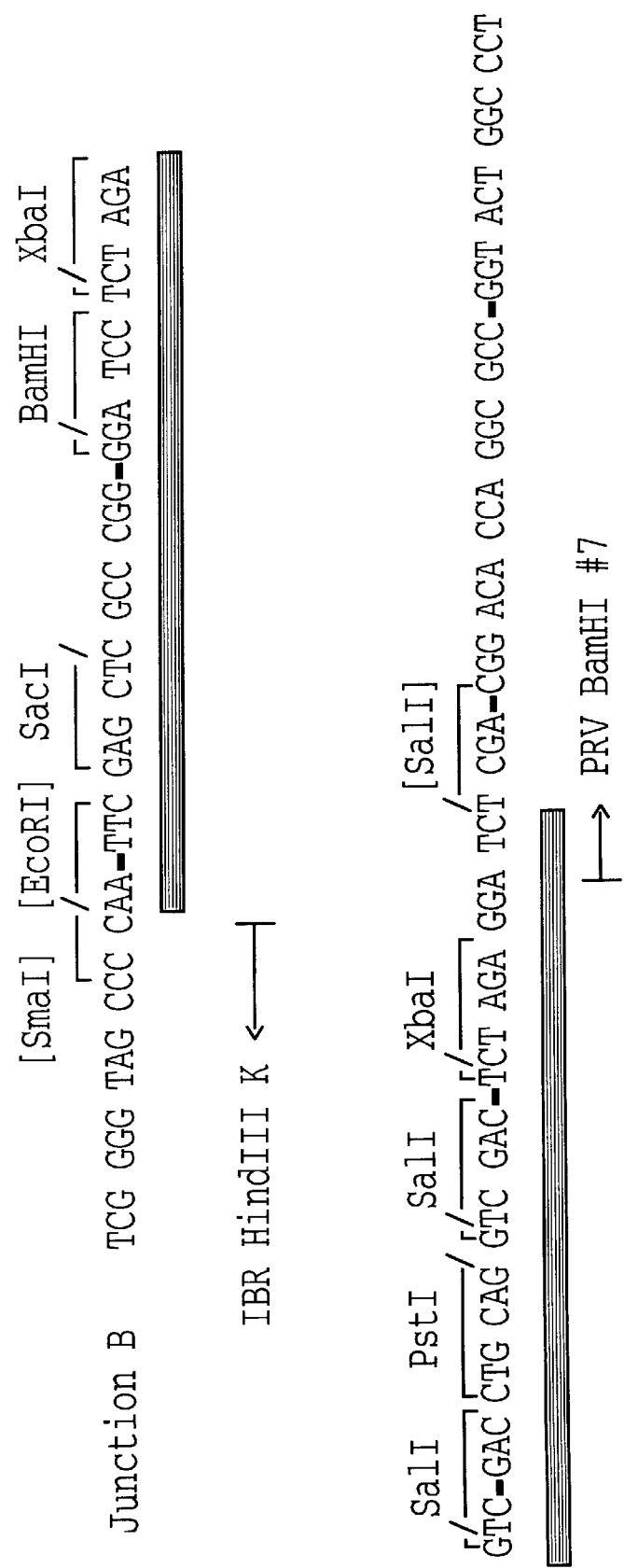
Figure 13E:
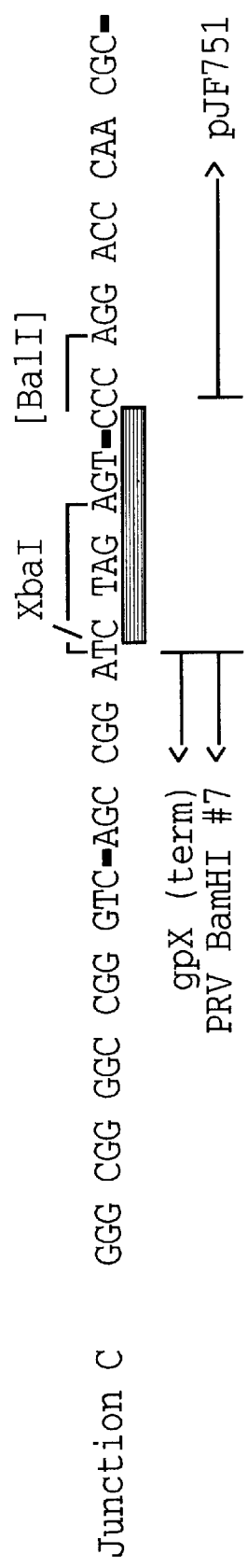
Figure 13F:
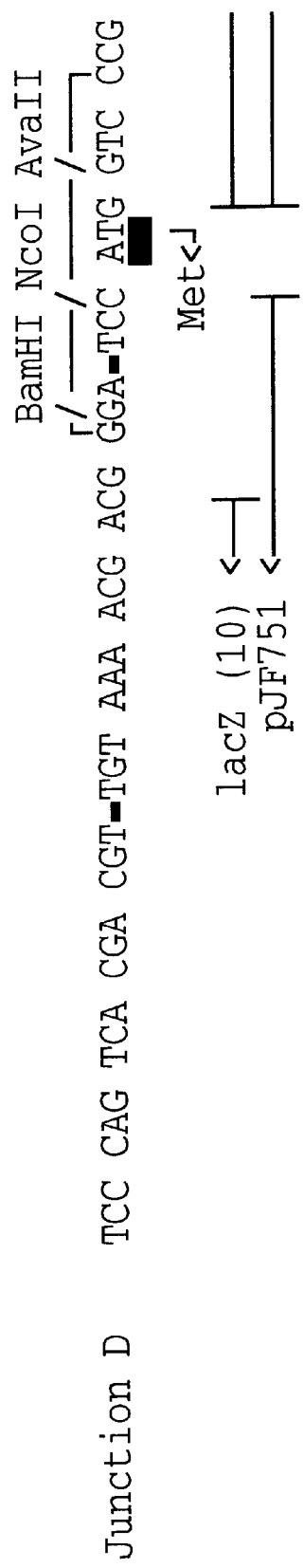
Figure 13G:
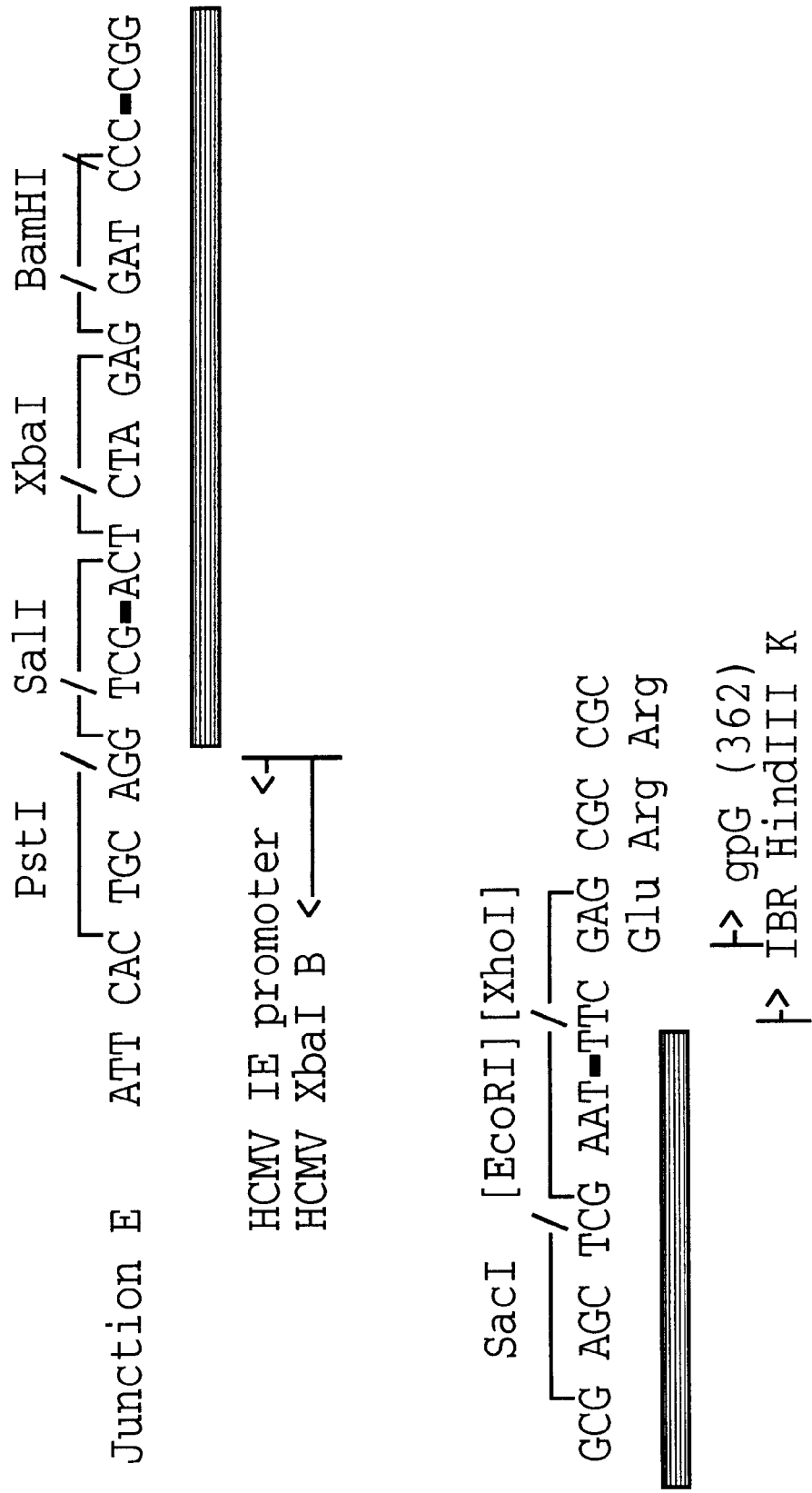
Figure 13H:
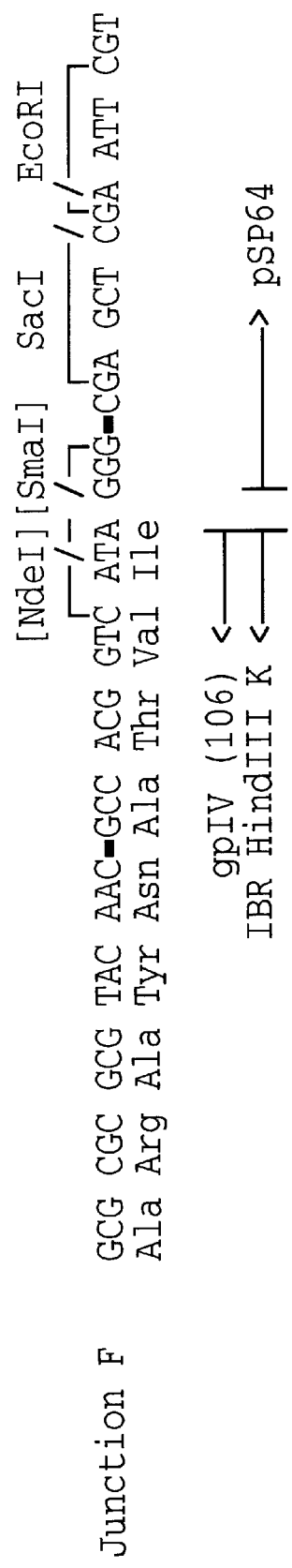
Figure 14B:
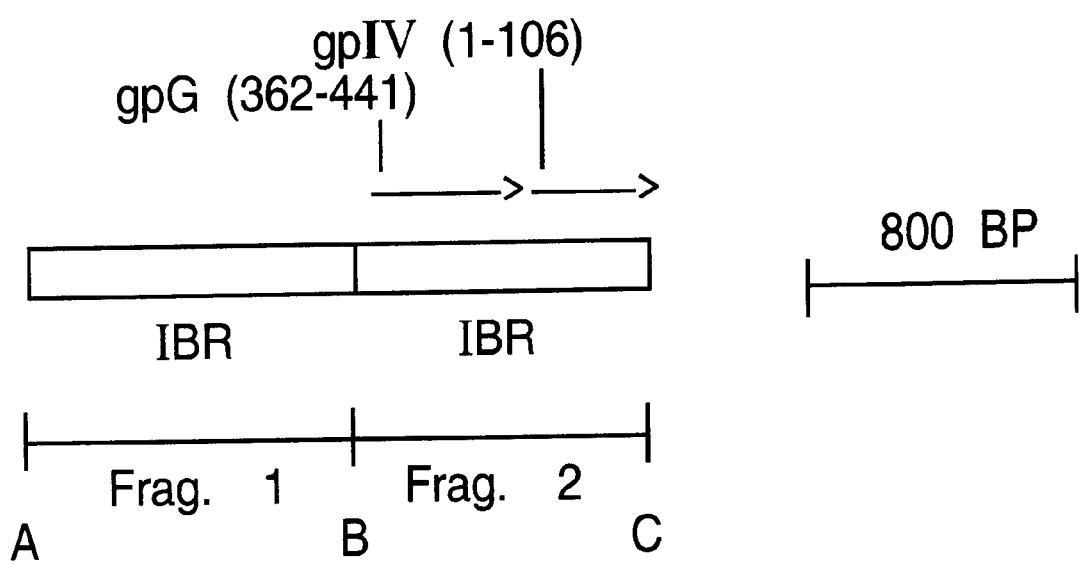
Figure 14C:
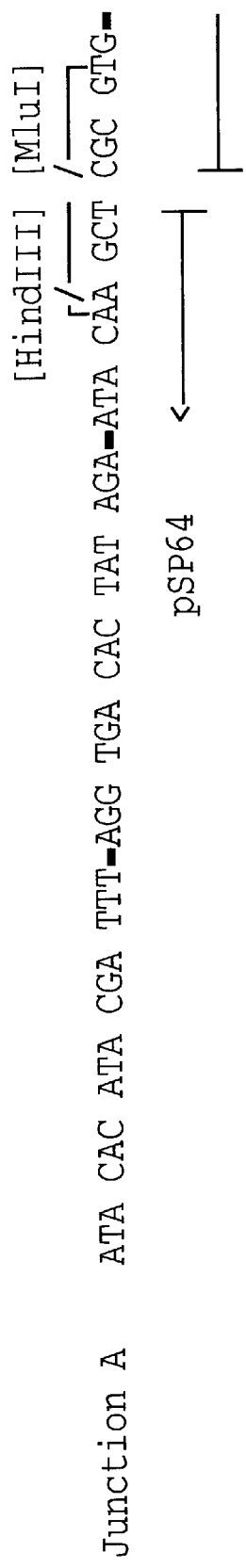
Figure 14D:
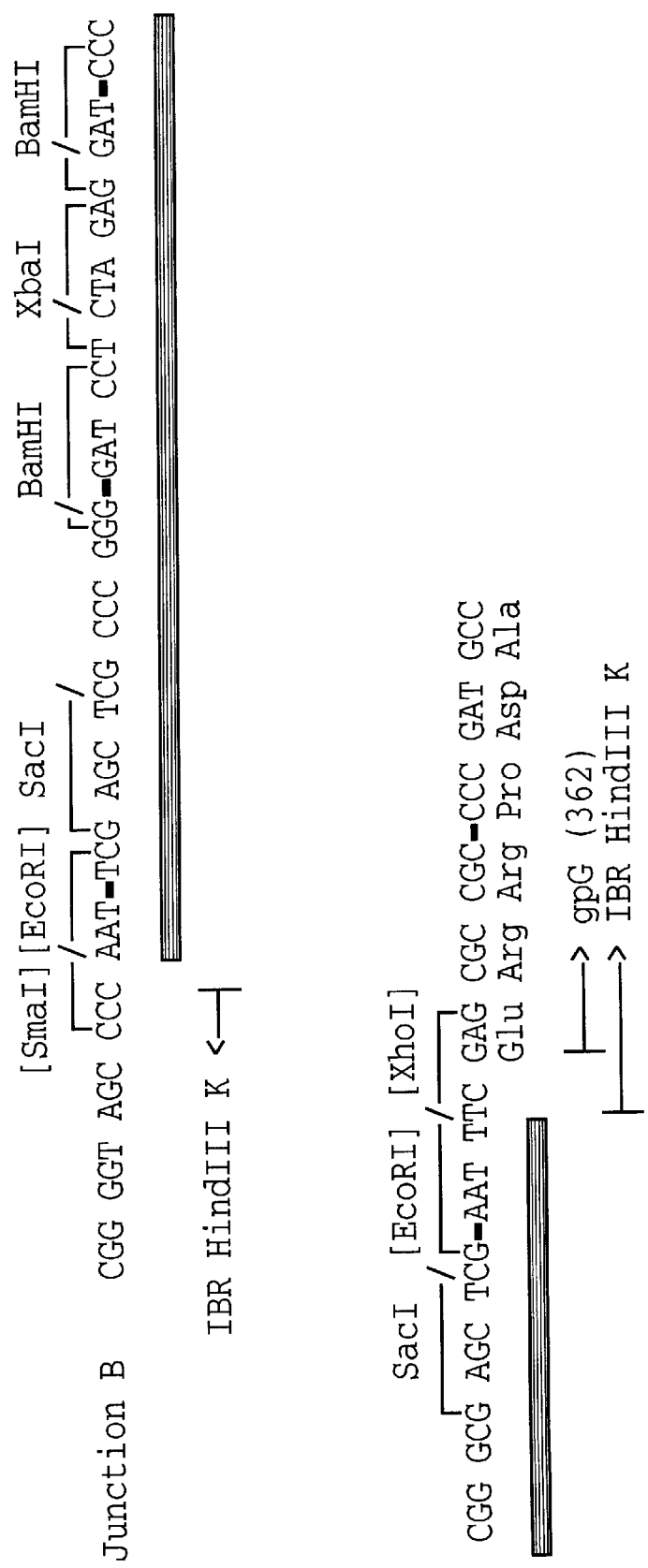
Figure 14E:
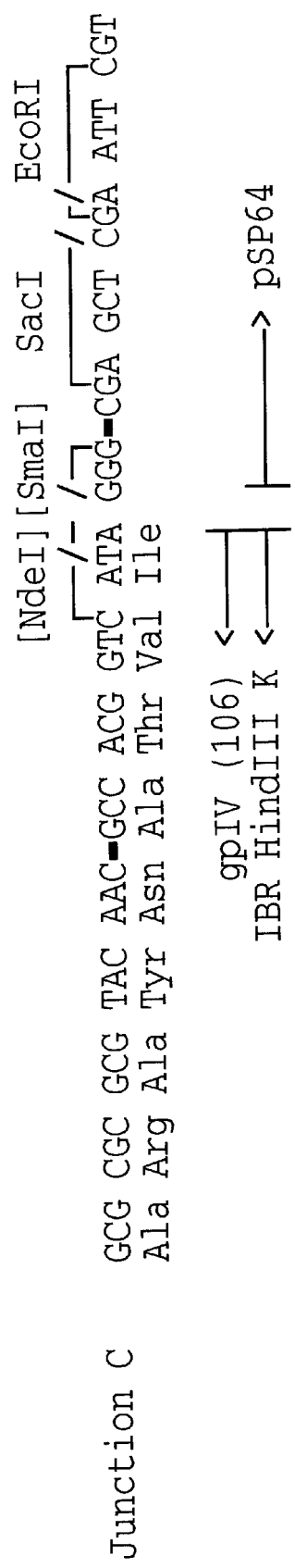

To confirm the expression of the IBR virus gG gene product, cells were infected with IBR virus and samples of media from infected cultures were subjected to SDS-polyacrylamide gel electrophoresis. The gel was blotted and analyzed using the WESTERN BLOTTING PROCEDURE. The anti-serum used was a mouse hyper-immune serum raised against chemically-synthesized gG peptides (amino acids 242–254 and 269–289) linked to keyhole limpet hemocyanin. As shown in FIG. 10, gG is prominent in the media of cells infected with wild type virus (S-IBR-000), but is not detected in media of mock infected cells.

Example 6

S-PRV-160

S-PRV-160 is a pseudorabies virus that has a deletion in the TK gene in the long unique region, a deletion in the repeat region, and an approximately 1414 base pair deletion in the gX coding region. The gene for E.coli β-galactosidase (lacZ gene) was inserted in the place of the gX gene and is under the control of the gX promoter. A chimeric gene coding for an IBR virus gG, PRV gIII and PRV gX fusion protein was inserted at the HindIII sites located in each repeat.

S-PRV-160 was constructed utilizing plasmid 459-12.6, pseudorabies virus S-PRV-013 (see U.S. Ser. No. 823,102, filed Jan. 27, 1986 now U.S. Pat. No. 5,068,192 issued Nov. 26, 1991 and U.S. Ser. No. 07/192,866, filed May 11, 1988 now U.S. Pat. No. 5,047,237 issued Sep. 10, 1991) and the restriction enzyme HindIII in the DIRECT LIGATION PROCEDURE FOR GENERATING RECOMBINANT HERPESVIRUS. Several clones were screened by digestion with HindIII for the presence of the HindIII band containing the chimeric gene insert from plasmid 459-12.6. One clone exhibiting the correct HindIII insert band was chosen and designated S-PRV-160.

S-PRV-160 was constructed so that it would express precisely the gG specific amino acids that were deleted in S-IBR-037. This allows the gG fusion protein expressed in S-PRV-160 to be used as an antigen to identify antibodies directed against the wild type virus as opposed to antibodies directed against S-IBR-037. Note that gX, the PRV homologue of IBR virus gG, has been deleted from S-PRV-160 to prevent any confusion resulting from cross reactivity that might exist between the two proteins. To confirm that S-PRV-160 does express IBR virus gG, a Western blot analysis was performed. As can be seen in FIG. 10, gG specific antibody does react with an appropriately sized media protein from S-PRV-160.

S-PRV-160 may also be utilized as an antigen for the production of gG specific monoclonal antibodies. Such antibodies are useful in the development of diagnostic tests specific for the gG protein. Monoclonal antibodies were generated in mice utilizing S-PRV-160 according to the PROCEDURE FOR GENERATING MONOCLONAL ANTIBODIES. One of these antibodies' clone 3-1G7 was shown to react specifically with purified gG in the gG ELISA assay.

Example 7

S-IBR-035

S-IBR-035 is an IBR virus that has two deletions in the short unique region of the genome. The first deletion is approximately 2500 base pairs and begins in the HindIII K fragment approximately 1750 base pairs downstream of the HindIII O/HindIII K junction and extends back through that junction. This deletion removes the US2 gene. The second deletion is approximately 294 base pairs and begins in the HindIII K fragment approximately 3900 base pairs downstream of the HindIII K/HindIII O junction and extends back toward that junction. This deletion removes amino acids 263 to 361 of the gG gene. The gene for *E.coli* β-galactosidase (lacZ gene) was inserted into the deletion in the gG gene and is under the control of the HCMV immediate early promoter.

S-IBR-035 was derived from S-IBR-000 (Cooper strain). This was accomplished utilizing the homology vector 439-01.31 (see Materials and Methods) and virus S-IBR-000 in the HOMOLOGOUS RECOMBINATION PROCEDURE FOR GENERATING RECOMBINANT HERPESVIRUS. The transfection stock was screened by the BLUOGAL™ SCREEN FOR RECOMBINANT HERPESVIRUS. The final result of blue plaque purification was the recombinant virus designated S-IBR-035. This virus was characterized by restriction mapping and the SOUTHERN BLOTTING DNA procedure. This analysis confirmed the insertion of the β-galactosidase (lacZ) marker gene and the deletion of approximately 294 base pairs of the gG gene. It was also confirmed that an approximately 2500 base pair deletion had occurred in the region of the US2 gene.

Example 8

S-IBR-036

S-IBR-036 is an IBR virus that has two deletions in the short unique region of the genome. The first deletion is approximately 2500 base pairs and is similar to the deletion in S-IBR-035 (see Example 7) which removes the US2 gene. The second deletion is approximately 1230 base pairs and begins in the HindIII K fragment approximately 3900 base pairs downstream of the HindIII O/HindIII K junction and extends back toward that junction. This deletion removes amino acids 1 to 361 of the gG gene. The gene for *E.coli* β-galactosidase (lacZ gene) was inserted into the deletion in the gG gene and is under the control of the HCMV immediate early promoter.

S-IBR-036 was derived from S-IBR-000 (Cooper strain). This was accomplished utilizing the homology vector 439-21.69 (see Materials and Methods) and virus S-IBR-000 in the HOMOLOGOUS RECOMBINATION PROCEDURE FOR GENERATING RECOMBINANT HERPESVIRUS. The transfection stock was screened by the BLUOGAL SCREEN FOR RECOMBINANT HERPESVIRUS. The final result of blue plaque purification was the recombinant virus designated S-IBR-036. This virus was characterized by restriction mapping and the SOUTHERN BLOTTING DNA procedure. This analysis confirmed the insertion of the β-galactosidase (lacZ) marker gene and the deletion of approximately 1230 base pairs of the gG gene. It was also confirmed that an approximately 2500 base pair deletion had occurred in the region of the US2 gene (see above).

Example 9

S-IBR-037

S-IBR-037 is an IBR virus that has two deletions in the short unique region of the genome. The first deletion is approximately 2500 base pairs and begins in the HindIII K fragment approximately 1750 base pairs downstream of the HindIII O/HindIII K junction and extends back through that junction. This deletion removes the US2 gene. The second deletion is approximately 1230 base pairs and begins in the HindIII K fragment approximately 3900 base pairs downstream of the HindIII O/HindIII K junction and extends back toward that junction. This deletion removes amino acids 1 to 361 of the gG gene.

S-IBR-037 was derived from S-IBR-035. This was accomplished utilizing the homology vector 439-70.4 (see Materials and Methods) and virus S-IBR-035 in the HOMOLOGOUS RECOMBINATION PROCEDURE FOR GENERATING RECOMBINANT HERPESVIRUS. The transfection stock was screened by the BLUOGAL™ SCREEN FOR RECOMBINANT HERPESVIRUS. The result of white plaque purification was the recombinant virus designated S-IBR-037. This virus was characterized by restriction mapping and the SOUTHERN BLOTTING DNA procedure. This analysis confirmed the deletion of the β-galactosidase (lacZ) marker gene and the deletion of approximately 1230 base pairs of the gG gene. It was also confirmed that an approximately 2500 base pair deletion had occurred in the region of the US2 gene (see above). S-IBR-037 was deposited on Apr. 16, 1991 pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. VR 2320.

To test the efficacy of S-IBR-037 as an inactivated IBR virus vaccine in protecting susceptible calves against virulent IBR virus challenge, a study was performed according to the VACCINATION STUDIES IN CALVES WITH INACTIVATED IBR VIRUS. The following results were observed.

Virus neutralization antibody titers were elicited in animals after the first vaccination (see Table 3). Antibody titers were not significantly different between animals that received a vaccine dose of $10^{7.3}$ virus and animals vaccinated with $10^{8.0}$ virus. After the second vaccination, mean antibody titers increased to 1:19 and 1:32, respectively, for the $10^{7.3}$ and $10^{8.0}$ vaccine groups. Control animals remained seronegative to IBR virus throughout the vaccination period. Antibody titers in both vaccinate groups showed an increase typical of an anamnestic response after challenge with virulent IBR virus. By 13 days post challenge, mean antibody titers were 1:152 and 1:215 for the $10^{7.3}$ and $10^{8.0}$ vaccinate groups respectively. In contrast, mean antibody titers in challenged control animals were 1:4 at 7 days and 1:8 at 13 days post challenge.

Nasal swabs were collected from challenged animals to determine whether vaccination decreased the time of virus shedding (Table 4). The most dramatic difference between vaccinates and control animals was observed at 12 days post challenge. At this time, seventy-five percent of control animals continue to shed, whereas, only twenty-five percent of both vaccinate groups shed virus. Virus was not isolated from control or vaccinated groups at 15 days post challenge.

TABLE 3

Generation of virus neutralizing antibody in animals vaccinated with inactivated S-IBR-037 vaccine.

| | Antibody titer[a] on days: | | | | | |
|---|---|---|---|---|---|---|
| | Post Vaccination | | | | Post Challenge | |
| Animal No. | 7 | 21 | 28 | 42 | 7 | 13 |
| Controls | | | | | | |
| 9 | ≦2 | ≦2 | ≦2 | ≦2 | 4 | 4 |
| 22 | ≦2 | ≦2 | ≦2 | ≦2 | 4 | 8 |
| 32 | ≦2 | ≦2 | ≦2 | ≦2 | 4 | 16 |
| 64 | ≦2 | ≦2 | ≦2 | ≦2 | 4 | 8 |
| GMT | ≦2 | ≦2 | ≦2 | ≦2 | 4 | 8 |
| Vaccinates dose $10^{7.3}$ | | | | | | |
| 1 | ≦2 | 8 | 32 | 64 | 64 | 128 |
| 20 | ≦2 | 8 | 32 | 64 | 64 | 256 |
| 25 | ≦2 | 8 | 16 | 8 | 64 | 512 |
| 36 | ≦2 | 4 | 16 | 4 | 16 | ≧32 |
| GMT | ≦2 | 6.7 | 22.6* | 19.0* | 45.34 | 152.2 |
| Vaccinates dose $10^{8.0}$ | | | | | | |
| 7 | ≦2 | 4 | 32 | 8 | 64 | 256 |
| 30 | ≦2 | ≧8 | 64 | 128 | 128 | ≧128 |
| 33 | ≦2 | 16 | 32 | 128 | 128 | 256 |
| 69 | ≦2 | 4 | 16 | 8 | 128 | 256 |
| GMT | ≦2 | 6.7 | 32* | 32* | 107.6 | 215.3 |

*Statistically greater than controls (p ≦ 0.05)
[a]Expressed as reciprocal of dilution.

TABLE 4

Isolation of IBR virus from vaccinated and unvaccinated control animals after challenge with virulent IBR virus.

| | IBR virus isolated (+/−) from animals on days post challenge | | | | |
|---|---|---|---|---|---|
| Animal No. | 3 | 6 | 9 | 12 | 15 |
| Controls | | | | | |
| 9 | − | + | + | + | − |
| 22 | − | + | + | − | − |
| 32 | − | + | + | + | − |
| 64 | − | + | + | + | − |
| Vaccinates dose $10^{7.3}$ | | | | | |
| 1 | − | + | + | − | − |
| 20 | − | + | + | − | − |
| 25 | − | + | + | − | − |
| 36 | − | + | + | + | − |
| Vaccinates dose $10^{8.0}$ | | | | | |
| 7 | − | + | + | − | − |
| 30 | − | − | − | − | − |
| 33 | − | + | + | + | − |
| 69 | − | + | + | − | − |

TABLE 5

Vaccinated animals demonstrate reduced clinical signs of IBR.

| | Clinical scores post challenge | | | | |
|---|---|---|---|---|---|
| Animal No. | Attitude[a] | Ulcers[b] | Serious Discharge[c] | Mucopurulent Discharge[d] | Temperature[e] |
| Controls | | | | | |
| 9 | 5 | 3 | 11 | 5 | 3 |
| 22 | 2 | 2 | 12 | 3 | 1 |
| 32 | 5 | 3 | 11 | 0 | 4 |
| 64 | 6 | 3 | 11 | 1 | 1 |
| GMS | 4.5 | 2.8 | 11.3 | 2.3 | 2.3 |
| Vaccinates dose $10^{7.3}$ | | | | | |
| 1 | 0 | 2 | 1 | 0 | 0 |
| 20 | 0 | 1 | 3 | 0 | 0 |
| 25 | 0 | 2 | 6 | 2 | 0 |
| 36[f] | 6 | 2 | 1 | 13 | 0 |
| GMS | 1.5 | 1.8 | 2.8* | 2.3 | 0 |
| Vaccinates dose $10^{8.0}$ | | | | | |
| 7 | 1 | 2 | 1 | 0 | 0 |
| 30 | 1 | 2 | 2 | 2 | 0 |
| 33 | 1 | 2 | 0 | 0 | 0 |
| 69 | 1 | 2 | 0 | 0 | 0 |
| GMS | 1 | 2 | 0.8* | 0.5 | 0 |

[a]Days with depressed attitude.
[b]Number of ulcers.
[c]Days with serous discharge.
[d]Days with mucopurulent discharge.
[e]Days with ≧2° F. above baseline temperature.
[f]Animal exhibited mucopurulent discharge on the day of challenge and for 13 days post challenge.
*Statistically greater than controls (p ≦ 0.05)

Animals were observed daily for 13 days post challenge for clinical signs of IBR infection. Clinical disease was evaluated with respect to attitude, the number of ulcers, extent of serious and mucopurulent discharge and the number of days with elevated temperature. The results presented in Table 5 show that vaccinated animals exhibited less severe disease than did unvaccinated control animals. Control animals showed clinical depression ("Attitude" in Table 5) for 4.5 days compared with 1 to 1.5 days for vaccinated animals. The amount and extent of serous discharge was substantially reduced in both vaccinate groups compared with controls. The extent of mucopurulent discharge was also reduced in vaccinated animals, although to a lesser degree. However, vaccinate animal #36 did have mucopurulent discharge on the day of challenge and is not consistent with the results for other vaccinates. None of the vaccinates exhibited temperatures of $\geq 2°$ F. above baseline. In contrast, all control animals exhibited elevated temperatures of $\geq 2°$ F. over baseline and 2 of 4 control animals had temperatures of 104° F. and above.

Vaccination of calves with inactivated S-IBR-037 vaccine protected the animals against virulent wild-type IBR virus challenge. Virus neutralization titers were statistically greater in vaccinated than in control animals. An anamnestic response in antibody titer was observed 7 days post challenge, indicating the development of humoral memory response. Except for 7 days post challenge, neutralization titers between the $10^{7.3}$ and $10^{8.0}$ vaccinate groups were not statistically different. Fewer vaccinated animals shed virulent challenge virus than control animals. These results suggest that virulent IBR virus is cleared more rapidly in vaccinated than in unvaccinated animals. Clinical symptoms of IBR virus infection were also reduced in vaccinated animals. After challenge, both vaccinate groups exhibited fewer days of depressed attitude, reduced serous discharge, and no elevated temperature compared with controls.

In order to show that gG antibody is produced in vaccinated calves following exposure to wild-type virus, serum samples taken pre- and post-exposure to wild-type viruses were subjected to the ELISA assay. Samples taken at the day of challenge and at 13 days post-challenge were analyzed. As seen in Table 6, the post-challenge absorbance readings for gG increase for each animal (ratio of >1.0), indicating that within 13 days of infection a detectable immune response to gG is present.

TABLE 6

Detection of antibody to gG in serum of animals vaccinated with S-IBR-037 and challenged with wild type.

| Animal No. | Ratio of pre- vs. post challenge[a] |
|---|---|
| Controls | |
| 9 | 1.22 |
| 22 | 1.96 |
| 32 | 1.87 |
| 64 | 2.19 |
| Vaccinates dose $10^{7.3}$ | |
| 1 | 1.39 |
| 20 | 1.40 |
| 25 | 1.84 |
| 36 | 1.18 |
| Vaccinates dose $10^{8.0}$ | |
| 7 | 1.19 |
| 30 | 1.29 |
| 33 | 1.52 |
| 69 | 2.66 |

[a]Animals were challenged with $10^{7.6}$ PFU of wild type IBR virus. Pre-challenge serum from day of challenge, post-challenge serum from 13 days post challenge. Data reflects the average of the ratio of absorbance readings for three independent ELISA determinations.

Example 10
S-IBR-038

S-IBR-038 is an IBR virus that has two deletions in the short unique region of the genome. The first deletion is approximately 2500 base pairs and begins in the HindIII K fragment approximately 1750 base pairs downstream of the HindIII O/HindIII K junction and extends back through that junction. This deletion removes the US2 gene. The second deletion is approximately 294 base pairs and begins in the HindIII K fragment approximately 3900 base pairs downstream of the HindIII K/HindIII O junction and extends back toward that junction. This deletion removes amino acids 261 to 359 of the gG gene.

S-IBR-038 resulted from the removal of the marker gene from S-IBR-035 (see above). This was accomplished by digestion of S-IBR-035 with XbaI as described in the DIRECT LIGATION PROCEDURE FOR GENERATING RECOMBINANT HERPESVIRUS. The structure of S-IBR-035 was confirmed by restriction enzyme analysis with HindIII, BamHI and XbaI.

Example 11
Glycoprotein E Gene

Deletion of the PRV gI gene has been shown to be valuable both as an attenuating lesion and a negative serological marker (3,42). In the studies described below the unique short region of infectious bronchitis virus virus was shown to contain a gene homologous to the gI gene of PRV.

Figure 16A:
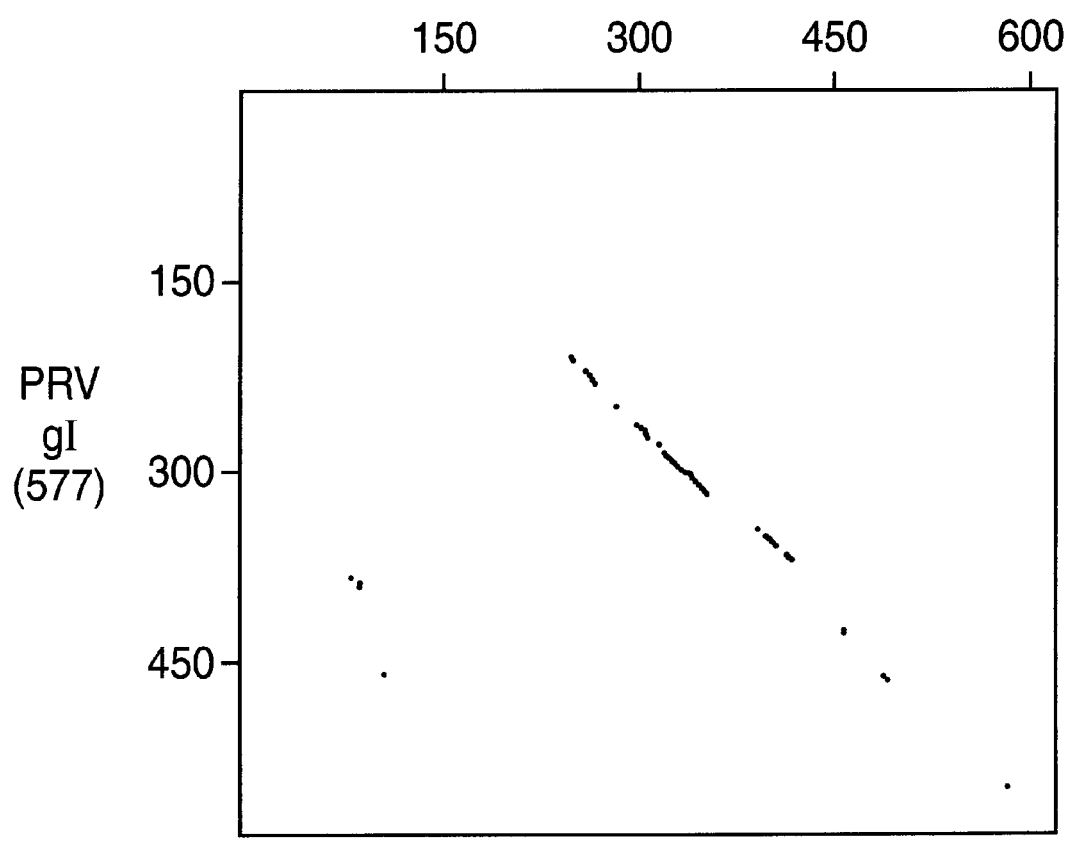
Figure 17B:
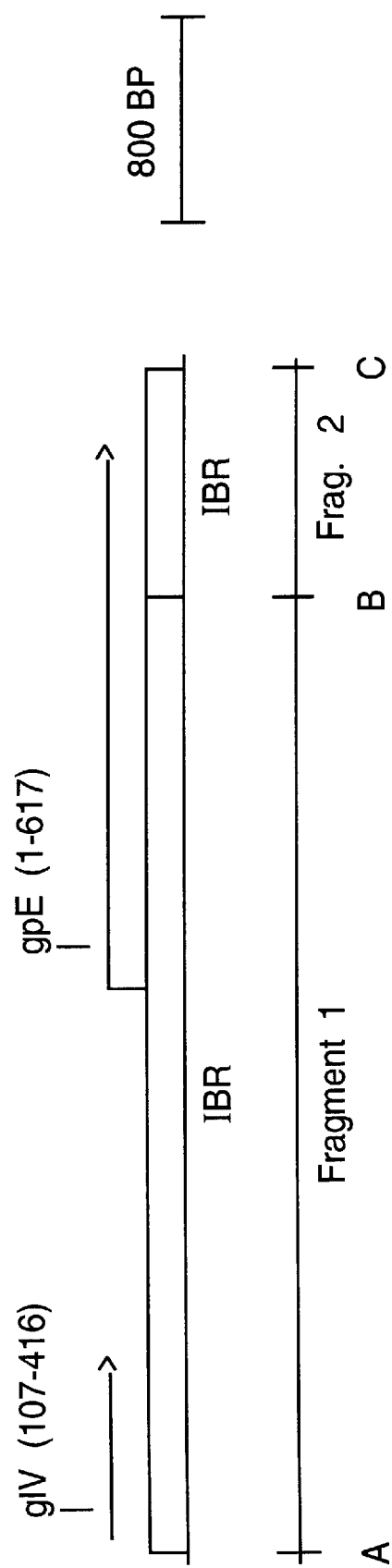
Figure 17C:
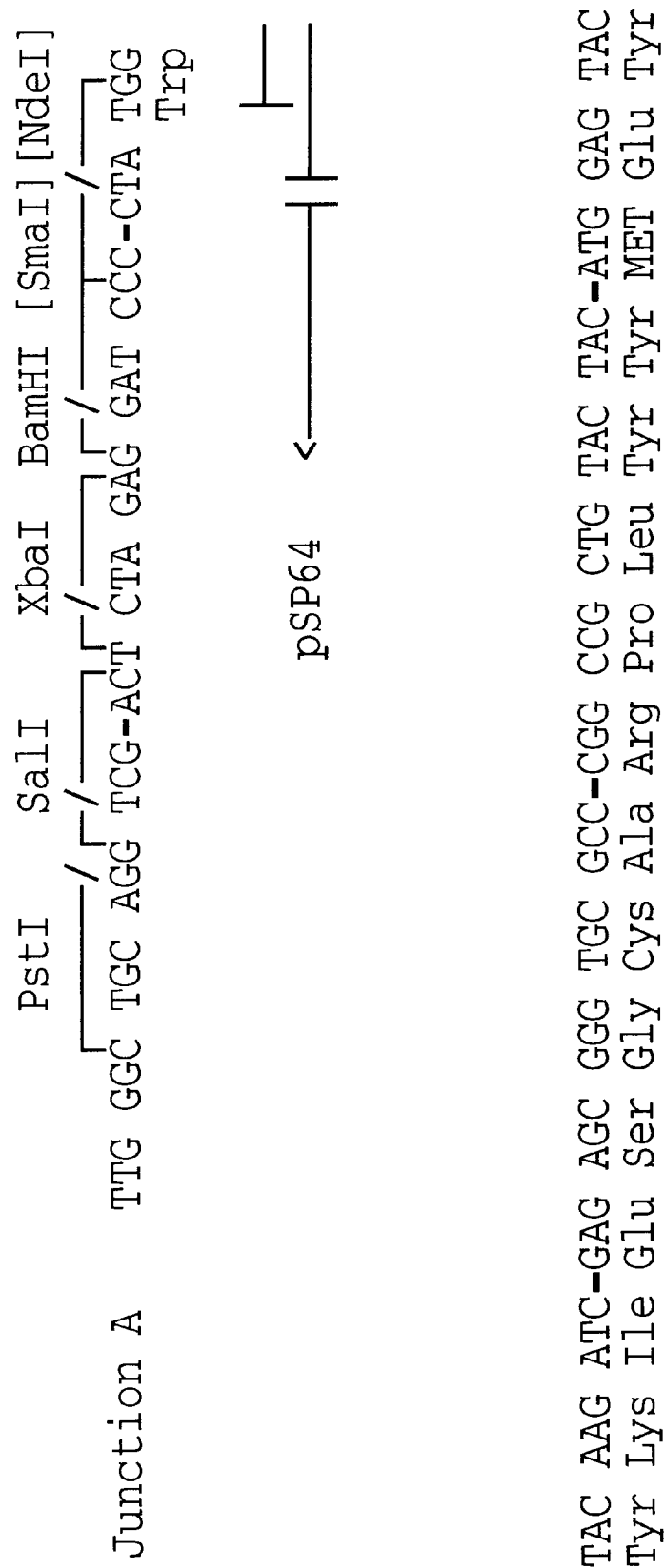
Figure 17D:
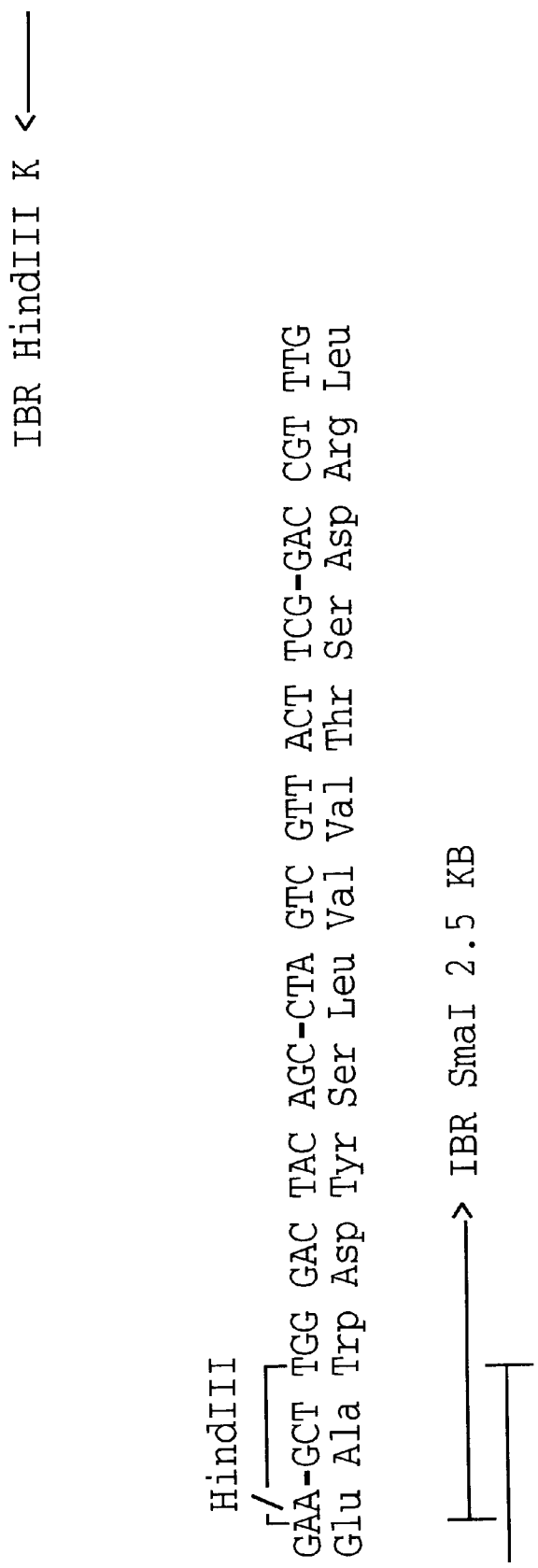
Figure 17E:
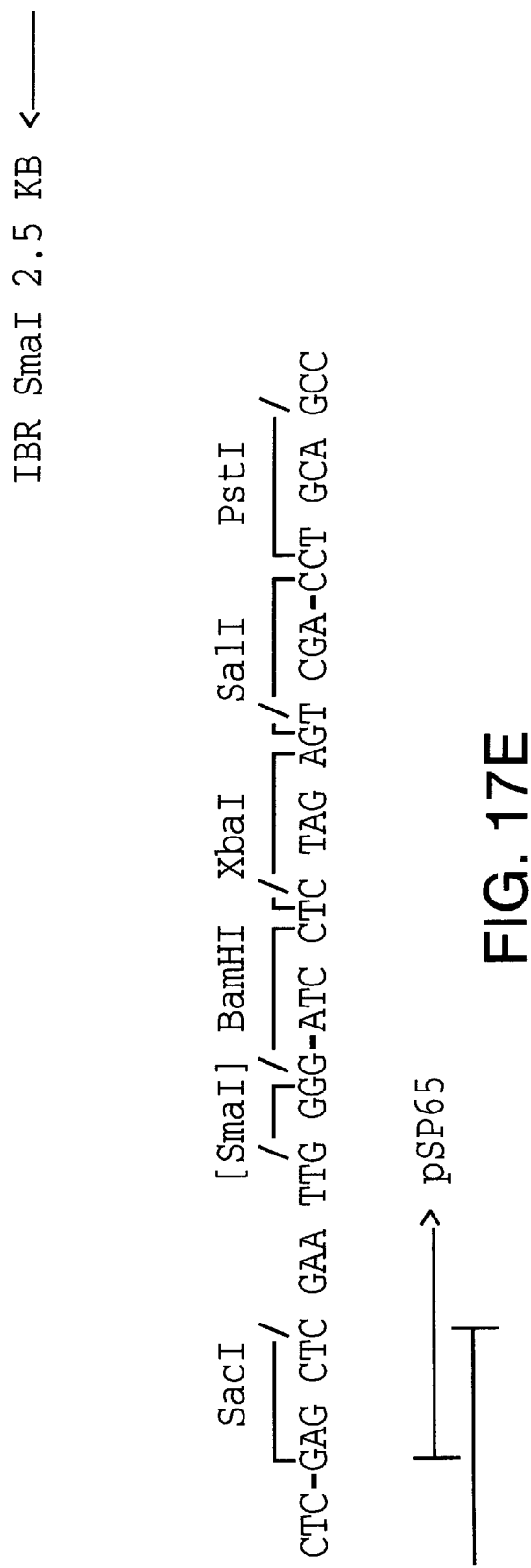
Figure 18B:
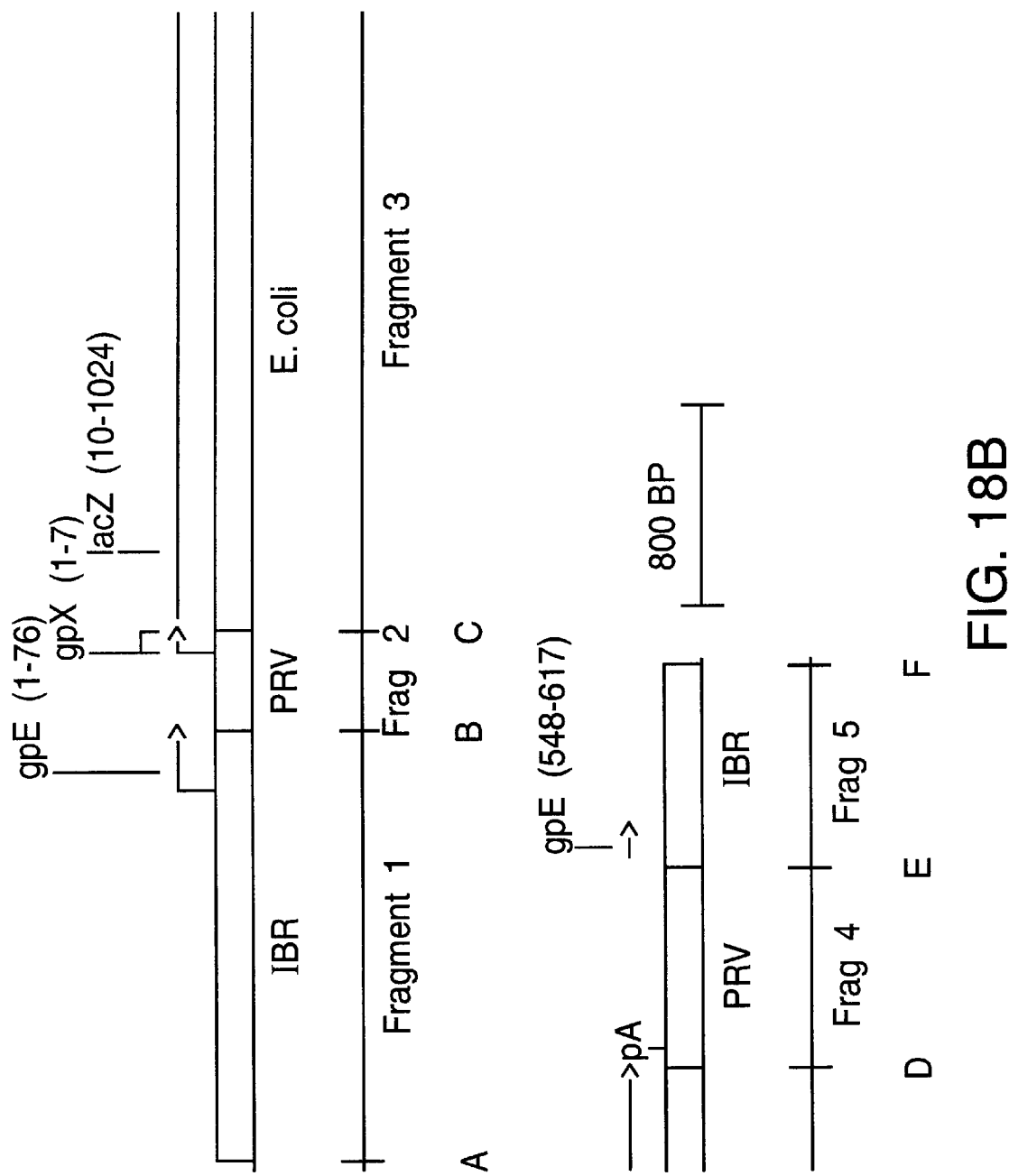
Figure 18D:
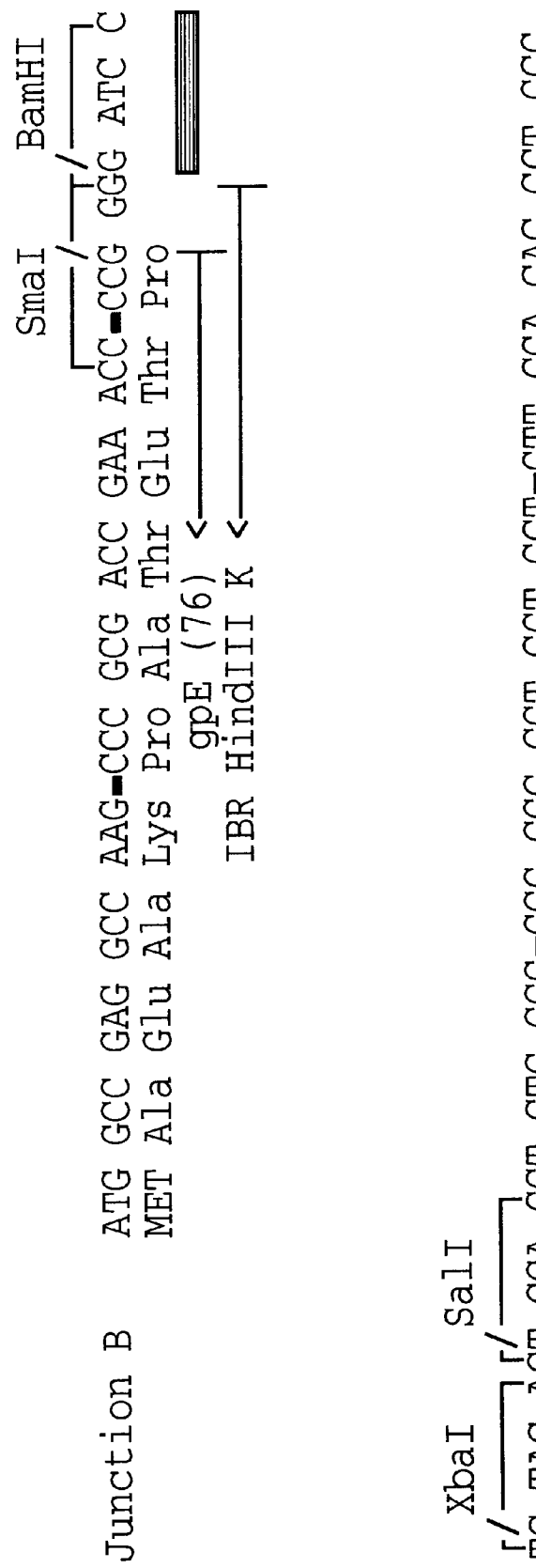
Figure 18E:
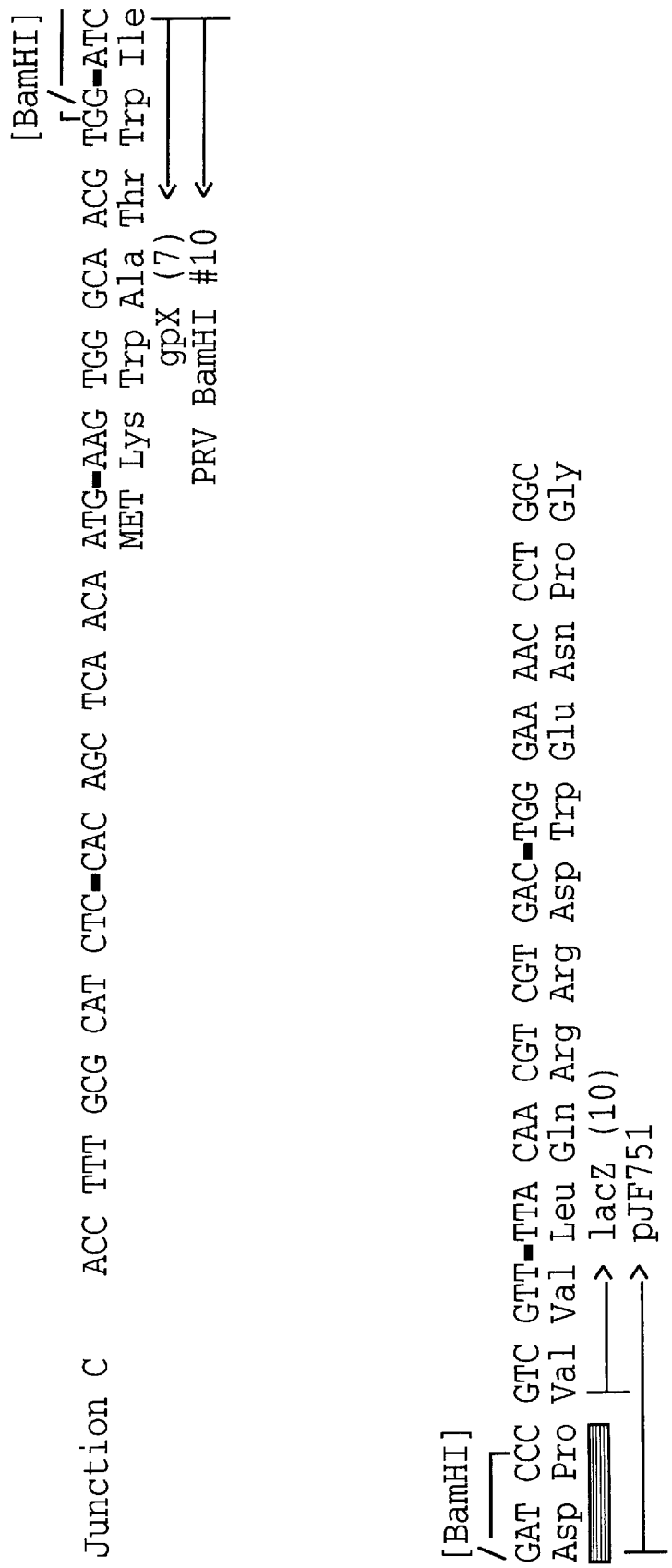
Figure 18F:
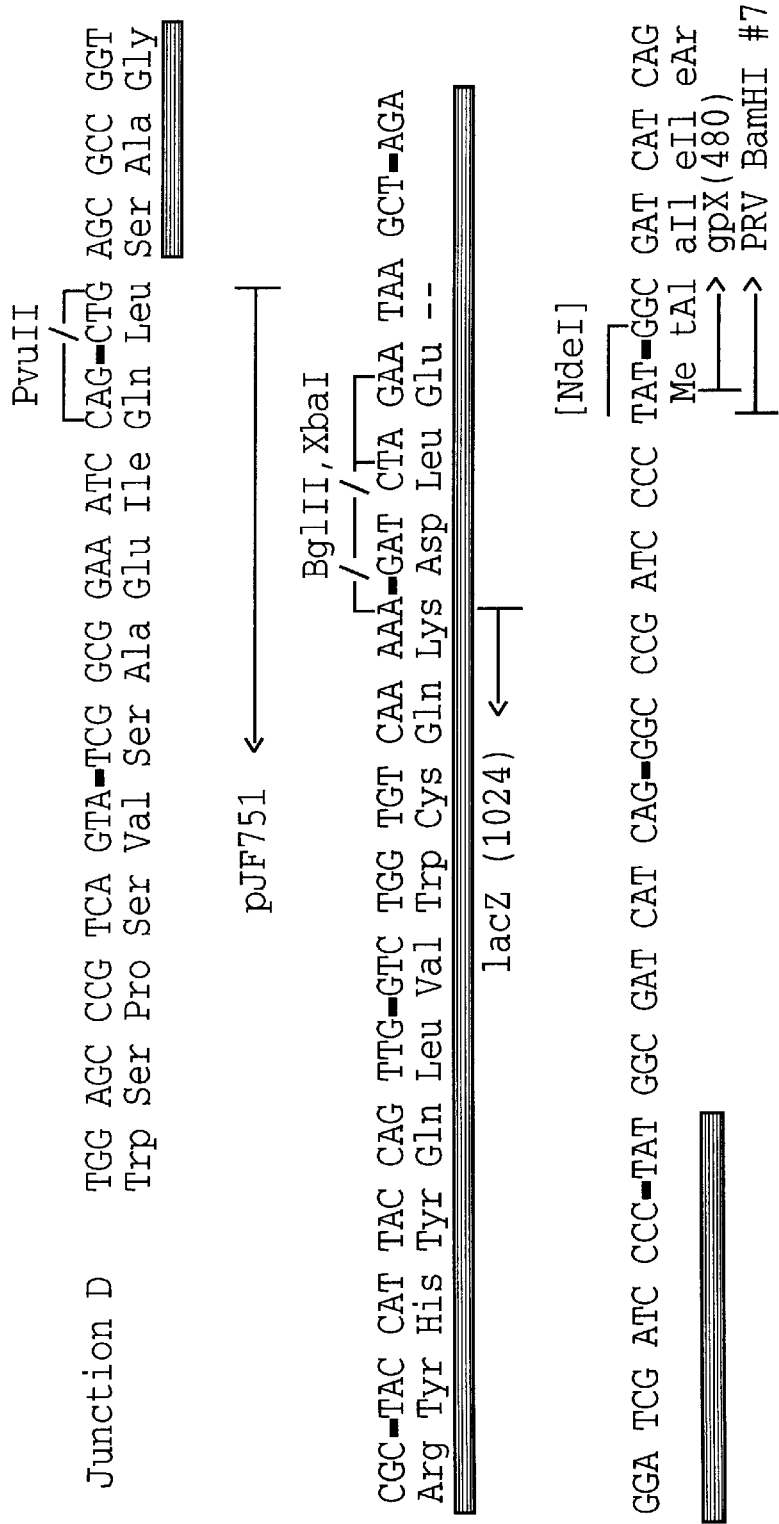
Figure 18G:
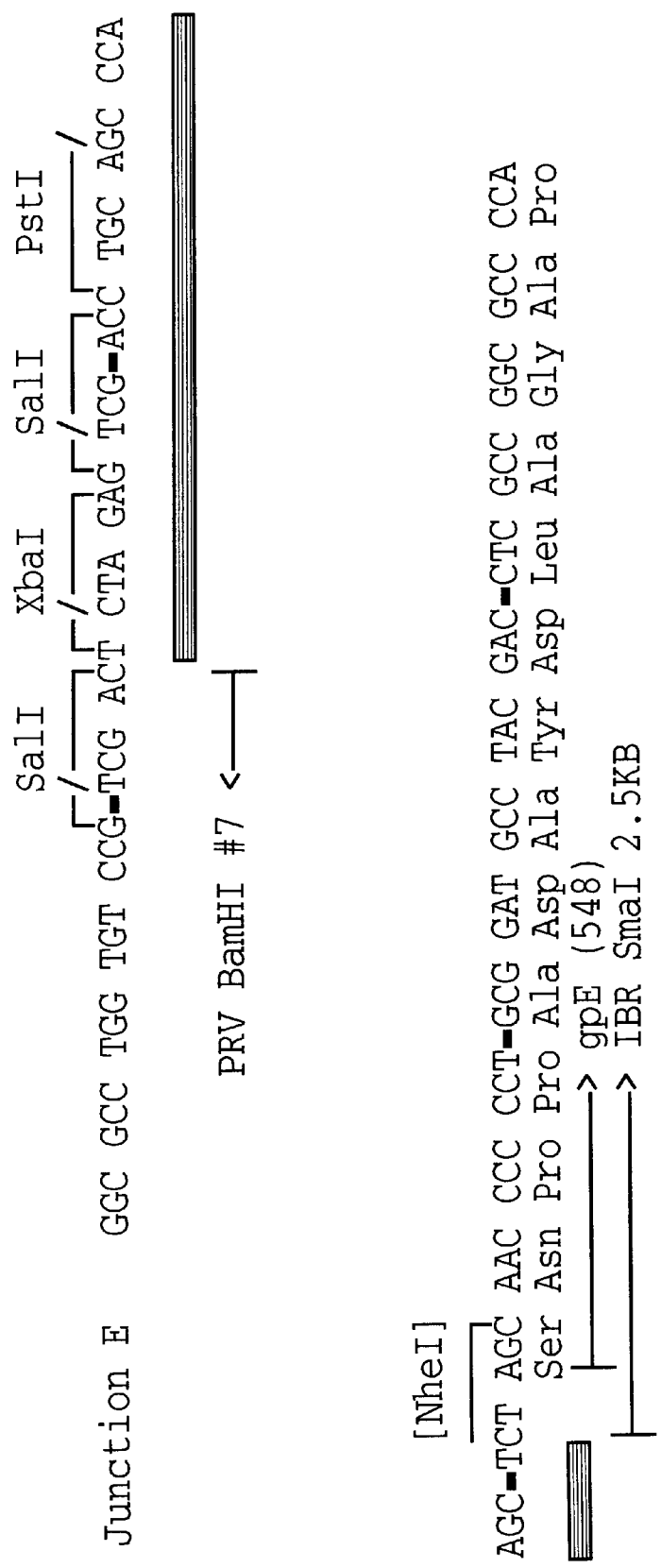

The sequence of 2038 base pairs of the IBR unique short region, starting approximately 1325 base pairs upstream of the HindIII K/HindIII F junction in the HindIII K fragment was determined. This region was found to contain an ORF coding for 617 amino acids translated in the direction away from the HindIII K/HindIII O junction (see FIG. 1). The ORF is 70.5% G+C and encodes a protein with a predicted molecular weight of approximately 88,980. Comparison of the sequence of the predicted protein with sequences of gene products of HSV-1, VZV, and PRV in the unique short region indicated that this ORF is homologous to the herpesvirus gE gene (see FIGS. 16A–16B).

The DNA encoding the gE gene has been cloned in two plasmids, PSY1644 and PSY1645. The amino-terminal half of the gene (encoding amino acids 1–276) was cloned as an approximately 2300 base pair fragment resulting from a partial SmaI digest of wild type S-IBR-000 (Cooper Strain) DNA. This fragment was inserted into the plasmid pSP64 to yield PSY1644. This plasmid, designated PSY1644, was deposited on Jul. 16, 1991 pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. 68651. The carboxyl-terminal half of the gene (encoding amino acids 277–617) was cloned as an approximately 2400 base pair SmaI fragment. The fragment was inserted into the plasmid pSP64 to yield PSY1645. This plasmid, designated PSY1645, was deposited on Jul. 16, 1991 pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. 68650. These plasmids may be used to confirm the sequence of the gE gene.

Example 12
Pseudorabies Virus Expressing IBR Virus qE

A pseudorabies virus analogous to S-PRV-160 may be constructed for the purpose of expressing the IBR virus gE.

This may be accomplished by inserting the gene coding for IBR virus gE into S-PRV-002 (U.S. Pat. No. 4,877,737).

Such an expression vector may be constructed utilizing the IBR virus gE plasmid described in the methods section, pseudorabies virus S-PRV-002 and the restriction enzyme XbaI in the DIRECT LIGATION PROCEDURE FOR GENERATING RECOMBINANT HERPESVIRUS. Viruses resulting from this procedure may be screened by digestion with XbaI for the presence of the XbaI band containing the IBR virus gE gene.

The gE protein expressed from this vector may be used as an antigen to identify antibodies directed against the wild type virus as opposed to antibodies directed against gE deleted viruses. This virus may also be utilized as an antigen for the production of gE specific monoclonal antibodies. Such antibodies are useful in the development of diagnostic tests specific for the gE protein. Monoclonal antibodies may be generated in mice utilizing this virus according to the PROCEDURE FOR GENERATING MONOCLONAL ANTIBODIES.

Example 13
Glycoprotein E Deleted IBR Viruses

The HOMOLOGY VECTOR 536-03.5 was used to generate various gE-deleted IBR viruses. Utilizing the general strategy described in CONSTRUCTION OF DELETION VIRUSES, a gE deletion of approximately 1410 base pairs (amino acids 77–547) was introduced into two different IBR virus backbones, S-IBR-000 (Cooper Strain) and S-IBR-037. The virus resulting from the S-IBR-000 parent contains the gE deletion alone. The virus resulting from the S-IBR-037 parent contains the gE deletion in conjunction with the US2 and gG deletions. The lacZ marker gene may be removed from these viruses utilizing the procedures outlined in the methods section.

These gE-deleted viruses are of great value as IBR vaccines. Their combination of different deletions will provide the varying degrees of attenuation which are required for a superior vaccine. These viruses will also provide a negative serological marker which may be used to distinguish vaccinated from infected animals. The virus containing both gG and gE deletions should be of even greater value by having two negative markers. The availability of two negative markers permits one marker to be used as a confirmatory test, greatly increasing the reliability of such a diagnostic determination.

Example 14
S-IBR-004

S-IBR-004 is an IBR recombinant virus carrying an inserted foreign gene, Tn5 NEO (aminoglycoside 3'-phosphotransferase) gene, under the control of the pseudorabies virus (PRV) glycoprotein X promoter.

Figure 19:
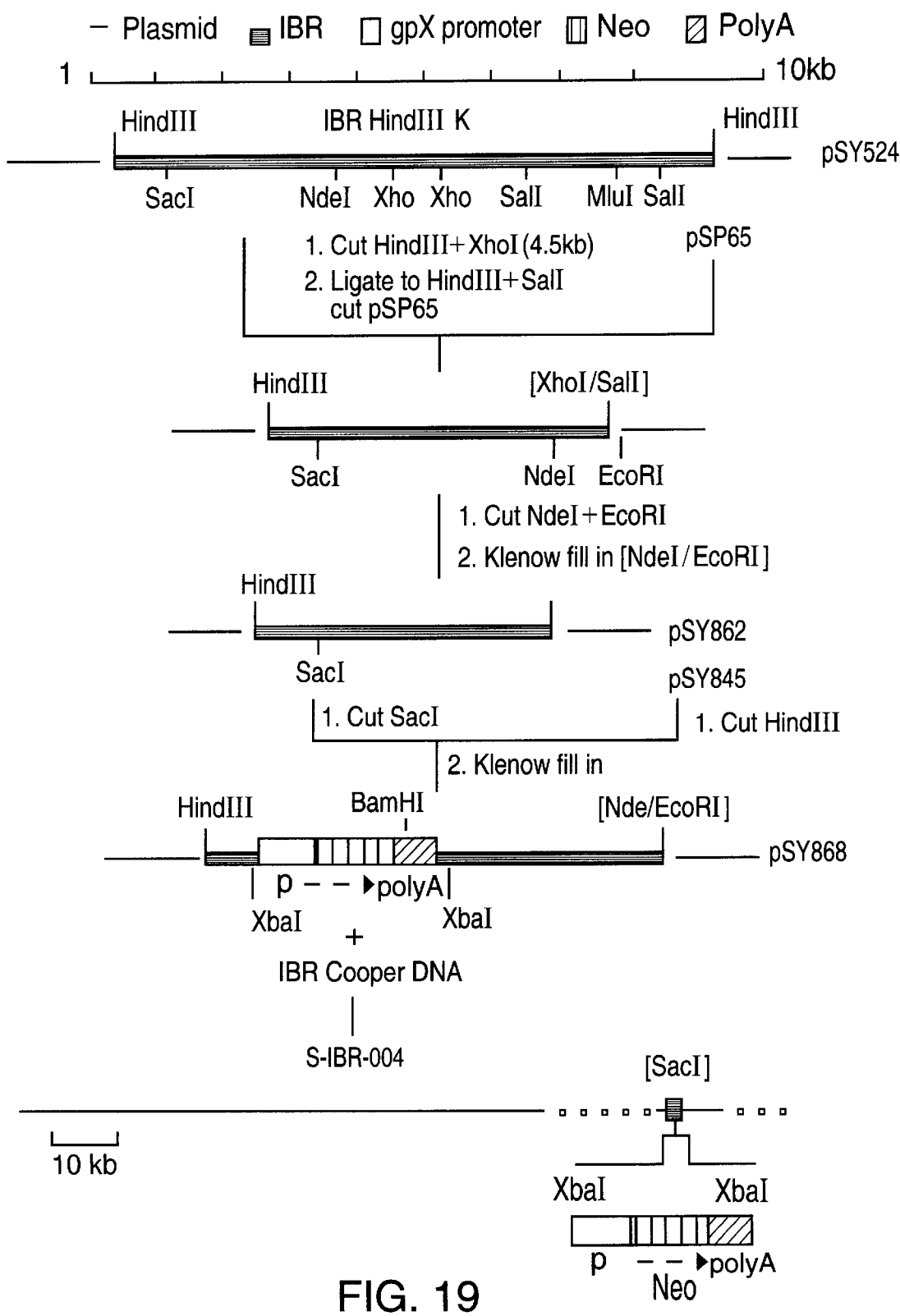

To construct this virus, the HindIII K DNA fragment from wild type IBR virus was cloned into the plasmid pSP64 at the HindIII site. This plasmid was designated pSY524. A map of the HindIII K fragment is shown in FIG. 19. The DNA from the XhoI site to the HindIII site and containing the NdeI site from pSY524 was cloned into plasmid pSP65 and called pSY846. The NdeI to EcoRI fragment was removed from pSY846 by digestion with NdeI and EcoRI restriction enzymes, followed by POLYMERASE FILL-IN REACTION and LIGATION. The resulting plasmid was called pSY862. The plasmid pNEO (P.L. Biochemicals, Inc.) contains the aminoglycoside 3'-phosphotransferase (NEO) gene and confers resistance to ampicillin and neomycin on *E. coli* hosts. The coding region of this gene (BglII-BamHI fragment) was isolated and cloned between the PRV gX promoter and the HSV-TK poly A sequence in a plasmid called pSY845.

The NEO gene construct in pSY845 was excised with HindIII, made blunt ended by the POLYMERASE FILL-IN REACTION, and cloned into the SacI site of plasmid pSY862. The final product was called pSY868.

Wild type IBR DNA was mixed with pSY868 DNA and the mixture was transfected into rabbit skin cells to generate recombinant IBR. The recombinant IBR virus carrying a functional NEO gene was then isolated and purified according to the SELECTION OF G418 RESISTANT IBR VIRUS method.

S-IBR-004 recombinant IBR was shown to express the NEO gene by the fact that cells infected with this virus were resistant to the toxicity of G418. A detailed map of the plasmid construction is shown in FIG. 19. The structure of S-IBR-004 is also shown in FIG. 19. S-IBR-004 was deposited on May 23, 1986 pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. VR 2134.

Example 15
S-IBR-008

S-IBR-008 is an IBR virus that has a deletion in the short unique region, and an insertion of the bovine rotavirus glycoprotein 38 (g38) gene in the XbaI site in the long unique region. The Xba I site is located in the intergenic region upstream of the lactency-related transcripts promoter and downstream of a potential ORF.

Figure 20:
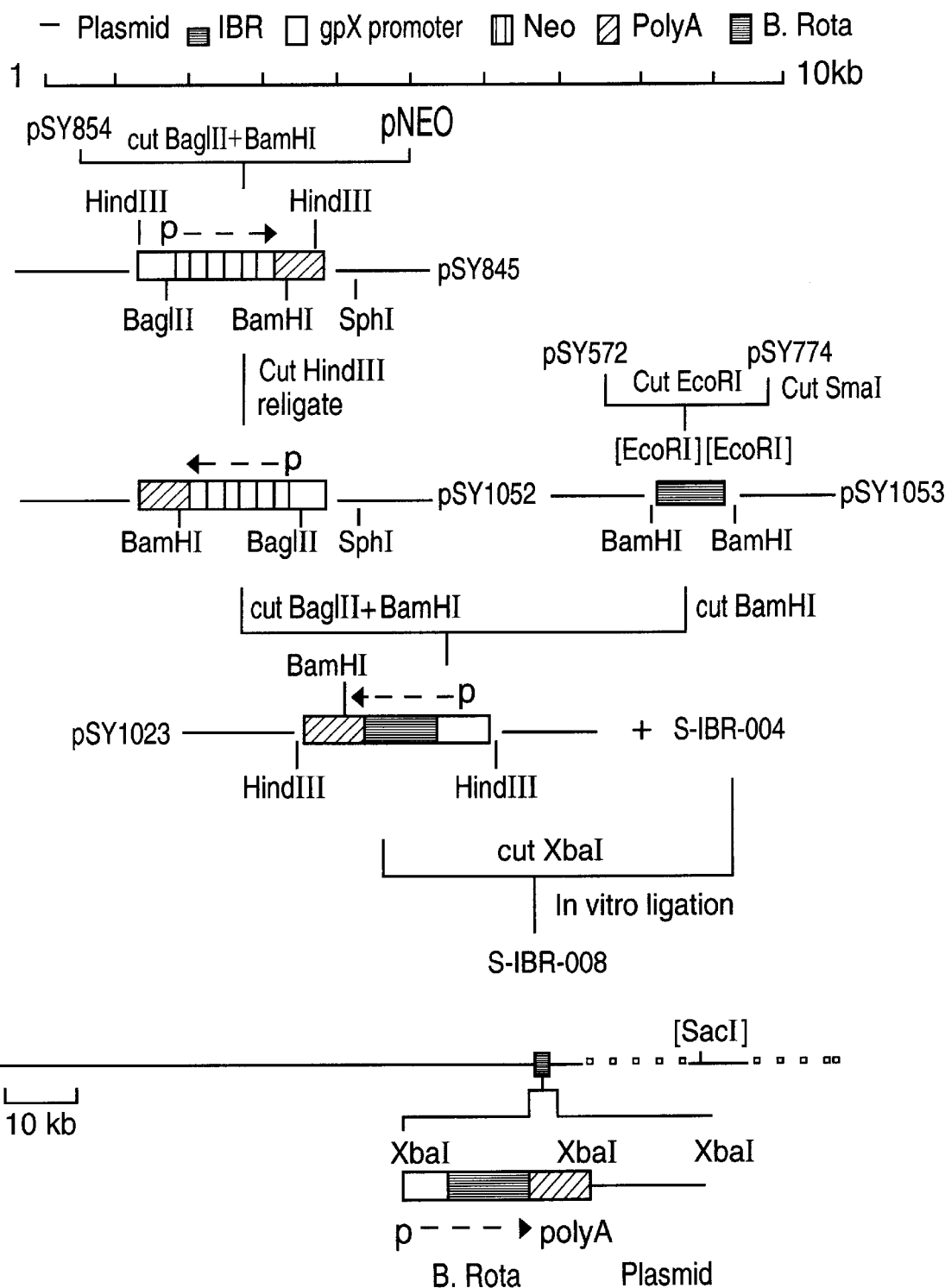
Figure 22A:
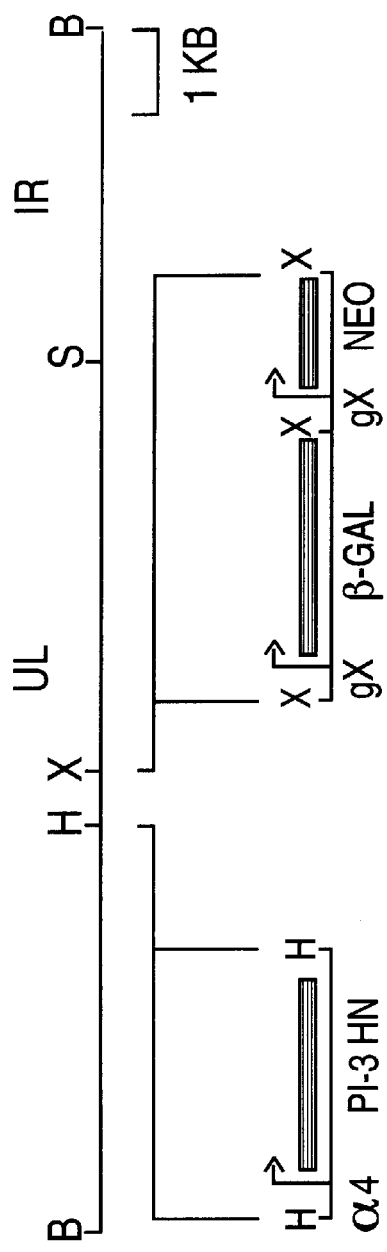
Figure 22B:
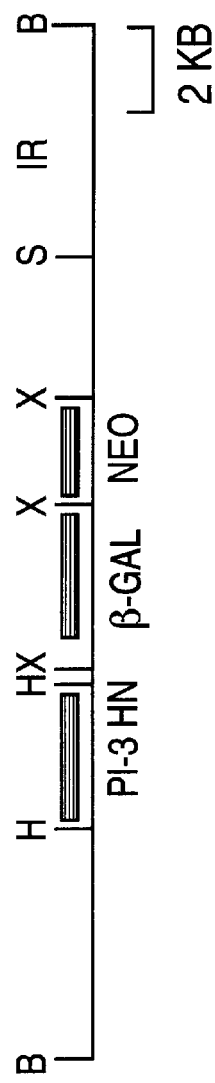
Figure 22C:
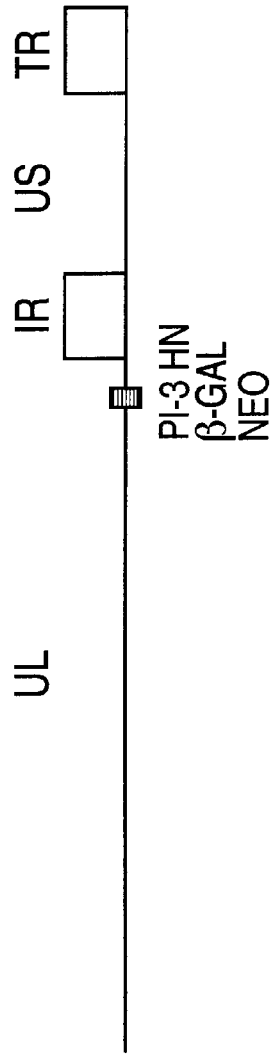
Figure 23A:
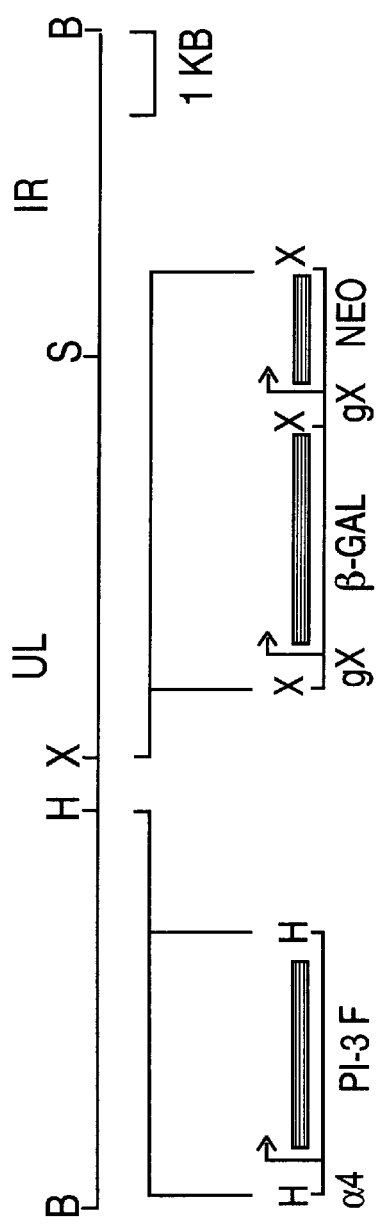
Figure 23B:
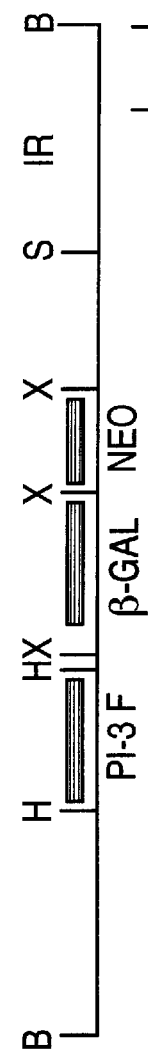
Figure 23C:
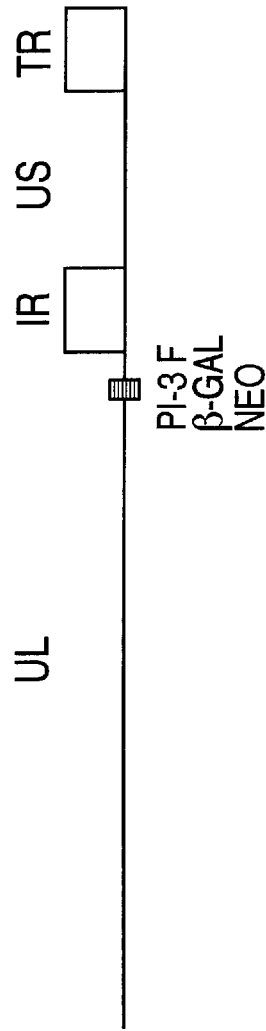
Figure 24:
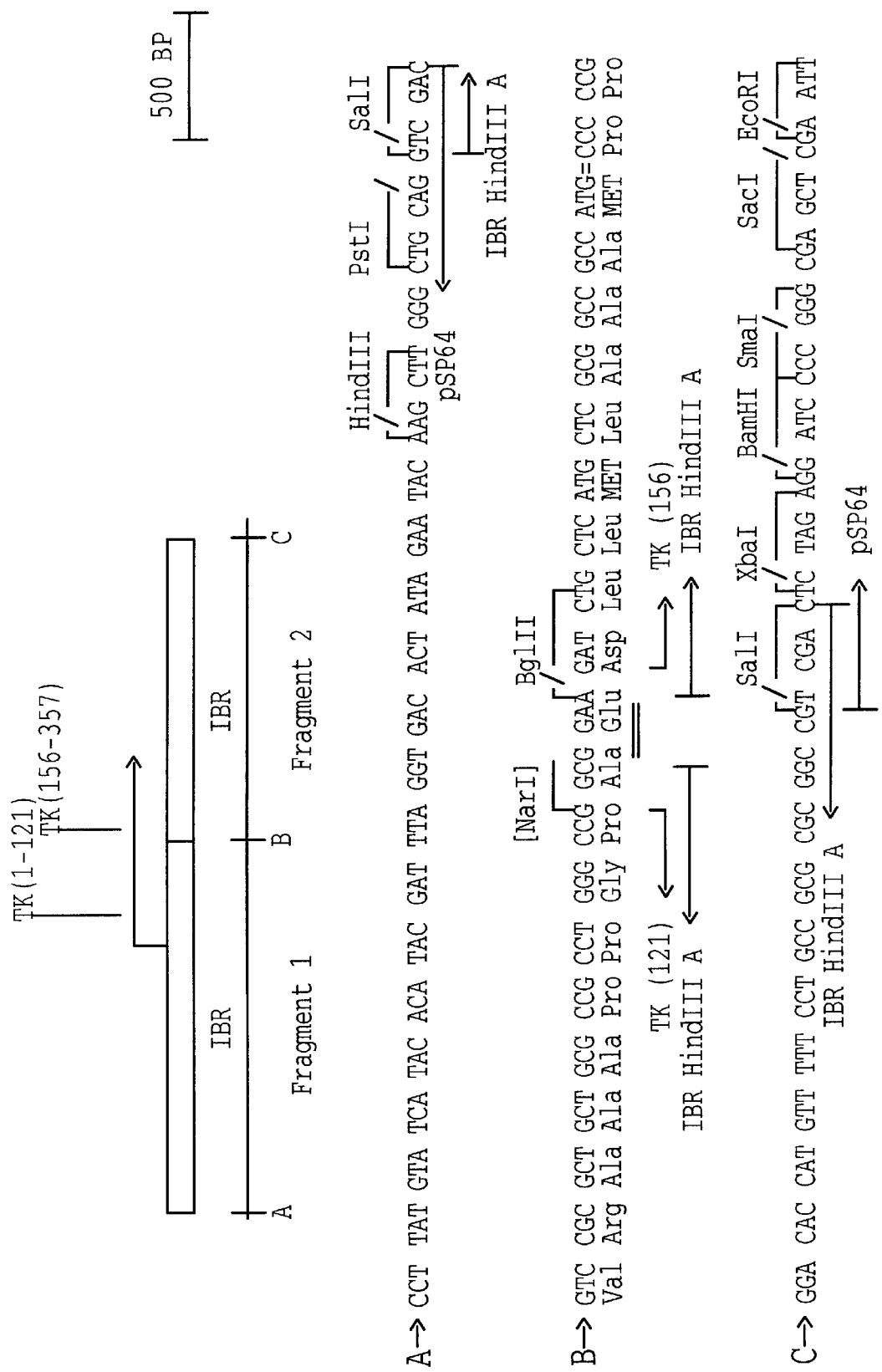
Figures 25, 25A:
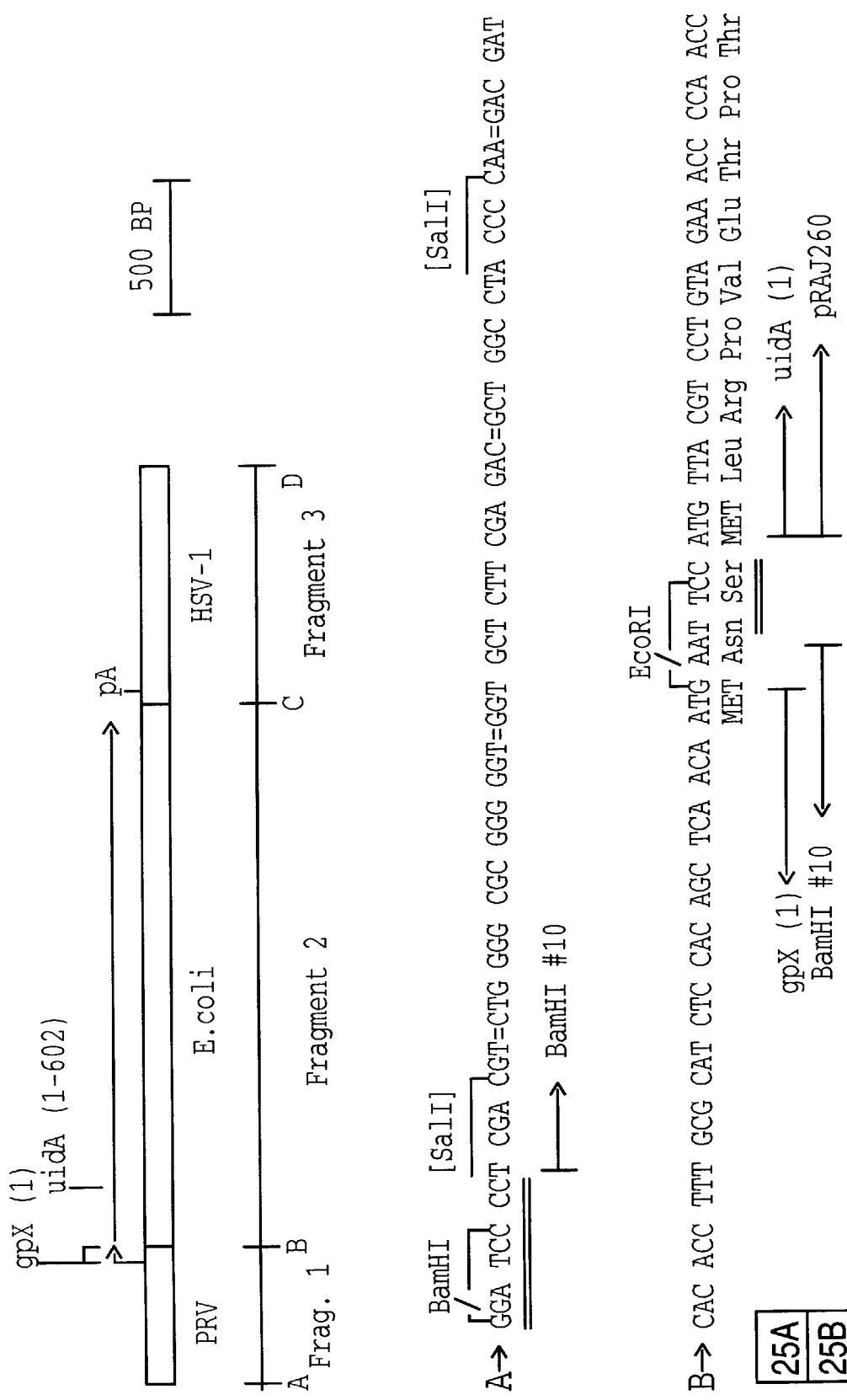
Figure 25B:
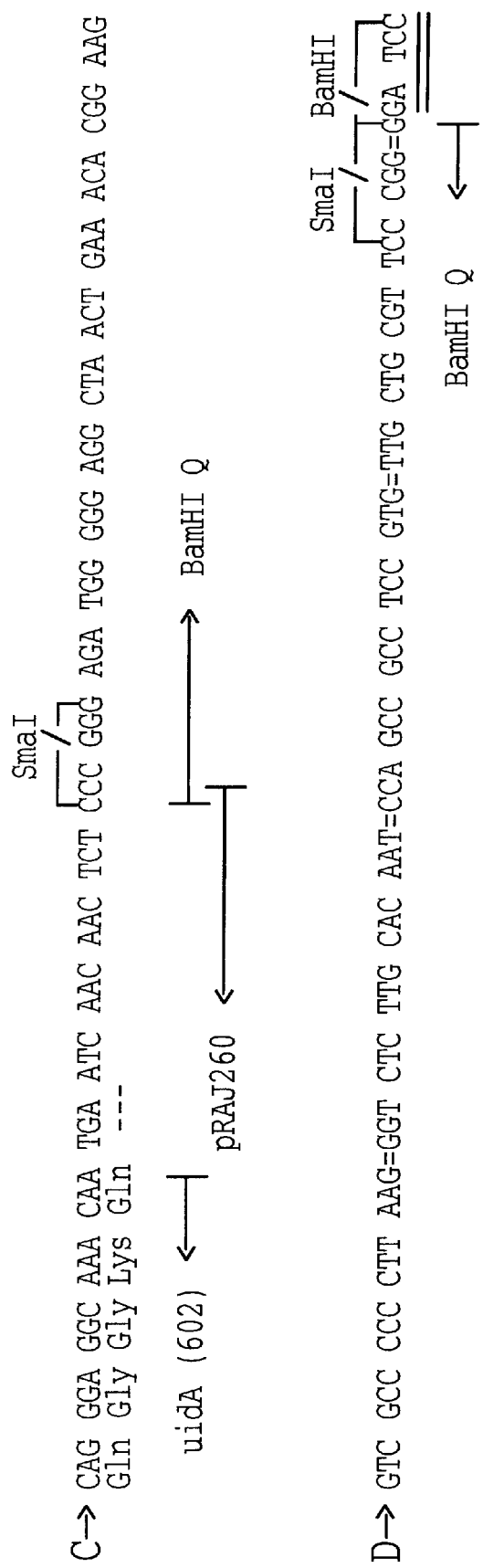
Figures 26, 26A:
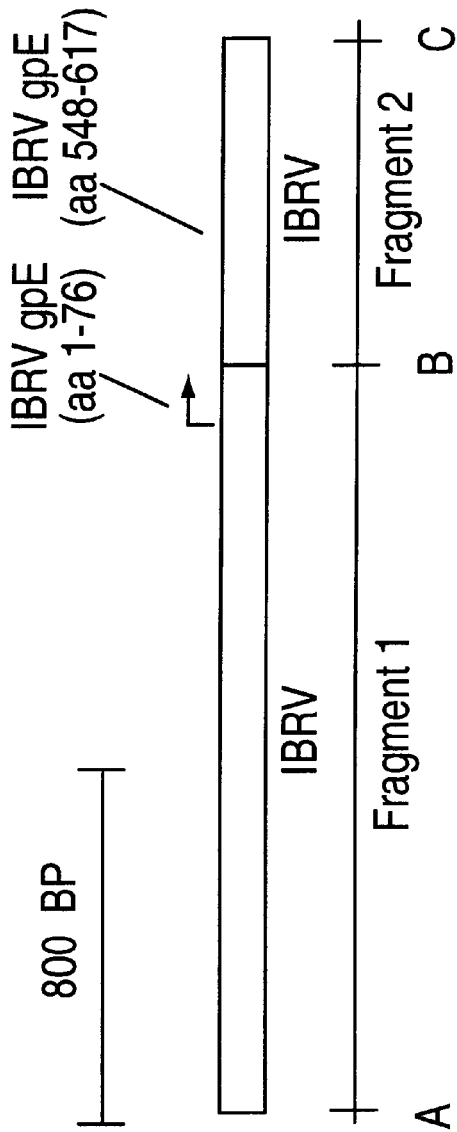
Figure 26B:
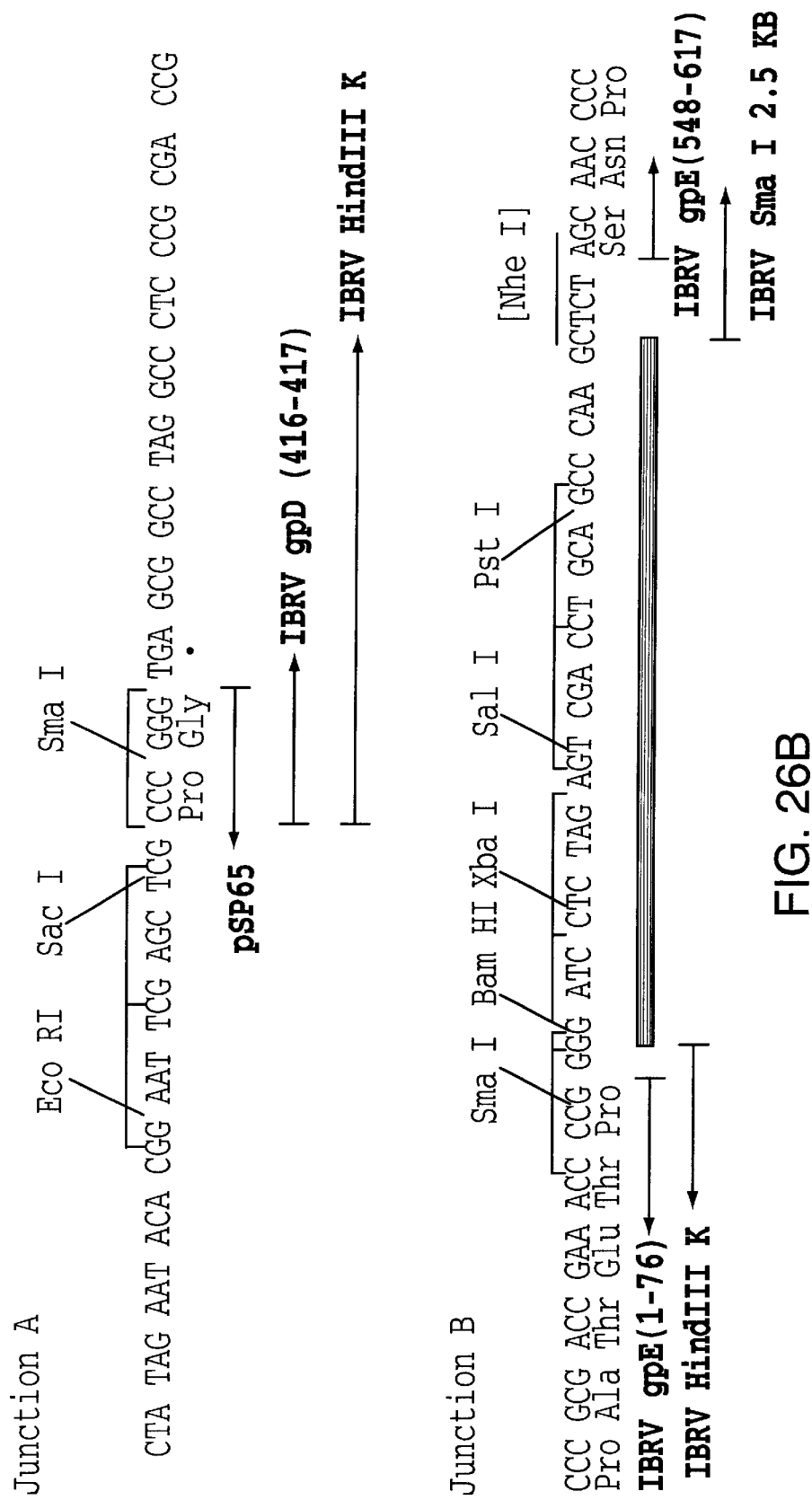

The bovine rotavirus g38 gene was cloned utilizing the METHOD FOR cDNA CLONING BOVINE ROTAVIRUS g38 GENE. The bovine rotavirus g38 gene was then engineered to contain herpesvirus regulatory signals as shown in FIG. 20. This was accomplished by cloning the g38 gene BamHI fragment contained in pSY1053 between the BamHI and BglII sites in pSY1052. The resulting plasmid, pSY1023, contained the PRV gX promoter in front of the g38 gene, and the HSV-1 TK polyadenylation signal behind the g38 gene. The entire construct was flanked by XbaI sites to allow for the insertion of the XbaI fragment into IBR by direct ligation.

S-IBR-004 was the starting virus for the generation of S-IBR-008. S-IBR-004 DNA and pSY1023 DNA were mixed together, cut with XbaI, and transfected into rabbit skin cells according to the DIRECT LIGATION PROCEDURE FOR GENERATING RECOMBINANT HERPESVIRUS. The transfection stock was screened for recombinant virus by the ANTIBODY SCREEN FOR RECOMBINANT HERPESVIRUS procedure using antibodies prepared against the rotavirus g38 protein.

One of the viruses purified by this screen was S-IBR-008, which has the following characteristics. It contains the rotavirus g38 gene plus the plasmid DNA inserted into the XbaI site in the long unique region of the virus genome, but no longer contains the NEO gene of parent S-IBR-004 in the unique short region. In fact, a small deletion was created in the unique short region at the location of the NEO gene, as evidenced by the absence of an XbaI site at this location in S-IBR-008.

S-IBR-008 was shown to be expressing the rotavirus g38 gene by analysis of RNA transcription in infected cells, and by the ANTIBODY SCREEN FOR RECOMBINANT HERPESVIRUS procedure using antibodies specific for the g38 gene. S-IBR-008 was deposited on Jun. 18, 1986 pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. VR 2141. The structure of S-IBR-008 is shown in FIG. 20.

Example 16

S-IBR-018

S-IBR-018 is an IBR virus that has three foreign genes inserted: the E. coli beta-galactosidase gene and the neomycin resistance gene in the XbaI site in the unique long region, and the parainfluenza type 3 (PI-3) virus (ATCC No. VR-281) hemagglutinin gene (HN) in the HindIII site in the unique long region adjacent to the Xba I site. The Xba I site is located in the intergenic region upstream of the lactency-related transcripts promoter and downstream of a potential ORF. The Hind III site is located within a potential ORF upstream of the latency-related transcripts.

For cloning the PI-3 HN gene, the SF-4 strain of PI-3 was grown in MADIN-DARBY bovine kidney (MDBK) cells in culture and RNA was extracted from infected cells. The RNA was used in a reverse transcription protocol as outlined in the cDNA CLONING procedure using poly-dT as primer for reverse transcriptase. From this procedure, a series of clones was obtained that comprised parts of the genome of the PI-3 virus. The location of the gene for the human PI-3 HN gene has been published (25,26) and this information was used to locate the gene in applicants' bovine PI-3 clones. The entire open reading frame of the bovine PI-3 HN gene was sequenced by applicants and is given in FIGS. 21A–21B.

The HSV ICP4 promoter was used to express the PI-3 HN gene and the HSV TK poly-A signal was used to terminate transcription. The engineering of this construct was done as shown in FIGS. 22A–22C. The construct contained (5' to 3') the HSV ICP4 promoter, the ICP4 TATA box, the ICP4 cap site, a fusion within the ICP4 5' untranslated region to the PI-3 HN gene at the HhaI site, the HN gene start codon, the HN structural gene, the HN stop codon, a fusion within the HN 3' untranslated region to the HSV TK untranslated 3' region, and the HSV TK poly-A signal sequence.

This plasmid also contained the beta-galactosidase (lacZ) gene under the control of the PRV gX promoter with the gX poly-A termination signal, as well as the neomycin resistance gene under the control of the gX promoter with the TK poly-A termination signal. These latter two genes were cloned in tandem at the XbaI site in BamHI-C fragment (FIGS. 22A–22C). This BamHI-C fragment contained the homology regions for use in the DNA TRANSFECTION FOR GENERATING RECOMBINANT VIRUS procedure. After the transfection step in the procedure, the resulting recombinant virus from the transfection stock was selected for by the SELECTION OF G418 RESISTANT IBR VIRUS procedure, followed by the BLUOGAL™ SCREEN FOR RECOMBINANT HERPESVIRUS procedure, and subsequently analyzed for the insertion of the PI-3 HN gene by the SOUTHERN BLOTTING OF DNA procedure. The virus that resulted from this screening was designated S-IBR-018.

S-IBR-018 was deposited on Jul. 21, 1987 pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. VR 2180. The structure of S-IBR-018 is shown in FIGS. 22A–22C.

Example 17

S-IBR-019

S-IBR-019 is an IBR virus that has three foreign genes inserted: the *E. coli* beta-galactosidase (lacZ) gene and the neomycin resistance gene in the XbaI site in the unique long region, and the parainfluenza type 3 (PI-3) virus fusion gene (F) in the HindIII site in the long unique region adjacent to the XbaI site.

For cloning the PI-3 F gene, the SF-4 strain of PI-3 was grown in MDBK cells in culture and RNA was extracted from infected cells. The RNA was used in a reverse transcription protocol as outlined in the cDNA CLONING procedure using poly-dT as primer for reverse transcriptase. From this procedure, a series of clones was obtained that comprised parts of the genome of the PI-3 virus. The location of the gene for the Sendai virus F gene has been published (27) and this comparative sequence information was used to locate the homologous gene in applicants' bovine PI-3 clones.

The HSV alpha-4 promoter was used to express the PI-3 F gene and the HSV TK poly-A signal was used to terminate transcription. The construct contained (5' to 3') the HSV alpha-4 promoter, the alpha-4 TATA box, the alpha-4 cap site, a fusion in the alpha-4 5' untranslated region to the PI-3 F gene, the F start codon, the F structural gene, the F stop codon, a fusion in the F 3' untranslated region to the HSV TK 3' untranslated region, and the TK poly-A signal sequence.

This plasmid also contained the beta-galactosidase (lacZ) gene under the control of the PRV gX promoter with the gX poly-A termination signal, as well as the neomycin resistance gene under the control of the gX promoter with the TK poly-A termination signal. These latter two genes were cloned in tandem at the XbaI site in BamHI-C fragment (FIGS. 23A–23C). This BamHI-C fragment contained the homology regions for use in the DNA TRANSFECTION FOR GENERATING RECOMBINANT VIRUS procedure. After the transfection step in the procedure, the resulting recombinant virus from the transfection stock was selected for by the SELECTION OF G418 RESISTANT HERPESVIRUS procedure, followed by the BLUOGAL™ SCREEN FOR RECOMBINANT HERPESVIRUS procedure, and subsequently analyzed for the insertion of the PI-3 F gene by SOUTHERN BLOTTING OF DNA procedure. The virus that resulted from this screening was designated S-IBR-019.

The structure of S-IBR-019 is shown in FIGS. 23A–23C.

Example 18

S-IBR-032

S-IBR-032 is an IBR virus that has two foreign genes inserted: the *Escherichia coli* beta-galactosidase (lacZ) gene with the bovine viral diarrhea virus (BVDV) g53 gene fused to the lacZ C-terminus and inserted in the long unique region at the XbaI restriction endonuclease site.

For cloning the BVDV g53 gene, the Singer strain of BVDV was grown in MADIN-DARBY bovine kidney (MDBK) cells in culture and the RNA was extracted from infected cells. The RNA was used in a reverse transcriptase procedure as outlined in the cDNA CLONING procedure using random primers for reverse transcriptase. From this procedure, a series of clones was obtained that comprised parts of the genome of BVDV. The location of the gene for BVDV g53 has been published (66) and this comparative sequence information was used to locate the homologous gene in the applicant's BVDV clones.

The PRV gX promoter was used to express lacZ with a region of BVDV g53 fused to the C-terminus, and the PRV poly-A signal was used to terminate transcription. A plasmid construct was engineered that contained (5' to 3') the PRV gX promoter and then the coding region consisting of amino acid codons 1–7 of the PRV gX gene, 10–1024 of the *Escherichia coli* lacZ gene, and 684–758 of the BVDV major open reading frame, and the PRV poly-A sequence.

This lacZ fusion gene cassette was then excised from the plasmid vector at the flanking XbaI sites and cloned into the unique XbaI site in IBR-002 using the in vitro ligation method described in CONSTRUCTION OF DELETION VIRUSES. After the transfection step in DNA TRANSFECTION FOR GENERATING RECOMBINANT VIRUS procedure, the resulting recombinant virus was screened and isolated from the transfection stock using the BLUOGAL™ SCREEN FOR RECOMBINANT HERPESVIRUS procedure, and subsequently analyzed for the insertion of the BVDV g53 region by SOUTHERN BLOTTING OF DNA procedure. The virus that resulted from this screening was designated S-IBR-032.

Example 19

S-IBR-039

S-IBR-039 is an IBR virus that has three deletions in the short unique region of the genome. The first deletion is approximately 2500 base pairs and begins in the HindIII K fragment approximately 1750 base pairs downstream of the HindIII O/HindIII K junction and extends back through that junction. This deletion removes the US2 gene. The second deletion is approximately 1230 base pairs and begins in the HindIII K fragment approximately 3900 base pairs downstream of the HindIII O/Hind K junction and extends back toward that junction. This deletion removes amino acids 1 to 361 of the gG gene. The third deletion is approximately 1410 base pairs and removes amino acids 77–547 of the gE gene.

S-IBR-039 was derived from S-IBR-037. This was accomplished utilizing the homology vector 536-03.5 (see MATERIALS AND METHODS) and virus S-IBR-037 in the HOMOLOGOUS RECOMBINATION PROCEDURE FOR GENERATING RECOMBINANT HERPESVIRUS. The transfection stock was screened by the SCREEN FOR RECOMBINANT HERPESVIRUS EXPRESSING ENZYMATIC MARKER GENES. The result of blue plaque purification was the recombinant virus designated S-IBR-039. This virus was characterized by restriction mapping and the SOUTHERN BLOTTING DNA procedure. This analysis confirmed the insertion of the β-galactosidase (lacZ) marker gene and the deletion of approximately 1230 base pairs of the gG gene. It was also confirmed that an approximately 1410 base pair deletion has occurred in the region of the gE gene (see above).

S-IBR-039 contains a deletion in the IBRV US2 gene which not only attenuates the virus but also has an unexpected effect of rendering the virus fetal safe. Therefore, S-IBR-039 can be formulated into a vaccine which is superior from other IBRV vaccines in that in addition to being safe and effective in protecting cattle from infections with IBR virus, it is also safe for use in pregnant animals.

Such vaccine comprises an effective immunizing amount of S-IBR-039 and a suitable carrier. This vaccine may contain either inactivated or live infectious bovine rhinotracheitis virus S-IBR-039.

Suitable carriers for the infectious bovine rhinotracheitis virus are well known in the art and include proteins, sugars, etc. One example of such a suitable carrier is a physiologically balanced culture medium containing one or more stabilizing agents such as stabilized, hydrolyzed proteins, lactose, etc.

In general, the vaccine of this invention contains an effective immunizing amount of S-IBR-039 virus from about $10^3$ to $10^8$ PFU/dose. Preferably, the effective immunizing amount is from about $10^4$ to $10^7$ PFU/dose for the live vaccine. Preferably, the live vaccine is created by taking tissue culture fluids and adding stabilizing agents such as stabilized, hydrolyzed proteins. Preferably, the inactivated vaccine uses tissue culture fluids directly after inactivation of the virus.

The present invention also provides a method of immunizing an animal, particularly a bovine, against disease caused by infectious bovine rhinotracheitis virus which comprises administering to the animal an effective immunizing dose of the vaccine comprising S-IBR-039. The vaccine may be administered by any of the methods well known to those skilled in the art, for example, by intramuscular, subcutaneous, intraperitoneal or intravenous injection. Alternatively, the vaccine may be administered intranasally or orally.

Another notable characteristic of S-IBR-039 is that it contains deletions in the gG and gE genes so that no functional gG or gE is produced upon viral replication. Said deletions in gG and gE, therefore, provides two negative serological markers for differentiating the virus from naturally-occurring IBR virus.

Accordingly, the present invention also provides a method for distinguishing an animal vaccinated with the infectious bovine rhinotracheitis virus S-IBR-039 from an animal infected with naturally-occurring infectious bovine rhinotracheitis virus. This method comprises analyzing a sample of a body fluid from the animal for the presence of IBRV gG or gE and at least one other antigen which is normally expressed in an animal infected by a naturally-occurring infectious bovine rhinotracheitis virus and determining whether the antigen and gG or gE are present in the body fluid. The presence of the antigen and the absence of gG or gE in the body fluid is indicative of an animal vaccinated with the vaccine and not infected with a naturally-occurring infectious bovine rhinotracheitis virus.

The presence of the antigen and of gG or gE in the body fluid may be determined by various methods, for example, by detecting in the body fluid antibodies specific for the antigen and for gG or gE.

S-IBR-039 has been deposited pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A.

A study was conducted to determine the serological and clinical response of young calves following intramuscular administration of S-IBR-037 and S-IBR-039. These results are presented in Table 7. Three calves were inoculated intramuscularly with $10^7$ PFU of S-IBR-037 and S-IBR-039. All calves inoculated with S-IBR-037 and S-IBR-039 developed significant neutralizing antibody to IBR virus above the antibody levels of the contact control. Attenuation of S-IBR-039 was demonstrated by the absence of clinical signs in animals inoculated with the S-IBR-039 virus.

TABLE 7

Serum Neutralizing Antibody Titers in Young Calves Following Vaccination with S-IBR-037 and S-IBR-039

| Virus | | Serum Antibody Titer[a] Days Post Inoculation | | |
|---|---|---|---|---|
| Construct | Calf # | 0 | 14 | 28 |
| S-IBR-037 | 01 | <2 | 9 | 5 |
| | 06 | <2 | 16 | 16 |
| | 17 | <2 | 5 | 7 |
| | Mean | <2 | 10.0 | 9.3 |
| S-IBR-039 | 11 | <2 | 5 | 4 |
| | 14 | <2 | 12 | 9 |
| | 07 | <2 | 16 | 4 |

TABLE 7-continued Serum Neutralizing Antibody Titers in Young Calves Following Vaccination with S-IBR-037 and S-IBR-039

| Virus Construct | Calf # | Serum Antibody Titer[a] Days Post Inoculation | | |
|---|---|---|---|---|
| | | 0 | 14 | 28 |
| | Mean | <2 | 11.0 | 5.7 |
| Control | Mean | <2 | <2 | <2 |

[a]Expressed as reciprocal of dilution

Example 20

S-IBR-045

S-IBR-045, a recombinant IBR virus with deletions in the Tk, US2, gG and gE genes may be constructed in the following manner. S-IBR-045 would be derived from S-IBR-039 (see example 19) through the construction of two intermediate viruses. The first intermediate virus, S-IBR-043, would be constructed utilizing the homology vector 591-46.12 (see MATERIALS AND METHODS) and virus S-IBR-039 in the HOMOLOGOUS RECOMBINATION PROCEDURE FOR GENERATING RECOMBINANT HERPESVIRUS. The transfection stock would be screened by the SCREEN FOR RECOMBINANT HERPESVIRUS EXPRESSING ENZYMATIC MARKER GENES for a white plaque recombinant virus (uida substrate). The resulting virus would have deletions of the Tk, US2, gG and gE genes and insertion of lacZ gene in the gE gene deletion. Finally, S-IBR-045 would be constructed, utilizing the homology vector 523-78.72 (see MATERIALS AND METHODS) and virus S-IBR-044 in the HOMOLOGOUS RECOMBINATION PROCEDURE FOR GENERATING RECOMBINANT HERPESVIRUS. The transfection stock would be screened by the SCREEN FOR RECOMBINANT HERPESVIRUS EXPRESSING ENZYMATIC MARKER GENES for a white plaque recombinant virus (lacZ substrate). This virus will be useful as a vaccine to protect cattle from infection with IBR. The combination of deletions will provide the appropriate attenuation which is required for a superior vaccine. This virus will also provides two negative serological markers which may be used to distinguish vaccinated from infected animals. The availability of two negative markers permits one marker to be used as a confirmatory test, greatly increasing the reliability of such a diagnostic determination.

Example 21

S-IBR-046

S-IBR-046, a recombinant IBR virus with deletions in the Tk, US2, gG and gE genes and the bovine viral diarrhea virus g53 gene inserted in place of the gE gene, may be constructed in the following manner. S-IBR-046 would be derived from S-IBR-044 (see example 20). It would be constructed utilizing the homology vector 523-78.72, into which the bovine viral diarrhea virus g53 gene has been inserted, and virus S-IBR-044 in the HOMOLOGOUS RECOMBINATION PROCEDURE FOR GENERATING RECOMBINANT HERPESVIRUS. Note that the bovine diarrhea virus gene would be cloned using techniques described in the methods section. The g53 gene would be placed under the control of the HCMV immediate early promoter. The transfection stock would be screened by the SCREEN FOR RECOMBINANT HERPESVIRUS EXPRESSING ENZYMATIC MARKER GENES for a white plaque recombinant virus (lacZ substrate). This virus will be useful as a vaccine to protect cattle from infection with IBR virus and bovine viral diarrhea virus.

Example 22

S-IBR-047

S-IBR-047, a recombinant IBR virus with deletions in the Tk, US2, gG and gE genes and the parainfluenza type 3 genes for hemagglutinin and fusion protein inserted in place of the gE gene may be constructed in the following manner. S-IBR-047 would be derived from S-IBR-044 (see example 20). It would be constructed utilizing the homology vector 523-78.72, into which the parainfluenza type 3 virus hemagglutinin and fusion genes has been inserted, and virus S-IBR-044 in the HOMOLOGOUS RECOMBINATION PROCEDURE FOR GENERATING RECOMBINANT HERPESVIRUS. Note that the parainfluenza type 3 virus genes would be cloned using techniques described in the methods section. The transfection stock would be screened by the SCREEN FOR RECOMBINANT HERPESVIRUS EXPRESSING ENZYMATIC MARKER GENES for a white plaque recombinant virus (lacZ substrate). This virus will be useful as a vaccine to protect cattle from infection with IBR virus and parainfluenza type 3 virus.

Example 23

S-IBR-049

S-IBR-049, a recombinant IBR virus with deletions in the Tk, US2, gG and gE genes and the bovine respiratory syncytial virus genes for the attachment, nucleocapsid and fusion proteins inserted in place of the gE gene may be constructed in the following manner. S-IBR-049 would be derived from S-IBR-044 (see example 20). It would be constructed utilizing the homology vector 523-78.72, into which the bovine respiratory syncytial virus attachment nucleocapsid and fusion genes had been inserted and virus S-IBR-044 in the HOMOLOGOUS RECOMBINATION PROCEDURE FOR GENERATING RECOMBINANT HERPESVIRUS. Note that the bovine respiratory syncytial virus genes would be cloned using techniques described in the methods section. The attachment protein gene would be placed under the control of the HCMV immediate early promoter and the fusion and nucleocapsid protein genes would be placed under the PRV gX promoter. The transfection stock would be screened by the SCREEN FOR RECOMBINANT HERPESVIRUS EXPRESSING ENZYMATIC MARKER GENES for a white plaque recombinant virus (lacZ substrate). This virus will be useful as a vaccine to protect cattle from infection with IBR virus and bovine respiratory syncytial.

Example 24

S-IBR-051

S-IBR-051, a recombinant IBR virus with deletions in the Tk, US2, gG and gE genes and the *Pasteurella haemolytica* genes for the leukotoxin and iron regulated outer membrane proteins inserted in place of the gE gene, may be constructed in the following manner. S-IBR-051 would be derived from S-IBR-044 (see example 20). It would be constructed utilizing the homology is vector 523-78.72, into which the *Pasteurella haemolytica* leukotoxin and iron regulated outer membrane protein genes had been inserted, and virus S-IBR-044 in the HOMOLOGOUS RECOMBINATION PROCEDURE FOR GENERATING RECOMBINANT HERPESVIRUS. Note that the *Pasteurella haemolytica* genes would be cloned using the techniques described in the methods section. The leukotoxin gene would be placed under the control of the HCMV immediate early promoter and the iron regulated outer membrane protein genes would be placed under the PRV gX promoter. The transfection stock would be screened by the SCREEN FOR RECOMBINANT HERPESVIRUS EXPRESSING ENZYMATIC MARKER GENES for a white plaque recombinant virus (lacz substrate). This virus will be useful as a vaccine to protect cattle from infection with IBR virus and *Pasteurella haemolytica*.

Example 25

S-IBR-052

S-IBR-052 is an IBR virus that has three deletions in the unique short region of the genome. The first deletion is approximately 2500 base pairs and begins in the HindIII K fragment approximately 1750 base pairs downstream of the HindIII O/HindIII K junction and extends back through that junction. This deletion removes the US2 gene. The second deletion is approximately 1230 base pairs and begins in the HindIII K fragment approximately 3900 base pairs downstream of the HindIII O/HindIII K junction and extends back toward that junction. This deletion removes amino acids 1 to 361 of the gG gene. The third deletion is approximately 1410 base pairs and removes amino acids 77–547 of the gE gene.

S-IBR-052 was derived from S-IBR-039. This was accomplished utilizing the homology vector 523-78.72 (see Materials and Methods) and virus S-IBR-039 in the HOMOLOGOUS RECOMBINATION PROCEDURE FOR GENERATING RECOMBINANT HERPESVIRUS. The transfection stock was screened by the BLUOGAL SCREEN FOR RECOMBINANT HERPESVIRUS. The result of white plaque purification was the recombinant virus designated S-IBR-052. This virus was characterized by restriction mapping and by PCR analysis. This analysis confirmed the deletion of the β-galactosidase (lacZ) marker gene and the deletion of approximately 1410 base pairs of the gE gene. It was also confirmed that deletions present in the parent S-IBR-039 virus were present in S-IBR-052.

S-IBR-052 contains a deletion in the IBRV US2 gene which not only attenuates the virus but also has an unexpected effect of rendering the virus fetal safe. Therefore, S-IBR-052 can be formulated into a vaccine which is superior from other IBRV vaccines in that in addition to being safe and effective in protecting cattle from infections with IBR virus, it is also safe for use in pregnant animals.

Another notable characteristic of S-IBR-052 is that it contains deletions in the gG and gE genes so that no functional gG or gE is produced upon viral replication. Said deletions in gG and gE, therefore, provides two negative serological markers for differentiating the virus from wild-type virus.

S-IBR-052 on Feb. 4, 1994 was deposited pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. VR 2443.

A study evaluating the safety of the S-IBR-052 vaccine demonstrates the absence of a clinical response in young calves following intranasal vaccination with S-IBR-052 when compared to S-IBR-000 (Cooper strain). Four weaned, IBRV antibody negative calves per group were inoculated intranasally with $2\times10^5$ PFU of S-IBR-052 or $4\times10^5$ PFU of S-IBR-000 (Cooper strain). Calves were observed daily over a 4-week period for increased body temperatures, respiratory disease, and ulcers of the nasal mucosa. As shown in Table 8, S-IBR-000 (Cooper) showed significant clinical signs whereas the S-IBR-052 showed no febrile signs or nasal ulcers and a reduced duration of respiratory signs. Since intranasal is the natural route of infection for IBR virus, it is significant that significant reduction in clinical signs are shown during S-IBR-052 vaccination compared to S-IBR-000 (Cooper) vaccination.

TABLE 8

Clinical Response of Young Calves Following Intramuscular and Intranasal Vaccination with S-IBR-052

| Virus Construct | Route of Innoculati | Febrile Signs (Days >104.5 F. °) | Respiratory Signs (Numbers of days) | Nasal Ulcers (Number of days) |
|---|---|---|---|---|
| S-IBR-000 (Cooper) | Intranasal | 4.7 | 20 | 4 |
| S-IBR-052 | Intranasal | .75 | 12 | 0 |

Example 26

Shipping Fever Vaccine

Shipping fever or bovine respiratory disease (BRD) complex is manifested as the result of a combination of infectious diseases of cattle and additional stress related factors (70). Respiratory virus infections, augmented by pathophysiological effects of stress, alter the susceptibility of cattle to Pasteurella organisms by a number of mechanisms. Control of the viral infections that initiate BRD as well as control of the terminal bacterial pneumonia is essential to preventing the disease syndrome (71).

The major infectious disease pathogens that contribute to BRD include but are not limited to infectious bovine rhinotracheitis virus (IBRV), prarinfluenza type 3 virus (PI-3), bovine viral diarrhea virus (BVDV), bovine respiratory syncytial virus (BRSV), and *Pasteurella haemolytica* (71). Through out this application, applicants have disclosed examples of recombinant IBR viruses that can be used as a vaccine to immunize animals against the various components of BRD.

The present invention also encompasses vaccines which are directed not only to one particular component of BRD but to a combination of several components responsible for the disease, so that the array of pathogens responsible for BRD can be controlled with a single immunization.

For example, a vaccine directed to several pathogens responsible for BRD can be formulated as follows: first, the various IBRV vectored antigens from BRSV, PI-3, BVDV and *P. haemolytica* can be combined in a single vaccine dose; secondly, the individual antigens from BRSV, PI-3, BVDV and *P. haemolytica* can be simultaneously cloned into the same IBR virus backbone.

A preferred embodiment of the IBR virus. backbone for vectoring one or more antigens from BRSV, PI-3, BVDV and *P. haemolytica* are S-IBR-039 (see example 19) and S-IBR-052(see example 25), both of which contain deletions of the US2, gG, and gE genes.

S-IBR-039 is particularly appropriate as a backbone virus for purposes of vectoring said antigens. S-IBR-039 is a superior vaccine since deletions of the US2 gene provides the unexpected property of fetal safety when used to vaccinate pregnant animals. In addition, deletions of the gG and gE genes provide multiple negative markers useful in distinguishing vaccinated from infected animals.

Using S-IBR-039 virus as a backbone, the following viruses have been constructed which contains BRSV, PI-3, or BVDV antigens:

S-IBR-053

S-IBR-053 has been constructed by inserting the gene for BVDV g53 into the gE deletion site of S-IBR-039. Expression of the BVDV g53 protein from S-IBR-053 grown in cell culture has been confirmed by immunofluorescence assay indicating that the correct immune reactive epitope of BVDV g53 is present.

S-IBR-054

S-IBR-054 has been constructed by inserting the genes for PI-3 F and HN into the gE deletion site of S-IBR-039. Expression of the PI-3 HN protein from S-IBR-054 grown in cell culture has been confirmed by immunofluorescence assay indicating that the correct immune reactive epitope of PI-3 HN is present.

S-IBR-055

S-IBR-055 has been constructed by inserting the gene for BRSV F and N into the gE deletion site and inserting the gene for BRSV G into the gG deletion site of the S-IBR-039 backbone.

S-IBR-059

S-IBR-059 has been constructed by inserting the gene for PI-3 F and HN into the gG deletion site and inserting the gene for BVDV g53 into the gE deletion site of the S-IBR-039 backbone.

IBR viruses designated S-IBR-053, S-IBR-054, S-IBR-055 and S-IBR-059 are presented as examples of recombinant IBR viruses containing one or more antigens from PI-3, BVDV, BRSV, and *Pasteurella haemolytica*, which have been constructed using S-IBR-039 as a backbone virus. Applicants' present invention extends beyond these examples to cover any recombinant IBRV containing one or more antigens from PI-3, BVDV, BRSV and *Pasteurella haemolytica* which is constructed using S-IBR-039 or S-IBR-052 as a backbone virus. The antigens to be inserted is selected from the following group: PI-3 HN and F, BVDV g53, BRSV F, N and G, and *Pasteurella haemolytica* leukotoxin. The following sites in S-IBR-039 or S-IBR-052 are used as insertion sites for these antigens: the gE deletion site, gG deletion site, or US2 deletion site of S-IBR-039 or S-IBR-052; Hind III or Xba I sites within the unique long region of IBRV contained on a 3900 base pair Apa I fragment (Homology vector 691-096.2) within the bamHI C fragment of IBRV. The Xba I site is located in the intergenic region upstream of the latency-related transcripts promoter and downstream of a potential ORF. The Hind III site is located within a potential ORF upstream of the latency-related transcripts; or 500 base pair EcoRV deletion within the repeat region of IBRV. Note that if a combination of antigens are inserted into one or more backbone viruses, this limits the number of IBR viruses required for BRD protection.

The following are several examples of how antigens from PI-3, BVDV, and BRSV are inserted into a backbone IBR virus, such as the S-IBR-039 backbone and the S-IBR-052 backbone.

1. Genes encoding BVDV g53, PI-3 HN and F, and BRSV F, N, and G are inserted in combination into the S-IBR-039 backbone or the S-IBR-052 backbone.

2. Genes encoding BVDV g53, BRSV F, N, and G are inserted in combination into the S-IBR-039 backbone or the S-IBR-052 backbone.

3. Genes encoding BRSV F, N, and G and PI-3 HN and F are inserted in combination into the S-IBR-039 backbone or the S-IBR-052 backbone.

Each of the above three IBR viruses are engineered further to include *Pasteurella haemolytica* leukotoxin.

The viruses described through out this section (example 26) can be used in combination as a vaccine against BRD. In addition, conventionally derived vaccines (killed virus, inactivated bacterins and modified live viruses) could be included with the recombinant multivalent vaccines as part of the BRD vaccine formulation should such vaccine components prove to be more effective.

The present invention also provides a method for distinguishing an animal vaccinated with the vaccine comprising the infectious bovine rhinotracheitis viruses described in this section (example 26). This method comprises analyzing a sample of a body fluid from the animal for the presence of gG or gE and at least one other antigen normally expressed in an animal infected by a naturally-occurring infectious bovine rhinotracheitis virus. The presence of the antigen and the absence of gG or gE in the body fluid is indicative of an animal vaccinated with the vaccine and not infected with a naturally-occurring IBR virus.

The presence of the antigen and of gG or gE in the body fluid may be determined by various methods, for example, by detecting in the body fluid antibodies specific for the antigen and for gG or gE.

Example 27

S-IBR-086

Figure 27:
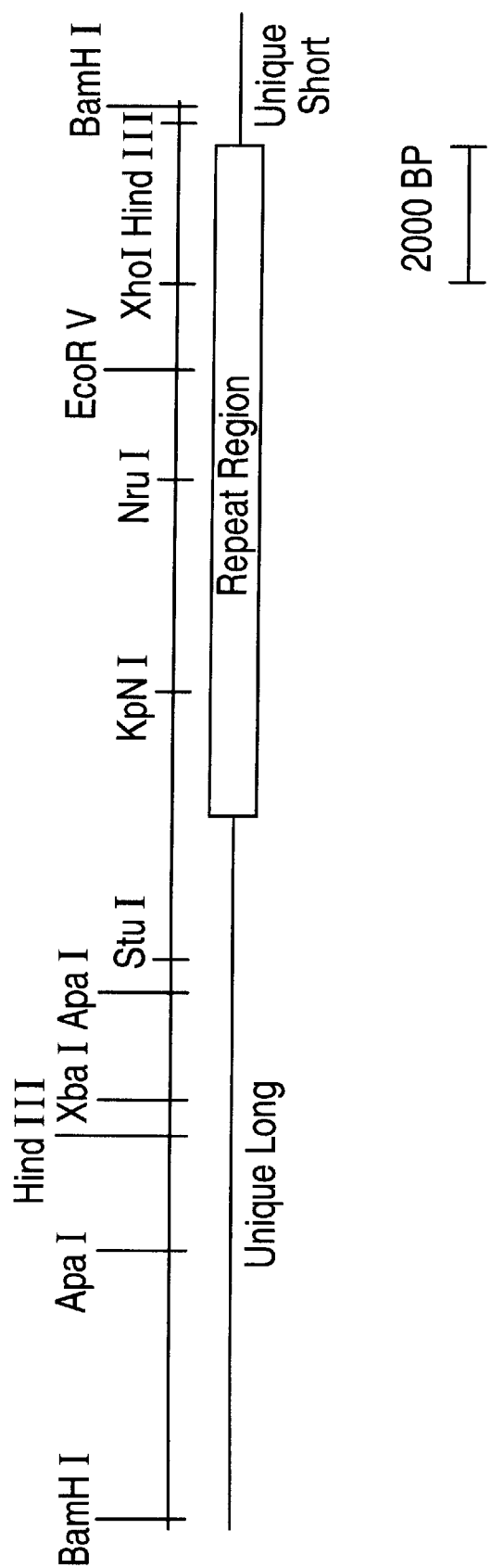

S-IBR-086 is an IBR virus that has three deletions in the short unique region of the genome and two foreign genes inserted into the unique long region of the genome. The deletions in the unique short are in the US2 gene, the gG gene, and the gE gene. The extent of these deletions are identical to those described for S-IBR-052 (Example 24). The genes for-the bovine viral diarrhea virus (BVDV) glycoprotein 53 (g53) (amno acids 1–394) under the control of the HCMV immediate early promoter and the *E. coli* uida under the control of the PRV gX promoter were inserted into a HindIII site within the BamHI C fragment of the IBRV genome (FIG. 27).

S-IBR-086 was derived from S-IBR-052. This was accomplished utilizing the homology vector 746-21.4 and virus S-IBR-052 in the HOMOLOGOUS RECOMBINATION PROCEDURE FOR GENERATING RECOMBINANT HERPESVIRUS. Homology vector 746-21.4 was constructed by inserting the HCMV IE promoter BVDV g53 gene and PRV gX promoter uida gene into the unique HindIII site of homology vector 691-096.2 (see Materials and Methods). The BVDV g53 gene was isolated by CLONING OF BOVINE VIRAL DIARRHEA VIRUS g53 and g48 GENES. The transfection stock was screened by the SCREEN FOR RECOMBINANT HERPESVIRUS EXPRESSING ENZYMATIC MARKER GENES. The result of blue plaque purification was the recombinant virus designated S-IBR-086. This virus was characterized by restriction mapping and by PCR analysis. This analysis confirmed the insertion of the β-glucuronidase (uidA) marker gene and the insertion of the BVDV g53 gene. Expression of the BVDV g53 was confirmed by immunoprecipitation using mouse monoclonal antibody to BVDV g53 protein. It was also confirmed that deletions present in the parent S-IBR-052 virus were present in S-IBR-086.

This virus is useful as a vaccine to protect cattle from infection with IBR virus and BVD virus. The deletion of the US2 gene attenuates the virus, and the deletions of the glycoproteins G and E genes from this virus provides two negative serological markers for distinguishing vaccinated from infected animals.

S-IBR-069

S-IBR-069 is an IBR virus that has three deletions in the short unique region of the genome and two foreign genes inserted into the unique long region of the genome. The deletions in the unique short are in the US2 gene, the gG gene, and the gE gene. The extent of these deletions are identical to those described for S-IBR-052 (Example 24).

The genes for the bovine viral diarrhea virus (BVDV) glycoprotein 53 (g53) (amino acids 1–394) under the control of the HCMV immediate early promoter, BVDV g48 gene (amino acid 1–226) under the control of the PRV gX promoter, and the *E. coli* lacZ gene under the control of the HSV-1 TK promoter were inserted into a HindIII site within the BamHI C fragment of the IBRV genome (FIG. 27).

S-IBR-069 was derived from S-IBR-052. This was accomplished utilizing the homology vector 756-15.5A and virus S-IBR-052 in the HOMOLOGOUS RECOMBINATION PROCEDURE FOR GENERATING RECOMBINANT HERPESVIRUS. Homology vector 756-15.5A was constructed by inserting the HCMV IE promoter BVDV g53 gene, PRV gX promoter BVDV g48 gene and HSV-1 TK promoter lacZ gene into the unique HindIII site of homology vector 691-096.2 (see Materials and Methods). The BVDV g53 and g48 genes were isolated by CLONING OF BOVINE VIRAL DIARRHEA VIRUS g53 and g48 GENES. The transfection stock was screened by the BLUOGAL™ SCREEN FOR RECOMBINANT HERPESVIRUS. The result of blue plaque purification was the recombinant virus designated S-IBR-069. This virus was characterized by restriction mapping and by PCR analysis. This analysis confirmed the insertion of the β-galactosidase (lacz) marker gene and the insertion of the BVDV g53 gene and the BVDV g48 gene. Expression of the BVDV g53 was confirmed by immunoprecipitation using mouse monoclonal antibody to BVDV g48 protein It was also confirmed that deletions present in the parent S-IBR-052 virus were present in S-IBR-069.

This virus is useful as a vaccine to protect cattle from infection with IBR virus and BVD virus. The deletion of the US2 gene attenuates the virus, an d the deletions of the glycoproteins G and E genes from this virus provides two negative serological markers for distinguishing vaccinated from infected animals.

S-IBR-074

S-IBR-074 is an IBR virus that has three deletions in the short unique region of the genome and two foreign genes inserted into the unique long region of the genome. The deletions in the unique short are in the US2 gene, the gG gene, and the gE gene. The extent of these deletions are identical to those described for S-IBR-052 (Example 24). The genes for the bovine viral diarrhea virus (BVDV) glycoprotein 53 (g53) (amino acids 1–394) under the control of the HCMV immediate early promoter, BVDV g48 gene (amino acids 1–226) under the control of the PRV gX promoter, and the *E. coli* lacZ gene under the control of the HSV-1 TK promoter were inserted into a HindIII site within the BamHI C fragment of the IBRV genome (FIG. 27). The PRV gX signal sequence is fused in frame to the 5' end of the BVDV g53 gene S-IBR-074 was derived from S-IBR-052. This was accomplished utilizing the homology vector 756-35.38 and virus S-IBR-052 in the HOMOLOGOUS RECOMBINATION PROCEDURE FOR GENERATING RECOMBINANT HERPESVIRUS. Homology vector 756-35.38 was constructed by inserting the HCMV IE promoter PRV gX signal/BVDV g53 gene, PRV gX promoter BVDV g48 gene and HSV-1 TK promoter lacZ gene into the unique HindIII site of homology vector 691-096.2 (see Materials and Methods). The BVDV g53 and g48 genes were isolated by CLONING OF BOVINE VIRAL DIARRHEA VIRUS g53 and g48 GENES. The transfection stock was screened by the BLUOGAL™ SCREEN FOR RECOMBINANT HERPESVIRUS. The result of blue plaque purification was the recombinant virus designated S-IBR-074.

This virus is useful as a vaccine to protect cattle from infection with IBR virus and BVD virus. The deletion of the US2 gene attenuates the virus, and the deletions of the glycoproteins G and E genes from this virus provides two negative serological markers for distinguishing vaccinated from infected animals.

Example 28

S-IBR-071

S-IBR-071 is an IBR virus that has three deletions in the short unique region of the genome and two foreign genes inserted into the unique long region of the genome. The deletions in the unique short are in the US2 gene, the gG gene, and the gE gene. The extent of these deletions are identical to those described for S-IBR-052 (Example 24). The genes for the bovine respiratory syncytial virus (BRSV) fusion (F) gene (amino acids 4–574) under the control of the HCMV immediate early promoter, BRSV attachment (G) gene (amnio acids 4–254) under the control of the PRV gX promoter, and the *E. coli* lacZ gene under the control of the HSV-1 TK promoter were inserted into a HindIII site within the BamHI C fragment of the IBRV genome (FIG. 27).

S-IBR-071 was derived from S-IBR-052. This was accomplished utilizing the homology vector 746-82.5B and virus S-IBR-052 in the HOMOLOGOUS RECOMBINATION PROCEDURE FOR GENERATING RECOMBINANT HERPESVIRUS. Homology vector 746-82.SB was constructed by inserting the HCMV IE promoter BRSV F gene, PRV gX promoter BRSV G gene, and HSV-1 TK promoter lacZ gene into the unique HindIII site of homology vector 691-096.2 (see Materials and Methods). The BRSV F and G genes were isolated by CLONING OF BOVINE RESPIRATORY SYNCYTIAL VIRUS FUSION PROTEIN AND NUCLEOCAPSID PROTEIN GENES. The transfection stock was screened by the BLUOGAL™ SCREEN FOR RECOMBINANT HERPESVIRUS. The result of blue plaque purification was the recombinant virus designated S-IBR-071.

This virus is useful as a vaccine to protect cattle from infection with IBR virus and BRSV. The deletion of the US2 gene attenuates the virus, and the deletions of the glycoproteins G and E genes from this virus provides two negative serological markers for distinguishing vaccinated from infected animals.

In an alternative embodiment of S-IBR-071 and S-IBR-072, a recombinant IBR virus is constructed that has three deletions (the US2 gene, the gG gene, and the gE gene) in the unique short and insertions of the BRSV F and G genes and lacZ gene in the HindIII site in the unique long and the BRSV N gene and uidA gene in the EcoRV site in the repeat region. The recombinant IBR viruses derived utilizing the HOMOLOGOUS RECOMBINATION PROCEDURE FOR GENERATING RECOMBINANT HERPESVIRUS from S-IBR-071 and a homology vector containing the BRSV N gene and uida gene with appropriate promoters inserted at the EcoRV site of homology vector 769-73.1 (see Materials and Methods). The transfection stock is screened by the SCREEN FOR RECOMBINANT HERPESVIRUS EXPRESSING ENZYMATIC MARKER GENES. The result of blue plaque purification is the recombinant IBR virus as described.

S-IBR-072

S-IBR-072 is an IBR virus that has three deletions in the short unique region of the genome and two foreign genes inserted into the unique long region of the genome. The deletions in the unique short are in the US2 gene, the gG gene, and the gE gene. The extent of these deletions are identical to those described for S-IBR-052 (Example 24). The genes for the bovine respiratory syncytial virus (BRSV) nucleocapsid (N) gene (amino acids 1–399) under the control of the PRV gX promoter, and the *E. coli* lacZ gene under the control of the HSV-1 TK promoter were inserted into a EcoRV site within the BamHI C fragment in the repeat region of the IBRV genome (FIG. 27).

S-IBR-072 is derived from S-IBR-052. A homology vector is constructed by inserting PRV gX promoter BRSV N gene and HSV-1 TK promoter lacZ gene into the unique EcoRV site of homology vector 769-73.1 (see Materials and Methods). The BRSV N gene is isolated by CLONING OF BOVINE RESPIRATORY SYNCYTIAL VIRUS FUSION PROTEIN AND NUCLEOCAPSID PROTEIN GENES. S-IBR-072 is accomplished utilizing the homology vector and virus S-IBR-052 in the HOMOLOGOUS RECOMBINATION PROCEDURE FOR GENERATING RECOMBINANT HERPESVIRUS. The transfection stock is screened by the BLUOGAL™ SCREEN FOR RECOMBINANT HERPESVIRUS. The result of blue plaque purification is the recombinant virus designated S-IBR-072.

This virus is useful as a vaccine to protect cattle from infection with IBR virus and BRSV. The deletion of the US2 gene attenuates the virus, and the deletions of the glycoproteins G and E genes from this virus provides two negative serological markers for distinguishing vaccinated from infected animals.

S-IBR-073

S-IBR-073 is an IBR virus that has three deletions in the short unique region of the genome and two foreign genes inserted into the unique long region of the genome. The deletions in the unique short are in the US2 gene, the gG gene, and the gE gene. The extent of these deletions are identical to those described for S-IBR-052 (Example 24). The genes for the parainfluenza virus type 3 (PI-3) fusion (F) gene (amino acids 4–540) under the control of the HCMV immediate early promoter, PI-3 haemagglutinin/neuraminidase (HN) gene (amino acids 1–573) under the control of the PRV gX promoter, and the *E. coli* lacZ gene under the control of the HSV-1 TK promoter were inserted into the gG deletion site within the unique short of the IBRV genome.

S-IBR-073 was derived from S-IBR-052. This was accomplished utilizing the homology vector 756-11.17 and virus S-IBR-052 in the HOMOLOGOUS RECOMBINATION PROCEDURE FOR GENERATING RECOMBINANT HERPESVIRUS. The PI-3 F and HN genes were isolated by CLONING OF PARAINFLUENZA-3 FUSION AND HEMAGGLUTININ GENES. The transfection stock was screened by the BLUOGAL™ SCREEN FOR RECOMBINANT HERPESVIRUS. The result of blue plaque purification was the recombinant virus designated S-IBR-073.

This virus is useful as a vaccine to protect cattle from infection with IBR virus and PI-3 virus. The deletion of the US2 gene attenuates the virus, and the deletions of the glycoproteins G and E genes from this virus provides two negative serological markers for distinguishing vaccinated from infected animals.

REFERENCES

1. J. L. Cantello et al., Journal of Virology 65, 1584–1588 (1991).
2. U. K. Laemnli, Nature 227, 680–685 (1970).
3. B. Lomniczi et al., Journal of Virology 49, 970–979 (1984).
4. R. Longnecker and B. Roizman, Science 236, 573–576 (1987).
5. S. Mackem and B. Roizman, Proc. Natl. Acad. Sci. USA 79, 4917–4921 (1982).
6. T. Maniatis et al., *Molecular Cloning: A Laboratory Manual*, Cold Spring Harbor Press (1982).
7. J. E. Mayfield et al., Journal of Virology 47, 259–264 (1983).
8. D. J. McGeoch et al., Journal of Molecular Biology 181, 1–13 (1985).
9. D. J. McGeoch et al., Journal of General Virology 68, 19–38 (1987).
10. D. J. McGeoch et al., Journal of General Virology 69, 1531–1574 (1988).
11. E. A. Petrovskis et al., Journal of Virology 60, 116–169 (1986).
12. T. J. Rea et al., Journal of Virology 54, 21–29 (1985).
13. A. K. Robbins et al., Journal of Virology 58, 339–347 (1986).
14. J. Sambrook et al., *Molecular Cloning: A Laboratory Manual*, Second Edition, Cold Spring Harbor Press (1989).
15. G. A. Smith et al., Journal of General Virology 71, 2417–2424 (1990).
16. D. R. Thomsen et al., Gene 16, 207–217, (1981)
17. S. K. Tikoo et al., Journal of Virology 64, 5132–5142 (1990).
18. C. E. Aronson, ed., *Veterinary Pharmaceuticals and Biologicals*, Veterinary Medicine Publ. Co., Lenexa, Kans., pp. 138–139 (1982–1983).
19. P. C. Weber et al., Science 236, 576–579 (1987).
20. U. S. Wirth et al., Journal of Virology 65, 195–205 (1991).
21. M. Zijil et al., Journal of Virology 71, 1747–1755 (1990).
22. L. Villarreal and P. Berg, Science 196, 183–185 (1977).
23. U. Gubler and B. J. Hoffman, Gene 25, 263–269 (1983).
24. F. L. Graham and A. Van der Eb, Virology 52, 556–567 (1973).
25. N. Elango et al., Journal of Virology 57, 481–489 (1986).
26. M. K. Spriggs and P. L. Collins, Journal of Virology 59, 646–654 (1986).
27. B. M. Blumberg et al., Journal of General Virology 66, 317–331 (1985).
28. R. W. Price and A. Kahn, Infection and Immunity 34, 571–580 (1981).
29. P. B. Tenser et al., J. of General Virology 64, 1369–1373 (1983).
30. B. Roizman et al., Cold Spring Harbor Conference on New Approaches to Viral Vaccines (September, 1983).
31. R. L. Thompson et al., Virology 131, 180–192 (1983).
32. K. Fukuchi et al., Proc. Natl. Acad. Sci. U.S.A. 82, 751–754, 1985.
33. J. M. Koomey et al., J. of Virology 50, 662–665, 1984.
34. S. B. Mohanty and S. K. Dutta, *Veterinary Virology*, Lea and Febiger, Philadelphia (1981).
35. R. Crandell in *Current Veterinary Therapy*, pages 543–546, W. B. Saunders, Philadelphia (1981).
36. H. Ludwig in *The Herpesviruses*, Vol. 2, B. Roizman, ed., Plenum Press (1983).
37. A. J. Davison, EMBO Journal, 2, 2203–2209 (1983).
38. F. A. Ferrari et al., J. of Bacteriology 161, 556–562 1985.
39. V. T. Oi and L. A. Herzenberg, *Selected Methods in Cellular Immunology*, Freeman Publ. Co., San Francisco (1980). pp. 351–372.
40. S. Ihara et al., Virology 122, 268–278 (1982).
41. D. Hanahan, Molecular Biology 166, 557–580 (1983).
42. M. W. Mellencamp et al., J. of Clinical Microbiology 27, 2208–2213 (1989).
43. Kit et al., U.S. Pat. No. 4,824,667, issued Apr. 25, 1989.
44. Kit et al., U.S. Pat. 4,703,011, issued Oct. 27, 1987.

45. Kit et al., The Veterinary Record 127, 363–364 (1990).
46. European Patent Publication EP 0 326 127 A2, published Aug. 2, 1989.
47. Federal Register, Vol. 55, No. 90, pp. 19245–19253 (May 9, 1990).
48. Fitzpatrick et al., J. of Virol. 62, 4239–4288 (1988).
49. T. Ben-Porat et al., Virol. 154, 325–334 (1986).
50. F. Zuckerman et al., in Vaccination and Control of Auieszky's Disease, Ed. J. van Oirschot, Kluwer, London (1989). pp. 107–117.
51. L. E. Post et al., J. Reprod. Fert. Suppl. 41, 97–104 (1990).
52. Wirth et al., J. of Virol. 63, 4882–4889 (1989).
53. B. Moss, Science 252, 1662–1667 (1991).
54. R. W. Honess, J. of General Virology 65, 2077–2107 (1984).
55. Cook & Stevens, J. of General Virology 31, 75–80 (1976).
56. Desrosiers et al., Molecular and Cellular Biology 5, 2796–2803 (1985).
57. Thomsen et al., Gene 57, 261–265 (1987).
58. Weir and Narayanan, Nucleic Acids Research 16, 10267–10282 (1988).
59. Spaete and Mocarski, Proceedings of the National Academy of Sciences U.S.A. 84, 7213–7217 (1987).
60. Whealy et al., Journal of Virology 62, 4185–4194 (1988).
61. Shih et al., Proceedings of the National Academy of Sciences U.S.A. 81, 5867–5870 (1984).
62. Edwards et al., in Technological Advances in Vaccine Development, pp. 223–234, Alan Riss Inc. (1988).
63. Proceeding of the 94th Annual Meeting of the United States Animal Health Association, pp. 66–75 (1990).
64. E. A. Petrovskis et al., Journal of Virology 60, 185–193 (1986).
65. Todd et al., U.S. Pat. No. 4,132,775, issued Jan. 2, 1979.
66. M. S. Collett et al., Journal of Virology 65, 200–208, (1988).
67. M. A. Innis et al., PCR Protocols: A Guide to Methods and Applications, 84–91, Academic Press, Inc. San Diego (1990).
68. R. D. Walker, et al., Am. J. Vet Res. 65, 1230–1234 (1984)
69. E. Harlow, and D. Lane, Antibodies: A Laboratory Manual, Cold Spring Harbor Press, New York (1988).
70. C. A. Hjerpe, The Bovine Respiratory Disease Complex. In: Current Veterinary Therapy 2: Food Animal Practice. Ed. by J. L. Howard, Philadelphia, W. B. Saunders Co., 1986, pp 670–680.
71. F. Fenner, et al., "Mechanisms of Disease Production: Acute Infections", Veterinary Virology. Academic Press, Inc., Orlando, Fla., 1987, pp 183–202.
72. T. Inque, et al., Journal of General Virology 70, 919–934 (1989).

What is claimed is:

1. A recombinant infectious bovine rhinotracheitis virus comprising a foreign DNA sequence inserted into an infectious bovine rhinotracheitis viral genome, wherein the foreign DNA sequence is inserted within the BamHI C fragment of the infectious bovine rhinotracheitis viral genome and is capable of being expressed in an infectious bovine rhinotracheitis virus infected host cell.

2. The recombinant infectious bovine rhinotracheitis virus of claim 1, wherein the foreign DNA sequence is inserted within the largest BamHI-KpnI subfragment of the BamHI C fragment of the infectious bovine rhinotracheitis viral genome.

3. The recombinant infectious bovine rhinotracheitis virus of claim 2, wherein the foreign DNA sequence is inserted within a HindIII site located within the largest BamHI-KpnI subfragment of the infectious bovine rhinotracheitis viral genome.

4. The recombinant infectious bovine rhinotracheitis virus of claim 2, wherein the foreign DNA sequence is inserted within an XbaI site located within the largest BamHI-KpnI subfragment of the infectious bovine rhinotracheitis viral genome.

5. The recombinant infectious bovine rhinotracheitis virus of claim 1, wherein the foreign DNA sequence is inserted within the smallest KpnI-BamHI subfragment of the BamHI C fragment of the infectious bovine rhinotracheitis viral genome.

6. The recombinant infectious bovine rhinotracheitis virus of claim 5, wherein the foreign DNA sequence is inserted within an EcoRV site located within the smallest KpnI-BamHI subfragment of the infectious bovine rhinotracheitis viral genome.

7. The recombinant infectious bovine rhinotracheitis virus of claim 1, further comprising a deletion in a non-essential region of the infectious bovine rhinotracheitis viral genome.

8. The recombinant infectious bovine rhinotracheitis virus of claim 7, wherein the deletion is in a US2 gene, a gG gene or a gE gene region.

9. The recombinant infectious bovine rhinotracheitis virus of claim 1, wherein the foreign DNA sequence encodes a polypeptide.

10. The recombinant infectious bovine rhinotracheitis virus of claim 9, wherein the polypeptide is antigenic in an animal into which the recombinant infectious bovine rhinotracheitis virus is introduced.

11. The recombinant infectious bovine rhinotracheitis virus of claim 9, wherein the polypeptide is *E. coli* beta-galactosidase.

12. The recombinant infectious bovine rhinotracheitis virus of claim 1, wherein the foreign DNA sequence encodes a cytokine or cytokine receptor.

13. The recombinant infectious bovine rhinotracheitis virus of claim 12, wherein the cytokine or cytokine receptor is selected from the group consisting of: chicken myelomonocytic growth factor (cMGF), chicken interferon (cIFN), interleukin-2, interleukin-6, interleukin-12, interferons, granulocyte-macrophage colony stimulating factors, transforming growth factor beta, epidermal growth factors, fibroblast growth factors, hepatocyte growth factor, insulin-like growth factors, B-nerve growth factor, platelet-derived growth factor, vascular endothelial growth factor, interleukin 1, IL-1 receptor antagonist, interleukin 3, interleukin 4, interleukin 5, IL-6 soluble receptor, interleukin 7, interleukin 8, interleukin 9, interleukin 10, interleukin 11, interleukin 13, angiogenin, chemokines, colony stimulating factors, erythropoietin, interferon gamma, leukemia inhibitory factor, oncostatin M, pleiotrophin, secretory leukocyte protease inhibitor, stem cell factor, tumor necrosis factors, soluble TNF receptors and interleukin receptors.

14. The recombinant infectious bovine rhinotracheitis virus of claim 10, wherein the antigenic polypeptide is an equine influenza virus neuroaminidase or an equine influenza virus hemagglutinin.

15. The recombinant infectious bovine rhinotracheiti virus of claim 10, wherein the antigenic polypeptide is selected from the group consisting of equine influenza virus type A/Alaska 91 neuraminidase, equine influenza virus type A/Alaska 91 hemagglutinin, equine influenza virus type A/Prague 56 neuraminidase, equine influenza virus type A/Prague 56 hemagglutinin, equine influenza virus type A/Miami 63 neuraminidase, equine influenza virus type A/Miami 63 hemagglutinin, equine influenza virus type A/Kentucky 81 neuraminidase equine influenza virus type A/Kentucky 81 hemagglutinin, equine herpesvirus type 1 glycoprotein B, and equine herpesvirus type 1 glycoprotein D.

16. The recombinant infectious bovine rhinotracheitis virus of claim 10, wherein the antigenic polypeptide is selected from the group consisting of hog cholera virus gE1, hog cholera virus gE2, swine influenza virus hemagglutinin, neuraminidase, matrix protein, nucleoprotein, pseudorabies virus gB, pseudorabies virus gC, pseudorabies virus gD, and PRRS virus ORF7.

17. The recombinant infectious bovine rhinotracheitis virus of claim 10, wherein the antigenic polypeptide is selected from the group consisting of: bovine respiratory syncytial virus attachment protein (BRSV G), bovine respiratory syncytial virus fusion protein (BRSV F), bovine respiratory syncytial virus nucleocapsid protein (BRSV N), bovine coronavirus, bovine rotavirus glycoprotein 38, bovine parainfluenza virus type 3 fusion protein, and bovine parainfluenza virus type 3 hemagglutinin neuraminidase.

18. The recombinant infectious bovine rhinotracheitis virus of claim 10, wherein the antigenic polypeptide is bovine viral diarrhea virus (BVDV) glycoprotein 48 or bovine viral diarrhea virus (BVDV) glycoprotein 53.

19. The recombinant infectious bovine rhinotracheitis virus of claim 10, wherein the antigenic polypeptide is selected from the group consisting of Marek's disease virus gA, Marek's disease virus gB, Marek's disease virus gD, Newcastle disease virus HN, Newcastle disease virus F, infectious laryngotracheitis virus gB, infectious laryngotracheitis virus gI, infectious laryngotracheitis virus gD, infectious bursal disease virus VP2, infectious bursal disease virus VP3, infectious bursal disease virus VP4, infectious bursal disease virus polyprotein, infectious bronchitis virus spike, infectious bronchitis virus matrix and chick anemia virus matrix.

20. The recombinant infectious bovine rhinotracheitis virus of claim 1, wherein the foreign DNA sequence is under the control of an endogenous infectious bovine rhinotracheitis virus promoter.

21. The recombinant infectious bovine rhinotracheitis virus of claim 20, wherein the foreign DNA sequence is under the control of a heterologous herpesvirus promoter.

22. The recombinant infectious bovine rhinotracheitis virus of claim 21, wherein the promoter is selected from the group consisting of a herpes simplex virus type 1 (HSV-1) ICP4 protein promoter, an HSV-1 TK promoter, a pseudorabies virus (PRV) glycoprotein X promoter, a PRV gX promoter, an HCMV immediate early promoter, a Marek's disease virus gA promoter, a Marek's disease virus gB promoter, a Marek's disease virus gD promoter, an infectious laryngotracheitis virus gB promoter, a BHV-1.1 VP8 promoter and an infectious laryngotracheitis virus gD promoter.

23. A vaccine which comprises an effective immunizing amount of the recombinant infectious bovine rhinotracheitis virus of claim 1 and a carrier.

24. The vaccine of claim 23, wherein the carrier is a physiologically balanced culture medium containing stabilizing agents.

25. The vaccine of claim 23, wherein the effective immunizing amount is from about $10^3$ to about $10^8$ PFU/dose.

26. The vaccine of claim 25, wherein the effective immunizing amount is from about $10^4$ to about $10^7$ PFU/dose.

27. The vaccine of claim 25, wherein the effective immunizing amount is from about $10^4$ to about $10^6$ PFU/dose.

28. A method of immunizing an animal against disease caused by infectious bovine rhinotracheitis virus which comprises administering to the animal an effective immunizing dose of the vaccine of claim 23.

29. The recombinant infectious bovine rhinotracheitis virus of claim 10, wherein the antigenic polypeptide is from an organism or virus selected from the group consisting of *Streptococcus equi*, equine infectious anemia virus, equine encephalitis virus, equine rhinovirus and equine rotavirus.

30. The recombinant infectious bovine rhinotracheitis virus of claim 10, wherein the antigenic polypeptide is from an organism or virus selected from the group consisting of avian encephalomyelitis virus, avian reovirus, avian paramyxovirus, avian influenza virus, avian adenovirus, fowlpox virus, avian coronavirus, avian rotavirus, chick anemia virus, Salmonella spp., *E. coli*, Pasteurella spp., Bordetella spp., Eimeria spp., Histomonas spp., Trichomonas spp., poultry nematodes, cestodes, trematodes, poultry mites, poultry lice and poultry protozoa.

* * * * *

SEQUENCE LISTING

<160> NUMBER OF SEQ ID NOS: 78

<210> SEQ ID NO 1
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide primer derived from sequence of
      bovine rotavirus

<400> SEQUENCE: 1
gggaattctg caggtcacat catacaattc taatctaag                              39

<210> SEQ ID NO 2
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide primer derived from sequence of
      bovine rotavirus

<400> SEQUENCE: 2
gggaattctg caggctttaa aagagagaat ttccgtttgg cta                        43

<210> SEQ ID NO 3
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide primer derived from sequence of
      bovine rotavirus

<400> SEQUENCE: 3
acgtcggatc ccttaccaaa ccacgtctta ctcttgtttt cc          42

<210> SEQ ID NO 4
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide primer derived from sequence of
      bovine rotavirus

<400> SEQUENCE: 4
acataggatc ccatgggaga aaacataaca cagtggaacc            40

<210> SEQ ID NO 5
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide primer derived from sequence of
      bovine rotavirus

<400> SEQUENCE: 5
cttggatcct catccatact gagtccctga ggccttctgt tc          42

<210> SEQ ID NO 6
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide primer derived from sequence of
      bovine rotavirus

<400> SEQUENCE: 6
catagatctt gtggtgctgt ccgacttcgc a                     31

<210> SEQ ID NO 7
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide primer derived from sequence of
      bovine rotavirus

<400> SEQUENCE: 7
cgtcggatcc ctcacagttc cacatcattg tctttgggat            40

<210> SEQ ID NO 8
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide primer derived from sequence of
      bovine rotavirus

<400> SEQUENCE: 8
cttaggatcc catggctctt agcaaggtca aactaaatga c          41

<210> SEQ ID NO 9
<211> LENGTH: 41
<212> TYPE: DNA
<213> ORGANISM: Artificial Sequence
<220> FEATURE:
<223> OTHER INFORMATION: Description of Artificial Sequence:  Synthetic

```
        oligonucleotide primer derived from sequence of
        bovine rotavirus

<400> SEQUENCE: 9
cgttggatcc ctagatctgt gtagttgatt gatttgtgtg a                    41

<210> SEQ ID NO 10
<211> LENGTH: 41
<212> TYPE: DNA
<213> ORGANISM: Artificial Sequence
<220> FEATURE:
<223> OTHER INFORMATION: Description of Artificial Sequence:Synthetic
        oligonucleotide primer derived from sequence of
        bovine rotavirus

<400> SEQUENCE: 10
ctctggatcc tcatacccat catcttaaat tcaagacatt a                    41

<210> SEQ ID NO 11
<211> LENGTH: 37
<212> TYPE: DNA
<213> ORGANISM: Artificial Sequence
<220> FEATURE:
<223> OTHER INFORMATION: Description of Artificial Sequence:Synthetic
        oligonucleotide primer derived from sequence of
        bovine rotavirus

<400> SEQUENCE: 11
tgcaggatcc tcatttacta aaggaaagat tgttgat                         37

<210> SEQ ID NO 12
<211> LENGTH: 35
<212> TYPE: DNA
<213> ORGANISM: Artificial Sequence
<220> FEATURE:
<223> OTHER INFORMATION: Description of Artificial Sequence:Synthetic
        oligonucleotide primer derived from sequence of
        bovine rotavirus

<400> SEQUENCE: 12
ctctggatcc tacagccatg aggatgatca tcagc                           35

<210> SEQ ID NO 13
<211> LENGTH: 34
<212> TYPE: DNA
<213> ORGANISM: Artificial Sequence
<220> FEATURE:
<223> OTHER INFORMATION: Description of Artificial Sequence:Synthetic
        oligonucleotide primer derived from sequence of
        bovine rotavirus

<400> SEQUENCE: 13
ttatggatcc tgctgctgtg ttgaacaact ttgt                            34

<210> SEQ ID NO 14
<211> LENGTH: 38
<212> TYPE: DNA
<213> ORGANISM: Artificial Sequence
<220> FEATURE:
<223> OTHER INFORMATION: Description of Artificial Sequence:Synthetic
        oligonucleotide primer derived from sequence of
        bovine rotavirus

<400> SEQUENCE: 14
ccgcggatcc catgaccatc acaaccataa tcatagcc                        38

<210> SEQ ID NO 15
```

```
<210> SEQ ID NO 15
<211> LENGTH: 43
<212> TYPE: DNA
<213> ORGANISM: Artificial Sequence
<220> FEATURE:
<223> OTHER INFORMATION: Description of Artificial Sequence:  Synthetic
      oligonucleotide primer derived from sequence of
      bovine rotavirus

<400> SEQUENCE: 15
cgtcggatcc cttagctgca gttttttgga acttctgttt tga                         43

<210> SEQ ID NO 16
<211> LENGTH: 40
<212> TYPE: DNA
<213> ORGANISM: Artificial Sequence
<220> FEATURE:
<223> OTHER INFORMATION: Description of Artificial Sequence:  Synthetic
      oligonucleotide primer derived from sequence of
      bovine rotavirus

<400> SEQUENCE: 16
cataggatcc catggaatat tggaaacaca caaacagcac                             40

<210> SEQ ID NO 17
<211> LENGTH: 31
<212> TYPE: DNA
<213> ORGANISM: Artificial Sequence
<220> FEATURE:
<223> OTHER INFORMATION: Description of Artificial Sequence:  Synthetic
      oligonucleotide primer derived from sequence of
      bovine rotavirus

<400> SEQUENCE: 17
tatagatctt agacttacaa ccctaaaaaa c                                      31

<210> SEQ ID NO 18
<211> LENGTH: 36
<212> TYPE: DNA
<213> ORGANISM: Artificial Sequence
<220> FEATURE:
<223> OTHER INFORMATION: Description of Artificial Sequence:  Synthetic
      oligonucleotide primer derived from sequence of
      bovine rotavirus

<400> SEQUENCE: 18
cgtggatcca actctataat gtgtgaaaca atatag                                 36

<210> SEQ ID NO 19
<211> LENGTH: 1079
<212> TYPE: DNA
<213> ORGANISM: Infections Bovine Rhinotracheitis Virus

<400> SEQUENCE: 19
ttaagcgttg ccgtggcggt cgccatggtg actatagtca cgtgtggccg gataggcgcg        60
gcgccttcca ggcaagccca gacgtgcgcc gcgcgggtgt ggcgtttcct tgccgagcag       120
agccgggcgc tgacggcaag ccggctgggg acgacggtcg ttgtcttcga tcacgcccta       180
gtaaaaacgg cgaagggctg cacgtcgacg tcaacgtcaa gccagcggcg cgggtggctt       240
ttgtcgacac agcgcccttg gcccgggcgc cggcttagcc cgccaccgcc aaccggcgag       300
tgggtcagct ggtcgacggc tacaaacttg ctgaaactcg gccgcgcgag ggctcggccc       360
ttccacatgt gggttttttgg cgccgccgat ttgtacgcgc ctatttttgc gcacattgcc       420
gccacgacgc gcttggttta cgcgcagctg gactgtacgt ttgcgggagc ggcgtggcgg       480
ctcccgcggc gcggcccggc catcgctagc ccgtggccgc cctacgatac cccgacactc       540
```

```
cctgagctgg tggccggtgg tgtccttttc cggctggtct acgaagtcgt agaccgcggg    600
cggcgccccg ccccgccaaa cgcgagcccc cgtgccccag gggctcgccc ccgcgcgcgc    660
catgtgctat cctttaaagg ccgcacccag cgccggcgtt tggtcatttg ctttgtgacc    720
gcgccgaggg accatgttcc gccagggcac ccccaaccgc gtggtgatca gcacagtgcc    780
gttgagcaga gaggcgaccg cgaccgcgac cgccggcacc ggtcccggat gcagggggg     840 gcttggtggc tggcgactct ttacagtgcc gccacgagca agaagacggc ctgtatgcta    900
tcgtcccgcc ggactatttt ccggtggtgc cctcgtccaa gccctgctg gtgaaagttc     960 ccgctcccgg cgcgagtccc gaccgaactg ggggcgcagt tcactttgaa tgtgttcccg    1020
cgccgcgccg accgctgcag ttctttcgtc agctttacga cggttcattc gttaagctt    1079
```

<210> SEQ ID NO 20
<211> LENGTH: 17
<212> TYPE: PRT
<213> ORGANISM: 'Axial Seamount' polynoid polychaete

<400> SEQUENCE: 20

Met Trp Val Phe Gly Ala Ala Asp Leu Tyr Ala Pro Ile Phe Ala His
 1               5                  10                  15
Ile

<210> SEQ ID NO 21
<211> LENGTH: 17
<212> TYPE: PRT
<213> ORGANISM: Herpes Simplex Virus 1

<400> SEQUENCE: 21

Leu Trp Val Val Gly Ala Ala Asp Leu Cys Val Pro Phe Leu Glu Tyr
 1               5                  10                  15
Ala

<210> SEQ ID NO 22
<211> LENGTH: 17
<212> TYPE: PRT
<213> ORGANISM: Parvovirus

<400> SEQUENCE: 22

Leu Trp Ile Leu Gly Ala Ala Asp Leu Cys Asp Gln Val Leu Leu Ala
 1               5                  10                  15
Ala

<210> SEQ ID NO 23
<211> LENGTH: 17
<212> TYPE: PRT
<213> ORGANISM: Herpes Simplex Virus 2

<400> SEQUENCE: 23

Leu Trp Val Val Gly Ala Ala Asp Leu Cys Val Pro Phe Phe Glu Tyr
 1               5                  10                  15
Ala

<210> SEQ ID NO 24
<211> LENGTH: 19
<212> TYPE: PRT
<213> ORGANISM: Marek's Disease Virus

<400> SEQUENCE: 24

```
His Ser Leu Trp Ile Val Gly Ala Ala Asp Ile Cys Arg Ile Ala Leu
  1               5                  10                  15

Glu Cys Ile
```

<210> SEQ ID NO 25
<211> LENGTH: 60
<212> TYPE: DNA
<213> ORGANISM: Artificial Sequence
<220> FEATURE:
<223> OTHER INFORMATION: Description of Artificial Sequence:  IBRV
      Cooper Strain

<400> SEQUENCE: 25
tgagcgcgcg ccgctgcatg ctggtgcgaa ctcacgccga gcgcgcgtgc gagcaagctt        60

<210> SEQ ID NO 26
<211> LENGTH: 60
<212> TYPE: DNA
<213> ORGANISM: Artificial Sequence
<220> FEATURE:
<223> OTHER INFORMATION: Description of Artificial Sequence:  IBRV
      Nasalgen Strain

<400> SEQUENCE: 26
ctagtaaaaa cggcgaaggg ctggtgcgaa ctcacgccga gcgcgcgtgc gagcaagctt        60

<210> SEQ ID NO 27
<211> LENGTH: 60
<212> TYPE: DNA
<213> ORGANISM: Artificial Sequence
<220> FEATURE:
<223> OTHER INFORMATION: Description of Artificial Sequence:  IBRV
      Cooper Strain

<400> SEQUENCE: 27
ctagtaaaaa cggcgaaggg ctgcacgtcg acgtcaacgt caagccagcg gcgcgggtgg        60

<210> SEQ ID NO 28
<211> LENGTH: 48
<212> TYPE: DNA
<213> ORGANISM: Artificial Sequence
<220> FEATURE:
<223> OTHER INFORMATION: Description of Artificial Sequence:  Synthetic
      Linker Sequences

<400> SEQUENCE: 28
gatttaggtg acactataga atacacggaa ttcgagctcg ccccatgg                    48

<210> SEQ ID NO 29
<211> LENGTH: 99
<212> TYPE: DNA
<213> ORGANISM: Artificial Sequence
<220> FEATURE:
<223> OTHER INFORMATION: Description of Artificial Sequence:  Synthetic
      Linker Sequences

<400> SEQUENCE: 29
ttaagtggga tcccggcgcg caggcgcgca cgtcggtcgc ggtcgcgcgc catgggggat       60
cctctagagc ttgggctgca ggtcctgatt gatacactg                              99

<210> SEQ ID NO 30
<211> LENGTH: 99
<212> TYPE: DNA
<213> ORGANISM: Artificial Sequence
<220> FEATURE:
<223> OTHER INFORMATION: Description of Artificial Sequence:  Synthetic Linker Sequences

<400> SEQUENCE: 30

| gccccgatcg tccacacgga gcgcggctgc cgacacggat ctgatcaaga gacaggatga | 60 |
| ggatcgtttc gcatgattga acaagatgga ttgcacgca | 99 |

<210> SEQ ID NO 31
<211> LENGTH: 100
<212> TYPE: DNA
<213> ORGANISM: Artificial Sequence
<220> FEATURE:
<223> OTHER INFORMATION: Description of Artificial Sequence: Synthetic
      Linker Sequences

<400> SEQUENCE: 31

| ggaccttgca caagatagcg tggtccggcc aggacgacga ggcttgcagg atcctctaga | 60 |
| gtcgggagat gggggaggct aactgaaaca cggaaggaga | 100 |

<210> SEQ ID NO 32
<211> LENGTH: 124
<212> TYPE: DNA
<213> ORGANISM: Artificial Sequence
<220> FEATURE:
<223> OTHER INFORMATION: Description of Artificial Sequence: Synthetic
      Linker Sequences

<400> SEQUENCE: 32

| gtgttgctgc gttcccgacc tgcagcccaa gctctagagt cgacctgcag cccaagctct | 60 |
| agagtcgacc tgcagcccaa gctcagatct gctcatgctc gcggccgcca tgccccggga | 120 |
| agcg | 124 |

<210> SEQ ID NO 33
<211> LENGTH: 60
<212> TYPE: DNA
<213> ORGANISM: Artificial Sequence
<220> FEATURE:
<223> OTHER INFORMATION: Description of Artificial Sequence: Synthetic
      Linker Sequences

<400> SEQUENCE: 33

| aggcagatct gagcttggcg taatcatggt catagctgtt tcctgtgtga aattgttatc | 60 |

<210> SEQ ID NO 34
<211> LENGTH: 1386
<212> TYPE: DNA
<213> ORGANISM: 'Axial Seamount' polynoid polychaete

<400> SEQUENCE: 34

| gcgatcatgc ctgccgcccg gaccggcacc ttggccgccg tcgccctaat cctgctctgc | 60 |
| ggggccgccg ttttgcggcc ccgcgcccga cgacctctgt ttcgccgacg tgcgccgcac | 120 |
| tggcatggcg ccctcccgcc cgctgggcc cgtcctgaac ctagcggcct cggatttgac | 180 |
| ctcgcgggtt tcggtgcgcg cggtggagct tcgcgcgctg cgcccggcc ctcttggaca | 240 |
| tggcggagac ggtggtgccc ggcggaccgc gagccscacg tcgtcgacgt cggctgggct | 300 |
| taccaagacg gggactgcat ggtgcctctg gcatatcgcc agtactttaa ctgcacgggg | 360 |
| ggcgcgctgc ccggccaaaa cgtctgcgcc gggctctctg agaccgcat ccgcggtggc | 420 |
| tttggaacct ccgactacgc gctctacggg acgtcgctag tactgcgccc cggcctgtac | 480 |
| gaccgcggga cctacatcta cttccttgga tacggcccag acgacatcta cgtgggcagc | 540 |

-continued

```
gtcacgctca tggtgggcgc cgacatccac aaatacccct gcgggctgga ccgagggctc    600
ggtgtggccc tgcaccacaa gagcggaccg gcccgacctc tgacagagga cgacgccacc    660
ggcgactggg cctgcggctg cttccccgcc cttgttgagg ttgacgcggt gtggggcaac    720
gtaagcgccg cagagctggg cctggccgac ccgatcgact acgccgacga agggggtgag    780
gtcgaagtgc tcgaggacga agccgggagc gccagcggaa acctgccgca ggacgacccc    840
gaccccgacc tcgcagattg ccggaccgtc gggctcttta gcgaaagcga catgttccgg    900
accgccagcg ggcccgaatc gctgctgatc ggcgccgttg ccaaggacgt cctgacggtg    960
cccctcaatc tgccgcccgg ccgctcttac gaggccctgc gaaacgcatc gctggagtgc   1020
aactcccgcc cgcgcgagac cggcgacgca gcggtggtgg tgatgtctct ccaggagccc   1080
gctcgcctcg agcgccgccc cgatgcccgc gccaccgatc cggagtttgg gctctttggc   1140
ctgcccgatg acccgccgt gcgcgcggca ttctcatcgg cctcgcgatc gctctgctgg   1200
tgctgctgtt tcgctggtga tcgtgctcgt ctgcgcctgc cggctcgccc gcccagccaa   1260
ggctgcgcga cgccccgcgc cgccacgttc gccaagagca acccgcgta cgagccgatg   1320 ctcagcgtct gatcgccggc accccacgcc gccccgaccc cgctgtcccg cgtttacaat   1380
aaacag                                                              1386
```

<210> SEQ ID NO 35
<211> LENGTH: 34
<212> TYPE: PRT
<213> ORGANISM: Parvovirus

<400> SEQUENCE: 35

Val Gly Trp Ala Tyr Gln Asp Gly Asp Cys Met Val Pro Leu Ala Tyr
1               5                   10                  15

Arg Gln Tyr Phe Asn Cys Thr Gly Gly Ala Leu Pro Gly Asn Val Leu
            20                  25                  30

Cys Ala

<210> SEQ ID NO 36
<211> LENGTH: 34
<212> TYPE: PRT
<213> ORGANISM: Parvovirus

<400> SEQUENCE: 36

Val Ala Trp Phe Phe Asp Gly Gly His Cys Lys Val Pro Leu Val His
1               5                   10                  15

Arg Glu Tyr Tyr Gly Cys Pro Gly Asp Ala Met Pro Ser Val Glu Thr
            20                  25                  30

Cys Thr

<210> SEQ ID NO 37
<211> LENGTH: 34
<212> TYPE: PRT
<213> ORGANISM: Herpes Simplex Virus - 2

<400> SEQUENCE: 37

Val Thr Tyr Tyr Arg Leu Thr Arg Ala Cys Arg Gln Pro Ile Leu Leu
1               5                   10                  15

Arg Gln Tyr Gly Gly Cys Arg Gly Gly Glu Pro Pro Ser Pro Lys Thr
            20                  25                  30

Cys Gly

<210> SEQ ID NO 38
<211> LENGTH: 102
<212> TYPE: DNA
<213> ORGANISM: Artificial Sequence
<220> FEATURE:
<223> OTHER INFORMATION: Description of Artificial Sequence: Synthetic
      Linker Sequences

<400> SEQUENCE: 38
cacatacgat ttaggtgaca ctatagaata caagcttggg ctgcaggtcg actctagagt      60
cgacctgcag tgaataataa aatgtgtgtt tgtccgaaat ac                        102

<210> SEQ ID NO 39
<211> LENGTH: 102
<212> TYPE: DNA
<213> ORGANISM: Artificial Sequence
<220> FEATURE:
<223> OTHER INFORMATION: Description of Artificial Sequence: Synthetic
      Linker Sequences

<400> SEQUENCE: 39
gcgtttgaga tttctgtccc gactaaattc atgtcgcgcg atagtggtgt ttatcgccga      60
tagagatggc gatattggaa aaatcgatat ttgaaaatat gg                        102

<210> SEQ ID NO 40
<211> LENGTH: 102
<212> TYPE: DNA
<213> ORGANISM: Artificial Sequence
<220> FEATURE:
<223> OTHER INFORMATION: Description of Artificial Sequence: Synthetic
      Linker Sequences

<400> SEQUENCE: 40
catattgaaa atgtcgccga tgtgagtttc tgtgtaactg atcgcgtgtt tggaggcaac      60
cggggcctgc tcccgacggc cagcgacgac gtggtgctca ag                        102

<210> SEQ ID NO 41
<211> LENGTH: 102
<212> TYPE: DNA
<213> ORGANISM: Artificial Sequence
<220> FEATURE:
<223> OTHER INFORMATION: Description of Artificial Sequence: Synthetic
      Linker Sequences

<400> SEQUENCE: 41
atgtctctcc aggagcccgc tcgcctcgag ggcctgccct cgcagctgcc cgtcttcgag      60
gacacgcagc gctacgacgc ctcccccgcg tccgtgagct gg                        102

<210> SEQ ID NO 42
<211> LENGTH: 102
<212> TYPE: DNA
<213> ORGANISM: Artificial Sequence
<220> FEATURE:
<223> OTHER INFORMATION: Description of Artificial Sequence: Synthetic
      Linker Sequences

<400> SEQUENCE: 42
cccgtgagca gcatgatcgt cgtcatcgcc ggcatcggga tcctggccat cgtgctggtc      60
atccatatgg cgatcatcag ggcccgggcc cggaacgacg gc                        102

<210> SEQ ID NO 43
<211> LENGTH: 75
<212> TYPE: DNA
<213> ORGANISM: Artificial Sequence
<220> FEATURE:
<223> OTHER INFORMATION: Description of Artificial Sequence: Synthetic
      Linker Sequences

<400> SEQUENCE: 43
gggccagtac cggcgcctgg tgtccgtcga ctctagagtc gacctgcagc ccaagctttg      60
gcgtaatcat ggtca                                                      75

<210> SEQ ID NO 44
<211> LENGTH: 57
<212> TYPE: DNA
<213> ORGANISM: Artificial Sequence
<220> FEATURE:
<223> OTHER INFORMATION: Description of Artificial Sequence: Synthetic
      Linker Sequences

<400> SEQUENCE: 44
acatacgatt taggtgacac tatagaatac aagcttaacg aatgaaccgt cgtaaag         57

<210> SEQ ID NO 45
<211> LENGTH: 96
<212> TYPE: DNA
<213> ORGANISM: Artificial Sequence
<220> FEATURE:
<223> OTHER INFORMATION: Description of Artificial Sequence: Synthetic
      Linker Sequences

<400> SEQUENCE: 45
gtcgaagtgc tcgaaattcg agctcgcccg gggatcctct agagtcgacc tgcaggtgga      60
ctctagagga tctcgacgga caccaggcgc cggtac                               96

<210> SEQ ID NO 46
<211> LENGTH: 57
<212> TYPE: DNA
<213> ORGANISM: Artificial Sequence
<220> FEATURE:
<223> OTHER INFORMATION: Description of Artificial Sequence: Synthetic
      Linker Sequences

<400> SEQUENCE: 46
gggcggggcc gggtcagccg gatctagagt cccaggaccc aacgctgccc gagtttg         57

<210> SEQ ID NO 47
<211> LENGTH: 57
<212> TYPE: DNA
<213> ORGANISM: Artificial Sequence
<220> FEATURE:
<223> OTHER INFORMATION: Description of Artificial Sequence: Synthetic
      Linker Sequences

<400> SEQUENCE: 47
tcccagtcac gacgttgtaa aacgacggga tccatggtcc cggtgtcttc tatggag         57

<210> SEQ ID NO 48
<211> LENGTH: 57
<212> TYPE: DNA
<213> ORGANISM: Artificial Sequence
<220> FEATURE:
<223> OTHER INFORMATION: Description of Artificial Sequence: Synthetic
      Linker Sequences

<400> SEQUENCE: 48
attcactgca ggtcgactct agaggatccc cgggcgagct cgaatttcga gcgccgc         57

<210> SEQ ID NO 49

```
<211> LENGTH: 57
<212> TYPE: DNA
<213> ORGANISM: Artificial Sequence
<220> FEATURE:
<223> OTHER INFORMATION: Description of Artificial Sequence:   Synthetic
      Linker Sequences

<400> SEQUENCE: 49
gcgcgcgcgt acaacgccac ggtcataggg cgagctcgaa ttcgtaatca tggtcat         57

<210> SEQ ID NO 50
<211> LENGTH: 57
<212> TYPE: DNA
<213> ORGANISM: Artificial Sequence
<220> FEATURE:
<223> OTHER INFORMATION: Description of Artificial Sequence:   Synthetic
      Linker Sequences

<400> SEQUENCE: 50
atacacatac gatttaggtg acactataga atacaagctc gcgtgtttgg aggcaac         57

<210> SEQ ID NO 51
<211> LENGTH: 102
<212> TYPE: DNA
<213> ORGANISM: Artificial Sequence
<220> FEATURE:
<223> OTHER INFORMATION: Description of Artificial Sequence:   Synthetic
      Linker Sequences

<400> SEQUENCE: 51
tcggggtagc cccaattcga gctcgcccgg ggatcctcta gagtcgacct gcaggtcgac      60
tctagaggat ctcgacggac accaggcgcc ggtactggcc ct                       102

<210> SEQ ID NO 52
<211> LENGTH: 57
<212> TYPE: DNA
<213> ORGANISM: Artificial Sequence
<220> FEATURE:
<223> OTHER INFORMATION: Description of Artificial Sequence:   Synthetic
      Linker Sequences

<400> SEQUENCE: 52
gggcggggcc gggtcagccg gatctagagt cccaggaccc aacgctgccc gagtttg         57

<210> SEQ ID NO 53
<211> LENGTH: 57
<212> TYPE: DNA
<213> ORGANISM: Artificial Sequence
<220> FEATURE:
<223> OTHER INFORMATION: Description of Artificial Sequence:   Synthetic
      Linker Sequences

<400> SEQUENCE: 53
tcccagtcac gacgttgtaa aacgacggga tccatggtcc cggtgtcttc tatggag         57

<210> SEQ ID NO 54
<211> LENGTH: 57
<212> TYPE: DNA
<213> ORGANISM: Artificial Sequence
<220> FEATURE:
<223> OTHER INFORMATION: Description of Artificial Sequence:   Synthetic
      Linker Sequences

<400> SEQUENCE: 54
attcactgca ggtcgactct agaggatccc cgggcgagct cgaatttcga gcgccgc         57
```

```
<210> SEQ ID NO 55
<211> LENGTH: 57
<212> TYPE: DNA
<213> ORGANISM: Artificial Sequence
<220> FEATURE:
<223> OTHER INFORMATION: Description of Artificial Sequence:   Synthetic
      Linker Sequences

<400> SEQUENCE: 55
gcgcgcgcgt acaacgccac ggtcataggg cgagctcgaa ttcgtaatca tggtcat          57

<210> SEQ ID NO 56
<211> LENGTH: 57
<212> TYPE: DNA
<213> ORGANISM: Artificial Sequence
<220> FEATURE:
<223> OTHER INFORMATION: Description of Artificial Sequence:   Synthetic
      Linker Sequences

<400> SEQUENCE: 56
atacacatac gatttaggtg acactataga atacaagctc gcgtgtttgg aggcaac          57

<210> SEQ ID NO 57
<211> LENGTH: 84
<212> TYPE: DNA
<213> ORGANISM: Artificial Sequence
<220> FEATURE:
<223> OTHER INFORMATION: Description of Artificial Sequence:   Synthetic
      Linker Sequences

<400> SEQUENCE: 57
cggggtagcc ccaattcgag ctcgcccggg gatcctctag aggatccccg ggcgagctcg       60
aatttcgagc gccgccccga tgcc                                              84

<210> SEQ ID NO 58
<211> LENGTH: 57
<212> TYPE: DNA
<213> ORGANISM: Artificial Sequence
<220> FEATURE:
<223> OTHER INFORMATION: Description of Artificial Sequence:   Synthetic
      Linker Sequences

<400> SEQUENCE: 58
gcgcgcgcgt acaacgccac ggtcataggg cgagctcgaa ttcgtaatca tggtcat          57

<210> SEQ ID NO 59
<211> LENGTH: 2040
<212> TYPE: DNA
<213> ORGANISM: IBRV

<400> SEQUENCE: 59
gcgggcaagg cggaggaaga ccgggggcag gagctgcgtg gagggcggag ccgttgagcg       60
gcccgaccgc cgccgggttg ttaaatgggt ctcgcgcggc tcgtggttcc acaccgcgcc      120
ggagaaccag cgcgcagctt cgctgcgtgt gtcccgcgag ctgcgttccg gggaacggcg      180
cgcgcgagag ggttcgaaaa gggcatttgg caatgcaacc caccgcgccg ccccggcssg      240
gttgcgccgc tgctgctgcc gcagttattg cttttcgggc tgatggccga ggccaagccc      300
gcgaccgaaa cccgggctc ggcttcggtc gacacggtct tcacgcgcg cgctggcgcg       360 cccgtctttc tcccagggcc cgcggcgcgc ccggacgtgc gcgccgttcg cggctggagc      420
gtcctcgcgg ccgcctgctc gccgcccgtg ccggagcccg tctgcctcga cgaccgcgag      480
tgcttcaccg acgtggccct ggacgcggcc tgcctgcgaa ccgcccgcgt ggccccgctg      540
```

-continued

```
gccatcgcgg agctcgccga gcggcccgac tcaacgggcg acaaagagtt tgttctcgcc         600
gacccgcacg tctcggcgca gctgggtcgc aacgcgaccg gggtgctgat cgcggccgca         660
gccgaggagg acggcggcgt gtacttcctg tacgaccggc tcatcggcga cgccggcgac         720
gaggagacgc agttggcgct gacgctgcag gtcgcgacgg ccggcgcgca gggcgccgcg         780
cgggacgagg agagggaacc agcgaccggg cccaccccg gccgccgcc ccaccgcacg           840 acgacacgcg cgccccgcg gcggcacggc gcgcgcttcc gcgtgctgcc gtaccactcc          900
cacgtataca ccccgggcga ttcctttctg ctatcggtgc gtctgcagtc tgagtttttc         960
gacgaggctc ccttctcggc cagcatcgac tggtacttcc tgcggacggc cggcgactgc        1020
gcgctcatcc gcatatacga gacgtgcatc ttccaccccg aggcaccggc ctgcctgcac        1080
cccgccgacg cgcagtgcag cttcgcgtcg ccgtaccgct ccgagaccgt gtacagccgg        1140
ctgtacgagc agtgccgccc ggaccctgcc ggtcgctggc cgcacgagtg cgagggcgcc        1200
gcgtacgcgg cgcccgttgc gcacctgcgt cccgccaata acagcgtaga cctggtctttt      1260 gacgacgcgc cggctgcggc ctccgggctt tacgtctttg tgctgcagta caacggccac        1320
gtggaagctt gggactactg cctagtcgtt acttcggacc gtttggtgcg cgcggtcacc        1380
gaccacacgc gccccgaggc cgcagccgcc gacgctcccg agccaggccc accgctcacc        1440
agcgagccgg cggggsgcc caccgggccc gcgccctggc ttgtggtgct ggtgggcgcg        1500
cttggactcg cgggactggt gggcatcgca gccctcgccg ttcgggtgtg cgcgcgccgc        1560
gcaagccaga agcgcaccta cgacatcctc aacccccttcg ggcccgtata caccagcttg      1620
ccgaccaacg agccgctcga cgtggtggtg ccagttagcg acgacgaatt tttccctcgac      1680 gaagactctt ttgcggatga cgacagcgac gatgacgggc ccgctagcaa ccccccctgcg      1740 gatgcctacg acctcgccgg cgccccagag ccaactagcg ggtttgcgcg agccccccgcc      1800 aacggcacgc gctcgagtcg ctctgggttc aaagtttggt ttagggaccc gcttgaagac       1860
gatgccgcgc cagcgcggac cccggccgca ccagattaca ccgtggtagc agcgcgactc       1920
aagtccatcc tccgctaggc gccccccccc gcgcgctgtg ccgtctgacg gaaagcaccc       1980
gcgtgtaggg ctgcatataa atgagcgct cacacaaagc ctcgtgcggc tgcttcgaag        2040
```

<210> SEQ ID NO 60
<211> LENGTH: 720
<212> TYPE: DNA
<213> ORGANISM: IBRV

<400> SEQUENCE: 60

```
gcgtgtaggg ctgcatataa atggagcgct cacacaaagc ctcgtgcggc tgcttcgaag    720

<210> SEQ ID NO 61
<211> LENGTH: 50
<212> TYPE: PRT
<213> ORGANISM: HSV-1

<400> SEQUENCE: 61

Trp Leu Arg Phe Asp Val Pro Thr Ser Cys Ala Glu Met Arg Ile Tyr
 1               5                  10                  15

Glu Ser Cys Leu Tyr His Pro Gln Leu Pro Glu Cys Leu Ser Pro Ala
            20                  25                  30

Asp Ala Pro Cys Ala Ala Ser Thr Trp Thr Ser Arg Leu Ala Val Arg
        35                  40                  45

Ser Tyr
    50

<210> SEQ ID NO 62
<211> LENGTH: 53
<212> TYPE: PRT
<213> ORGANISM: PRV

<400> SEQUENCE: 62

Trp Tyr Tyr Ala Arg Ala Pro Pro Arg Cys Leu Leu Tyr Tyr Val Tyr
 1               5                  10                  15

Glu Pro Cys Ile Tyr His Pro Arg Ala Pro Glu Cys Leu Arg Pro Val
            20                  25                  30

Asp Pro Ala Cys Ser Phe Thr Ser Pro Ala Ala Arg Ala Ala Leu Val
        35                  40                  45

Ala Arg Arg Ala Tyr
    50

<210> SEQ ID NO 63
<211> LENGTH: 52
<212> TYPE: PRT
<213> ORGANISM: VZV

<400> SEQUENCE: 63

Trp Leu Tyr Val Pro Ile Asp Pro Thr Cys Gln Pro Met Arg Leu Tyr
 1               5                  10                  15

Ser Thr Cys Leu Tyr His Pro Asn Ala Pro Gln Cys Leu Ser His Met
            20                  25                  30

Asn Ser Gly Cys Thr Phe Thr Ser Pro His Leu Ala Gln Arg Val Ala
        35                  40                  45

Ser Thr Val Tyr
    50

<210> SEQ ID NO 64
<211> LENGTH: 52
<212> TYPE: PRT
<213> ORGANISM: IBRV

<400> SEQUENCE: 64

Trp Tyr Phe Leu Arg Thr Ala Gly Asp Cys Ala Leu Ile Arg Ile Tyr
 1               5                  10                  15

Glu Thr Cys Ile Phe His Pro Glu Ala Pro Ala Cys Leu His Pro Ala
            20                  25                  30

Asp Ala Gln Cys Ser Phe Ala Ser Pro Tyr Arg Ser Glu Thr Val Tyr
        35                  40                  45

Ser Arg Leu Tyr
    50

<210> SEQ ID NO 65
<211> LENGTH: 85
<212> TYPE: DNA
<213> ORGANISM: Artificial Sequence
<220> FEATURE:
<223> OTHER INFORMATION: Description of Artificial Sequence: Synthetic
      Linker Sequences

<400> SEQUENCE: 65
ttgggctgca ggtcgactct agaggatccc ctatggtaca agatcgagag cgggtgccgc    60
ccggccgctg tactacatgg agtac                                          85

<210> SEQ ID NO 66
<211> LENGTH: 84
<212> TYPE: DNA
<213> ORGANISM: Artificial Sequence
<220> FEATURE:
<223> OTHER INFORMATION: Description of Artificial Sequence: Synthetic
      Linker Sequence

<400> SEQUENCE: 66
tccgggcttt acgtctttgt gctgcagtac aacggccacg tggaagcttg ggactacagc    60
ctagtcgtta cttcggaccg tttg                                           84

<210> SEQ ID NO 67
<211> LENGTH: 84
<212> TYPE: DNA
<213> ORGANISM: Artificial Sequence
<220> FEATURE:
<223> OTHER INFORMATION: Description of Artificial Sequence: Synthetic
      Linker Sequences

<400> SEQUENCE: 67
ccttcaccgc cgccggaagg ctccatcgtg tccatcccca tcctcgagct cgaattgggg    60
atcctctaga gtcgacctgc agcc                                           84

<210> SEQ ID NO 68
<211> LENGTH: 60
<212> TYPE: DNA
<213> ORGANISM: Artificial Sequence
<220> FEATURE:
<223> OTHER INFORMATION: Description of Artificial Sequence: Synthetic
      Linker Sequences

<400> SEQUENCE: 68
ctatagaata cacggaattc gagctcgccc gggtgagcgg cctaggcccct ccccgaccg    60

<210> SEQ ID NO 69
<211> LENGTH: 90
<212> TYPE: DNA
<213> ORGANISM: Artificial Sequence
<220> FEATURE:
<223> OTHER INFORMATION: Description of Artificial Sequence: Synthetic
      Linker Sequences

<400> SEQUENCE: 69
atggccgagg ccaagcccgc gaccgaaacc ccggggatcc tctagagtcg acgtctgggg    60 cgcggggtg gtgctcttcg agacgctgcc                                      90

<210> SEQ ID NO 70

-continued

```
<211> LENGTH: 90
<212> TYPE: DNA
<213> ORGANISM: Artificial Sequence
<220> FEATURE:
<223> OTHER INFORMATION: Description of Artificial Sequence:   Synthetic
      Linker Sequence

<400> SEQUENCE: 70
acctttgcgc atctccacag ctcaacaatg aagtgggcaa cgtggatcga tcccgtcgtt     60
ttacaacgtc gtgactggga aaaccctggc                                      90

<210> SEQ ID NO 71
<211> LENGTH: 201
<212> TYPE: DNA
<213> ORGANISM: Artificial Sequence
<220> FEATURE:
<223> OTHER INFORMATION: Description of Artificial Sequence:   Synthetic
      Linker Sequences

<400> SEQUENCE: 71
tggagcccgt cagtatcggc ggaaatccag ctgagcgccg gtcgctacca ttaccagttg     60
gtctggtgtc aaaaagatct agaataagct agaggatcga tcccctatgg cgatcatcag    120
ggcccgatcc cctatggcga tcatcagggc ccgggcccgg aacgacggct accgccacgt    180
ggcctccgcc tgacccggcc c                                              201

<210> SEQ ID NO 72
<211> LENGTH: 90
<212> TYPE: DNA
<213> ORGANISM: Artificial Sequence
<220> FEATURE:
<223> OTHER INFORMATION: Description of Artificial Sequence:   Synthetic
      Linker Sequences

<400> SEQUENCE: 72
ggcgcctggt gtccgtcgac tctagagtcg acctgcagcc caagctctag caacccccct     60
gcggatgcct acgacctcgc cggcgcccca                                      90

<210> SEQ ID NO 73
<211> LENGTH: 1880
<212> TYPE: DNA
<213> ORGANISM: IBRV

<400> SEQUENCE: 73
aggaacaaag ttgttcaaca cagcagcagc gaacagaccc aaaggcagcg cagaggcgac     60
accgaaccca aaatggaata ttggaaacac acaaacagca caaaaaacac caacaatgaa    120
accgaaacaa ccagaggcaa acacagtagc aaggttacaa atatcataat gtacaccttc    180
tggacaataa catcaacaat attattagtc atttttataa tgatattgac aaacttaatt    240
caagagaaca atcataataa attaatgttg caggaaataa gaaaagaatt cgcggcaata    300
gacaccaaga ttcagaggac ctcggatgac attggaacct caatacagtc aggaataaat    360
acaagacttc tcacaattca gagtcatgtt caaaactata tcccactatc actaacacaa    420
caaatgtcag atctcagaaa atttatcaat gatctaacaa ataaaagaga acatcaagaa    480
gtgccaatac agagaatgac tcatgataga ggtatagaac ccctaaatcc agacaagttc    540
tggaggtgta catctggtaa cccatctcta acaagtagtc ctaagataag gttaatacca    600
gggccaggtt tattagcaac atctactaca gtaaatggct gtattagaat cccatcgtta    660
gcaatcaatc atttaatcta cgcttacacc tctaatctta tcacccaggg ctgtcaaaat    720
```

-continued

| | |
|---|---|
| ataggggaaat cttaccaagt actacaaata gggataatta ctataaattc ggacctagta | 780 |
| cctgatttaa atcccagagt cacacataca tttaatattg atgataatag gaaatcttgc | 840 |
| tctctggcac tattgaatac agatgtttat cagttatgct caacaccaaa agttgatgag | 900 |
| agatccgatt atgcatcaac aggtattgag gatattgtac ttgacattgt cactaataat | 960 |
| ggattaatta taacaacaag gtttacaaat aataatataa cttttgataa accgtatgca | 1020 |
| gcattgtatc catcagtagg accaggaatc tattataagg gtaaagttat ctttctcgga | 1080 |
| tatggaggtc tagagcatga agaaaacgga gacgtaatat gtaatacaac tggttgtcct | 1140 |
| ggcaaaacac agagagactg taatcaggct tcttatagcc catggttctc aaataggaga | 1200 |
| atggtaaact ctattattgt tgttgataaa ggcatagatg caacttttag cttgagggtg | 1260 |
| tggactattc caatgagcca aaattattgg ggatcagaag gaagattact tttattaggt | 1320 |
| gacagaatat acatatatac tagatccaca agttggcaca gtaaattaca gttaggggta | 1380 |
| attgatattt ctgattataa taatataaga ataaattgga cttggcataa tgtaccatca | 1440 |
| cggccaggaa atgatgaatg tccatggggt cattcatgcc cagacggatg tataacagga | 1500 |
| gtttacactg atgcatatcc gctaaaccca tcggggagtg ttgtatcatc agtaattctt | 1560 |
| gactcacaaa agtctagaga aaacccaatc attacctact caacagctac aaatagaata | 1620 |
| aatgaattag ctatatataa cagaacactt ccagctgcat atacaacaac aaattgtatc | 1680 |
| acacattatg ataaagggta ttgttttcat atagtagaaa taaatcacag aagtttgaat | 1740 |
| acgtttcaac ctatgttatt caaaacgaaa gttccaaaaa actgcagcta aatgatcatc | 1800 |
| gcatatcgga tgccagatga cattaaaaga gaccaccaga cagacaacac aggagatgat | 1860 |
| gcaagatata aaggaataat | 1880 |

<210> SEQ ID NO 74
<211> LENGTH: 900
<212> TYPE: DNA
<213> ORGANISM: IBRV
<220> FEATURE:
<221> NAME/KEY: unsure
<222> LOCATION: (812)
<223> OTHER INFORMATION: Where n=unsure

<400> SEQUENCE: 74

| | |
|---|---|
| gtttacaaat aataatataa cttttgataa accgtatgca gcattgtatc catcagtagg | 60 |
| accaggaatc tattataagg gtaaagttat ctttctcgga tatggaggtc tagagcatga | 120 |
| agaaaacgga gacgtaatat gtaatacaac tggttgtcct ggcaaaacac agagagactg | 180 |
| taatcaggct tcttatagcc catggttctc aaataggaga atggtaaact ctattattgt | 240 |
| tgttgataaa ggcatagatg caacttttag cttgagggtg tggactattc caatgagcca | 300 |
| aaattattgg ggatcagaag gaagattact tttattaggt gacagaatat acatatatac | 360 |
| tagatccaca agttggcaca gtaaattaca gttaggggta attgatattt ctgattataa | 420 |
| taatataaga ataaattgga cttggcataa tgtaccatca cggccaggaa atgatgaatg | 480 |
| tccatggggt cattcatgcc cagacggatg tataacagga gtttacactg atgcatatcc | 540 |
| gctaaaccca tcggggagtg ttgtatcatc agtaattctt gactcacaaa agtctagaga | 600 |
| aaacccaatc attacctact caacagctac aaatagaata aatgaattag ctatatataa | 660 |
| cagaacactt ccagctgcat atacaacaac aaattgtatc acacattatg ataaagggta | 720 |
| ttgttttcat atagtagaaa taaacacaga agtttgaata cgtttcaacc tatgttattc | 780 |
| aaaacagaag ttccaaaaaa ctgcagctaa antgatcatc gcatatcgga tgccagatga | 840 |

-continued

```
cattaaaaga gaccaccaga cagacaacac aggagatgat gcaagatata aaggaataat      900

<210> SEQ ID NO 75
<211> LENGTH: 198
<212> TYPE: DNA
<213> ORGANISM: Artificial Sequence
<220> FEATURE:
<223> OTHER INFORMATION: Description of Artificial Sequence:  Synthetic
      Linker

<400> SEQUENCE: 75
ccttatgtat catacacata cgatttaggt gacactatag aatacaagct tgggctgcag       60
gtcgacgtcc gcgctgctgc gccgcctggg ccggcggaag atctggtcat gctcgcggcc      120
gccatgcccc cgggacacca tgtttttcct gccgcgcgcg gccgtcgact ctagaggatc      180
cccgggcgag ctcgaatt                                                    198

<210> SEQ ID NO 76
<211> LENGTH: 132
<212> TYPE: DNA
<213> ORGANISM: Artificial Sequence
<220> FEATURE:
<223> OTHER INFORMATION: Description of Artificial Sequence:  Synthetic
      Linker

<400> SEQUENCE: 76
ggatcccctc gacgtctggg gcgcggggt ggtgctcttc gagacgctgg cctacccaa         60 gacgatcaca cctttgcgca tctccacagc tcaacaatga attccatgtt acgtcctgta      120
gaaaccccaa cc                                                          132

<210> SEQ ID NO 77
<211> LENGTH: 132
<212> TYPE: DNA
<213> ORGANISM: Artificial Sequence
<220> FEATURE:
<223> OTHER INFORMATION: Description of Artificial Sequence:  Synthetic
      Linker

<400> SEQUENCE: 77
cagggaggca aacaatgaat caacaactct cccgggagat ggggaggct aactgaaaca        60 cggaaggtcg cccccttaa gggtctcttg cacaatccag ccgcctccgt gttgctgcgt      120
tcccggggat cc                                                          132

<210> SEQ ID NO 78
<211> LENGTH: 122
<212> TYPE: DNA
<213> ORGANISM: Artificial Sequence
<220> FEATURE:
<223> OTHER INFORMATION: Description of Artificial Sequence:  Synthetic
      Linker

<400> SEQUENCE: 78
ctatagaata cacggaattc gagctcgccc gggtgagcgg cctaggccct cccccgaccg       60
cccgcgaccg aaacccgggg gatcctctag agtcgacctg cagcccaagc tctagcaacc     120
cc                                                                     122
```